(12) United States Patent
Kokubo et al.

(10) Patent No.: US 8,822,459 B2
(45) Date of Patent: *Sep. 2, 2014

(54) COMPOUND CONTAINING BASIC GROUP AND USE THEREOF

(75) Inventors: Masaya Kokubo, Mishima-gun (JP); Yoshikazu Takaoka, Mishima-gun (JP); Shiro Shibayama, Tsukuba (JP)

(73) Assignee: Ono Pharmaceutical Co., Ltd., Osaka (JP)

(*) Notice: Subject to any disclaimer, the term of this patent is extended or adjusted under 35 U.S.C. 154(b) by 357 days.

This patent is subject to a terminal disclaimer.

(21) Appl. No.: 13/027,957

(22) Filed: Feb. 15, 2011

(65) Prior Publication Data

US 2011/0142856 A1 Jun. 16, 2011

Related U.S. Application Data

(62) Division of application No. 11/661,270, filed as application No. PCT/JP2005/016066 on Aug. 26, 2005, now Pat. No. 7,951,816.

(30) Foreign Application Priority Data

Aug. 27, 2004 (JP) ................................. 2004-248431
Mar. 30, 2005 (JP) ................................. 2005-100039
Jun. 29, 2005 (JP) ................................. 2005-190741

(51) Int. Cl.
| | | |
|---|---|---|
| A61K 31/535 | (2006.01) |
| C07D 265/28 | (2006.01) |
| C07D 471/10 | (2006.01) |
| C07D 233/90 | (2006.01) |
| C07D 401/14 | (2006.01) |
| C07D 487/10 | (2006.01) |
| C07D 233/16 | (2006.01) |
| C07D 233/84 | (2006.01) |
| C07D 403/12 | (2006.01) |
| C07D 403/14 | (2006.01) |

(52) U.S. Cl.
CPC ............ *C07D 471/10* (2013.01); *C07D 233/90* (2013.01); *C07D 401/14* (2013.01); *C07D 487/10* (2013.01); *C07D 233/16* (2013.01); *C07D 233/84* (2013.01); *C07D 403/12* (2013.01); *C07D 403/14* (2013.01)
USPC ........................................ 514/230.5; 544/71

(58) Field of Classification Search
None
See application file for complete search history.

(56) References Cited

U.S. PATENT DOCUMENTS

| | | | |
|---|---|---|---|
| 3,301,857 A | | 1/1967 | Berger et al. |
| 5,534,537 A * | | 7/1996 | Ciccarone et al. ............ 514/397 |
| 5,962,462 A | | 10/1999 | Mills et al. |
| 6,291,469 B1 | | 9/2001 | Fisher et al. |
| 7,176,227 B2 | | 2/2007 | Yamazaki et al. |
| 7,883,991 B1 * | | 2/2011 | Wu et al. ........................ 438/459 |
| 8,168,783 B2 * | | 5/2012 | Kokubo et al. ................. 544/71 |
| 2002/0018124 A1 | | 2/2002 | Mottur et al. |
| 2003/0018046 A1 | | 1/2003 | Bridger et al. |
| 2003/0187023 A1 | | 10/2003 | Kubo et al. |
| 2003/0220341 A1 | | 11/2003 | Bridger et al. |
| 2004/0019058 A1 | | 1/2004 | Bridger et al. |
| 2004/0254221 A1 * | | 12/2004 | Yamazaki et al. ............ 514/332 |
| 2005/0165063 A1 | | 7/2005 | Yamazaki et al. |
| 2007/0208007 A1 | | 9/2007 | Saitou |
| 2007/0208033 A1 | | 9/2007 | Yamazaki et al. |
| 2008/0009495 A1 | | 1/2008 | Kokuto et al. |
| 2008/0303976 A1 | | 12/2008 | Nishizawa et al. |
| 2009/0169567 A1 | | 7/2009 | Kokubo et al. |
| 2009/0192182 A1 * | | 7/2009 | Kusumi et al. ................ 514/278 |
| 2012/0101280 A1 * | | 4/2012 | Yoshida et al. ................ 546/16 |

FOREIGN PATENT DOCUMENTS

| | | |
|---|---|---|
| EP | 0070171 B1 | 1/1983 |
| EP | 1308439 A1 | 5/2003 |
| EP | 1378510 A1 | 1/2004 |
| EP | 2003104884 | 3/2004 |
| EP | 1724263 A1 | 11/2006 |
| EP | 1961744 A1 | 8/2008 |
| JP | 49-013184 A | 2/1974 |
| JP | 49-072332 A | 7/1974 |
| JP | 04-018092 A | 1/1992 |
| JP | 11321508 A | 11/1999 |

(Continued)

OTHER PUBLICATIONS

Ohkanda. Journal of Medicinal Chemistry, 2004, 47, 432-445.*

(Continued)

*Primary Examiner* — Noble Jarrell
(74) *Attorney, Agent, or Firm* — Sughrue Mion, PLLC

(57) ABSTRACT

The present invention relates to a compound represented by formula (I-0):

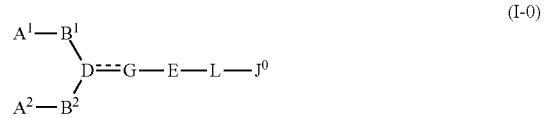

wherein symbols in formula have the same meanings as described in the present specification, a salt thereof, an N-oxide thereof or a solvate thereof or a prodrug thereof, and medical use thereof.

The compound of the present invention has an antagonistic activity against CXCR4 and is therefore useful as a preventive and/or therapeutic agent for CXCR4-mediated diseases, for example, inflammatory and immune diseases (for example, rheumatoid arthritis, arthritis, retinopathy, pulmonary fibrosis, transplanted organ rejection, etc.), allergic diseases, infections (for example, human immunodeficiency virus infection, acquired immunodeficiency syndrome, etc.), psychoneurotic diseases, cerebral diseases, cardiovascular disease, metabolic diseases, and cancerous diseases (for example, cancer, cancer metastasis, etc.), or an agent for regeneration therapy.

9 Claims, No Drawings

(56) References Cited

FOREIGN PATENT DOCUMENTS

| | | | |
|---|---|---|---|
| JP | 2002-348288 A | 12/2002 | |
| JP | 20030104884 A | 4/2003 | |
| JP | 2004-508421 A | 3/2004 | |
| JP | 2004-508422 A | 3/2004 | |
| JP | 2005-518397 A | 6/2005 | |
| WO | 9501358 A1 | 1/1995 | |
| WO | 97/11940 A1 | 4/1997 | |
| WO | 9711940 A1 | 4/1997 | |
| WO | 98/25605 A1 | 6/1998 | |
| WO | 9825605 A1 | 6/1998 | |
| WO | 01/13917 A1 | 3/2001 | |
| WO | WO 01/14376 A1 | 3/2001 | |
| WO | 01/94346 A1 | 12/2001 | |
| WO | 02/22599 A2 | 3/2002 | |
| WO | 02/22600 A2 | 3/2002 | |
| WO | 2002/022599 A2 | 3/2002 | |
| WO | 2002/022600 A2 | 3/2002 | |
| WO | 02/074770 A1 | 9/2002 | |
| WO | 03/020721 A1 | 3/2003 | |
| WO | 03/024941 A1 | 3/2003 | |
| WO | 03/029218 * | 4/2003 | ........... C07D 213/38 |
| WO | 03/029218 A1 | 4/2003 | |
| WO | 03/055876 A1 | 7/2003 | |
| WO | 03/057698 A2 | 7/2003 | |
| WO | 2003/055876 A1 | 7/2003 | |
| WO | WO 03/076443 A1 | 9/2003 | |
| WO | 2004/024697 A1 | 3/2004 | |
| WO | 2004024697 A1 | 3/2004 | |
| WO | 2005/085209 A1 | 9/2005 | |
| WO | 2006/022454 A1 | 3/2006 | |

OTHER PUBLICATIONS

Ookubo. Journal of the American Chemical Society, 1996, 118, 701-702.*
Mashuta. Journal of the American Chemical Society, 1992, 114, 3815-27.*
Sorrell. Inorganic Chemistry, 1991, 30, 207-10.*
Final Office Action dated Feb. 12, 2013, issued by the United States Patent and Trademark Office in counterpart U.S. Appl. No. 12/332,716.
Bleicher et al., "Parallel Solution-and Solid-Phase Synthesis of Spirohydantion Derivatives as Neurokinin-Receptor Ligands"; Bioorganic & Medicinal Chemistry Letters (2002), vol. 12 No. 18,pp. 2519-2522.
United States Office Action; dated Dec. 22, 2010, issued in related U.S. Appl. No. 12/301,194 to Kusumi et al.
H. Van De Waterbeemd; "Property-Based Design: Optimization of Drug Absorption and Pharmacokinetics", Journal of Medicinal Chemistry, vol. 44, No. 9, Apr. 26, 2011, pp. 1313-1333.
Non-Final Office Action dated Mar. 29, 2011, in related U.S. Appl. No. 12/332,716.
Winters, G. et al. "Sintesi Di Spiroidantoine Da Chetoni Eterociclici Basici", Farmaco, Edizione Scientifica, 1970, vol. 25, No. 9, p. 681-693.
Mailey, Everett A. et al., "Synthesis of Derivatives of Alkylated and Arylated Piperidones and Piperidinols", Journal of Organic Chemistry, 1957, vol. 22, p. 1061-1065.
Japanese Office Action mailed May 6, 2012 issued by the Japanese Patent Office in counterpart Japanese Patent Application No. 2006-531995.
European Patent Office, Communication, dated Jun. 1, 2012, issued in counterpart European Application No. 06832893.9.
US Office Action issued in related U.S. Appl. No. 12/094,100 on Jul. 27, 2011.
Extended European Search Report issued in European Application No. 07743395.1 on Jul. 12, 2011.
US Office Action issued in related U.S. Appl. No. 12/332,716 on Jul. 29, 2011.
European Office Action issued in European Application No. 06832893.9 on Oct. 20, 2010.
Ishihara et al., Chemical & Pharmaceutical Bulletin (1992), 40(5), pp. 1177-1185.
Extended European Search Report issued in corresponding European application No. 10013312.3 on Aug. 16, 2011.
Skerlj, R et al., "Synthesis and SAR of Novel CXCR4 Antagonists that are Potent Inhibitors of T Tropic (XR) HIV-1 Replication," Bioorg. & Med. Chem. Letters. vol. 21 (2011). pp. 262-266.
Rautio, J. et al., "Prodrugs: design and clinical applications". Nature Reviews: Drug Discovery. vol. 7. Mar. 2008. pp. 255-270.
European Office Action, dated Aug. 4, 2011, issued in corresponding European Application No. 05776646.1.
Notification of Reasons for Refusal dated Aug. 14, 2012 issued by the Japanese Patent Office in corresponding Japanese Patent Application No. 2007-545323.
Office Action dated Oct. 1, 2012 issued by the United States Patent and Trademark Office in counterpart U.S. Appl. No. 12/332,716.
Carrera, George M., et al., "Synthesis of Novel Substituted Spirohydantoins", Journal of Heterocyclic Chemistry, Jul. 1992, vol. 29, pp. 847-850.
Paul W Smith: "New Spiropiperidines as Potent and Selective Non-Peptide Tachykinin NK2 Receptor Antagonists". Journal of Medicinal Chemistry, American Chemical Society, Washington, US, vol. 38. No. 19. Published Jan. 1, 1995 (pp. 3772-3779).
Supplementary European Search Report issued Jul. 9, 2010 in European Application No. 047279985.6 counterpart of U.S. Appl. No. 12/332,716.
International Search Report for PCT/JP04/005493 corresponding to (parent) U.S. Appl. No. 10/553,596 dated Aug. 3, 2004.
Vippagunta et al., Advanced Drug Delivery Reviews 48 (2001) 3-26.
Lipinski, C.A., Bioisosterism in Drug Design; Annual Reports in Medicinal Chemistry, vol. 21, 1986, pp. 283-291.
Hirokazu Tamamura et al., "A future perspective on the development of chemokine receptor CXCR4 antagonists", Expert Opin. Drug Discov., 2008, pp. 1155-1166, vol. 3, No. 10.
Extended European Search Report issued May 29, 2009 in European Application No. 06832893.9, counterpart of U.S. Appl. No. 12/094,100.
American Cancer Society, "Can Cancer Be Prevented?"; http://www.cancer.org/docroot/CRI/content/CRI_2_4_2x_Can_cancer_be_prevented.asp, accessed May 27, 2010.
TeensHealth, "HIV and AIDS," http://kidshealth.org/teen/infections/stds/std_hiv.html,accessed May 27, 2010.
Renu Agarwal, et al.; Therapeutic potential of Curcuma longa, the golden spice of India, in drug discovery for ophthalmic diseases; Expert Opin. Drug Discon. (2009) 4(2): 147-158 pp. 1-12.
Sudha R. Vippagunta, et al.; Crystalline solids; Advanced Drug Delivery Reviews 48 (2001)3-26.
H. Soto, et al.; Gene Array Analysis Comparison between Rat Collagen-induced Arthritis and Human Rheumatoid Arthritis; Journal compilation(c)2008 Blackwell Publishing Ltd. Scandinavian Journal of Immunology 68, 43-57.
Rheumatoid Arthritis—Prevention http://www.webmed.com/rheumatoid-arthritis/tc/rheumatoid-arthritis-prevention retrieved (1 of 3) Aug. 28, 2009.
James E. Pease, et al.; Chemokine receptor antagonists: part 2; Expert Opin Ther. Patents (2009) 19(2):199-221.
Cara A. Mosley, et al.: Recent patents regarding the discovery of small molecule CXCR4 antagonists; Expert Opin. Ther. Patents (2009)19(1):23-38.
Tara Mirzadegan, et al.: Identification of the Binding Site for a Novel Class of CCR2b Chemokine Receptor Antagonists: The Journal of Biological Chemistry; vol. 275, No. 33, Issue of Aug. 18, pp. 25562-25571, 2000.
Borna Mehrad, et al.: Fibrocyte CXCR4 regulation as a therapeutic target in pulmonary fibrosis; The International Journal of Biochemistry & Cell Biology 41 (2009) 1708-1718.
Christopher A. Lipinski; Section VI-Topics in Chemistry and Drug Design; Annual Reports in Medicinal Chemistry—21; pp. 283-291; 1986.
Jason M. Link, et al.: Clues to the etiology of autoimmune diseases through analysis of immunoglobulin genes; Arthritis Res 2002, 4:80-83.
Jantzen and Robinson; Modern Pharmaceutics; p. 596; 1996.

(56) References Cited

OTHER PUBLICATIONS

Definition of Cancer; Medicine Net.com; http://www.medterms.com/script/main/art.asp?articlekey=(1 of 3), retrieved Nov. 27, 2007, pp. 1-3.
Jan A. Burger; CXCR4 chemokine receptor antagonists: perspectives in SCLC; Expert Opin. Investig. Drugs (2009) 18(4):481-490.
Arthritis Basics; http://www.webmed.com/osteoarthritis/guide/arthritis-basic (1 of 4); Apr. 26, 2010.
Extended European Search Report issued in Application No. 05776646.1, dated Aug. 10, 2010.
CA 1983:470751. See CA registry #85732-34-9 and CA registry #85732-35-0.
CA 1984:510946. See CA registry #85732-35-0 and CA registry #85732-42-9.
CA 1989:407312. See CA registry #85732-35-0 and CA registry #121061-07-2.
CA 2003:282402. See CA registry #508240-62-8 and CA registry #508240-61-7.
CA 2003:991516. See CA registry #635713-68-7 and CA registry #635713-67-6.
Notification of Reasons for Refusal, dated Nov. 19, 2013, issued by the Japanese Patent Office in counterpart Japanese Application No. 2012-053565.

* cited by examiner

COMPOUND CONTAINING BASIC GROUP AND USE THEREOF

This is a Divisional of application Ser. No. 11/661,270 filed Feb. 27, 2007 (now U.S. Pat. No. 7,951,816) which is a national stage of PCT/JP2005/016066 filed Aug. 26, 2005, claiming priority based on Japanese Application No. 2004-248431 filed Aug. 27, 2004, Japanese Application No. 2005-100039 filed Mar. 30, 2005 and Japanese Application No. 2005-190741 filed Jun. 29, 2005, the contents of all of which are incorporated herein by reference in their entirety.

TECHNICAL FIELD

The present invention relates to compounds having a basic group which is useful as medicaments, and use thereof.

More specifically, the present invention relates to (1) compounds represented by formula (I):

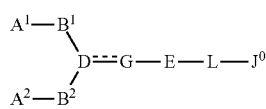

(I-0)

wherein all symbols have the same meanings as described hereinafter, and salts thereof, N-oxides thereof or solvates thereof or prodrugs thereof, (2) use thereof, and (3) a method for producing the same.

BACKGROUND ART

Chemokine is known as a basic protein which has chemotaxis and an activating activity against endogenous leucocytes and also has strong heparin-binding abilities. It is now considered that chemokine is associated with not only control of infiltration of specific leucocytes upon inflammatory and immune responses, but also development, homing of lymphocytes under physiological conditions and migration of hemocyte precursor cells and somatic cells.

Differentiation, proliferation and cell death of blood cells are controlled by various cytokines. Inflammation occurs at a local region in a living body. Differentiation and maturation of lymphocytes, and the like are carried out at a specific site. More particularly, required various cells migrate and accumulate in the specific site and a sequence of inflammatory and immune responses arise. Thus, in addition to differentiation, proliferation and death of cells, cell migration is also an essential phenomenon to an immune system.

In the living body, migration of blood cells start with sifting hemopoiesis that started at AGM (Aorta Gonad Mesonephros) region via fetal liver to permanent hematopoiesis at bone marrow in a development course. Moreover, precursors of T cells and thymus dendritic cells migrate from fetal liver into bone marrow and then into the thymus gland. They differentiate under thymus environment. The T cells are subjected to clonal selection migrates into secondary lymphoid tissues, where they contribute to immune responses in periphery. Skin Langerhans cells that caught antigen, thereby undergone activation and differentiation migrate to T cell region in a topical lymph node, where they activate naive T cells therein as dendritic cells. The memory T cells again perform its homing into the lymph node via lymphatic and blood vessels. In addition, B cells, T cells in intestinal epithelia, γδT cells, NKT cells, and dendritic cells migrate from bone marrow not via thymus, differentiate and contribute to immune responses.

Chemokine is closely associated with such a migration of the various cells. For example, SDF-1 (Stromal cell derived factor-1) and its receptor, CXCR4 also act on various immune- and inflammatory reactions. For example, they have been reported to be associated with accumulation and activation of CD4+T cells in a synovial membrane from a human patient suffering from rheumatoid arthritis (*J. Immunol.*, 165, 6590-6598 (2000)). In addition, in a CIA model mouse, CXCR4 inhibitor inhibited accumulation of leucocytes in a joint and dramatically reduced arthritis score (*J. Immunol.*, 167, 4648-4692 (2001)). In a mouse OVA-induced airway hypersensitive model, an anti-CXCR4 antibody reduced the number of eosinophiles accumulating in pulmonary interstitial tissues and prevented airway hypersensitivity (*J. Immunol.*, 165, 499-508 (2000)).

There has been reported that SDF-1 and its receptor, CXCR4 play an important role in maintaining hemopoietic stem cells in bone marrow *J. Exp. Med.*, 185, 111-120 (1997), *Blood*, 97, 3354-3360 (2001)). Accordingly, control of SDF-1 and CXCR4 is expected to modulate recruitment of hemopoietic stem cells to peripheral blood and are useful for peripheral blood stem cell transplantation and reproduction transplantation treatment.

SDF-1 and CXCR4 are associated with infiltration of various cancer cells such as breast cancer, prostate cancer, and ovarian cancer (*Nature*, 410, 50-56 (2001), *Cancer Res.*, 62, 1832-1837 (2002), *Cancer Res.*, 62, 5930-5938 (2002)). In a model of transferring a human breast cancer cell strain into a SCID mouse, an anti-CXCR4 antibody prevented metastasis of breast cancer cells to lung (*Nature*, 410, 50-56 (2001)). In human ovarian epithelial tumor, highly expression of SDF-1 promotes accumulation of plasmacytoid dendritic cells and inhibits the act of bone marrow dendritic cells associated with tumor immune and suppresses tumor immune (*Nat. Med.*, 12, 1339 (2001)). Moreover, SDF-1 is associated with proliferation and migration of non-Hodgkin's lymphoma cells, and in a model of transferring a human non-Hodgkin's lymphoma cells into a NOD/SCID mouse, an anti-CXCR4 antibody inhibited proliferation of the tumor cells and improved mouse mortality (*Cancer Res.*, 62, 3106-3112 (2002)).

SDF-1 and CXCR4 play an important role for formation of hippocampus dentate gyrus granulocyte, that is essential for memory and learning and are associated with development of a disease associated with adult plasticity and pathology of hippocampus, for example Alzheimer's disease, stroke and epilepsy (*Development*, 129, 4249-4260 (2002), *Trends in Neuroscience*, 25, 548-549 (2002)).

SDF-1 and CXCR4 are essential for a function of self-reactive B cells associated with development of diabetes. In NOD mouse, an anti-SDF-1 antibody reduced blood glucose level and the number of mature IgM+B cells in a periphery tissue (*Immunology*, 107, 222-232 (2002)). In a human arteriosclerotic plaque, SDF-1 was highly expressed and activated blood platelets (*Circ. Res.*, 86, 131-138 (2000)).

SDF-1 and CXCR4 are associated with residence of hemopoietic stem cells and hemopoietic precursor cells in bone marrow. CXCR4 antagonist, AMD 3100 in combination with G-CSF increased the numbers of hemopoietic stem cells and hemopoietic precursor cells in periphery blood (*Journal Experimental Medicine*, 2001, 1307-1318 (2005)).

In addition, the results of SDF-1/CXCR4 knock-out mice showed that SDF-1 is essential for functions of central nervous system, heart and vessels of gastrointestinal tract in addition to lymphocytes (*Nature*, 382, 635-639 (1996), *Nature*, 393, 591-594 (1998), *Nature*, 393, 595-599 (1998)). Accordingly, it may be associated with a disease of these tissues.

Thus, chemokine receptors are expressed at various specific cells and at a specific time. They are largely associated with the control of inflammatory- and immune-responses through a mechanism by which their effector cells accumulate in a site where chemokine is produced.

Acquired immunodeficiency syndrome (also called AIDS) that caused by infection of human immunodeficiency virus (hereinafter abbreviated to HIV) is one of diseases for which therapies are the most eagerly desired lately. Once HIV infection has been established in a main target cell, CD4+ cell, HIV repetitively proliferates in a patient's body and in the event deathly destroys T cells responsible for immunological functions by necrosis. In this process, immunological functions are gradually deteriorated, various immunocompromised states become to develop such as fever, diarrhea and swelling of a lymph node, and various opportunistic infections such as carinii pneumonia are easily complicated. It is well known that such a state is the onset of AIDS and induces malignant tumors such as Kaposi's sarcoma and becomes severe.

Currently, there are tried various preventive and therapeutic treatments for AIDS as follows: for example, (1) inhibition of HIV proliferation by administration of reverse transcriptase inhibitors and protease inhibitors, and (2) prevention or alleviation of opportunistic infections by administration of an immunostimulant, etc.

HIV mainly infects helper T cells which play a key role in the immune system. Since 1985, it has been known that in this process HIV utilizes a membrane protein CD4 that is expressed on the membrane of T cells (*Cell,* 52, 631 (1985)). CD4 molecule consists of 433 amino acid residues and is expressed in macrophages, some B cells, vascular endothelial cells, Langerhans cells in skin tissues, dendritic cells located in lymphatic tissues, glia cells of central nervous system and the like in addition to mature helper T cells. However, as it becomes obvious that HIV infection cannot be established with only CD4 molecule, the possible presence of some factor that is responsible for infection of cell with HIV, other than CD4 molecule, has been suggested.

In 1996, a cell membrane protein called Fusin has been identified as a factor responsible for HIV infection other than a CD4 molecule (*Science,* 272, 872 (1996)). This Fusin molecule has been demonstrated to be a receptor for SDF-1, namely, CXCR4. In addition, it has been shown that SDF-1 specifically inhibits infection of T cell-directed (X4) HIV in vitro (*Nature,* 382, 829 (1996), *Nature,* 382, 833 (1996)). This may be considered that SDF-1 binds to CXCR4 prior to HIV, thereby taking away a scaffold for infecting a cell from HIV resulting in inhibition of HIV infection.

Also, at the same period, there has been found that another chemokine receptor CCR5, that is a receptor for RANTES, MIP-1α, and MIP-1β, is utilized at infection of macrophage-directed (R5) HIV (*Science,* 272, 1955 (1996)).

Accordingly, those which can compete with HIV for CXCR4 and CCR5 or those which bind to a HIV virus and prevent for said virus from binding to CXCR4 and CCR5 may be a HIV infection inhibitor. In addition, there is a case where a low molecular weight compound discovered as a HIV infection inhibitor was showed to be indeed an antagonist of CXCR4 (*Nature Medicine,* 4, 72 (1998)).

As described above, compounds having an antagonistic activity against CXCR4 is effective, such as, for prevention and/or treatment of inflammatory and immune diseases, allergic diseases, infections, particularly HIV infection, and diseases associated with the infection, psychoneurotic diseases, cerebral diseases, cardiovascular diseases, metabolic diseases, cancerous diseases and the like. Also, the compounds are useful for cell medical treatment and regeneration therapy.

Heretofore, some compounds having an antagonistic activity against CXCR4 have been reported. For example, it is disclosed that a compound represented by formula (X):

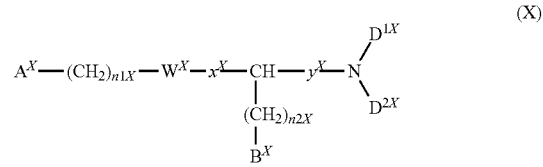

wherein $A^X$ represents

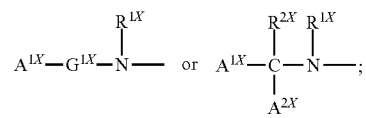

$A^{1X}$ and $A^{2X}$ each independently represents a hydrogen atom, an optionally substituted monocyclic or polycyclic heteroaromatic ring, or an optionally substituted monocyclic or polycyclic aromatic ring;

$G^{1X}$ represents a single bond or —$CR^{2X}R^{3X}$—;

$R^{1X}$; $R^{2X}$ and $R^{3X}$ represent an optionally substituted alkyl group having 1 to 6 carbon atom(s);

$W^X$ represents an optionally substituted alkylene group having 1 to 7 carbon atom(s), an optionally substituted monocyclic or polycyclic heteroaromatic ring, or an optionally substituted monocyclic or polycyclic aromatic ring;

$x^X$ represents -$z^{1X}$-CO-$z^{2X}$-;

$z^{1X}$ and $z^{2X}$ each independently represents a single bond or $NR^{13X}$;

$y^X$ represents —CO—;

$D^{1X}$ and $D^{2X}$ each h c independently represents a hydrogen atom or -$G^{1X}$-$R^{4X}$; $G^{2X}$ represents an optionally substituted alkylene group having 1 to 15 carbon atom(s);

$R^{4X}$ represents a hydrogen atom, an optionally substituted monocyclic or polycyclic heteroaromatic ring, or an optionally substituted monocyclic or polycyclic aromatic ring;

n2X represents 0 to 4;

n1X represents 0 to 3; and

BX represents —$NR^{6X}R^{7X}$, and only required portions were extracted with respect to definition of each group), or a pharmaceutically acceptable salt has an antagonistic activity against CXCR4 (see WO03/029218 pamphlet).

Also, it is disclosed that a compound represented by formula (Y):

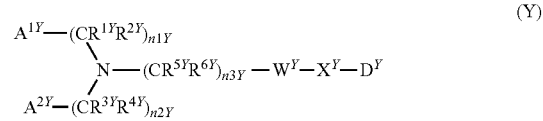

wherein n1Y, n2Y and n3Y represent 0 to 3;

$R^{1Y}$, $R^{2Y}$, $R^{3Y}$, $R^{4Y}$, $R^{5Y}$ and $R^{6Y}$ each independently represents a hydrogen atom, or an optionally substituted alkyl group having 1 to 15 carbon atom(s);

$A^{1Y}$ and $A^{2Y}$ each independently represents an optionally substituted monocyclic or polycyclic heteroaromatic ring;

$W^Y$ represents an optionally substituted alkylene group having 1 to 15 carbon atom(s); $X^Y$ represents O, $CH_2$, or $NR^{11Y}$;

$D^Y$ represents $-Q^Y-Y^Y-B^Y$;

$Q^Y$ represents a single bond or —CO— when $X^Y$ is $NR^{11Y}$;

$Y^Y$ represents $-(CR^{18Y}R^{19Y})_{m3Y}-$;

$R^{18Y}$ and $R^{19Y}$ each independently represents a hydrogen atom, or an optionally substituted alkyl group having 1 to 15 carbon atom(s);

m3Y represents 0 to 6; $B^Y$ represents $-NR^{25Y}R^{26Y}$; and $R^{25Y}$ and $R^{26Y}$ represent a hydrogen atom or an optionally substituted alkyl group having 1 to 15 carbon atom(s) when $X^Y$ is not $CH_2$, and only required portions were extracted with respect to definition of each group), or a pharmaceutically acceptable salt or a prodrug thereof has an antagonistic activity against CXCR4 (see WO2004/024697 pamphlet).

DISCLOSURE OF THE INVENTION

It is earnestly desired to develop a CXCR4 antagonist which is useful as a preventive and/or therapeutic agent for inflammatory and immune diseases (for example, rheumatoid arthritis, arthritis, retinopathy, pulmonary fibrosis, transplanted organ rejection, etc.), allergic diseases, infections (for example, human immunodeficiency virus infection, acquired immunodeficiency syndrome, etc.), and cancerous diseases (for example, cancer, cancer metastasis, etc.), or an agent for regeneration therapy, and also causes less side effect and is safe.

The present, inventors have intensively studied and found that a compound represented by formula (I-0) described hereinafter surprisingly has a strong antagonistic activity against CXCR4, and thus the present invention has been completed.

Namely, the present invention relates to:

[1] A compound represented by formula (I-0):

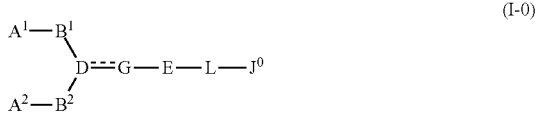

(I-0)

wherein $A^1$ and $A^2$ each independently represents a group having a basic group;

$B^1$ and $B^2$ each independently represents a bond or a spacer having 1 to 4 atom(s) in its main chain;

E represents a spacer having 1 to 10 atom(s) in its main chain; L represents a bond or a spacer having 1 to 4 atom(s) in its main chain;

$J^0$ represents (1) an aliphatic hydrocarbon group which is substituted with a group having a basic group, and also may have a substituent(s), (2) a cyclic group which is substituted with a group having a basic group, and also may have a substituent(s), (3) a spiro-bound cyclic group which may be substituted with a group having a basic group, and also may have a substituent(s), or (4) a bridged cyclic group which may be substituted with a group having a basic group, and also may have a substituent(s);

⁒ represents a single bond or a double bond;

when ⁒ represents a single bond, D represents a nitrogen atom or a carbon atom which may have a substituent(s), G represents a carbon atom which may have a substituent(s), a carbonyl group, an oxygen atom, a nitrogen atom which may have a substituent, or a sulfur atom which may be oxidized, when ⁒ represents a double bond, D represents a carbon atom; and G represents a carbon atom which may have a substituent(s), or a nitrogen atom, and wherein when $J^0$ represents the above group (1) or (2) and also D represents a nitrogen atom, G represents a carbonyl group, an oxygen atom, a nitrogen atom which may have a substituent, or a sulfur atom which may be oxidized, or $B^1$ represents a spacer having 1 to 4 atom(s) in its main chain, which has at least one selected from —O—, —S—, —CO—, —SO—, —SO$_2$—, and a divalent nitrogen atom which may have a substituent) or a salt thereof, an N-oxide thereof or a solvate thereof, or a prodrug thereof;

[2] The compound according to the above-described [1], which is represented by formula (I):

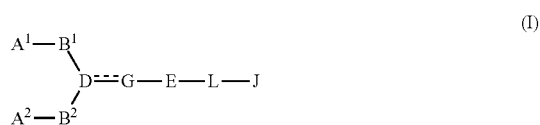

(I)

wherein J has the same meaning as in (1) or (2) in $J^0$ described in [1], and other symbols have the same meanings as described in [1], and wherein when D represents a nitrogen atom, G represents a carbonyl group, an oxygen atom, a nitrogen atom which may have a substituent, or a sulfur atom which may be oxidized, or $B^1$ represents a spacer having 1 to 4 atom(s) in its main chain, which has at least one selected from —O—, —S—, —CO—, —SO—, —SO$_2$—, and a divalent nitrogen atom which may have a substituent;

[3] The compound according to the above-described [1], wherein $J^0$ is (3) or (4) described in the above [1]:

[4] The compound according to the above-described [3], wherein $J^0$ is a spiro-bound heterocyclic ring or bridged heterocyclic ring which may be substituted with a group having a basic group, and also may have at least one nitrogen atom which may have a substituent, and also may have an oxygen atom and/or a sulfur atom which may be oxidized;

[5] The compound according to the above-described [3], wherein $J^0$ is a spiro-bound carbocyclic ring or bridged carbocyclic ring which may be substituted with a group having a basic group, and also may have a substituent(s);

[6] The compound according to the above-described [4], wherein the spiro-bound heterocyclic ring or bridged heterocyclic ring which may have at least one nitrogen atom and also may have an oxygen atom and/or a sulfur atom which may be oxidized is

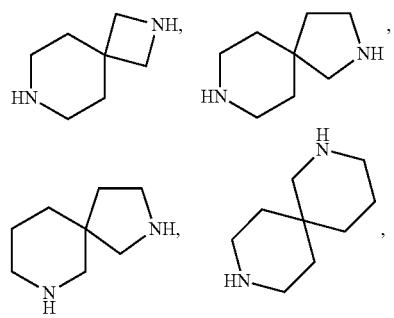

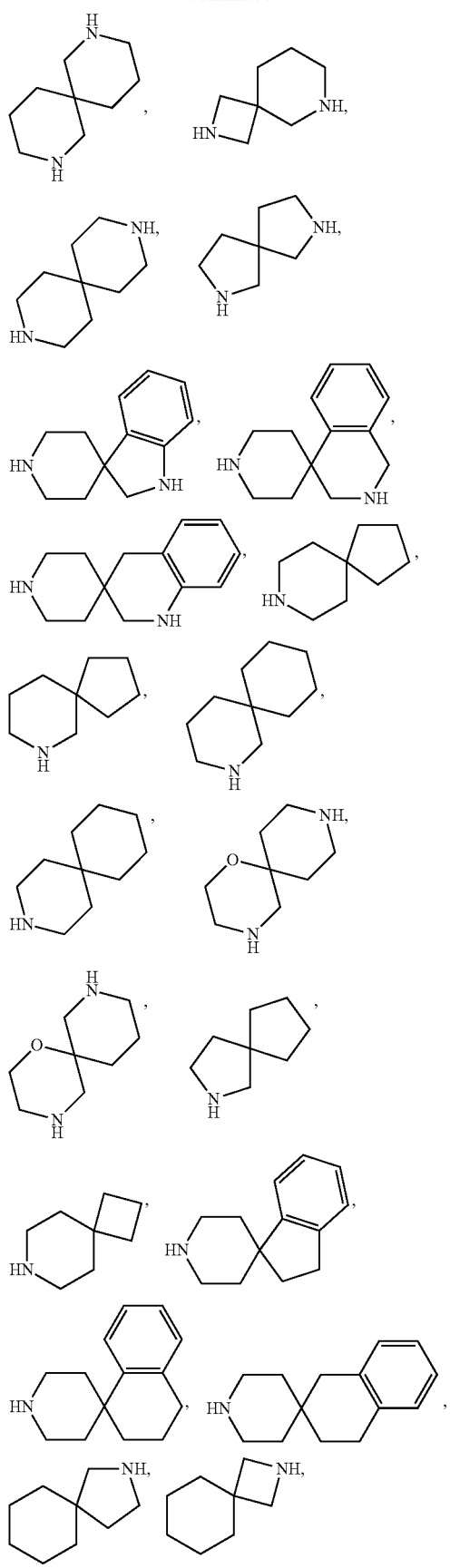

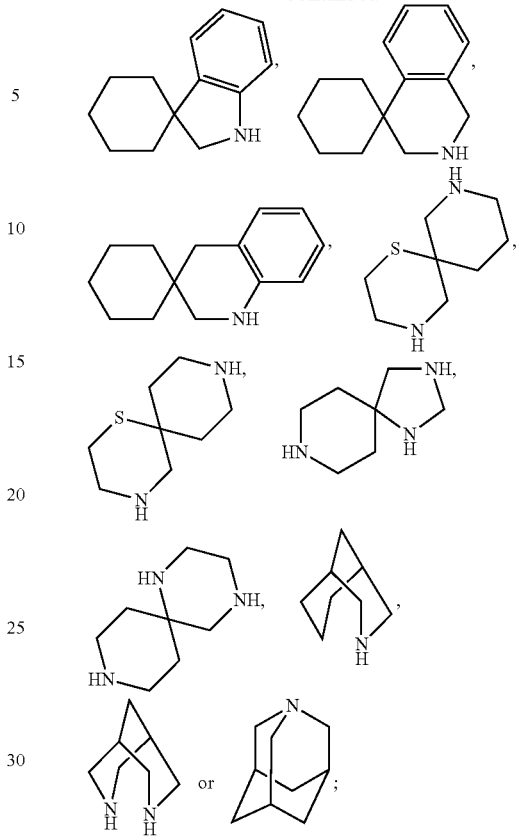

[7] The compound according to the above-described [4], wherein the ring constituting the spiro-bound heterocyclic ring is a 7- to 15-membered bicyclic spiro-bound heterocyclic ring comprising a monocycle having at least one nitrogen atom and carbon atom(s), and/or a monocycle having at least one nitrogen atom, one oxygen atom and carbon atoms;

[8] The compound according to the above-described [7], wherein the 7- to 15-membered bicyclic spiro-bound heterocyclic ring is

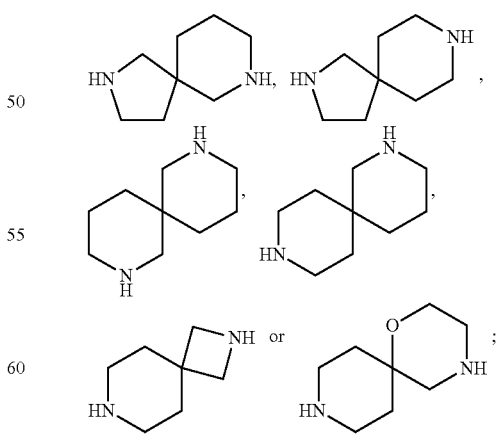

[9] The compound according to the above-described [5], wherein the spiro-bound carbocyclic ring or bridged carbocyclic ring is

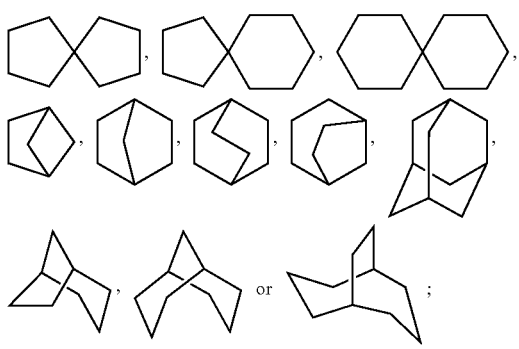

[10] The compound according to the above-described [1], wherein $A^1$ and $A^2$ each independently represents a nitrogen-containing hetrocyclic ring which may have a substituent(s);
[11] The compound according to the above-described [10], wherein the nitrogen-containing hetrocyclic ring is an imidazole ring or a benzimidazole ring;
[12] The compound according to the above-described [1], wherein the spacer having 1 to 4 atom(s) in its main chain represented by $B^1$ and $B^2$ each independently represents —CO—, —$SO_2$— or —$CH_2$—;
[13] The compound according to the above-described [1], wherein D is a nitrogen atom;
[14] The compound according to the above-described [1], wherein G is —CO—, —$SO_2$— or —$CH_2$—;
[15] The compound according to the above-described [1], wherein E is a divalent 3- to 8-membered monocyclic cyclic group which may have a substituent(s);
[16] The compound according to the above-described [15], wherein the 3- to 8-membered monocyclic cyclic group is a benzene ring;
[17] The compound according to the above-described [1], wherein L is —$CH_2$—, —CONH— or —$CH_2$—NH— in which $J^0$ is bound to the right side of each group;
[18] The compound according to the above-described [2], wherein the basic group is a mono- or di-substituted amino group;
[19] The compound according to the above-described [18], wherein the substituent of the di-substituted amino group is a C1-8 alkyl group and/or a cyclic group;
[20] The compound according to the above-described [19], wherein the di-substituted amino group is a dipropylamino group, or an N-cyclohexyl-N-propylamino group;
[21] The compound according to the above-described [2], wherein the aliphatic hydrocarbon group is a butyl group, or the cyclic group is a cyclohexyl group;
[22] The compound according to the above-described [2], which is represented by formula (I-3):

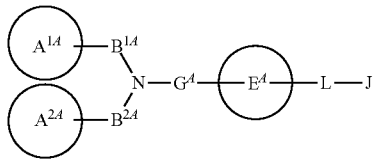

(I-3)

wherein ring $A^{1A}$ and ring $A^{2A}$ each independently represents a nitrogen-containing hetrocyclic ring which may have a substituent(s);

$B^{1A}$, $B^{2A}$ and $G^A$ each independently represents —CO—, —$SO_2$— or —$CH_2$—;
ring $E^A$ represents a divalent 3- to 8-membered monocyclic cyclic group which may have a substituent(s), or a divalent 9- or 10-membered polycyclic cyclic group which may have a substituent(s);
L has the same meaning as described in [1]; and
J has the same meaning as described in [2], and
wherein any of $B^{1A}$ and $G^A$ represents —CO— or —$SO_2$—;
[23] The compound according to the above-described [22], wherein L is a bond, —$CH_2$—, —CONH—, —$CH_2$—NH—, —O—$CH_2$—, —S—$CH_2$—, or —$CH_2$—$CH_2$— in which J is bound to the right side of each group;
[24] The compound according to the above-described [1], which is represented by formula (I-4):

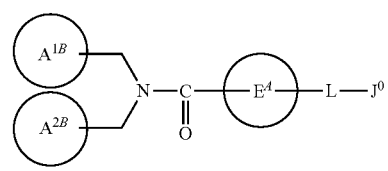

(I-4)

wherein ring $A^{1B}$ and ring $A^{2B}$ each independently represents imidazole or benzimidazole which may have a substituent(s),
ring $E^A$ has the same meaning as described in [22], and
other symbols have the same meanings as described in [1]:
[25] The compound according to the above-described [1], wherein
-L-$J^0$ is

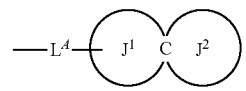

in the group,
(a) when $L^A$ is -(a C1-3 aliphatic hydrocarbon group which may have a substituent(s))-(nitrogen atom which may have a substituent)-, ring $J^1$ represents (i) a C3-10 monocyclic or bicyclic carbocyclic ring, or (ii) a 3- to 10-membered monocyclic or bicyclic hetrocyclic ring comprising a carbon atom, an oxygen atom and/or a sulfur atom which may be oxidized,
(b) when $L^A$ is a divalent C1-4 aliphatic hydrocarbon group which may have a substituent(s), ring J represents a 3- to 10-membered monocyclic or bicyclic hetrocyclic ring which may have at least one nitrogen atom and also may have an oxygen atom and/or a sulfur atom which may be oxidized,
ring $J^2$ represents (i) a C3-10 monocyclic or bicyclic carbocyclic ring substituted with a group having a basic group; (ii) a 3- to 10-membered monocyclic or bicyclic hetrocyclic ring which may be substituted with a group having a basic group and which comprises a carbon atom, an oxygen atom and/or a sulfur atom which may be oxidized; or (iii) a 3- to 10-membered monocyclic or bicyclic hetrocyclic ring which may be substituted with a group having a basic group, and also may have at least one nitrogen atom, and also may have an oxygen atom or a sulfur atom which may be oxidized, and
ring $J^1$ and ring $J^2$ may have 1 to 8 substituent(s) at the substitutable position and, when two or more substituents are present, plural substituents may be the same or different, wherein the nitrogen atom which may have a substituent in L$^A$ is bound to ring J$^1$;
[26] The compound according to the above-described [25], wherein
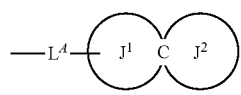
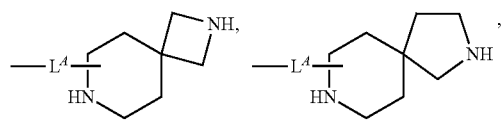
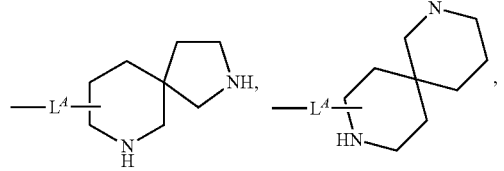
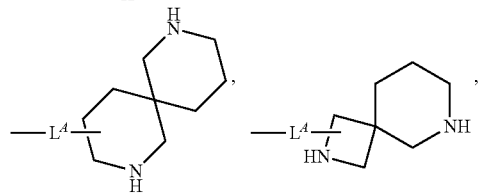
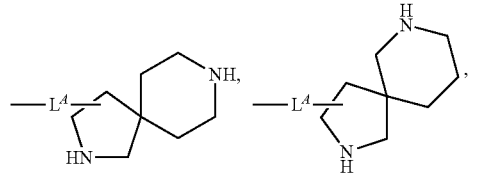
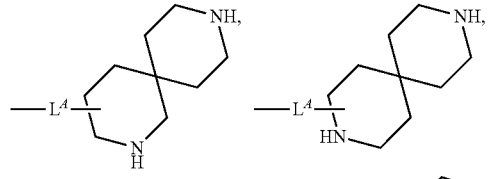
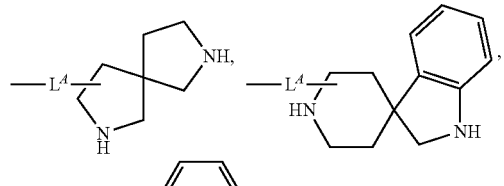
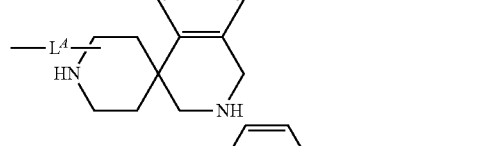
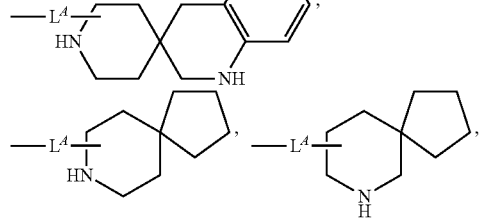
-continued
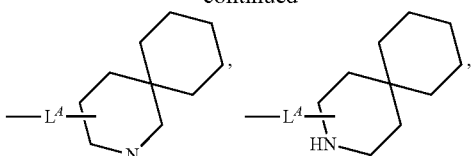
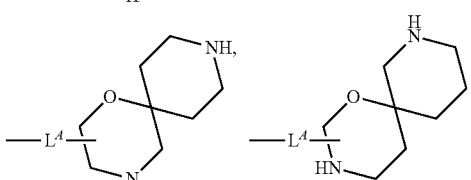
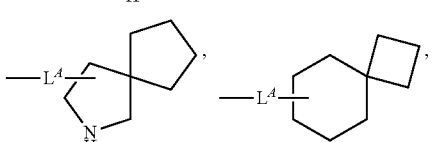
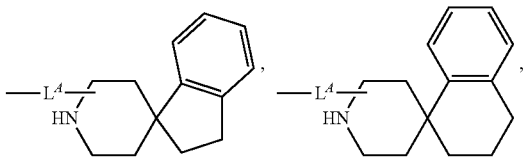
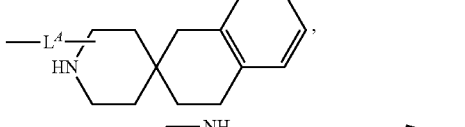
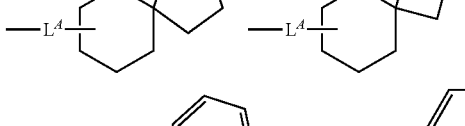
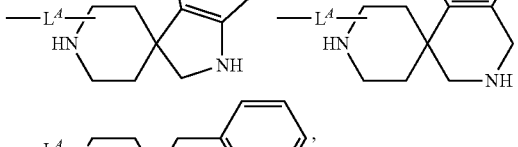
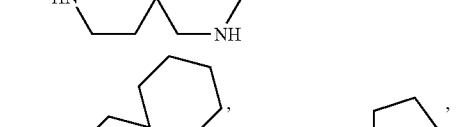
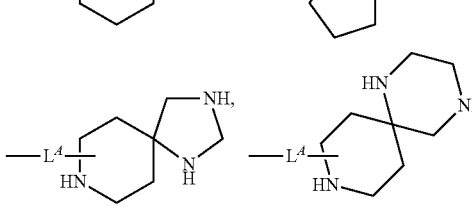

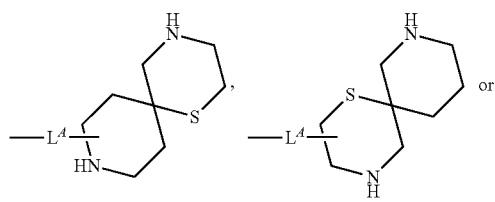

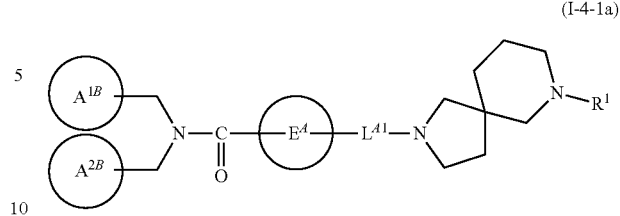

(I-4-1a)

or formula (I-4-1b):

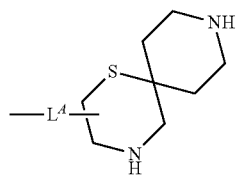

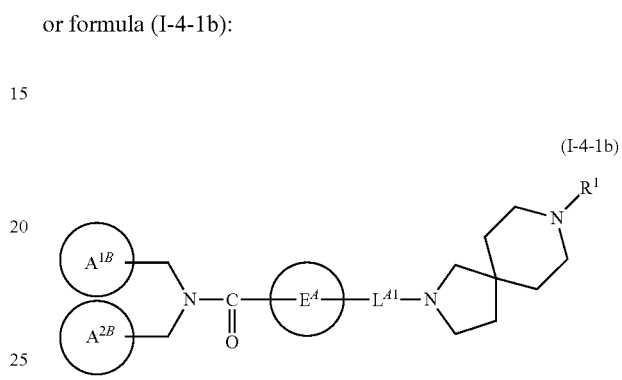

(I-4-1b)

in the group, $L^A$ has the same meaning as described in [25], wherein $L^A$ may be bound to a nitrogen atom of —NH— and the nitrogen atom of —NH— may have a substituent;

[27] The compound according to the above-described [25], wherein wherein $L^{A1}$ represents a divalent C1-4 aliphatic hydrocarbon group which may have a substituent(s);

$R^1$ represents a hydrogen atom or a substituent; and other symbols have the same meanings as described in [24];

[29] The compound according to the above-described [24], which is represented by formula (I-4-2):

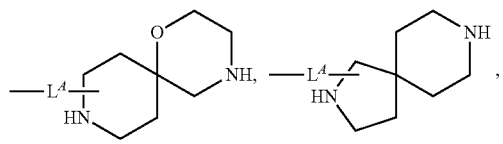

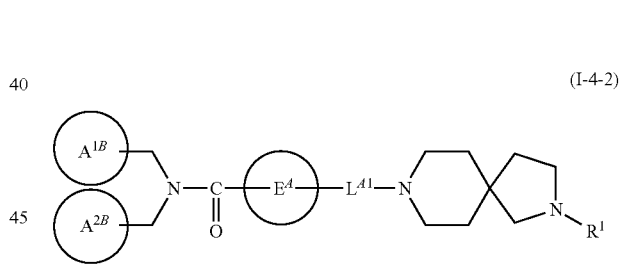

(I-4-2)

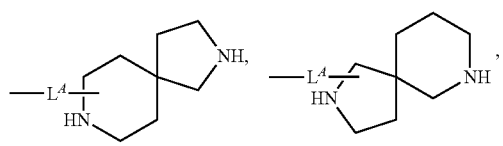

wherein all symbols have the same meanings as described in [24] and [28];

[30] The compound according to the above-described [24], which is represented by formula (I-4-3a):

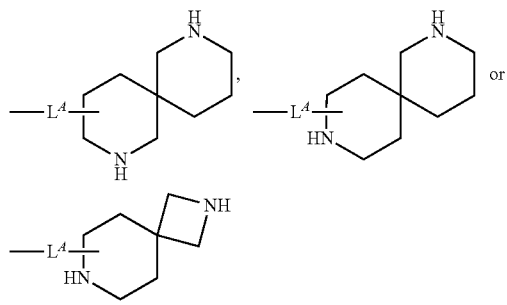

(I-4-3a)

in the group, $L^A$ has the same meaning as described in [25], wherein $L^A$ may be bound to a nitrogen atom of —NH— and the nitrogen atom of —NH— may have a substituent;

[28] The compound according to the above-described [24], which is represented by formula (I-4-1a):

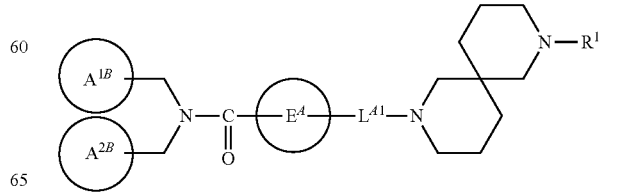

or formula (I-4-3b):

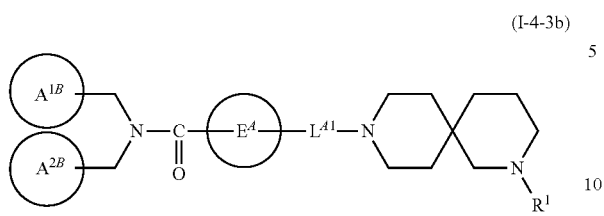

(I-4-3b)

wherein all symbols have the same meanings as described in [24] and [28];

[31] The compound described in [24], which is represented by formula (I-4-4):

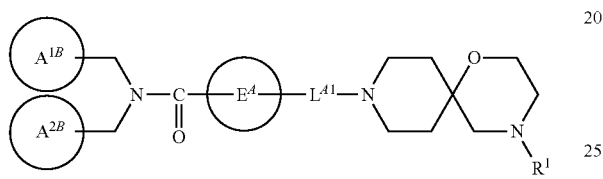

(I-4-4)

wherein all symbols have the same meanings as described in [24] and [28];

[32] The compound according to the above-described [24], which is represented by formula (I-4-5):

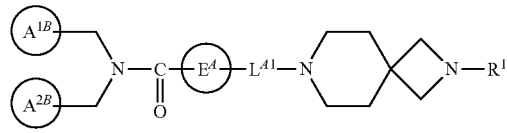

(I-4-5)

wherein all symbols have the same meanings as described in [24] and [28];

[33] The compound according to the above-described any one of [28] to [32], wherein the substituent represented by $R^1$ is an aliphatic hydrocarbon group, a cyclic group, or an aliphatic hydrocarbon group substituted with a cyclic group;

[34] The compound according to the above-described [24], wherein
-L-$J^0$ is

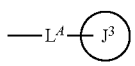

in the group, ring $J^3$ represents (i) a bridged polycyclic carbocyclic ring substituted with a group having a basic group; (ii) a bridged polycyclic hetrocyclic ring substituted with a group having a basic group, which is composed of a carbon atom, an oxygen atom and/or a sulfur atom which may be oxidized; or (iii) a bridged polycyclic hetrocyclic ring which may be substituted with a group having a basic group, and may have at least one nitrogen atom and also may have an oxygen atom and/or a sulfur atom which may be oxidized;

ring $J^3$ may have 1 to 8 substituent(s) on the substitutable position and, when two or more substituents are present, plural substituents are the same or different; and $L^A$ has the same meaning as described in [25];

[35] The compound according to the above-described [34], wherein the bridged polycyclic carbocyclic ring is

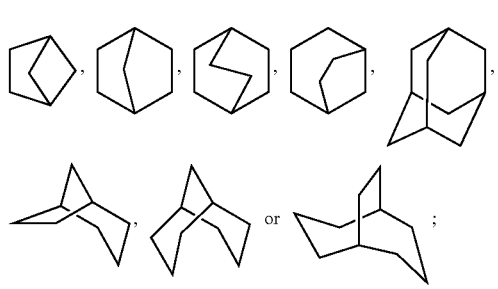

[36] The compound according to the above-described [34], wherein the bridged polycyclic hetrocyclic ring which has at least one nitrogen atom and also may have an oxygen atom and/or a sulfur atom which may be oxidized is

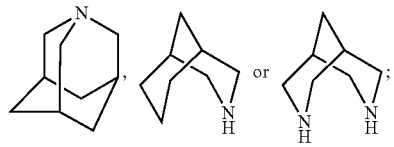

[37] The compound according to the above-described [24], wherein
-L-$J^0$ is

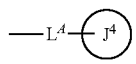

in the group, ring $J^4$ represents (i) a C3-15 monocyclic or condensed carbocyclic ring substituted with a group having a basic group; (ii) a 3- to 15-membered monocyclic or condensed hetrocyclic ring substituted with a group having a basic group, which is composed of a carbon atom, an oxygen atom and/or a sulfur atom which may be oxidized; or (iii) a 3- to 15-membered monocyclic or condensed hetrocyclic ring which may be substituted with a group having a basic group, and also may have at least one nitrogen atom and also may have an oxygen atom and/or a sulfur atom which may be oxidized, ring $J^4$ may have 1 to 8 substituent(s) on the substitutable position and, when two or more substituents are present, plural substituents are the same or different; and $L^A$ has the same meaning as described in [25]);

[38] The compound according to the above-described [37], wherein the C3-15 monocyclic or condensed carbocyclic ring is

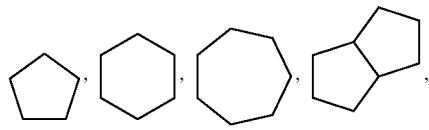

-continued

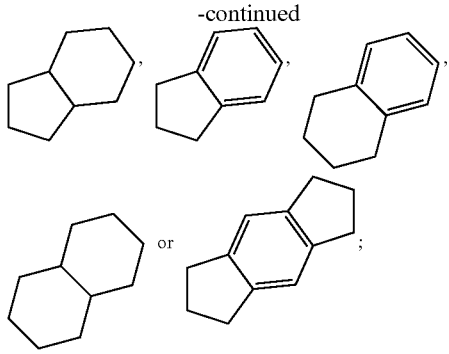

[39] The compound according to the above-described [38], wherein the C3-15 monocyclic or condensed carbocyclic ring is a cyclohexyl group;

[40] The compound according to the above-described [24], which is represented by formula (I-4-6):

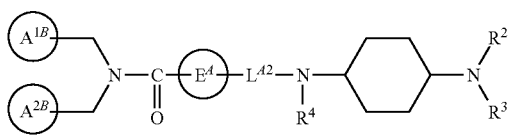

(I-4-6)

wherein $L^{A2}$ represents a C1-3 aliphatic hydrocarbon group which may have a substituent(s);

$R^2$, $R^3$ and $R^4$ each independently represent a hydrogen atom or a substituent; and $R^2$ and $R^3$ may be combined with the nitrogen atom to which they are attached to form a ring which may have a substituent(s); and other symbols have the same meanings as described in [24];

[41] The compound according to the above-described [40], wherein $R^2$ and $R^3$ each independently represents a hydrogen atom, an aliphatic hydrocarbon group, a C3-15 monocyclic or condensed carbocyclic ring, or an aliphatic hydrocarbon group substituted with a C3-15 monocyclic or condensed carbocyclic ring, or may be combined with the nitrogen atom to which $R^2$ and $R^3$ are attached to form a monocyclic or condensed hetrocyclic ring; and wherein an atom(s) other than a nitrogen atom, which constitutes a hetrocyclic ring, is/are a carbon atom;

[42] The compound described in [40], wherein $R^4$ is a hydrogen atom, an aliphatic hydrocarbon group, or an aliphatic hydrocarbon group substituted with a hydroxyl group;

[43] The compound according to the above-described [37], wherein the 3- to 15-membered monocyclic or condensed hetrocyclic ring which has at least one nitrogen atom and also may have an oxygen atom and/or a sulfur atom which may be oxidized is

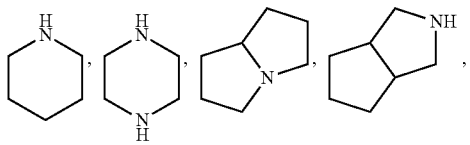

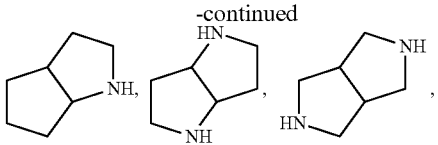

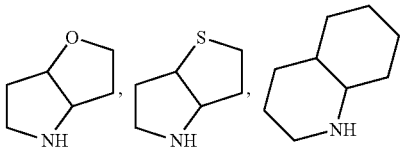

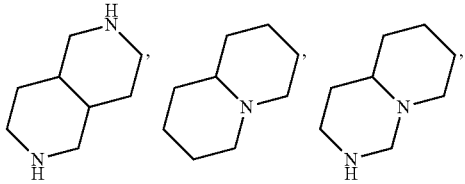

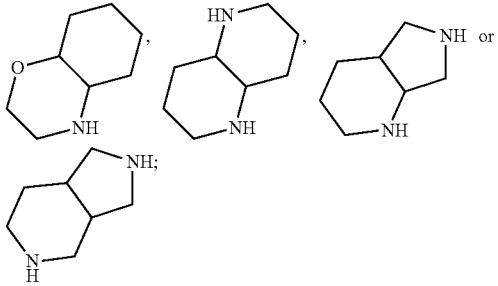

[44] The compound according to the above-described [1], which is represented by formula (I-8):

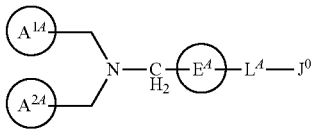

(I-8)

wherein ring $A^{1A}$, ring $A^{2A}$ and ring $E^A$ have the same meanings as described in [22];

$L^A$ has the same meaning as described in [25]; and $J^0$ has the same meaning as described in (3) or (4) in $J^0$ described in [1];

[45] The compound according to the above-described [44], wherein $-L^A-J^0$ is

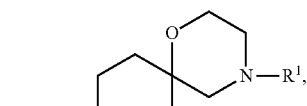

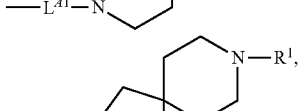

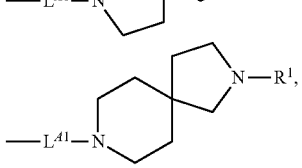

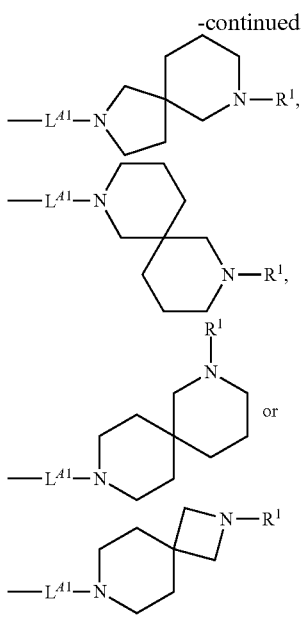

in the group, $L^{A1}$ and $R^1$ have the same meanings as described in [28];

[46] The compound according to the above-described [45], wherein the substituent represented by R' is an aliphatic hydrocarbon group, a cyclic group, or an aliphatic hydrocarbon group substituted with a cyclic group;

[47] The compound according to the above-described [1], which is 4-({[4-(dipropylamino)butyl]amino}methyl)-N,N-bis(1H-imidazol-2-ylmethyl)benzamide;

4-({[3-(dibutylamino)propyl]amino}methyl)-N,N-bis(1H-imidazol-2-ylmethyl)benzamide;

4-({[5-(dipropylamino)pentyl]amino}methyl)-N,N-bis(1H-imidazol-2-ylmethyl)benzamide;

4-({4-[(dipropylamino)methyl]-1-piperidinyl}methyl)-N,N-bis(1H-imidazol-2-ylmethyl)benzamide;

4-({[4-(dipropylamino)cyclohexyl]amino}methyl)-N,N-bis(1H-imidazol-2-ylmethyl)benzamide;

4-({[3-(dipropylamino)propyl]amino}methyl)-N,N-bis(1H-imidazol-2-ylmethyl)benzamide;

4-[(2-benzyl-2,9-diazaspiro[5.5]undec-9-yl)methyl]-N,N-bis(1H-imidazol-2-ylmethyl)benzamide;

4-[(2-cyclohexyl-2,9-diazaspiro[5.5]undec-9-yl)methyl]-N,N-bis(1H-imidazol-2-ylmethyl)benzamide;

2-[4-(dipropylamino)butyl]-N,N-bis(1H-imidazol-2-ylmethyl)-1,2,3,4-tetrahydro-6-isoquinolinecarboxamide;

N-[4-({[4-(dipropylamino)butyl]amino}methyl)benzyl]-N-(1H-imidazol-2-ylmethyl)-1H-imidazole-2-carboxamide;

4-({[4-(dipropylamino)butyl]amino}methyl)-N,N-bis(1H-imidazol-2-ylmethyl)benzenesulfonamide;

4-[({trans-4-[cyclohexyl(propyl)amino]cyclohexyl}amino)methyl]-N,N-bis(1H-imidazol-2-ylmethyl)benzamide;

4-[(2-cyclohexyl-2,8-diazaspiro[4.5]dec-8-yl)methyl]-N,N-bis(1H-imidazol-2-ylmethyl)benzamide; or 4-[(8-cyclohexyl-2,8-diazaspiro[4.5]dec-2-yl)methyl]-N,N-bis(1H-imidazol-2-ylmethyl)benzamide;

[48] The compound according to the above-described [1], which is

4-[(2-cyclohexyl-2,8-diazaspiro[4.5]dec-8-yl)methyl]-N,N-bis(1H-imidazol-2-ylmethyl)benzamide;

4-[(8-cyclohexyl-2,8-diazaspiro[4.5]dec-2-yl)methyl]-N,N-bis(1H-imidazol-2-ylmethyl)benzamide;

4-[(2-cyclohexyl-2,8-diazaspiro[4.5]dec-8-yl)methyl]-N,N-bis(1H-imidazol-2-ylmethyl)benzamide;

4-[(8-cyclohexyl-2,8-diazaspiro[4.5]dec-2-yl)methyl]-N,N-bis(1H-imidazol-2-ylmethyl)benzamide;

N,N-bis(1H-imidazol-2-ylmethyl)-4-{[8-(2-thienylmethyl)-2,8-diazaspiro[4.5]dec-2-yl]methyl}benzamide;

N-(1H-benzoimidazol-2-ylmethyl)-4-[(8-cyclohexyl-2,8-diazaspiro[4.5]dec-2-yl)methyl]-N-(1H-imidazol-2-ylmethyl)benzamide;

4-[(8-cycloheptyl-2,8-diazaspiro[4.5]dec-2-yl)methyl]-N,N-bis(1H-imidazol-2-ylmethyl)benzamide;

N,N-bis(1H-imidazol-2-ylmethyl)-4-({8-[(3-methyl-2-thienyl)methyl]-2,8-diazaspiro[4.5]dec-2-yl}methyl)benzamide; or 4-{[8-(1-ethylpropyl)-2,8-diazaspiro[4.5]dec-2-yl]methyl}-N,N-bis(1H-imidazol-2-ylmethyl)benzamide;

[49] The compound according to the above-described [1], which is

4-[({trans-4-[cyclohexyl(propyl)amino]cyclohexyl}amino)methyl]-N,N-bis(1H-imidazol-2-ylmethyl)benzamide;

4-[({trans-4-[benzyl(propyl)amino]cyclohexyl}amino)methyl]-N,N-bis(1H-imidazol-2-ylmethyl)benzamide;

4-({[4-(1-azepanyl)cyclohexyl]amino}methyl)-N,N-bis(1H-imidazol-2-ylmethyl)benzamide;

N-(1H-benzoimidazol-2-ylmethyl)-4-[({trans-4-[cyclohexyl(propyl)amino]cyclohexyl}amino)methyl]-N-(1H-imidazol-2-ylmethyl)benzamide;

4-[({trans-4-[(1-ethylpropyl)(propyl)amino]cyclohexyl}amino)methyl]-N,N-bis(1H-imidazol-2-ylmethyl)benzamide;

4-{[{trans-4-[cyclohexyl(propyl)amino]cyclohexyl}(methyl)amino]methyl}-N,N-bis(1H-imidazol-2-ylmethyl)benzamide;

4-{[{trans-4-[cyclohexyl(propyl)amino]cyclohexyl}(2-hydroxyethyl)amino]methyl}-N,N-bis(1H-imidazol-2-ylmethyl)benzamide; or 4-[({trans-4-[(1-ethylpropyl)(2-hydroxyethyl)amino]cyclohexyl}amino)methyl]-N,N-bis(1H-imidazol-2-ylmethyl)benzamide;

[50] A pharmaceutical composition comprising a compound represented by formula (I-0) described in [1], a salt thereof, an N-oxide thereof or a solvate thereof, or a prodrug thereof;

[51] The pharmaceutical composition according to the above-described [50], which is a CXCR4 antagonist;

[52] The pharmaceutical composition described in [51], which is an agent for preventing and/or treating CXCR4-mediated diseases, or an agent for regeneration therapy;

[53] The pharmaceutical composition according to the above-described [52], wherein the CXCR4-mediated disease is human immunodeficiency virus infection, acquired immunodeficiency syndrome, cancer, cancer metastasis, rheumatoid arthritis, arthritis, retinopathy, pulmonary fibrosis or transplanted organ rejection, or the agent for regeneration therapy is an agent for transplantation medical treatment;

[54] The pharmaceutical composition according to the above-described [52], wherein the CXCR4-mediated disease is human immunodeficiency virus infection;

[55] A pharmaceutical composition comprising a compound represented by formula (I-0) depicted in [1], a salt thereof, an N-oxide thereof or a solvate thereof, or a prodrug thereof, and one or more kinds selected from reverse transcriptase inhibitor, protease inhibitor, CCR2 antagonist, CCR3 antagonist, CCR4 antagonist, CCR5 antagonist, CXCR4 antagonist, HIV integrase inhibitor, fusion inhibitor, CD4 antagonist, antibody against surface antigen of HIV, short interfering RNA, and vaccine of HIV;

[56] A method for antagonizing CXCR4 in a mammal, which comprises administering an effective dosage of a compound represented by formula (I-0) depicted in [1], a salt thereof, an N-oxide thereof or a solvate thereof, or a prodrug thereof to the mammal:

[57] A method of preventing and/or treating CXCR4-mediated diseases in a mammal, which comprises administering an effective dosage of a compound represented by formula (I-0) depicted in [1], a salt thereof, an N-oxide thereof or a solvate thereof, or a prodrug thereof to the mammal;

[58] Use of a compound represented by formula (I-0) described in [1], a salt thereof, an N-oxide thereof or a solvate thereof or a prodrug thereof for production of a CXCR4 antagonist;

[59] Use of a compound represented by formula (I-0) depicted in [1], a salt thereof, an N-oxide thereof or a solvate thereof or a prodrug thereof for production of an agent for preventing and/or treating CXCR4-mediated diseases;

[60] A compound represented by formula (1):

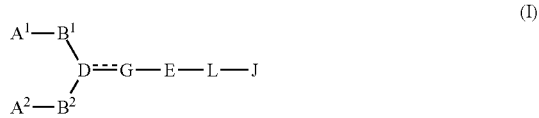

wherein $A^1$ and $A^2$ each independently represents a group having a basic group;

$B^1$ and $B^2$ each independently represents a bond or a spacer having 1 to 4 atom(s) in its main chain;

E represents a spacer having 1 to 10 atom(s) in its main chain;

L represents a bond or a spacer having 1 to 2 atom(s) in its main chain;

J represents an aliphatic hydrocarbon group which is substituted with a group having a basic group, and also may be substituted by a substituent(s), or a cyclic group which is substituted with a group having a basic group, and also may be substituted by a substituent(s);

⸺ represents a single bond or a double bond;

when ⸺ represents a single bond, D represents a nitrogen atom or a carbon atom which may have a substituent(s), G represents a carbon atom which may have a substituent(s), a carbonyl group, an oxygen atom, or a sulfur atom which may be oxidized, when ⸺ represents a double bond, D represents a carbon atom, and G represents a carbon atom which may have a substituent(s), or a nitrogen atom;

wherein when D represents a nitrogen atom, G represents a carbonyl group, an oxygen atom, or a sulfur atom which may be oxidized, or $B^1$ represents a spacer having a main chain of 1 to 4 atom(s), which has at least one selected from —O—, —S—, —CO—, —SO—, —SO$_2$—, a divalent nitrogen atom which may have a substituent and a divalent 3- and 8-membered monocyclic cyclic group which may have a substituent(s)) or a salt thereof, an N-oxide thereof or a solvate thereof, or a prodrug thereof; or

[61] A method for producing a compound represented by formula (I-0), a salt thereof, an N-oxide thereof or a solvate thereof, or a prodrug thereof.

In the present specification, "cyclic group" includes, for example, a carbocyclic ring or a hetrocyclic ring. Examples of the "carbocyclic ring" include C3-15 monocyclic or polycyclic carbocyclic ring. The "C3-15 monocyclic or polycyclic carbocyclic ring" includes a C3-15 monocyclic or polycyclic unsaturated carbocyclic ring, or partially or completely saturated one thereof, a spiro-bound polycyclic carbocyclic ring and a bridged polycyclic carbocyclic ring. Examples of the "C3-15 monocyclic or polycyclic unsaturated carbocyclic ring, or partially or completely saturated one thereof" include cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene, and 1,2,3,5,6,7-hexahydro-s-indacene rings; examples of the "spiro-bound polycyclic carbocyclic ring" include spiro[4.4]nonane, spiro[4.5]decane, spiro[5.5]undecane, spiro[3.4]octane, and spiro[3.5]nonane rings; and examples of the "bridged polycyclic carbocyclic ring" include bicyclo[2.2.1]heptane, bicyclo[2.2.1]hept-2-ene, bicyclo[3.1.1]heptane, bicyclo[3.1.1]hept-2-ene, bicyclo[3.2.1]octane, bicyclo[2.2.2]octane, bicyclo[2.2.2]oct-2-ene, adamantane, noradamantane, bicyclo[2.1.1]hexane, bicyclo[3.3.1]nonane, bicyclo[3.2.1]octane, bicyclo[3.3.2]decane ring. Among these, examples of the "C3-15 monocyclic or polycyclic aromatic carbocyclic ring" include benzene, azulene, naphthalene, phenanthrene, and anthracene rings.

Examples of the hetrocyclic ring includes "3- to 15-membered monocyclic or polycyclic hetrocyclic ring having, as a hetero atom, 1 to 4 nitrogen atom(s), 1 to 2 oxygen atom(s) and/or 1 to 2 sulfur atom(s)". The "3- to 15-membered monocyclic or polycyclic hetrocyclic ring having, as a hetero atom, 1 to 4 nitrogen atom(s), 1 to 2 oxygen atom(s) and/or 1 to 2 sulfur atom(s)" includes, 3- to 15-membered monocyclic or polycyclic unsaturated hetrocyclic ring having, as a hetero atom, 1 to 4 nitrogen atom(s), 1 to 2 oxygen atom(s) and/or 1 to 2 sulfur atom(s), or partially or completely saturated one thereof, a spiro-bound polycyclic hetrocyclic ring and a bridged polycyclic hetrocyclic ring. Examples of the "3- to 15-membered monocyclic or polycyclic unsaturated hetrocyclic ring having, as a hetero atom, 1 to 4 nitrogen atom(s), 1 to 2 oxygen atom(s) and/or 1 to 2 sulfur atom(s), or partially or completely saturated one thereof" include pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzoazepine, benzodiazepine, benzofurazan, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydro benzoazepin, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindane, benzodioxane, chroman, benzodithiolane, benzodithiane, 6,7-dihydro-5H-cyclopenta[b]pyrazine, 5H-cyclopenta[b]pyrazine, imidazo[2,1-b][1,3]thiazole, pyrido[2,3-b]pyrazine, pyrido[3,4-b]pyrazine, [1,3]thiazolo[4,5-b]pyrazine, thieno[2,3-b]pyrazine, 3,4-dihydro-2H-pyrazino[2,3-b][1,4]oxazine, 6,7-dihydro-5H-cyclopenta[b]pyrazine, imidazo[1,2-a]pyrazine, 6,7-dihydro-5H-cyclopenta[b]pyridine, furo[3,2-b]pyridine, pyrido[2,3-d]pyrimidine, 2,3-dihydro-1H-pyrrolo[2,3-b]pyridine, 5,6,7,8-tetrahydro-1,6-naphthylidine, 6,7,8,9-tetrahydro-5H-pyrido[2,3-d]azepine, 3,4-dihydro-2H-pyrano[3,2-c]pyridine, 2,3-dihydrofuro[3,2-c]pyridine, hexahydro-1H-pyrrolidine, octahydrocyclopenta[c]pyrrole, octahydrocyclopenta[b]pyrrole, octahydropyrrolo[3,2-b]pyrrole, octahydropyrrolo[3,4-c]pyrrole, hexahydro-2H-furo[3,2-b]pyrrole, hexahydro-2H-thieno[3,2-b]pyrrole, decahydroquinoline, decahydro-2,6-naphthylidine, octahydro-2H-quinolidine, octahydro-1H-pyrido[1,2-c]pyrimidine, octahydro-2H-1,4-benzooxazine, decahydro-1,5-naphthylidine, octahydro-1H-pyrrolo[3,4-b]pyridine, and octahydro-1H-pyrrolo[3,4-c]pyridine rings; examples of the "spiro-bound polycyclic hetrocyclic ring" include azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane, 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 7-azaspiro[4.5]decane, 3-azaspiro[5.5]undecane, 2-azaspiro[5.5]undecane, 1-oxa-4,8-diazaspiro[5.5]undecane, 1-oxa-4,9-diazaspiro[5.5]undecane, 3,4-dihydrospiro[chromene-2,4'-piperidine], 2-azaspiro[4.4]nonane, 7-azaspiro[3.5]nonane, 2,3-dihydrospiro[indene-1,4'-piperidine], 3,4-dihydro-2H-spiro[naphthalene-1,4'-piperidine], 3,4-dihydro-1H-spiro[naphthalene-2,4'-piperidine], 2-azaspiro[4.5]decane, 2-azaspiro[3.5]nonane, 1',2'-dihydrospiro[cyclohexane-1,3'-indole], 2',3'-dihydro-1'H-spiro[cyclohexane-1,4'-isoquinoline], 1',4'-dihydro-2'H-spiro[cyclohexane-1,3'-quinoline], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, and 1-thia-4,8-diazaspiro[5.5]undecane rings; and examples of the "bridged polycyclic hetrocyclic ring" include azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, 1-azatricyclo[3.3.1.1$^{3,7}$]decane, 3-azabicyclo[3.3.1]nonane, and 3,7-diazabicyclo[3.3.1]nonane rings. Among these, examples of the "3- to 15-membered monocyclic or polycyclic aromatic hetrocyclic ring having, as a hetero atom, 1 to 4 nitrogen atom(s), 1 to 2 oxygen atom(s) and/or 1 to 2 sulfur atom(s)" include pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthylidine, quinoxaline, quinazoline, cinnoline, benzoxazole, benzothiazole, benzimidazole, benzofurazan, benzothiadiazole, benzotriazole, carbazole, β-carboline, acridine, phenazine, dibenzofuran, dibenzothiophene, phenanthridine, phenanthroline, perimidine rings.

In the present specification, "aliphatic hydrocarbon group" includes, for example, "linear or branched aliphatic hydrocarbon group". Examples of the "linear or branched aliphatic hydrocarbon group" include "aliphatic hydrocarbon group having 1 to 8 carbon atom(s)", and examples of "aliphatic hydrocarbon group having 1 to 8 carbon atom(s)" include C1-8 alkyl group, C2-8 alkenyl group, and C2-8 alkynyl group.

Examples of the C1-8 alkyl group include methyl, ethyl, propyl, isopropyl, butyl, sec-butyl, tert-butyl, pentyl, hexyl, heptyl, and octyl groups, and isomer groups thereof.

Examples of the C2-8 alkenyl group include vinyl, propenyl, butenyl, pentenyl, hexenyl, heptenyl, octenyl, butadienyl, pentadienyl, hexadienyl, heptadienyl, octadienyl, hexatrienyl, heptatrienyl, and octatrienyl groups, and isomer groups thereof.

Examples of the C2-8 alkynyl group include ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, and octatriynyl groups, and isomer groups thereof.

In the present specification, "group having a basic group" represented by $A^1$ and $A^2$ is not specifically limited as long as it has a basic group. Examples thereof include (1) basic group, (2) aliphatic hydrocarbon group which is substituted with a basic group, and also may have a substituent(s), and (3) cyclic group which is substituted with a basic group, and also may have a substituent(s).

The "aliphatic hydrocarbon group" in the "aliphatic hydrocarbon group which is substituted with a basic group, and also may have a substituent(s)" has the same meaning as in the aliphatic hydrocarbon group.

The "cyclic group" in the "cyclic group which is substituted with a basic group, and also may have a substituent(s)" has the same meaning as in the cyclic group.

The "substituent" in the "aliphatic hydrocarbon group which is substituted with a basic group, and also may have a substituent(s)" or the "cyclic group which is substituted with a basic group, and also may have a substituent(s)" is not specifically limited as long as it is a substituent. Examples thereof include the following substituents defined as T.

Examples of T include:
(1) aliphatic hydrocarbon group,
(2) C1-8 alkylidene group (for example, methylidene, ethylidene, propylidene, butylidene, pentylidene, hexylidene, heptylidene, or octylidene group, and isomer thereof, etc.),
(3) cyclic group,
(4) aliphatic hydrocarbon group substituted with a cyclic group (for example, cyclopropylmethyl, cyclopentylmethyl, cyclohexylmethyl, phenylmethyl, naphthylmethyl, pyridinylmethyl, cyclopropylethyl, cyclopentylethyl, cyclohexylethyl, phenylethyl, naphthylethyl, pyridinylethyl, cyclopropylpropyl, cyclopentylpropyl, cyclohexylpropyl, phenylmethyl, phenylpropyl, naphthylpropyl, pyridinylpropyl, etc.),
(5) hydroxyl group,
(6) —O-aliphatic hydrocarbon group (for example, methoxy, ethoxy, propoxy, isopropoxy, butoxy, isobutoxy, tert-butoxy, pentoxy, hexyloxy, heptyloxy, octyloxy, propenyloxy, butenyloxy, pentenyloxy, hexenyloxy, propynyloxy, butynyloxy, pentynyloxy, hexynyloxy, etc.),
(7) —O-cyclic group (for example, cyclopropyloxy, cyclopentyloxy, cyclohexyloxy, phenoxy, naphthyloxy, pyridinyloxy, etc.),
(8) —O-aliphatic hydrocarbon group-cyclic group (for example, cyclopentylmethoxy, cyclohexylmethoxy, phenylmethoxy, etc.),
(9) mercapto group,
(10) —S-aliphatic hydrocarbon group (for example, methylthio, ethylthio, propylthio, isopropylthio, butylthio, isobutylthio, tert-butylthio, pentylthio, hexylthio, heptylthio, octylthio, propenylthio, butenylthio, pentenylthio, hexenylthio, propynylthio, butynylthio, pentynylthio, hexynylthio, etc.),
(11) —S-cyclic group (for example, cyclopropylthio, cyclopentylthio, cyclohexylthio, phenylthio, naphthylthio, pyridinylthio, etc.),
(12) —S-aliphatic hydrocarbon group-cyclic group (for example, cyclopentylmethylthio, cyclohexylmethylthio, phenylmethylthio, etc.),
(13) —S(O)-aliphatic hydrocarbon group (for example, methylsulfinyl, ethylsulfinyl, propylsulfinyl, isopropylsulfinyl, butylsulfinyl, isobutylsulfinyl, tert-butylsulfinyl, pentylsulfinyl, hexylsulfinyl, heptylsulfinyl, octylsulfinyl, propenylsulfinyl, butenylsulfinyl, pentenylsulfinyl, hexenylsulfinyl, propynylsulfinyl, butynylsulfinyl, pentynylsulfinyl, hexynylsulfinyl, etc.),
(14) —S(O)-cyclic group (for example, cyclopropylsulfinyl, cyclopentylsulfinyl, cyclohexylsulfinyl, phenylsulfinyl, naphthylsulfinyl, pyridinylsulfinyl, etc.),
(15) —S(O)-aliphatic hydrocarbon group-cyclic group (for example, cyclopentylmethylsulfinyl, cyclohexylmethylsulfinyl, phenylmethylsulfinyl, etc.),
(16) —$SO_2$-aliphatic hydrocarbon group (for example, methylsulfonyl, ethylsulfonyl, propylsulfonyl, isopropylsulfonyl, butylsulfonyl, isobutylsulfonyl, tert-butylsulfonyl, pentylsulfonyl, hexylsulfonyl, heptylsulfonyl, octylsulfonyl, propenylsulfonyl, butenylsulfonyl, pentenylsulfonyl, hexenylsulfonyl, propynylsulfonyl, butynylsulfonyl, pentynylsulfonyl, hexynylsulfonyl, etc.),
(17) —$SO_2$-cyclic group (for example, cyclopropylsulfonyl, cyclopentylsulfonyl, cyclohexylsulfonyl, phenylsulfonyl, naphthylsulfonyl, pyridinylsulfonyl, etc.),
(18) —$SO_2$-aliphatic hydrocarbon group-cyclic group (for example, cyclopentylmethylsulfonyl, cyclohexylmethylsulfonyl, phenylmethylsulfonyl, etc.),
(19) —O—CO-aliphatic hydrocarbon group (for example, methanoyloxy, ethanoyloxy, propanoyloxy, isopropanoyloxy, butanoyloxy, isobutanoyloxy, tert-butanoyloxy, pentanoyloxy, hexanoyloxy, heptanoyloxy, octanoyloxy, propenoyloxy, butenoyloxy, pentenoyloxy, hexenoyloxy, propynoyloxy, butynoyloxy, pentynoyloxy, hexynoyloxy, etc.),
(20) —O—CO-cyclic group (for example, cyclopropylcarbonyloxy, cyclopentylcarbonyloxy, cyclohexylcarbonyloxy, phenylcarbonyloxy, naphthylcarbonyloxy, pyridinylcarbonyloxy, etc.),
(21) —O—CO-aliphatic hydrocarbon group-cyclic group (for example, cyclopentylmethanoyloxy, cyclohexylmethanoyloxy, phenylmethanoyloxy, etc.),
(22) —CO-aliphatic hydrocarbon group (for example, methanoyl, ethanoyl, propanoyl, isopropanoyl, butanoyl, isobutanoyl, tert-butanoyl, pentanoyl, hexanoyl, heptanoyl, octanoyl, propenoyl, butenoyl, pentenoyl, hexenoyl, propynoyl, butynoyl, pentynoyl, hexynoyl, etc.),
(23) —CO-cyclic group (for example, cyclopropylcarbonyl, cyclopentylcarbonyl, cyclohexylcarbonyl, phenylcarbonyl, naphthylcarbonyl, pyridinylcarbonyl, etc.),
(24) —CO-aliphatic hydrocarbon group-cyclic group (for example, cyclopentylmethanoyl, cyclohexylmethanoyl, phenylmethanoyl, etc.),
(25) oxo group,
(26) thioxo group,
(27) sulfino group,
(28) sulfo group,
(29) amino group,
(30) mono- or di-substituted amino group ("substituent" in "mono- or di-substituted amino group" herein includes, for example, (1) aliphatic hydrocarbon group, (2) cyclic group, and (3) aliphatic hydrocarbon group substituted with a cyclic group, and examples thereof include methylamino, ethylamino, propylamino, isopropylamino, butylamino, isobutylamino, tert-butylamino, pentylamino, hexylamino, heptylamino, octylamino, dimethylamino, diethylamino, dipropylamino, dibutylamino, dipentylamino, dihexylamino, diheptylamino, dioctylamino, N-methyl-N-ethylamino, cyclopropylamino, cyclopentylamino, cyclohexylamino, phenylamino, diphenylamino, dibenzylamino, N-phenyl-N-methylamino, N-phenyl-N-ethylamino, N-benzyl-N-methylamino, N-benzyl-N-ethylamino, N-cyclohexyl-N-propylamino, etc.),

(31) sulfamoyl group,

(32) mono- or di-substituted sulfamoyl group ("substituent" in "mono- or di-substituted sulfamoyl group" include, for example, (1) aliphatic hydrocarbon group, (2) cyclic group, and (3) aliphatic hydrocarbon group substituted with a cyclic group, and examples thereof include N-methylsulfamoyl, N-ethylsulfamoyl, N-propylsulfamoyl, N-isopropylsulfamoyl, N-butylsulfamoyl, N-isobutylsulfamoyl, N-(tert-butyl)sulfamoyl, N-pentylsulfamoyl, N-hexylsulfamoyl, N-heptylsulfamoyl, N-octylsulfamoyl, N,N-dimethylsulfamoyl, N,N-diethylsulfamoyl, N,N-dipropylsulfamoyl, N,N-dibutylsulfamoyl, N,N-dipentylsulfamoyl, N,N-dihexylsulfamoyl, N-methyl-N-ethylsulfamoyl, N-cyclopropylsulfamoyl, N-cyclopentylsulfamoyl, N-cyclohexylsulfamoyl, N-phenylsulfamoyl, N,N-diphenylsulfamoyl, N,N-dibenzylsulfamoyl, N-phenyl-N-methylsulfamoyl, N-phenyl-N-ethylsulfamoyl, N-benzyl-N-methylsulfamoyl, N-benzyl-N-ethylsulfamoyl, N-cyclohexyl-N-propylamino, etc.),

(33) carboxy group,

(34) —COO-aliphatic hydrocarbon group (for example, methoxycarbonyl, ethoxycarbonyl, propoxycarbonyl, isopropoxycarbonyl, butoxycarbonyl, isobutoxycarbonyl, tert-butoxycarbonyl, pentoxycarbonyl, hexyloxycarbonyl, heptyloxycarbonyl, octyloxycarbonyl, propenyloxycarbonyl, butenyloxycarbonyl, pentenyloxycarbonyl, hexenyloxycarbonyl, propynyloxycarbonyl, butynyloxycarbonyl, pentynyloxycarbonyl, hexynyloxycarbonyl, etc.),

(35) —COO-cyclic group (for example, cyclopropyloxycarbonyl, cyclopentyloxycarbonyl, cyclohexyloxycarbonyl, phenoxycarbonyl, naphthyloxycarbonyl, pyridinyloxycarbonyl, etc.),

(36) —COO-aliphatic hydrocarbon group-cyclic group (for example, cyclopentylmethoxycarbonyl, cyclohexylmethoxycarbonyl, phenylmethoxycarbonyl, etc.),

(37) carbamoyl group,

(38) mono- or di-substituted carbamoyl group ("substituent" in "mono- or di-substituted carbamoyl group" herein includes, for example, (1) aliphatic hydrocarbon group, (2) cyclic group, and (3) aliphatic hydrocarbon group substituted with a cyclic group, and examples thereof include N-methylcarbamoyl, N-ethylcarbamoyl, N-propylcarbamoyl, N-isopropylcarbamoyl, N-butylcarbamoyl, N-isobutylcarbamoyl, N-(tert-butyl)carbamoyl, N-pentylcarbamoyl, N-hexylcarbamoyl, N-heptylcarbamoyl, N-octylcarbamoyl, N-cyclopropylcarbamoyl, N-cyclopentylcarbamoyl, N-cyclohexylcarbamoyl, N-phenylcarbamoyl, N,N-dimethylcarbamoyl, N,N-diethylcarbamoyl, N,N-dipropylcarbamoyl, N,N-dibutylcarbamoyl, N,N-dipentylcarbamoyl, N,N-dihexylcarbamoyl, N-methyl-N-ethylcarbamoyl, N,N-diphenylcarbamoyl, N,N-dibenzylcarbamoyl, N-phenyl-N-methylcarbamoyl, N-phenyl-N-ethylcarbamoyl, N-benzyl-N-methylcarbamoyl, N-benzyl-N-ethylcarbamoyl, etc.),

(39) —NH—CO-aliphatic hydrocarbon group (for example, methanoylamino, ethanoylamino, propanoylamino, isopropanoylamino, butanoylamino, isobutanoylamino, tert-butanoylamino, pentanoylamino, hexanoylamino, heptanoylamino, octanoylamino, propenoylamino, butenoylamino, pentenoylamino, hexenoylamino, propynoylamino, butynoylamino, pentynoylamino, hexynoylamino, etc.),

(40) —NH—CO-cyclic group (for example, cyclopropylcarbonylamino, cyclopentylcarbonylamino, cyclohexylcarbonylamino, phenylcarbonylamino, naphthylcarbonylamino, pyridinylcarbonylamino, etc.),

(41) —NH—CO-aliphatic hydrocarbon group-cyclic group (for example, cyclopentylmethanoylamino, cyclohexylmethanoylamino, phenylmethanoylamino, etc.),

(42) —NH—SO$_2$-aliphatic hydrocarbon group (for example, methylsulfonylamino, ethylsulfonylamino, propylsulfonylamino, isopropylsulfonylamino, butylsulfonylamino, isobutylsulfonylamino, tert-butylsulfonylamino, pentylsulfonylamino, hexylsulfonylamino, heptylsulfonylamino, octylsulfonylamino, propenylsulfonylamino, butenylsulfonylamino, pentenylsulfonylamino, hexenylsulfonylamino, propynylsulfonylamino, butynylsulfonylamino, pentynylsulfonylamino, hexynylsulfonyl, etc.),

(43) —NH—SO$_2$-cyclic group (for example, cyclopropylsulfonylamino, cyclopentylsulfonylamino, cyclohexylsulfonylamino, phenylsulfonylamino, naphthylsulfonylamino, pyridinylsulfonyl, etc.),

(44) —NH—SO$_2$-aliphatic hydrocarbon group-cyclic group (for example, cyclopentylmethylsulfonylamino, cyclohexylmethylsulfonylamino, phenylmethylsulfonyl, etc.),

(45) cyano group,

(46) hydrazino group,

(47) nitro group,

(48) nitroso group,

(49) imino group,

(50) mono-substituted imino group ("substituent" in the mono-substituted imino group includes, for example, (1) aliphatic hydrocarbon group, (2) cyclic group, (3) aliphatic hydrocarbon group substituted with a cyclic group, (4) hydroxyl group, (5) —O-aliphatic hydrocarbon group, (6) —O-cyclic group, and (7) —O-aliphatic hydrocarbon group-cyclic group, and examples thereof include methylimino, ethylimino, propylimino, isopropylimino, butylimino, isobutylimino, (tert-butyl)imino, pentylimino, hexylimino, heptylimino, octylimino, cyclopropylimino, cyclopentylimino, cyclohexylimino, phenylimino, benzylimino, hydroxyimino, ethoxyimino, propoxyimino, isopropoxyimino, butoxyimino, cyclopentoxyimino, cyclohexyloxyimino, phenoxyimino, benzyloxyimino, etc.),

(51) halogen atom (for example, fluorine atom, chlorine atom, bromine atom, iodine atom, etc.),

(52) methyl group substituted with 1 to 3 halogen atom(s) (for example, fluoromethyl, difluoromethyl, trifluoromethyl, trichloromethyl, etc.), and

(53) methoxy group substituted with 1 to 3 halogen atom(s) (for example, fluoromethoxy, difluoromethoxy, trifluoromethoxy, trichloromethoxy, etc.). These optional substituents may be substituted on the optional substitutable position in optional substitutable number. The number of substituents is preferably from 1 to 8, and more preferably from 1 to 5. The "aliphatic hydrocarbon group" and the "cyclic group" in T have the same meanings as described above.

The "basic group" in the "group having a basic group" is not specifically limited as long as it has a basic nitrogen atom. Examples thereof include (a) amino group, (b) amidino group, (c) guanidino group, (d) hydrazino group, (e) mono- or di-substituted amino group, (f) mono-, di- or tri-substituted amidino group, (g) mono-, di-, tri- or tetra-substituted guanidino group, (h) mono-, di- or tri-substituted hydrazino group, and (i) nitrogen-containing hetrocyclic ring which may have a substituent(s). Examples of the "substituent" in the "mono- or di-substituted amino group" herein include (1) aliphatic hydrocarbon group (which has the same meaning as described above), (2) cyclic group (which has the same meaning as described above), (3) aliphatic hydrocarbon group substituted with a cyclic group (aliphatic hydrocarbon and cyclic group have the same meanings as described above), (4) cyclic group substituted with a substituent(s) (substituent has the same meaning as in T, and cyclic group has the same meaning as described above), (5) aliphatic hydrocarbon group substituted with a substituent(s) (substituent has the same meaning as in T, and aliphatic hydrocarbon has the same meaning as described above), (6) aliphatic hydrocarbon group substituted with a cyclic group substituted with a substituent(s) (substituent has the same meaning as in T, and aliphatic hydrocarbon and cyclic groups have the same meanings as described above), and (7) substituent T described above. These optional substituents may be substituted on the optional substitutable position in optional substitutable number. The number of substituents is preferably from 1 to 8, and more preferably from 1 to 5. Examples thereof include methylamino, ethylamino, propylamino, isopropylamino, butylamino, isobutylamino, tert-butylamino, pentylamino, hexylamino, heptylamino, octylamino, dimethylamino, diethylamino, dipropylamino, dibutylamino, dipentylamino, dihexylamino, diheptylamino, dioctylamino, N-methyl-N-ethylamino, cyclopropylamino, cyclopentylamino, cyclohexylamino, phenylamino, diphenylamino, dibenzylamino, N-phenyl-N-methylamino, N-phenyl-N-ethylamino, N-benzyl-N-methylamino, N-benzyl-N-ethylamino, N-benzyl-N-cyclohexylamino, N-cyclohexyl-N-propylamino, N-cyclohexyl-N-(3-hydroxypropyl)amino, N-(4-hydroxycyclohexyl)-N-propylamino, N-(4-hydroxycyclohexyl)-N-(3-hydroxypropyl)amino, N-(4-hydroxycyclohexyl)methyl-N-propylamino, N-cyclohexyl-N-acetylamino, N-(3-methoxypropyl)-N-propylamino, N-(2-carboxyethyl)-N-propylamino, N-(2-ethylpropyl)-N-propylamino, N-cyclohexyl-N-(methylsulfonyl)amino, N-(tetrahydropyran-4-yl)-N-propylamino, and N-(indan-2-yl)-N-propylamino. Examples of the "substituent" in the "mono-, di- or tri-substituted amidino group" include (1) aliphatic hydrocarbon group (which has the same meaning as described above), (2) cyclic group (which has the same meaning as described above), (3) aliphatic hydrocarbon group substituted with a cyclic group (aliphatic hydrocarbon and cyclic groups have the same meanings as described above). Examples of the "mono-, di- or tri-substituted amidino group" include methylamidino, ethylamidino, propylamidino, isopropylamidino, butylamidino, isobutylamidino, tert-butylamidino, pentylamidino, hexylamidino, heptylamidino, octylamidino, N,N-dimethylamidino, N,N'-dimethylamidino, N,N,N'-trimethylamidino, N,N-diethylamidino, N,N'-diethylamidino, N,N,N'-triethylamidino, N,N-dipropylamidino, N,N'-dipropylamidino, N,N,N'-tripropylamidino, N,N-dibutylamidino, N,N'-dibutylamidino, N,N,N'-tributylamidino, N,N-dipentylamidino, N,N'-dipentylamidino, N,N,N'-tripentylamidino, N,N-dihexylamidino, N,N'-dihexylamidino, N,N,N'-trihexylamidino, N,N-diheptylamidino, N,N'-diheptylamidino, N,N,N'-trioctylamidino, N,N'-dioctylamidino, N,N,N'-trioctylamidino, N-methyl-N-ethylamidino, N-methyl-N'-ethylamidino, cyclopropylamidino, cyclopentylamidino, cyclohexylamidino, phenylamidino, N,N-diphenylamidino, N,N'-diphenylamidino, N,N,N'-triphenylamidino, N,N-dibenzylamidino, N,N'-dibenzylamidino, N,N,N'-tribenzylamidino, N-phenyl-N'-methylamidino, N-phenyl-N'-ethylamidino, N-benzyl-N-methylamidino, and N-benzyl-N-ethylamidino.

Examples of the "substituent" in the "mono-, di-, tri- or tetra-substituted guanidino group" include (1) aliphatic hydrocarbon group (which has the same meaning as described above), (2) cyclic group (which has the same meaning as described above), and (3) aliphatic hydrocarbon group substituted with a cyclic group (aliphatic hydrocarbon and cyclic have the same meanings as described above). Examples of the "mono-, di-, tri- or tetra-substituted guanidino group" include, for example, methylguanidino, ethylguanidino, propylguanidino, isopropylguanidino, butylguanidino, isobutylguanidino, tert-butylguanidino, pentylguanidino, hexylguanidino, heptylguanidino, octylguanidino, N,N-dimethylguanidino, N,N'-dimethylguanidino, N,N,N'-trimethylguanidino, N,N,N',N''-tetramethylguanidino, N,N-diethylguanidino, N,N'-diethylguanidino, N,N,N'-triethylguanidino, N,N,N',N''-tetraethylguanidino, N,N-dipropylguanidino, N,N'-dipropylguanidino, N,N,N'-tripropylguanidino, N,N,N',N''-tetrapropylguanidino, N,N-dibutylguanidino, N,N'-dibutylguanidino, N,N,N'-tributylguanidino, N,N,N',N''-tetrabutylguanidino, N,N-dipentylguanidino, N,N'-dipentylguanidino, N,N,N'-tripentylguanidino, N,N,N',N''-tetrapentylguanidino, N,N-dihexylguanidino, N,N'-dihexylguanidino, N,N,N'-trihexylguanidino, N,N,N',N''-tetrahexylguanidino, N,N-diheptylguanidino, N,N'-diheptylguanidino, N,N,N'-triheptylguanidino, N,N,N',N''-tetraheptylguanidino, N,N-dioctylguanidino, N,N'-dioctylguanidino, N,N,N'-trioctylguanidino, N,N,N',N''-tetraoctylguanidino, N-methyl-N-ethylguanidino, N-methyl-N'-ethylguanidino, cyclopropylguanidino, cyclopentylguanidino, cyclohexylguanidino, phenylguanidino, N,N-diphenylguanidino, N,N'-diphenylguanidino, N,N,N'-triphenylguanidino, N,N,N',N''-tetraphenylguanidino, N,N-dibenzylguanidino, N,N'-dibenzylguanidino, N,N,N'-tribenzylguanidino, N,N,N',N''-tetrabenzylguanidino, N-phenyl-N'-methylguanidino, N-phenyl-N'-ethylguanidino, N-benzyl-N-methylguanidino, N-benzyl-N-ethylguanidino and the like.

Examples of the "substituent" in the "mono-, di- or tri-substituted hydrazino group" include (1) aliphatic hydrocarbon group (which has the same meaning as described above), (2) cyclic group (which has the same meaning as described above), and (3) aliphatic hydrocarbon group substituted with a cyclic group (aliphatic hydrocarbon and cyclic groups have the same meanings as described above). Examples of the "mono-, di- or tri-substituted hydrazino group" include, for example, methylhydrazino, ethylhydrazino, propylhydrazino, isopropylhydrazino, butylhydrazino, isobutylhydrazino, tert-butylhydrazino, pentylhydrazino, hexylhydrazino, heptylhydrazino, octylhydrazino, N,N-dimethylhydrazino, N,N'-dimethylhydrazino, N,N,N'-trimethylhydrazino, N,N-diethylhydrazino, N,N'-diethylhydrazino, N,N,N'-triethylhydrazino, N,N-dipropylhydrazino, N,N'-dipropylhydrazino, N,N,N'-tripropylhydrazino, N,N-dibutylhydrazino, N,N'-dibutylhydrazino, N,N,N'-tributylhydrazino, N,N-dipentylhydrazino, N,N'-dipentylhydrazino, N,N,N'-tripentylhydrazino, N,N-dihexylhydrazino, N,N'-dihexylhydrazino, N,N,N'-trihexylhydrazino, N,N-diheptylhydrazino. N,N'-diheptylhydrazino, N,N,N'-triheptylhydrazino, N,N-dioctylhydrazino, N,N'-dioctylhydrazino, N,N,N'-trioctylhydrazino, N-methyl-N-ethylhydrazino, N-methyl-N'-ethylhydrazino, cyclopropylhydrazino, cyclopentylhydrazino, cyclohexylhydrazino, phenylhydrazino, N,N-diphenylhydrazino, N,N'-diphenylhydrazino, N,N,N'-triphenylhydrazino, N,N-dibenzylhydrazino, N,N'-dibenzylhydrazino, N,N,N'-tribenzylhydrazino, N-phenyl-N'-methylhydrazino, N-phenyl-N'-ethylhydrazino, N-benzyl-N-methylhydrazino, N-benzyl-N-ethylhydrazino and the like.

Examples of the "nitrogen-containing hetrocyclic ring" in the "nitrogen-containing hetrocyclic ring which may have a substituent(s)" include, for example, pyrrole, imidazole, triazole, pyrazole, pyridine, pyrazine, pyrimidine, pyridazine, azepine, diazepine, oxazole, thiazole, isoxazole, isothiazole, indole, isoindole, quinoline, isoquinoline, benzoxazole, benzothiazole, benzimidazole, aziridine, azetidine, pyrrolidine, piperidine, piperazine, morpholine, thiomorpholine, perhydroazepine, perhydrodiazepine, indoline, isoindoline, quinazoline, tetrahydroquinoline, perhydroquinoline, tetrahydroisoquinoline, perhydroisoquinoline, tetrahydronaphthyridine, quinoxaline, tetrahydroquinoxaline, dihydrobenzimidazole, perhydrobenzimidazole, carbazole, tetrahydrocarbazole, azabicyclo[3.2.1]octane, quinuclidine, 2,8-diazaspiro[4.5]decane, 1,4,9-triazaspiro[5.5]undecane, 3,9-diazaspiro[5.5]undecane, 2,9-diazaspiro[5.5]undecane, 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane ring and the like.

The "substituent" in the "nitrogen-containing hetrocyclic ring which may have a substituent(s)" has the same meaning as in above described T. These optional substituent(s) may be substituted on the optional substitutable position in optional substitutable number. The number of substituents is preferably from 1 to 8, and more preferably from 1 to 5.

In the present specification, "nitrogen-containing hetrocyclic ring which may have a substituent(s)" represented by ring $A^{1A}$ and ring $A^{2A}$ has the same meaning as the "nitrogen-containing hetrocyclic ring which may have a substituent(s)" in $A^1$ and $A^2$.

In the present specification, examples of the "substituent" of the "imidazole or benzimidazole which may have a substituent" represented by ring $A^{1B}$ and ring $A^{2B}$ include those exemplified as for T in $A^1$ and $A^2$, and these optional substituents may be substituted on the substitutable position and the number of substituents is from 1 to 5, and preferably from 1 to 2.

In the present specification, "spacer having a main chain of 1 to 4 atom(s)" represented by $B^1$ and $B^2$, and "spacer having a main chain of 1 to 4 atom(s)" represented by L mean the space wherein 1 to 4 atom(s) of the main chain are arranged in a line. "Number of atoms of main chain" is counted so that the number of atoms of the main chain is minimized. For example, it is counted that the number of atoms of 1,2-cyclopentylene is 2 and the number of atoms of 1,3-cyclopentylene is 3. Examples of the "spacer having a main chain of 1 to 4 atom(s)" include divalent group composed of 1 to 4 groups selected optionally from —O—, —S—, —CO—, —SO—, —SO$_2$—, divalent nitrogen atom which may have a substituent, divalent aliphatic hydrocarbon group having 1 to 4 carbon atom(s) which may have a substituent(s), and divalent 3- to 8-membered monocyclic cyclic group which may have a substituent(s), wherein 1 to 4 atom(s) of the main chain are arranged in a line.

The "divalent nitrogen atom which may have a substituent" represents, in addition to —NH—, those wherein hydrogen atom in the "—NH-" group are optionally substituted with (1) aliphatic hydrocarbon group, (2) cyclic group, (3) aliphatic hydrocarbon group substituted with a cyclic group, (4) hydroxyl group, (5) —O-aliphatic hydrocarbon group, (6)-β-cyclic group, (7) —O-aliphatic hydrocarbon group-cyclic group, (8) —SO$_2$-aliphatic hydrocarbon group, (9) —SO$_2$-cyclic group, (10) —SO$_2$-aliphatic hydrocarbon group-cyclic group, (11) —CO-aliphatic hydrocarbon, (12) —CO-cyclic group, (13) —CO-aliphatic hydrocarbon group-cyclic group, (14) carboxy group, (15) —COO-aliphatic hydrocarbon, (16) —COO-cyclic group, or (17) —COO-aliphatic hydrocarbon group-cyclic group. The substituents (1) to (17) are have same meanings as described above.

Examples of the "divalent aliphatic hydrocarbon group having 1 to 4 carbon atom(s)" in the "divalent aliphatic hydrocarbon group having 1 to 4 carbon atom(s) which may have a substituent(s)" include C1-4 alkylene group (for example, —CH$_2$—, —(CH$_2$)$_2$—, —(CH$_2$)$_3$—, —(CH$_2$)$_4$—, etc.), C2-4 alkenylene group (for example, —CH=CH—, —CH$_2$—CH=CH—, —CH=CH—CH$_2$—, —(CH$_2$)$_2$—CH=CH—, —CH=CH—(CH$_2$)$_2$—, —CH$_2$—CH=CH—CH$_2$—, etc.), and C2-4 alkynylene group (for example, —C≡C—, —CH$_2$—C≡C—, —C≡C—CH$_2$—, —(CH$_2$)$_2$—C≡C—, —C≡C—(CH$_2$)$_2$—, —CH$_2$—C≡C—CH$_2$—, etc.). Examples of the "substituent" in the "divalent aliphatic hydrocarbon group having 1 to 4 carbon atom(s) which may have a substituent(s)" include those exemplified as for T in $A^1$ and $A^2$, and these optional substituents may be substituted on the substitutable position and the number of substituents is from 1 to 5, and preferably from 1 to 2.

Examples of the "divalent 3- to 8-membered monocyclic cyclic group" in the "divalent 3- to 8-membered monocyclic cyclic group which may have a substituent(s)" include divalent group which can be obtained by eliminating optional two hydrogen atoms from the "C3-8 monocyclic cyclic group". Examples of the "C3-8 monocyclic cyclic group" herein include "C3-8 monocyclic carbocyclic ring" and "3- to 8-membered monocyclic hetrocyclic ring". The "C3-8 monocyclic carbocyclic ring" includes C3-8 monocyclic unsaturated carbocyclic ring, and partially or completely saturated one thereof. Examples of the "C3-8 monocyclic unsaturated carbocyclic ring, and partially or completely saturated one thereof" include cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, and benzene rings. Among these, the "C3-8 monocyclic aromatic carbocyclic ring" includes, for example, benzene ring.

Examples of the "3- to 8-membered monocyclic hetrocyclic ring" include "3- to 8-membered monocyclic hetrocyclic ring having, as a hetero atom, 1 to 4 nitrogen atom(s), 1 to 2 oxygen atom(s) and/or 1 to 2 sulfur atom(s)". The 3- to 8-membered monocyclic hetrocyclic ring having, as a hetero atom, 1 to 4 nitrogen atom(s), 1 to 2 oxygen atom(s) and/or 1 to 2 sulfur atom(s)" herein includes 3- to 8-membered monocyclic unsaturated hetrocyclic ring having, as a hetero atom, 1 to 4 nitrogen atom(s), 1 to 2 oxygen atom(s) and/or 1 to 2 sulfur atom(s), and partially or completely saturated one thereof. Examples of the "3- to 8-membered monocyclic unsaturated hetrocyclic ring having, as a hetero atom, 1 to 4 nitrogen atom(s), 1 to 2 oxygen atom(s) and/or 1 to 2 sulfur atom(s), and partially or completely saturated one thereof" include pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolysine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane rings and the like. Among these, examples of the "3- to 8-membered monocyclic aromatic hetrocyclic ring having, as a hetero atom, 1 to 4 nitrogen atom(s), 1 to 2 oxygen atom(s) and/or 1 to 2 sulfur atom(s)" include pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole rings and the like. Examples of the "substituent" in the "divalent 3- to 8-membered monocyclic cyclic group which may have a substituent(s)" include those exemplified as for T in A' and $A^2$, and these optional substituents may be substituted on the substitutable position and the number of substituents is from 1 to 8, and preferably from 1 to 5.

In the present specification, "spacer having a main chain of 1 to 10 atom(s)" represented by E means the space wherein 1 to 10 atom(s) of the main chain are arranged in a line. "Number of atoms of main chain" is counted so that the number of atoms of the main chain is minimized. For example, it is counted that the number of atoms of

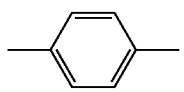

is 4 and the number of atoms of

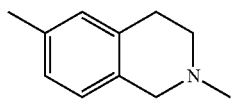

is 6.

Examples of the "spacer having a main chain of 1 to 10 atom(s)" include divalent group composed of 1 to 10 groups selected optionally from —O—, —S—, —CO—, —SO—, —SO$_2$—, divalent nitrogen atom which may have a substituent, divalent aliphatic hydrocarbon group having 1 to 10 carbon atom(s) which may have a substituent(s), and divalent 3- to 15-membered monocyclic cyclic group which may have a substituent(s), wherein 1 to 10 atom(s) of the main chain are arranged in a line. The "divalent nitrogen atom which may have a substituent" has the same meaning as described above. Examples of the "divalent aliphatic hydrocarbon group having 1 to 10 carbon atom(s)" in the "divalent aliphatic hydrocarbon group having 1 to 10 carbon atom(s) which may have a substituent(s)" include C1-10 alkylene group (methylene, ethylene, trimethylene, tetramethylene, pentamethylene, hexamethylene, heptamethylene, octamethylene, nonamethylene, decamethylene group, and isomers thereof), C2-10 alkenylene group (ethenylene, propenylene, butenylene, pentenylene, hexenylene, heptenylene, octenylene, nonenylene, decenylene group, and isomers thereof), and C2-10 alkynylene group (ethynylene, propynylene, butynylene, pentynylene, hexynylene, heptynylene, octynylene, nonynylene, decynylene group, and isomers thereof). Examples of the "substituent" in the "divalent aliphatic hydrocarbon group having 1 to 10 carbon atom(s) which may have a substituent(s)" include those exemplified as for T in $A^1$ and $A^2$, and these optional substituents may be substituted on the substitutable position and the number of substituents is from 1 to 5, and preferably from 1 to 2. Examples of the "divalent 3- to 15-membered cyclic group" in the "divalent 3- to 15-membered cyclic group which may have a substituent(s)" include divalent group obtained by eliminating optional two hydrogen atoms from the "3- to 15-membered cyclic group". Examples of the "3- to 15-membered cyclic group" include C3-15 monocyclic or polycyclic carbocyclic ring defined above, or 3- to 15-membered monocyclic or polycyclic hetrocyclic ring having, as a hetero atom, 1 to 4 nitrogen atom(s), 1 to 2 oxygen atom(s) and/or 1 to 2 sulfur atom(s). Examples of the "substituent" in the "divalent 3- to 15-membered cyclic group which may have a substituent(s)" include those exemplified as for T in $A^1$ and $A^2$, and these optional substituents may be substituted on the substitutable position and the number of substituents is from 1 to 5, and preferably from 1 to 2.

In the present specification, the "divalent 3- to 8-membered monocyclic cyclic group which may have a substituent(s)" of the "divalent 3- to 8-membered monocyclic cyclic group which may have a substituent(s), or divalent 9- or 10-membered polycyclic cyclic group which may have a substituent(s)" represented by ring $E^4$ has the same meaning as in the "divalent 3- to 8-membered monocyclic cyclic group which may have a substituent(s)" in B and $B^2$. As the "divalent 9- or 10-membered polycyclic cyclic group which may have a substituent(s)" of the "divalent 3- to 8-membered monocyclic cyclic group which may have a substituent(s), or divalent 9- or 10-membered polycyclic cyclic group which may have a substituent(s)" represented by ring $E^A$, a 9- or 10-membered cyclic group is selected from among the "divalent 3- to 15-membered cyclic group which may have a substituent(s)" in E.

In the present specification, "-(nitrogen atom which may have a substituent)-" in "-(aliphatic hydrocarbon group having 1 to 3 carbon atom(s) which may have a substituent(s))-(nitrogen atom which may have a substituent)-" represented by $L^4$ and $L^{41}$ has the same meaning as in the "divalent nitrogen atom which may have a substituent". Examples of the "aliphatic hydrocarbon group having 1 to 3 carbon atom(s)" in the "aliphatic hydrocarbon group having 1 to 3 carbon atom(s) which may have a substituent(s)" include C1 to 3 alkylene group (for example, methylene, ethylene, trimethylene, etc.), C2-3 alkenylene group (for example, ethenylene, propenylene, etc.), and C2-3 alkynylene group (for example, ethynylene, propynylene, etc.). Examples of the "substituent" in the "aliphatic hydrocarbon group having 1 to 3 carbon atom(s) which may have a substituent(s)" include those exemplified as for T in $A^1$ and $A^2$, and these optional substituents may be substituted on the substitutable position and the number of substituents is from 1 to 3.

In the present specification, the "divalent aliphatic hydrocarbon group having 1 to 4 carbon atom(s) which may have a substituent(s)" represented by $L^A$ and $L^{A2}$ has the same meaning as described above.

In the present specification, examples of the "aliphatic hydrocarbon group which is substituted with a group having a basic group, and also may have a substituent(s)" represented by $J^0$ include (1) aliphatic hydrocarbon group which is substituted with a basic group, and also may have a substituent(s), (2) aliphatic hydrocarbon group which is substituted with a cyclic group substituted with a basic group, and also may have a substituent(s), and (3) aliphatic hydrocarbon group which is substituted with an aliphatic hydrocarbon group substituted with a basic group, and also may have a substituent(s). Examples of the "cyclic group which is substituted with a group having a basic group, and also may have a substituent(s)" represented by $J^0$ include (1) cyclic group which is substituted with a basic group, and also may have a substituent(s), (2) cyclic group which is substituted with a cyclic group substituted with a basic group, and also may have a substituent(s), and (3) cyclic group which is substituted with an aliphatic hydrocarbon group substituted with a basic group, and also may have a substituent(s). Examples of the "spiro-bound cyclic group which may be substituted with a group having a basic group, and also may have a substituent(s)" represented by $J^0$ include (1) spiro-bound cyclic group which may be substituted with a basic group, and also may have a substituent(s), (2) spiro-bound cyclic group which may be substituted with a cyclic group substituted with a basic group, and also may have a substituent(s), and (3) spiro-bound cyclic group which may be substituted with an aliphatic hydrocarbon group substituted with a basic group, and also may have a substituent(s). Examples of the "bridged cyclic group which may be substituted with a group having a basic group, and also may have a substituent(s)" represented by $J^0$ include (1) bridged cyclic group which may be substituted with a basic group, and also may have a substituent(s), (2) bridged cyclic group which may be substituted with a cyclic group substituted with a basic group, and also may have a substituent(s), and (3) bridged cyclic group which may be substituted with an aliphatic hydrocarbon group substituted with a basic group, and also may have a substituent(s). The "spiro-bound cyclic group" in the "spiro-bound cyclic group which may be substituted with a group having a basic group, and also may have a substituent(s)" has the same meaning as in "spiro-bound polycyclic carbocyclic ring" of "carbocyclic ring" in the "cyclic group" or "spiro-bound polycyclic hetrocyclic ring" of "hetrocyclic ring" in the "cyclic group". The "bridged cyclic group" of the "bridged cyclic group which may be substituted with a group having a basic group, and also may have a substituent(s)" has the same meaning as in "bridged polycyclic carbocyclic ring" of "carbocyclic ring" in the "cyclic group" or "bridged polycyclic hetrocyclic ring" of "hetrocyclic ring". The "aliphatic hydrocarbon group" and "cyclic group" herein have the same meaning as described above. The "basic group" herein has the same meaning as in the "basic group" in $A^1$ and $A^2$. The "substituent" herein is not specifically limited. Examples thereof include those exemplified as for T in $A^1$ and $A^2$, and these optional substituents may be substituted on the substitutable position and the number of substituents is from 1 to 5.

In the present specification, the "spiro-bound heterocyclic ring or bridged heterocyclic ring which has at least one nitrogen atom, and also may have an oxygen atom and/or a sulfur atom which may be oxidized" in the "spiro-bound heterocyclic ring or bridged heterocyclic ring which may be substituted with a group having a basic group and also may have a substituent(s), and also may have at least one nitrogen atom and also may have an oxygen atom and/or a sulfur atom which may be oxidized" represented by $J^0$ includes spiro-bound heterocyclic ring which has at least one nitrogen atom, and may also have an oxygen atom and/or a sulfur atom which may be oxidized, and bridged heterocyclic ring which has at least one nitrogen atom, and also may have an oxygen atom and/or a sulfur atom which may be oxidized. Examples of the "spiro-bound heterocyclic ring which has at least one nitrogen atom, and also may have an oxygen atom and/or a sulfur atom" include, for example, azaspiro[4.4]nonane, oxazaspiro[4.4]nonane, azaspiro[4.5]decane, oxazaspiro[4.5]decane, azaspiro[5.5]undecane, 2,7-diazaspiro[3.5]nonane, 2,8-diazaspiro[4.5]decane, 2,7-diazaspiro[4.5]decane-2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 8-azaspiro[4.5]decane, 7-azaspiro[4.5]decane, 3-azaspiro[5.5]undecane, 2-azaspiro[5.5]undecane, 1-oxa-4,8-diazaspiro[5.5]undecane, 1-oxa-4,9-diazaspiro[5.5]undecane, 3,4-dihydrospiro[chromene-2,4'-piperidine], 2-azaspiro[4.4]nonane, 7-azaspiro[3.5]nonane, 2,3-dihydrospiro[indene-1,4'-piperidine], 3,4-dihydro-2H-spiro[naphthalene-1,4'-piperidine], 3,4-dihydro-1H-spiro[naphthalene-2,4'-piperidine], 2-azaspiro[4.5]decane, 2-azaspiro[3.5]nonane, 1',2'-dihydrospiro[cyclohexane-1,3'-indole], 2',3'-dihydro-1'H-spiro[cyclohexane-1,4'-isoquinoline], 1',4'-dihydro-2'H-spiro[cyclohexane-1,3'-quinoline], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane and the like. Examples of the "bridged heterocyclic ring which has at least one nitrogen atom, and also may have an oxygen atom and/or a sulfur atom include, for example, azabicyclo[2.2.1]heptane, azabicyclo[3.1.1]heptane, azabicyclo[3.2.1]octane, azabicyclo[2.2.2]octane, diazabicyclo[2.2.2]octane, 1-azatricyclo[3.3.1.1$^{3,7}$]decane, 3-azabicyclo[3.3.1]nonane, 3,7-diazabicyclo[3.3.1]nonane and the like.

In the present specification, the "7- to 15-membered bicyclic spiro-bound heterocyclic ring wherein a ring comprising the spiro-bound heterocyclic ring is a monocycle composed of at least one nitrogen atom and carbon atoms, and/or a monocycle composed of at least one nitrogen atom, one oxygen atom and carbon atoms" represented by $J^0$ includes (1) 7- to 15-membered bicyclic spiro-bound heterocyclic ring wherein a ring comprising the spiro-bound heterocyclic ring is two (a) 4- to 8-membered monocycles composed of at least one nitrogen atom and carbon atoms, (2) 7- to 15-membered bicyclic spiro-bound heterocyclic ring wherein a ring comprising the spiro-bound heterocyclic ring is (a) 4- to 8-membered monocycle composed of at least one nitrogen atom and carbon atoms, and (b) 4- to 8-membered monocycle composed of at least one nitrogen atom, one oxygen atom and carbon atoms, and (3) 7- to 15-membered bicyclic spiro-bound heterocyclic ring wherein a ring comprising the spiro-bound heterocyclic ring is two (b) monocycles composed of at least one nitrogen atom, one oxygen atom and carbon atoms.

"(1) 7- to 15-membered bicyclic spiro-bound heterocyclic ring wherein a ring comprising the spiro-bound heterocyclic ring is two (a) 4- to 8-membered monocycles composed of at least one nitrogen atom and carbon atoms" means that two rings selected optionally from "(a) 4- to 8-membered monocycle composed of at least one nitrogen atom and carbon atoms" share one carbon atom. The shared carbon atom may be any carbon atom as long as it is a carbon atom constituting the monocycle.

"(2) 7- to 15-membered bicyclic spiro-bound heterocyclic ring wherein a ring comprising the spiro-bound heterocyclic ring is (a) 4- to 8-membered monocycle composed of at least one nitrogen atom and carbon atoms, and (b) 4- to 8-membered monocycle composed of at least one nitrogen atom, one oxygen atom and carbon atoms" means that one ring selected optionally from "(a) 4- to 8-membered monocycle composed of at least one nitrogen atom and carbon atoms" and one ring selected optionally from "(b) 4- to 8-membered monocycle composed of at least one nitrogen atom, one oxygen atom and carbon atoms" share one carbon atom. The shared carbon atom may be any carbon atom as long as it is a carbon atom constituting the monocycle.

"(3) 7- to 15-membered bicyclic spiro-bound heterocyclic ring wherein a ring comprising the spiro-bound heterocyclic ring is two (b) monocycles composed of at least one nitrogen atom, one oxygen atom and carbon atoms" means that two rings selected optionally from "(b) monocycle composed of at least one nitrogen atom, one oxygen atom and carbon atoms" shares one carbon atom. The shared carbon atom may be any carbon atom as long as it is a carbon atom constituting the monocycle.

Examples of the "4- to 8-membered monocycle composed of at least one nitrogen atom and carbon atoms" include, for example, azetidine, pyrrolidine, piperidine, piperazine, azepane, 1,4-diazepane, azocane, 1,4-diazocane, 1,5-diazocane, morpholine and the like.

Examples of the "4- to 8-membered monocycle composed of at least one nitrogen atom, one oxygen atom and carbon atoms" include, for example, 1,4-oxazepane, 1,4-oxazocane, 1,5-oxazocane and the like.

Examples of "(1) 7- to 15-membered bicyclic spiro-bound heterocyclic ring wherein a ring comprising the spiro-bound heterocyclic ring is two (a) 4- to 8-membered monocycles composed of at least one nitrogen atom and carbon atoms" include, for example, 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 2,6-diazaspiro[3.5]nonane, 3,9-diazaspiro[5.5]undecane, 2,7-diazaspiro[4.4]nonane, 1,3,8-triazaspiro[4.5]decane, 1,4,9-triazaspiro[5.5]undecane and the like.

Examples of "(2) 7- to 15-membered bicyclic spiro-bound heterocyclic ring wherein a ring comprising the spiro-bound heterocyclic ring is (a) 4- to 8-membered monocycle composed of at least one nitrogen atom and carbon atoms, and (b) 4- to 8-membered monocycle composed of at least one nitrogen atom, one oxygen atom and carbon atoms" include 1-oxa-4,9-diazaspiro[5.5]undecane, and 1-oxa-4,8-diazaspiro[5.5]undecane.

Examples of "(3) 7- to 15-membered bicyclic spiro-bound heterocyclic ring wherein a ring comprising the spiro-bound heterocyclic ring is two (b) monocycles composed of at least one nitrogen atom, one oxygen atom and carbon atoms" include 2,9-dioxa-5,12-diazaspiro[6.6]tridecane.

In the present specification, examples of the "spiro-bound carbocyclic ring or bridged carbocyclic ring" in the "spiro-bound carbocyclic ring or bridged carbocyclic ring which is substituted with a group having a basic group, and also may have a substituent(s)" represented by $J^0$ include "spiro-bound polycyclic carbocyclic ring" or "bridged polycyclic carbocyclic ring" in the "cyclic group".

The "substituent" in the $J^0$ group is not specifically limited. Examples thereof include those exemplified as for T in $A^1$ and $A^2$, and these optional substituents may be substituted on the substitutable position and the number of substituents is from 1 to 5. Furthermore, the "aliphatic hydrocarbon group", "cyclic group" and "basic group" in the $J^0$ group have the same meaning as in the "aliphatic hydrocarbon group", the "cyclic group" and the "basic group" that are described above.

In the present specification, ring $J^1$ and ring $J^2$ represent a ring constituting a spiro ring.

In the present specification, the "C3-10 monocyclic or bicyclic carbocyclic ring" represented by ring $J^1$ and ring $J^{1a}$ includes a C3-10 monocyclic or bicyclic unsaturated carbocyclic ring, and partially or completely saturated one thereof. Examples thereof include, for example, benzene, azulene, naphthalene, cyclopropane, cyclobutane, cyclopentane, cyclohexane, cycloheptane, cyclooctane, cyclononane, cyclodecane, cyclohexene, cycloheptene, cyclooctene, cyclopentadiene, cyclohexadiene, cycloheptadiene, cyclooctadiene, pentalene, perhydropentalene, perhydroazulene, indene, perhydroindene, indane, dihydronaphthalene, tetrahydronaphthalene, perhydronaphthalene, heptalene, perhydroheptalene and the like.

In the present specification, the "3- to 10-membered monocyclic or bicyclic hetrocyclic ring composed of carbon atom, oxygen atom and/or sulfur atom which may be oxidized" represented by ring $J^1$ and ring $J^{1a}$ includes a 3- to 10-membered monocyclic or bicyclic unsaturated hetrocyclic ring composed of carbon atom, oxygen atom and/or sulfur atom which may be oxidized, and partially or completely saturated one thereof. Examples thereof include, for example, furan, pyran, oxepine, thiophene, thiopyran, thiepine, benzofuran, isobenzofuran, benzothiophene, isobenzothiophene, dithianaphthalene, chromene, benzoxepine, benzothiepine, oxirane, oxetane, dihydrofuran; tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, oxathiane, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, benzoxathiane, benzodioxepane, dioxolane, dioxane, dithiolane, dithiane, dioxaindane, benzodioxane, chroman, benzodithiolane, benzodithiane and the like.

In the present specification, the "3- to 10-membered monocyclic or bicyclic hetrocyclic ring which has at least one nitrogen atom, and also may have oxygen atom or sulfur atom which may be oxidized" represented by ring $J^1$ and ring $J^{1b}$ includes a 3- to 10-membered monocyclic or bicyclic unsaturated hetrocyclic ring which has at least one nitrogen atom and also may have oxygen atom or sulfur atom which may be oxidized, and partially or completely saturated one thereof.

Examples thereof include, for example, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, pyrrole, imidazole, triazole, tetrazole, pyrazole, pyridine, pyrazine, pyrimidine, pyridazine, azepine, diazepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, indazole, quinoline, isoquinoline, quinolizine, purine, phthalazine, pteridine, naphthyridine, quinoxaline, quinazoline, cinnoline, benzoxazole, benzothiazole, benzimidazole, benzoxazepine, benzoxadiazepine, benzothiepine, benzothiazepine, benzothiadiazepine, benzoazepine, benzodiazepine, benzofurazan, benzothiadiazole, benzotriazole and the like.

The "C3-10 monocyclic or bicyclic carbocyclic ring", "3- to 10-membered monocyclic or bicyclic hetrocyclic ring composed of carbon atom, oxygen atom and/or sulfur atom which may be oxidized", or "3- to 10-membered monocyclic or bicyclic hetrocyclic ring which has at least one nitrogen atom and also may have oxygen atom or sulfur atom which may be oxidized" in the "C3-10 monocyclic or bicyclic carbocyclic ring substituted with a group having a basic group", "3- to 10-membered monocyclic or bicyclic hetrocyclic ring composed of carbon atom, oxygen atom and/or sulfur atom which may be oxidized, which is substituted with a group having a basic group", or "3- to 10-membered monocyclic or bicyclic hetrocyclic ring which has at least one nitrogen atom and also may have oxygen atom or sulfur atom which may be oxidized, and also may be substituted with a group having a basic group" represented by ring $J^2$ has the same meaning as described above. The "C3-10 monocyclic or bicyclic carbocyclic ring" or "3- to 10-membered monocyclic or bicyclic hetrocyclic ring composed of carbon atom, oxygen atom and/or sulfur atom which may be oxidized" in the "C3-10 monocyclic or bicyclic carbocyclic ring substituted with a group having a basic group" or "3- to 10-membered monocyclic or bicyclic hetrocyclic ring composed of carbon atom, oxygen atom and/or sulfur atom which may be oxidized, which is substituted with a group having a basic group" represented by ring $J^{2a}$ has the same meaning as described above. The "3- to 10-membered monocyclic or bicyclic hetrocyclic ring which has at least one nitrogen atom and also may have oxygen atom or sulfur atom which may be oxidized" in the "3- to 10-membered monocyclic or bicyclic hetrocyclic ring which has at least one nitrogen atom and also may have oxygen atom or sulfur atom which may be oxidized, which may be substituted with a group having a basic group" represented by ring $J^{2b}$ has the same meaning as described above. The "group having a basic group" herein has the same meaning as in the "group having a basic group" in the "spiro-bound cyclic group which may be substituted with a group having a basic group, and also may have a substituent(s)".

In the present specification, the "bridged polycyclic carbocyclic ring" in the "bridged polycyclic carbocyclic ring substituted with a group having a basic group" represented by ring $J^3$ has the same meaning as in the above-described "bridged polycyclic carbocyclic ring" in the "cyclic group".

In the present specification, examples of the "bridged polycyclic hetrocyclic ring composed of carbon atom, oxygen atom and/or sulfur atom which may be oxidized" of the "bridged polycyclic hetrocyclic ring composed of carbon atom, oxygen atom and/or sulfur atom which may be oxidized, which is substituted with a group having a basic group" represented by ring $J^3$ include, for example, oxabicyclo[2.2.1]heptane oxabicyclo[3.2.1]octane and the like.

In the present specification, examples of the "bridged polycyclic hetrocyclic ring which has at least one nitrogen atom and also may have an oxygen atom and/or a sulfur atom which may be oxidized" of the "bridged polycyclic hetrocyclic ring which may have at least one nitrogen atom and also may have an oxygen atom and/or a sulfur atom which may be oxidized, which may be substituted with a group having a basic group" represented by ring $J^3$ include, for example, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, 1-azatricyclo[3.3.1.1$^{3,7}$]decane, 3-azabicyclo[3.3.1]nonane, 3,7-diazabicyclo[3.3.1]nonane and the like.

The "group having a basic group" in ring $J^3$ has the same meaning as in the "group having a basic group" in the "bridged cyclic group which may be substituted with a group having a basic group, and also may have a substituent(s)".

In the present specification, the "C3-15 monocyclic or condensed carbocyclic ring" in the "C3-15 monocyclic or condensed carbocyclic ring substituted with a group having a basic group" represented by ring $J^4$ has the same meaning as in the "C3-15 monocyclic or polycyclic unsaturated carbocyclic ring, and partially or completely saturated one thereof" in the "cyclic group".

In the present specification, the "3- to 15-membered monocyclic or condensed hetrocyclic ring" of the "3- to 15-membered monocyclic or condensed hetrocyclic ring composed of carbon atom, oxygen atom and/or sulfur atom which may be oxidized, which is substituted with a group having a basic group" represented by ring $J^4$ includes a 3- to 15-membered monocyclic or condensed unsaturated hetrocyclic ring composed of carbon atom, oxygen atom and/or sulfur atom which may be oxidized, and partially or completely saturated one thereof. Examples thereof include, for example, furan, pyran, oxepine, thiophene, thiopyran, thiepine, benzofuran, isobenzofuran, benzothiophene, isobenzothiophene, dithianaphthalene, chromene, benzoxepine, benzothiepine, dibenzofuran, xanthene, dibenzothiophene, phenoxathiin, thianthrene, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, oxathiane, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, benzoxathiane, benzodioxepane, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindane, benzodioxane, chroman, benzodithiolane, benzodithiane and the like.

In the present specification, the "3- to 15-membered monocyclic or condensed hetrocyclic ring which has at least one nitrogen atom and also may have an oxygen atom and/or a sulfur atom which may be oxidized" of the "3- to 15-membered monocyclic or condensed hetrocyclic ring which has at least one nitrogen atom and also may have an oxygen atom and/or a sulfur atom which may be oxidized, which may be substituted with a group having a basic group" represented by ring $J^4$ includes a monocyclic or condensed 3- to 15-membered unsaturated hetrocyclic ring which has at least one nitrogen atom and also may have an oxygen atom and/or a sulfur atom which may be oxidized, and partially or completely saturated one thereof. Examples thereof include, for example, pyrrole, imidazole, triazole, tetrazole, pyrazole, pyridine, pyrazine, pyrimidine, pyridazine, azepin, diazepin, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepin, indole, isoindole, indolizine, indazole, quinoline, isoquinoline, quinolizine, purine, phthalazine, pteridine, naphthyridine, quinoxaline, quinazoline, cinnoline, benzoxazole, benzothiazole, benzimidazole, benzoxazepine, benzoxadiazepine, benzothiazepin, benzothiadiazepine, benzoxazepine, benzodiazepine, benzofurazan, benzothiadiazole, benzotriazole, carbazole, β-carboline, acridine, phenazine, phenothiazine, phenoxazine, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, dihydrobenzoxazepine, tetrahydrobenzoxazepine, dihydrocarbazole, tetrahydrocarbazole, perhydrocarbazole, dihydroacridine, tetrahydroacridine, perhydroacridine, hexahydro-1H-pyrrolidine, octahydrocyclopenta[c]pyrrole, octahydrocyclopenta[b]pyrrole, octahydropyrrolo[3,2-b]pyrrole, octahydropyrrolo[3,4-c]pyrrole, hexahydro-2H-furo[3,2-b]pyrrole, hexahydro-2H-thieno[3,2-b]pyrrole, decahydroquinoline, decahydro-2,6-naphthylidine, octahydro-2H-quinolidine, octahydro-1H-pyrido[1,2-c]pyrimidine, octahydro-2H-1,4-benzooxazine, decahydro-1,5-naphthylidine, octahydro-1H-pyrrolo[3,4-b]pyridine, octahydro-1H-pyrrolo[3,4-c]pyridine and the like.

The "group having a basic group" in ring $J^4$ has the same meaning as in the "group having a basic group" in the above-described "cyclic group which is substituted with a group having a basic group, and also may have a substituent(s)".

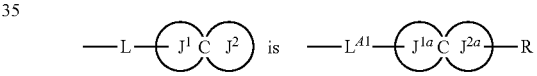

in the group, $L^{A1}$ represents -(aliphatic hydrocarbon group having 1 to 3 carbon atom(s) which may have a substituent(s))-(nitrogen atom which may have a substituent(s))-;

ring $J^{1a}$ and ring $J^{2a}$ each independently represents (i) a C3-10 monocyclic or bicyclic carbocyclic ring, or (ii) a 3- to 10-membered monocyclic or bicyclic hetrocyclic ring composed of a carbon atom, an oxygen atom and/or a sulfur atom which may be oxidized;

R represents a group having a basic group;

ring $J^{1a}$ and ring $J^{2a}$ may have the number of substituents capable of substituting on the substitutable position and, when two or more substituents are present, plural substituents may be the same or different, wherein (a nitrogen atom which may have a substituent) in $L^A$ is bonded to ring $J^1$),

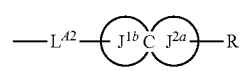

in the group, $L^{A2}$ represents a divalent aliphatic hydrocarbon group having 1 to 4 carbon atom(s) which may have a substituent(s);

ring $J^{1b}$ represents a 3- to 10-membered monocyclic or bicyclic hetrocyclic ring which has at least one nitrogen atom and may also have an oxygen atom and/or a sulfur atom which may be oxidized;

ring $J^{1b}$ may have the number of substituents capable of substituting on the substitutable position and, when two or more substituents are present, plural substituents may be the same or different;

other symbols have the same meanings as described above),

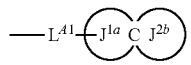

in the group, ring $J^{2b}$ represents a 3- to 10-membered monocyclic or bicyclic hetrocyclic ring which may have at least one nitrogen atom and also may have an oxygen atom or a sulfur atom which may be oxidized, which may be substituted with a group having a basic group;

ring $J^{2b}$ may have the number of substituents capable of substituting on the substitutable position and, when two or more substituents are present, plural substituents may be the same or different;

other symbols have the same meanings as described above), or

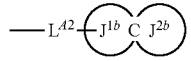

in the group, all symbols have the same meanings as described above.

includes, for example,

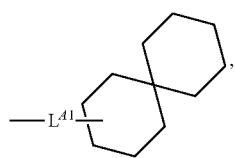 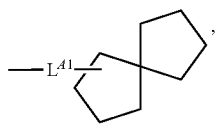

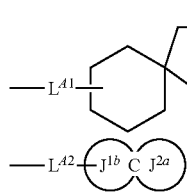

includes, for example,

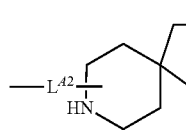 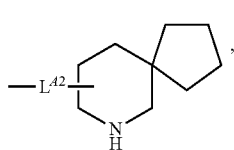

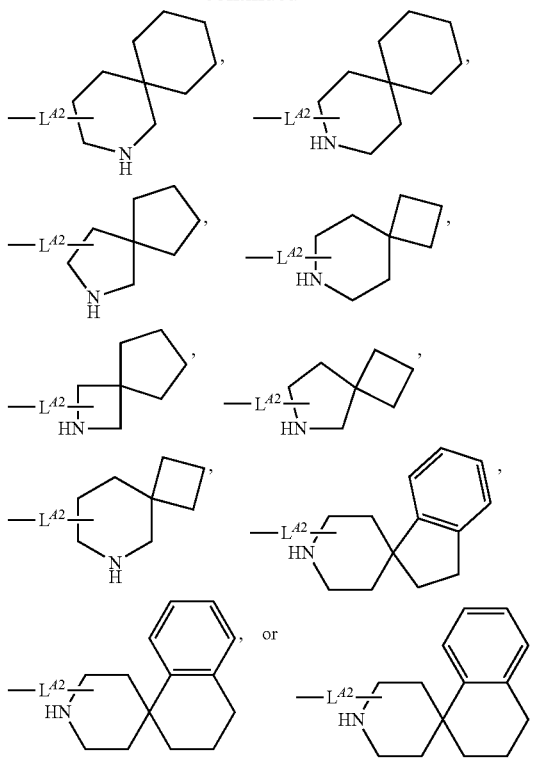

wherein $L^{A2}$ may be a substituent of a nitrogen atom of —NH—,

includes, for example,

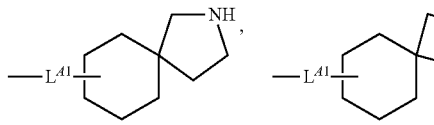 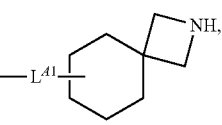

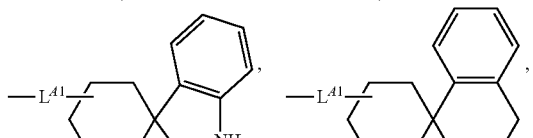 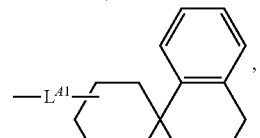

or 

wherein a nitrogen atom of —NH— may have a substituent, and

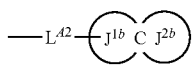

includes, for example,

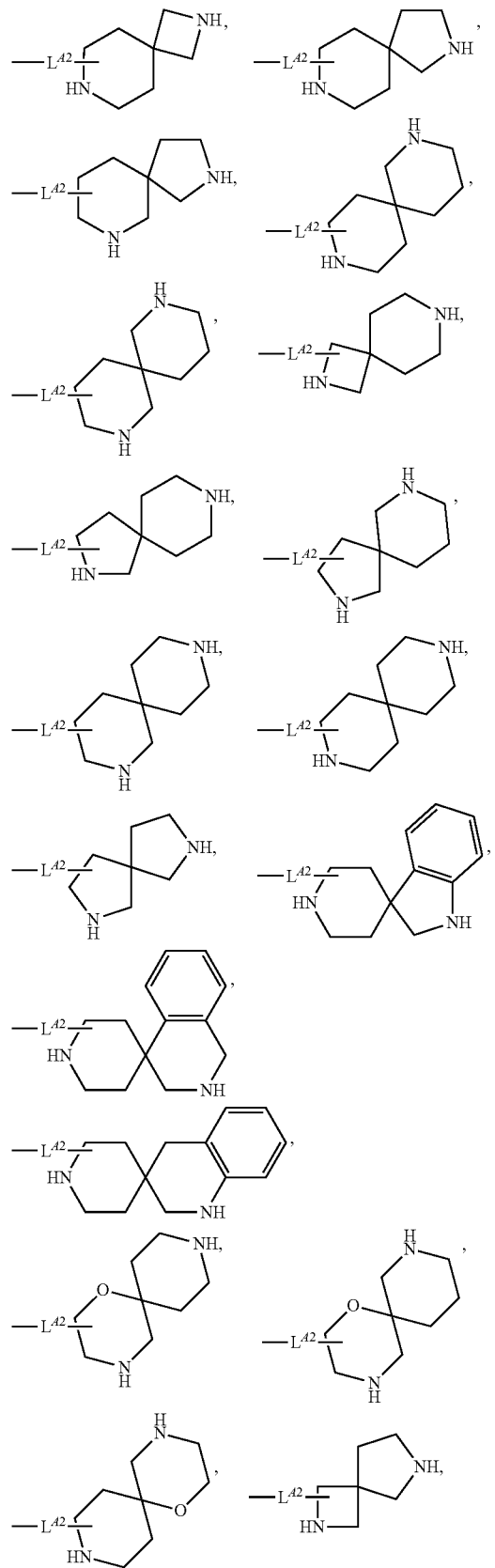
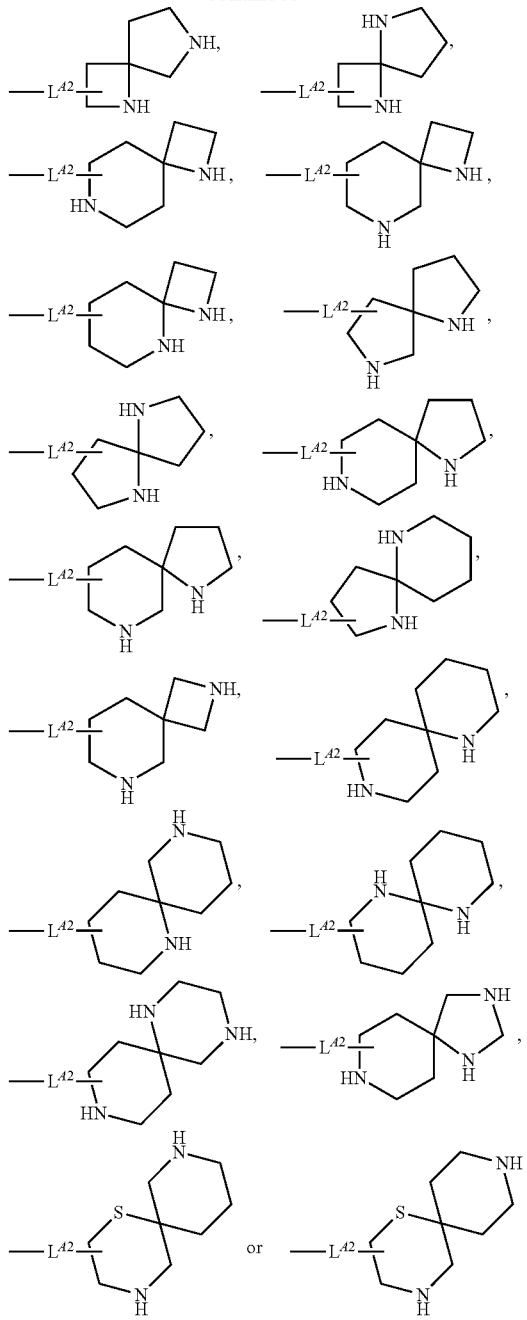

wherein $L^{A2}$ may be a substituent of a nitrogen atom of —NH—, and the nitrogen atom of —NH— may have a substituent.

In the present specification, the "group having a basic group" of R has the same meaning as in the "group having a basic group" of the "spiro-bound cyclic group which may be substituted with a group having a basic group, and also may have a substituent(s)".

In the present specification, the "substituent" of the "number of substituents capable of substituting on the substitutable position" of ring $J^1$, ring $J^2$, ring $J^3$, ring $J^4$, ring $J^{1a}$, ring $J^{1b}$, ring $J^{2a}$ and ring $J^{2b}$ is not specifically limited. Examples thereof include those exemplified as for T in $A^1$ and $A^2$, and these optional substituents may be substituted on the substitutable position and the number of substituents is preferably from 1 to 8, and more preferably from 1 to 5.

In the present specification, the "substituent" in the "carbon atom which may have a substituent(s)" represented by D and G is not specifically limited. Examples thereof include those exemplified as for T in $A^1$ and $A^2$, and these optional substituents may be substituted on the substitutable position and the number of substituents is from 1 to 2.

In the present specification, the "divalent nitrogen atom which may have a substituent" represented by G has the same meaning as in the "divalent nitrogen atom which may have a substituent".

In the present specification, the "sulfur atom which may be oxidized" means —S—, —SO—, or —$SO_2$—.

In the present specification, the "substituent" represented by $R^1$ and $R^4$ is not specifically limited. Examples thereof include (1) aliphatic hydrocarbon group which may have a substituent(s), (2) cyclic group which may have a substituent(s), (3) aliphatic hydrocarbon group substituted with a cyclic group which may have a substituent(s), and (4) substituent T described above. The "aliphatic hydrocarbon group" and "cyclic group" in the "aliphatic hydrocarbon group which may have a substituent(s)", "cyclic group which may have a substituent(s)" and "aliphatic hydrocarbon group substituted with a cyclic group which may have a substituent(s)" have the same meanings as described above, and examples of the "substituent" include those exemplified as for T in $A^1$ and $A^2$.

In the present specification, the "substituent" represented by $R^2$ and $R^3$ has the same meaning as in the "substituent" in (e) a mono- or di-substituted amino group among the "basic group" of the "group having a basic group" represented by $A^1$ and $A^2$.

The ring, which is formed by combining $R^2$ and $R^3$ with the nitrogen atom to which they are attached, has the same meaning as in the "3- to 10-membered monocyclic or condensed hetrocyclic ring which has at least one nitrogen atom and also may have an oxygen atom and/or a sulfur atom which may be oxidized" represented by ring $J^1$.

Examples of the "$R^2$ and $R^3$ which may be combined with the nitrogen atom to which $R^2$ and $R^3$ are attached to fond a monocyclic or condensed hetrocyclic ring, provided that an atom other than a nitrogen atom to be attached, which constitutes a hetrocyclic ring, is a carbon atom" include pyrrole, indole, isoindole, benzoxazepine, carbazole, acridine, aziridine, azetidine, pyrroline, pyrrolidine, dihydropyridine, tetrahydropyridine, piperidine, dihydroazepine, tetrahydroazepine, perhydroazepine, indoline, isoindoline, dihydroquinoline, tetrahydroquinoline, perhydroquinoline, dihydroisoquinoline, tetrahydroisoquinoline, perhydroisoquinoline, dihydrobenzoxazepine, tetrahydrobenzoxazepine, dihydrocarbazole, tetrahydrocarbazole, perhydrocarbazole, dihydroacridine, tetrahydroacridine and the like.

In the present invention, all isomers are included unless otherwise specified. For example, alkyl group, alkenyl group, alkynyl group, alkylene group, alkenylene group, alkynylene group, alkylidene group and the like include those which are linear and branched. Furthermore, all of isomers (E-, Z-, cis-, and trans-isomers) on the double bond, ring and condensed ring, isomers (R-isomer, S-isomer, α,β configuration, enantiomer, and diastereomer) due to the presence of asymmetric carbon, optically active substances with optical rotation (D-, L-, d-, and l-compounds), polar compounds (high polar compound and low polar compound) generated by chromatographic separation, equilibrium compounds, rotational isomers, mixtures in an optional mixing ratio and racemic mixtures are included in the present invention.

In the present invention, as is apparent to those skilled in the art, the symbol represents that it is bonded to the other side of the page (namely, α configuration), the symbol represents that it is bonded to this side of the page (namely, β configuration), and the symbol represents that it is a mixture of the α configuration and the β configuration.

[Salts]

Salts of the compound represented by formula (I-0) include all of nontoxic salts and pharmaceutically acceptable salts. The pharmaceutically acceptable salt is preferably a water soluble salt which shows less toxicity. Examples of the suitable salt of the compound represented by formula (I-0) include salts of alkali metal (potassium, sodium, lithium, etc.), salts of alkali earth metal (calcium, magnesium, etc.), ammonium salts (tetramethylammonium salt, tetrabutylammonium salt, etc.), salts of organic amine (triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salts [inorganic acid salts (hydrochloride, hydrobromide, hydroiodide, sulfate, phosphate, nitrate, etc.), and organic acid salts (acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, etc.)] and the like.

Furthermore, salts include quaternary ammonium salts. The quaternary ammonium salt is obtained by quaternizing a nitrogen atom of the compound represented by formula (I-0) with a $R^0$ group ($R^0$ group represents a C1-8 alkyl group, or a C1-8 alkyl group substituted with a phenyl group).

Also, salts include N-oxide. The compound of the present invention can be converted into N-oxide by an optional method. N-oxide is obtained by oxidizing a nitrogen atom of the compound represented by formula (I-0).

Examples of suitable solvate of the compound represented by formula (I-0) include solvates such as water, alcoholic solvent (for example, methanol, ethanol, etc.) and the like. The solvate is preferably nontoxic and water soluble. The solvate of the compound of the present invention also includes solvates of alkali (earth) metal salts, ammonium salts, salts of organic amine, and acid addition salts of the compound of the present invention.

The compound of the present invention can be converted into the above salts and solvates by a known method.

[Prodrugs]

A prodrug of the compound represented by formula (I-0) means a compound which is converted into the compound represented by formula (I-0) in the living body by the reaction with an enzyme, gastric acid or the like. Examples of the prodrug of the compound represented by formula (I-0) include compound wherein an amino group is acylated, alkylated, or phosphorylated (for example, compound wherein an amino group of the compound represented by formula (I-0) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.) when the compound represented by formula (I-0) has an amino group; compound wherein a hydroxyl group is acylated, alkylated, phosphorylated, boricated or the like (for example, compound wherein a hydroxyl group of the compound represented by formula (I-0) is acetylated, palmitoylated, propanoylated, pivaloylated, succinylated, fumarylated, alanylated, dimethylaminomethylcarbonylated, etc.) when the compound represented by formula (I-0) has a hydroxyl group; and compound wherein a carboxy group is esterificated, amidated or the like (for example, compound wherein a carboxy group of the compound represented by formula (I-0) is ethylesterificated, phenylesterificated, carboxymethylesterificated, dimethylaminomethylesterificated, pivaloyloxymethylesterificated, ethoxycarbonyloxyethylesterificated, phthalidylesterificated, (5-methyl-2-oxo-1,3-dioxolen-4-yl)methylesterificated, cyclohexyloxycarbonylethylesterificated, methylamidated, etc.) when the compound represented by formula (I-0) has a carboxy group. These compounds can be prepared by a per se known method. The prodrug of the compound represented by formula (I-0) may be either of a hydrate and a non-hydrate. Also, the prodrug of the compound represented by formula (I-0) may be converted into the compound represented by formula (I-0) under physiological conditions described in "Development of Drug" published in 1990 by Hirokawa Shoten, Vol. 7, "Molecular Design", pp. 163-198. Furthermore, the compound represented by formula (I-0) may be labelled with isotope (for example, $^3H$, $^{14}C$, $^{35}S$, $^{125}I$, etc.) and the like. The compound represented by formula (I-0) of the present invention, a salt thereof, a solvate thereof, or a prodrug thereof (hereinafter abbreviated to a compound of the present invention, sometimes) is a compound which is excellent in solubility and oral absorption and maintain its pharmacological activity for a long period of time, and is also less likely to be inhibited by a drug metabolizing enzyme and has low toxicity. These properties are most important physical, chemical and pharmacological properties required when preparations are developed, and the inventive compound satisfies these conditions and is expected to be useful for developing extremely excellent (see The Merck Manual of Diagnosis and Therapy (17th Ed.), Merck & Co.).

The fact that the compound of the present invention is useful as a drug can be evaluated by methods described in various tests and biological examples described hereinafter, and methods which can be carried out by appropriately improving the above methods. The fact that the compound of the present invention is kinetically excellent in length of half-life in blood, stability in alimentary canal, oral absorption and bioavailability can be easily evaluated by a known method, for example, a method described in "Drug Bioavailability (Science of Evaluation and Improvement)", Gendai Iryo-sha, published on Jul. 6, 1998.

In the formula (I-0) of the present invention, any of each definition by $A^1$, $A^2$, $B^1$, $B^2$, D, G, E, L, and $J^0$ is preferred. In the following, preferable groups will be listed. The symbols used herein have the same meaning as described above.

$A^1$ and $A^2$ each is preferably a basic group, and more preferably a nitrogen-containing hetrocyclic ring which may have a substituent(s), for example. The "nitrogen-containing hetrocyclic ring group" herein is preferably pyrrole, imidazole, triazole, pyrazole, pyridine, pyrazine, pyrimidine, benzimidazole, azabenzimidazole, or tetrahydroquinoline ring, more preferably imidazole or benzimidazole ring, and particularly preferably imidazol-2-yl or benzoimidazol-2-yl. The "substituent" herein is preferably none or an aliphatic hydrocarbon group, more preferably none, a C1-8 alkyl group or the like, and particularly preferably none or a methyl group, and most preferably none. $A^1$ and $A^2$ may be the same or different.

$B^1$ and $B^2$ each is preferably a spacer having a main chain of 1 atom, and more preferably —CO—, $SO_2$— or a methylene group (—$CH_2$—) which may have a substituent(s). The "substituent" herein is preferably none or a methyl group, and more preferably none. $B^1$ and $B^2$ may be the same or different.

D is preferably a nitrogen atom or a carbon atom which may have a substituent, and more preferably a nitrogen atom.

G is preferably a carbon atom which may have a substituent(s), a carbonyl group, or a sulfur atom which may be oxidized. The "substituent" herein is preferably none or a methyl group, and more preferably none. G is more preferably a carbonyl group (—CO—), a sulfonyl group (—$SO_2$—), or a methylene group which may have a substituent(s). The "substituent" in the "methylene group which may have a substituent(s)" is not specifically limited and examples thereof include those exemplified as for the "substituent" in $A^1$ and $A^2$, and these optional substituents may be substituted on the substitutable position and the number of substituents is from 1 to 2. The "methylene group which may have a substituent(s)" does not represent a carbonyl group (—CO—).

E is preferably a divalent aliphatic hydrocarbon group having 1 to 4 carbon atom(s) which may have a substituent(s), a divalent 3- to 8-membered monocyclic cyclic group which may have a substituent(s), or a divalent 9- or 10-membered polycyclic cyclic group may have a substituent(s), and more preferably a divalent 3- to 8-membered monocyclic cyclic group which may have a substituent(s), or a divalent 9- or 10-membered polycyclic cyclic group which may have a substituent(s). The "divalent 3- to 8-membered monocyclic cyclic group which may have a substituent(s)" has the same meaning as described in the above described $B^1$. The "3- to 8-membered monocyclic cyclic group" herein is preferably a C5-7 monocyclic carbocyclic ring (ring having 5 to 7 carbon atoms is selected from among the above described C3-8 monocyclic carbocyclic ring) or a 5- to 7-membered monocyclic hetrocyclic ring (5- to 7-membered hetrocyclic ring is selected from among the above described 3- to 8-membered monocyclic hetrocyclic ring), more preferably, a cyclopentane, cyclohexane, cyclohexene, cyclohexadiene, benzene, pyridine, pyrazine, pyrimidine, pyridazine, piperidine or piperazine ring, and particularly preferably a benzene ring.

Examples of the "divalent 9- or 10-membered polycyclic cyclic group" in the "divalent 9- or 10-membered polycyclic cyclic group which may have a substituent(s)" include divalent group obtained by eliminating optional two hydrogen atoms from the "9- or 10-membered polycyclic cyclic group". Examples of the "9- or 10-membered polycyclic cyclic group" herein include "9- or 10-membered polycyclic carbocyclic ring" and "9- or 10-membered polycyclic hetrocyclic ring". The "9- or 10-membered polycyclic carbocyclic ring" includes a 9- or 10-membered polycyclic unsaturated carbocyclic ring, and partially or completely saturated one thereof. Examples of the "9- or 10-membered polycyclic unsaturated carbocyclic ring, and partially or completely saturated one thereof" include azulene, naphthalene, perhydroazulene, indene, perhydroindene, indane, dihydronaphthalene, tetrahydronaphthalene, and perhydronaphthalene rings.

Examples of the "9- or 10-membered polycyclic hetrocyclic ring" include "9- or 10-membered polycyclic hetrocyclic ring having, as a hetero atom, 1 to 4 nitrogen atom(s), 1 to 2 oxygen atom(s) and/or 1 to 2 sulfur atom(s)". The "9- or 10-membered polycyclic hetrocyclic ring having, as a hetero atom, 1 to 4 nitrogen atom(s), 1 to 2 oxygen atom(s) and/or 1 to 2 sulfur atom(s)" includes a 9- or 10-membered polycyclic unsaturated hetrocyclic ring having, as a hetero atom, 1 to 4 nitrogen atom(s), 1 to 2 oxygen atom(s) and/or 1 to 2 sulfur atom(s), and partially or completely saturated one thereof. Examples of the "9- or 10-membered polycyclic unsaturated hetrocyclic ring having, as a hetero atom, 1 to 4 nitrogen atom(s), 1 to 2 oxygen atom(s) and/or 1 to 2 sulfur atom(s), and partially or completely saturated one thereof" include indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, and perhydrobenzimidazole rings.

The "9- or 10-membered polycyclic cyclic group" herein is preferably a 9- or 10-membered polycyclic heterocyclic ring group, and more preferably a tetrahydroisoquinoline ring.

The "substituent" of the "divalent 3- to 8-membered monocyclic cyclic group which may have a substituent(s)" or the "divalent 9- or 10-membered polycyclic cyclic group which may have a substituent(s)" is preferably none, a halogen atom or a methyl group, and more preferably none.

L is preferably a spacer having a main chain of 1 to 2 atom(s). The "spacer having a main chain of 1 to 2 atom(s)" is preferably a divalent group composed of 1 to 2 groups selected optionally from —O—, —S—, —CO—, —SO—, —SO$_2$—, divalent nitrogen atom which may have a substituent, divalent aliphatic hydrocarbon group having one carbon atom which may have a substituent(s), wherein 1 to 2 atom(s) of the main chain are arranged in a line, more preferably —CH$_2$—, —O—CH$_2$—, —S—CH$_2$—, —NH—CH$_2$—, —CH$_2$—CH$_2$—, —CH=CH—, —C≡C—, —CH$_2$—O—, —CH$_2$—S—, —CH$_2$—NH—, —CONH—, —NHCO— or —NHSO$_2$—, and particularly preferably —CH$_2$—, —CONH—, —CH$_2$—NH—, —O—CH$_2$—, —S—CH$_2$—, —CH$_2$—CH$_2$-(J$^0$ is bonded to the right side). A bond is also preferable.

J$^0$ is preferably an aliphatic hydrocarbon group which is substituted with a basic group, and also may have a substituent(s); a cyclic group which is substituted with an aliphatic hydrocarbon group substituted with a basic group, and also may have a substituent(s); or an aliphatic hydrocarbon group which is substituted with a cyclic group substituted with a basic group, and also may have a substituent(s). The "basic group" herein is preferably a mono- or di-substituted amino group, or a nitrogen-containing heterocyclic ring which may have a substituent(s). The "mono- or di-substituted amino group" herein is preferably a di-substituted amino group, more preferably dimethylamino, diethylamino, dipropylamino, dibutylamino, or N-cyclohexyl-N-propylamino, and particularly preferably dipropylamino or N-cyclohexyl-N-propylamino. The "nitrogen-containing heterocyclic ring which may have a substituent(s)" herein is preferably non-substituted nitrogen-containing heterocyclic ring, or a nitrogen-containing hetrocyclic ring substituted with a C1-8 alkyl group or an oxo group, and the "nitrogen-containing hetrocyclic ring" is preferably a pyrrolidine, piperidine, morpholine, thiomorpholine, perhydrodiazepine, tetrahydroisoquinoline, 2,8-diazaspiro[4.5]decane, 1,4,9-triazaspiro[5.5]undecane, 3,9-diazaspiro[5.5]undecane, or 2,9-diazaspiro[5.5]undecane ring.

The "aliphatic hydrocarbon group" in the "aliphatic hydrocarbon group which is substituted with a basic group, and also may have a substituent(s)" or "aliphatic hydrocarbon group which is substituted with a cyclic group substituted with a basic group, and also may have a substituent(s)" herein is preferably a C1-8 alkyl group or a C2-8 alkenyl group, and more preferably methyl, ethyl, propyl, butyl, pentyl, or hexyl. The "cyclic group" in the "cyclic group which is substituted with an aliphatic hydrocarbon group substituted with a basic group, and also may have a substituent(s)" is preferably a C5-7 monocyclic carbocyclic ring (ring having 5 to 7 carbon atoms is selected from among the above described C3-15 monocyclic or polycyclic carbocyclic ring) or a 5- to 7-membered monocyclic hetrocyclic ring (5- to 7-membered heterocyclic ring is selected from among the above described 3- to 15-membered monocyclic or polycyclic hetrocyclic ring), and more preferably a cyclopentane, cyclohexane, cyclohexene, adamantyl, cyclohexadiene, benzene, pyridine, pyrazine, tetrahydropyran, pyrimidine, pyridazine, piperidine, or piperazine ring. The "substituent" herein is preferably none, a halogen atom, a methyl group, a hydroxyl group, an amino group or an oxo group, and more preferably none.

Furthermore, J$^0$ is preferably a "cyclic group which is substituted with a group having a basic group, and also may have a substituent(s)", a "spirocyclic group which may be substituted with a group having a basic group, and also may have a substituent(s)", or a "bridged cyclic group which may be substituted with a group having a basic group, and also may have a substituent(s)". The "cyclic group" or "spirobound cyclic group", or "bridged cyclic group" is preferably (1) a spiro-bound cyclic group, (2) a bridged polycyclic carbocyclic ring, (3) a bridged polycyclic heterocyclic ring composed of a carbon atom, an oxygen atom and/or a sulfur atom which may be oxidized, (4) a bridged polycyclic heterocyclic ring which has at least one nitrogen atom, and also may have an oxygen atom and/or a sulfur atom which may be oxidized, (5) a C3-15 monocyclic or condensed carbocyclic ring, (6) a 3- to 15-membered monocyclic or condensed hetrocyclic ring composed of a carbon atom, an oxygen atom and/or a sulfur atom which may be oxidized, or (7) a 3- to 15-membered monocyclic or condensed hetrocyclic ring which has at least one nitrogen atom, and also has a carbon atom, oxygen atom and/or a sulfur atom which may be oxidized.

The "spiro-bound cyclic group" is preferably 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 8-azaspiro[4.5]decane, 7-azaspiro[4.5]decane, 3-azaspiro[5.5]undecane, 2-azaspiro[5.5]undecane, 1-oxa-4,8-diazaspiro[5.5]undecane, 1-oxa-4,9-diazaspiro[5.5]undecane, 3,4-dihydrospiro[chromene-2,4'-piperidine], 2-azaspiro[4.4]nonane, 7-azaspiro[3.5]nonane, 2,3-dihydrospiro[indene-1,4'-piperidine], 3,4-dihydro-2H-spiro[naphthalene-1,4'-piperidine], 3,4-dihydro-1H-spiro[naphthalene-2,4'-piperidine], 2-azaspiro[4.5]decane, 2-azaspiro[3.5]nonane, 1',2'-dihydrospiro[cyclohexane-1,3'-indole], 2',3'-dihydro-1'H-spiro[cyclohexane-1,4'-isoquinoline], 1',4'-dihydro-2'H-spiro[cyclohexane-1,3'-quinoline], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8- diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane, spiro[4.4]nonane, spiro[4.5]decane, spiro[5.5]undecane, spiro[3.4]octane, or spiro[3.5]nonane. The "spiro-bound cyclic group" is more preferably 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 1-oxa-4,8-diazaspiro[5.5]undecane, 1-oxa-4,9-diazaspiro[5.5]undecane, 3,4-dihydrospiro[chromene-2,4'-piperidine], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, or 1-thia-4,8-diazaspiro[5.5]undecane. The "spiro-bound cyclic group" is particularly preferably 2,7-diazaspiro[4.5]decane, 2,8-diazaspiro[4.5]decane, 2,8-diazaspiro[5.5]undecane, 2,9-diazaspiro[5.5]undecane, 2,7-diazaspiro[3.5]nonane, or 1-oxa-4,9-diazaspiro[5.5]undecane.

The "bridged polycyclic carbocyclic ring" is preferably bicyclo[2.1.1]hexane, bicyclo[2.2.1]heptane, bicyclo[2.2.2]octane, bicyclo[3.2.1]octane, adamantane, bicyclo[3.3.1]nonane, bicyclo[3.2.1]octane, or bicyclo[3.3.2]decane.

The "bridged polycyclic hetrocyclic ring which has at least one nitrogen atom, and also may have an oxygen atom and/or a sulfur atom which may be oxidized" is preferably 1-azatricyclo[3.3.1.1$^{3,7}$]decane, 3-azabicyclo[3.3.1]nonane, or 3,7-diazabicyclo[3.3.1]nonane.

The "7- to 15-membered bicyclic spiro-bound heterocyclic ring wherein a ring comprising the spiro-bound heterocyclic ring is a monocycle composed of at least one nitrogen atom and carbon atoms, and/or a monocycle composed of at least one nitrogen atom, one oxygen atom and carbon atoms" is preferably a 9- to 11-membered bicyclic spiro-bound heterocyclic ring wherein a ring comprising the spiro-bound heterocyclic ring is a monocycle composed of at least one nitrogen atom and carbon atoms, and/or a monocycle composed of at least one nitrogen atom, one oxygen atom and carbon atoms.

The "9 to 11-membered bicyclic spiro-bound heterocyclic ring wherein a ring comprising the spiro-bound heterocyclic ring is a monocycle composed of at least one nitrogen atom and carbon atom, and/or a monocycle composed of at least one nitrogen atom, one oxygen atom and carbon atoms" is preferably 2,7-diazaspiro[4.5]decane, 2,8-diazaspiro[4.5]decane, 2,8-diazaspiro[5.5]undecane, 2,9-diazaspiro[5.5]undecane, 2,7-diazaspiro[3.5]nonane, or 1-oxa-4,9-diazaspiro[5.5]undecane.

The "C3-15 monocyclic or condensed carbocyclic ring" is preferably cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, or 1,2,3,5,6,7-hexahydro-s-indacene. More preferably, it is cyclopentane, cyclohexane, or cyclooctane. Most preferably, it is cyclohexane.

The "3- to 15-membered monocyclic or condensed hetrocyclic ring composed of a carbon atom, an oxygen atom and/or a sulfur atom which may be oxidized" is preferably the partially or completely saturated 3- to 15-membered monocyclic or condensed hetrocyclic ring composed of a carbon atom, an oxygen atom and/or a sulfur atom which may be oxidized.

The "3- to 15-membered monocyclic or condensed hetrocyclic ring which has at least one nitrogen atom, and also has a carbon atom, an oxygen atom and/or a sulfur atom which may be oxidized" is preferably the partially or completely saturated 3- to 15-membered monocyclic or condensed hetrocyclic ring which has at least one nitrogen atom and also has a carbon atom, an oxygen atom and/or a sulfur atom which may be oxidized.

The "substituent" in the phrase "which may be substituted with the substituent" of ring $J^1$, ring $J^2$, ring $J^3$, and ring $J^4$ is preferably an aliphatic hydrocarbon group, a cyclic group, or an aliphatic hydrocarbon group substituted with a cyclic group, and more preferably an aliphatic hydrocarbon group having 1 to 8 carbon atom(s), or a C3-10 monocyclic or bicyclic carbocyclic ring.

The "substituent having a basic group" in the phrase "which is substituted with a group having a basic group", or "which may be substituted with a basic group" of ring $J^2$, ring $J^3$, and ring $J^4$ is preferably a mono- or di-substituted amino group, or a nitrogen-containing hetrocyclic ring which may have a substituent(s). The "monomer or di-substituted amino group" herein is preferably a di-substituted amino group, more preferably dimethylamino, diethylamino, dipropylamino, dibutylamino, or N-cyclohexyl-N-propylamino, and particularly preferably dipropylamino or N-cyclohexyl-N-propylamino.

R is preferably a mono- or di-substituted amino group or a nitrogen-containing hetrocyclic ring which may have a substituent(s). The "mono- or di-substituted amino group" herein is preferably a di-substituted amino group, more preferably dimethylamino, diethylamino, dipropylamino, dibutylamino, or N-cyclohexyl-N-propylamino, and particularly preferably dipropylamino or N-cyclohexyl-N-propylamino.

In the present invention, a compound of the formula (I-0), which has a combination of preferable groups listed above, is preferable.

Among the compound represented by formula (I-0), a preferable compound includes, for example, a compound represented by formula (I-1):

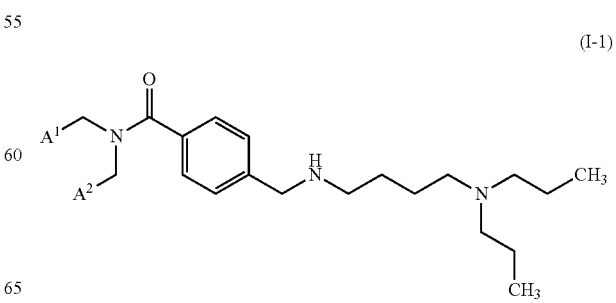

(I-1)

wherein all symbols have the same meanings as described above, formula (I-2):

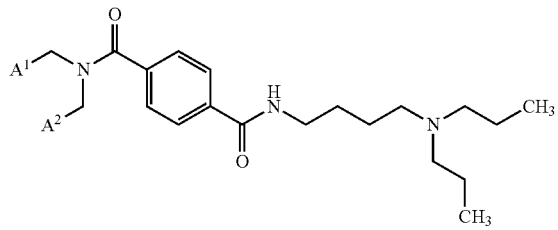
(I-2)

wherein all symbols have the same meanings as described above, formula (I-3):

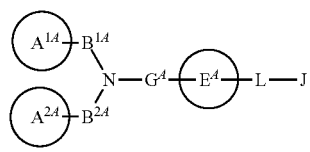
(I-3)

wherein a ring $A^{1A}$ and a ring $A^{2A}$ each independently represents a nitrogen-containing hetrocyclic ring which may have a substituent(s);

$B^{1A}$, $B^{2A}$ and $G^A$ each independently represents —CO—, —SO$_2$— or —CH$_2$—;

a ring $E^A$ represents divalent 3- to 8-membered monocyclic cyclic group which may have a substituent(s), or a divalent 9- or 10-membered polycyclic cyclic group which may have a substituent(s); and other symbols have the same meanings as described above, provided that any of $B^{1A}$ or $G^A$ represents —CO— or —SO$_2$—, formula (I-5-1):

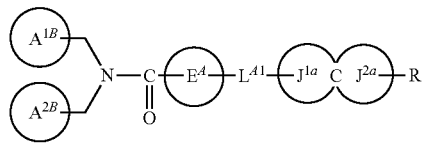
(I-5-1)

wherein all symbols have the same meanings as described above, formula (I-5-2):

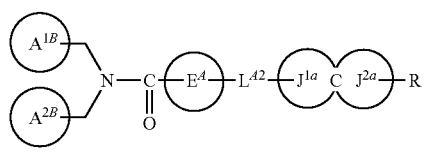
(I-5-2)

wherein all symbols have the same meanings as described above, formula (I-5-3):

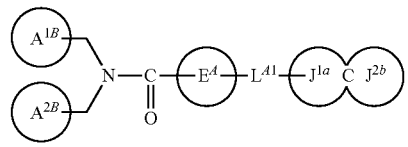
(I-5-3)

wherein all symbols have the same meanings as described above, formula (I-5-4):

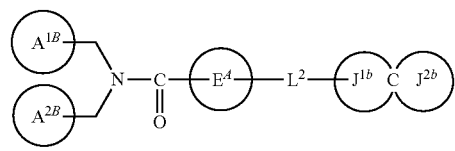
(I-5-4)

wherein all symbols have the same meanings as described above, formula (I-6):

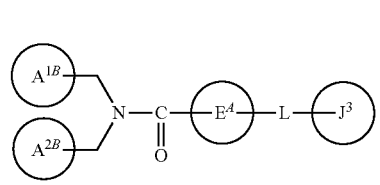
(I-6)

wherein all symbols have the same meanings as described above, formula (I-7):

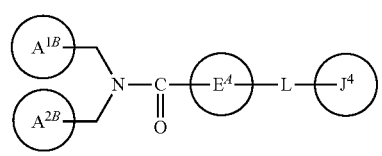
(I-7)

wherein all symbols have the same meanings as described above, formula (I-8-1):

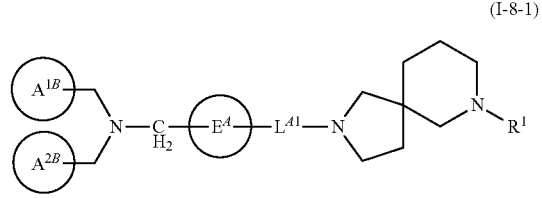
(I-8-1)

wherein all symbols have the same meanings as described above, formula (I-8-2):

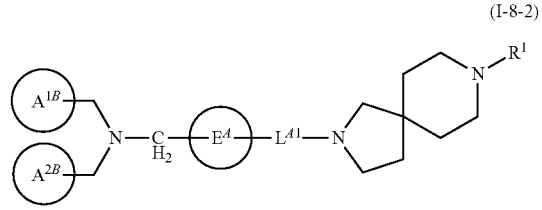
(I-8-2)

wherein all symbols have the same meanings as described above, formula (I-8-3):

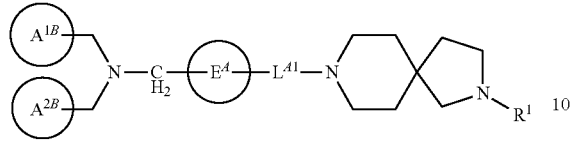

wherein all symbols have the same meanings as described above, formula (I-8-4):

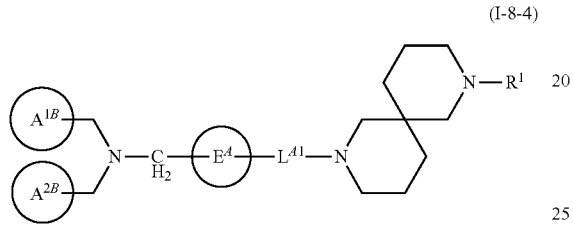

wherein all symbols have the same meanings as described above, formula (I-8-5):

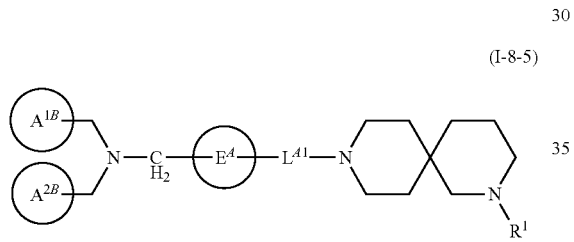

wherein all symbols have the same meanings as described above, formula (I-8-6):

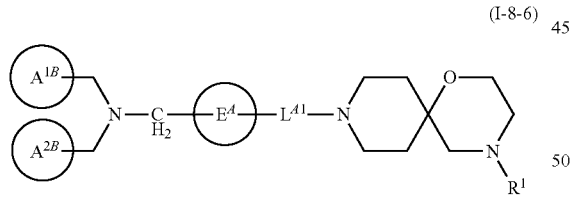

wherein all symbols have the same meanings as described above, formula (I-8-7):

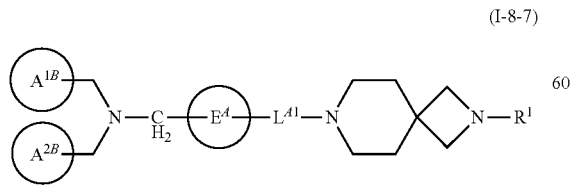

wherein all symbols have the same meanings as described above, formula (I-9-1):

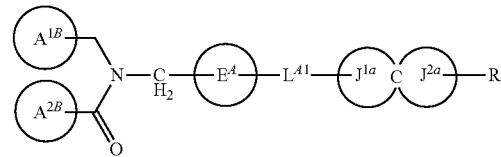

wherein all symbols have the same meanings as described above, formula (I-9-2):

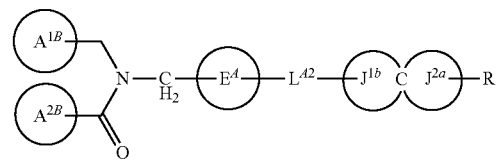

wherein all symbols have the same meanings as described above, formula (I-9-3):

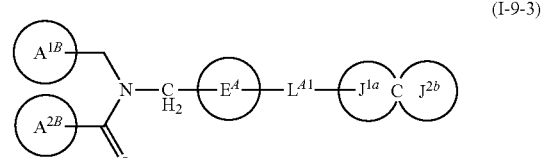

wherein all symbols have the same meanings as described above, formula (I-9-4):

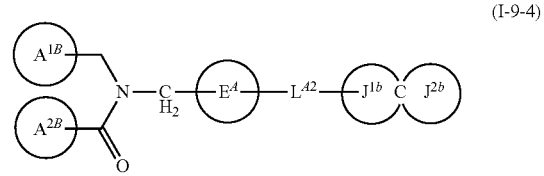

wherein all symbols have the same meanings as described above, formula (I-10):

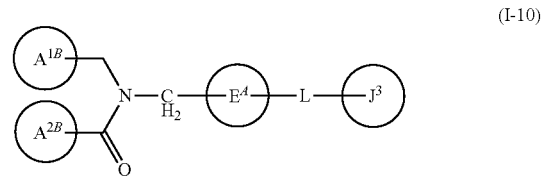

wherein all symbols have the same meanings as described above, or formula (I-11)

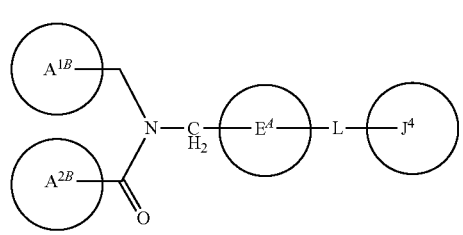

(I-11)

wherein all symbols have the same meanings as described above, a salt thereof, an N-oxide thereof or a solvate thereof or a prodrug thereof.

Among the compound represented by formula (I-0), more preferable compound is a compound represented by formula (I-4-1a):

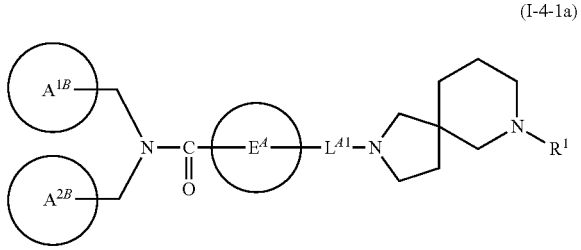

(I-4-1a)

wherein all symbols have the same meanings as described above, formula (I-4-1b):

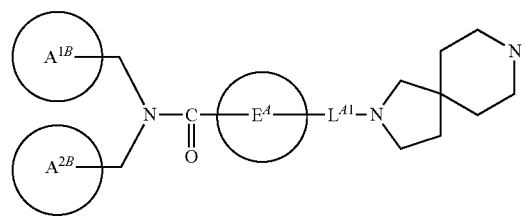

(I-4-1b)

wherein all symbols have the same meanings as described above, formula (I-4-2):

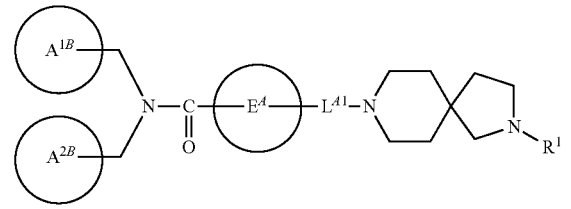

(I-4-2)

wherein all symbols have the same meanings as described above, formula (I-4-3a):

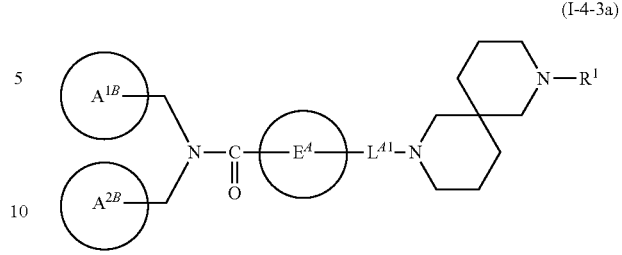

(I-4-3a)

wherein all symbols have the same meanings as described above, formula (I-4-3b):

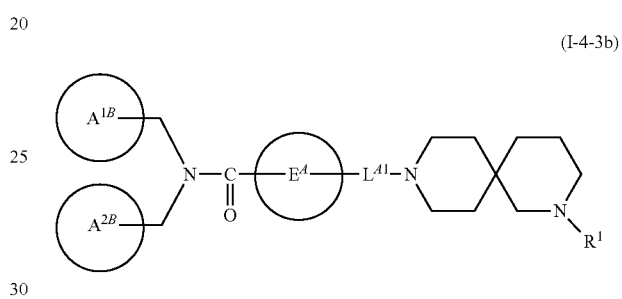

(I-4-3b)

wherein all symbols have the same meanings as described above, formula (I-4-4):

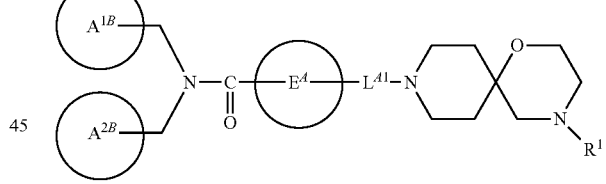

(I-4-4)

wherein all symbols have the same meanings as described above, formula (I-4-5):

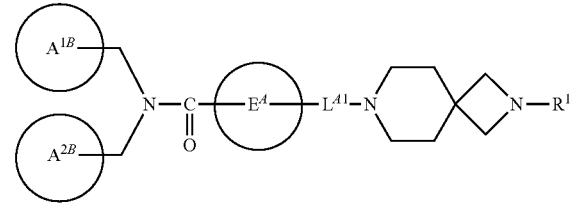

(I-4-5)

wherein all symbols have the same meanings as described above, formula (I-4-6):

(I-4-6)

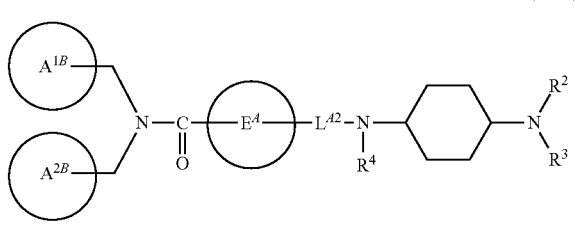

wherein all symbols have the same meanings as described above, formula (I-8-1):

(I-8-1)

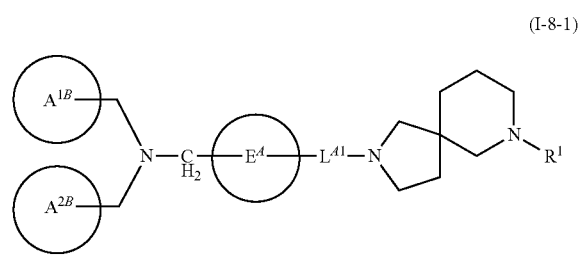

wherein all symbols have the same meanings as described above, or formula (I-8-2):

(I-8-2)

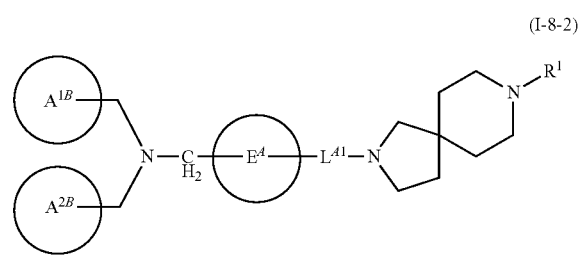

wherein all symbols have the same meanings as described above, a salt thereof, an N-oxide thereof or a solvate thereof or a prodrug thereof.

The substituent of ring $J^{2b}$ is preferably $R^1$.

$R^1$ is preferably a hydrogen atom, an aliphatic hydrocarbon group, a cyclic group, or an aliphatic hydrocarbon group substituted with a cyclic group. The aliphatic hydrocarbon group represented by $R^1$ is preferably a C1-8 alkyl group. The cyclic group represented by $R^1$ is preferably a C3-15 monocyclic or polycyclic unsaturated carbocyclic ring, or partially or completely saturated one thereof. It is more preferably a C3-8 monocyclic saturated carbocyclic ring, and particularly cyclopropane, cyclobutane, cyclopentane, cyclohexane, or cycloheptane. The "cyclic group" such as aliphatic hydrocarbon group substituted with a cyclic group is preferably thiophene.

$R^2$ or $R^3$ is preferably a hydrogen atom, an aliphatic hydrocarbon group, a cyclic group, or an aliphatic hydrocarbon group substituted with a cyclic group. The aliphatic hydrocarbon group represented by $R^2$ or $R^3$ is preferably a C1-8 alkyl group.

The "cyclic group" of the cyclic group or aliphatic hydrocarbon group substituted with a cyclic group represented by $R^2$ or $R^3$ is preferably a C3-15 monocyclic or polycyclic unsaturated carbocyclic ring, or partially or completely saturated one thereof. The "cyclic group" of the cyclic group, or aliphatic hydrocarbon group substituted with a cyclic group represented by $R^2$ or $R^3$ is preferably a C3-8 monocyclic saturated carbocyclic ring, and particularly preferably cyclopropane, cyclobutane, cyclopentane, cyclohexane, or cycloheptane.

The "hetrocyclic ring" of the hetrocyclic ring which may have a substituent(s), which is formed by combining $R^2$ and $R^3$ with the nitrogen atom to which they are attached, is preferably a 3- to 15-membered monocyclic or condensed hetrocyclic ring which has at least one nitrogen atom and also may have an oxygen atom and/or a sulfur atom which may be oxidized. More preferably, those composed of one nitrogen atom and carbon atoms are selected from among 3- to 15-membered monocyclic or condensed hetrocyclic rings which have at least one nitrogen atom and also may have an oxygen atom and/or a sulfur atom which may be oxidized. More preferably, it is pyrrolidine, piperidine, perhydroazepine, tetrahydroisoquinoline, tetrahydroquinoline, or perhydroisoquinoline.

$R^4$ is preferably a hydrogen atom, an aliphatic hydrocarbon group, or an aliphatic hydrocarbon group substituted with a substituent(s). The substituent of the aliphatic hydrocarbon group substituted with a substituent(s) represented by $R^4$ is preferably a hydroxyl group. The aliphatic hydrocarbon group or "aliphatic hydrocarbon group" of the aliphatic hydrocarbon group substituted with a substituent(s) is preferably a C3-8 aliphatic hydrocarbon group.

Specific examples of the compound of the present invention include compound shown in the following (1) to (64), compounds described in Examples, salts thereof, N-oxides thereof or solvates thereof or prodrugs thereof:

(1) N-[4-({[4-(diisopropylamino)butyl]amino}methyl)benzyl]-N-(1H-imidazol-2-ylmethyl)-1H-imidazole-2-carboxyamide; (2) 4-({[4-(diisopropylamino)butyl]amino}methyl)-N,N-bis(1H-imidazol-2-ylmethyl)benzene sulfonamide; (3) N-[4-({[4-(diisopropylamino)butyl]amino}methyl)benzyl]-N-(1H-imidazol-2-ylmethyl)-1H-imidazole-2-sulfonamide; (4) $N^1$-[4-(diisopropylamino)butyl]-$N^4$,$N^4$-bis(1H-imidazol-2-ylmethyl)terephthalamide; (5) $N^5$-[4-(diisopropylamino)butyl]-$N^2$,$N^2$-bis(1H-imidazol-2-ylmethyl)pyridine-2,5-dicarboxyamide; (6) $N^2$-[4-(diisopropylamino)butyl]-$N^5$,$N^5$-bis(1H-imidazol-2-ylmethyl)pyridine-2,5-dicarboxyamide; (7) $N^2$-[4-(diisopropylamino)butyl]-$N^5$,$N^5$-bis(1H-imidazol-2-ylmethyl)pyrazine-2,5-dicarboxyamide; (8) $N^5$-[4-(diisopropylamino)butyl]-$N^2$,$N^2$-bis(1H-imidazol-2-ylmethyl)pyrimidine-2,5-dicarboxyamide; (9) $N^2$-[4-(diisopropylamino)butyl]-$N^5$,$N^5$-bis(1H-imidazol-2-ylmethyl)pyrimidine-2,5-dicarboxyamide; (10) $N^2$-[4-(diisopropylamino)butyl]-$N^5$,$N^5$-bis(1H-imidazol-2-ylmethyl)-1H-pyrrole-2,5-dicarboxyamide; (11) $N^2$-[4-(diisopropylamino)butyl]-$N^5$,$N^5$-bis(1H-imidazol-2-ylmethyl)-1H-imidazole-2,5-dicarboxyamide; (12) $N^1$[4-(diisopropylamino)butyl]-$N^2$,$N^2$-bis(1H-imidazol-2-ylmethyl)-1H-imidazole-2,5-dicarboxyamide; (13) $N^5$-[4-(diisopropylamino)butyl]-$N^2$,$N^2$-bis(1H-imidazol-2-ylmethyl)-1,3-oxazole-2,5-dicarboxyamide; (14) $N^2$-[4-(diisopropylamino)butyl]-$N^5$,$N^5$-bis(1H-imidazol-2-ylmethyl)-1,3-oxazole-2,5-dicarboxyamide; (15) $N^2$-[4-(diisopropylamino)butyl]-$N^5$,$N^5$-bis(1H-imidazol-2-ylmethyl)-1,3-thiazole-2,5-dicarboxyamide; (16) $N^5$-[4-(diisopropylamino)butyl]-$N^2$,$N^2$-bis(1H-imidazol-2-ylmethyl)-1,3-thiazole-2,5-dicarboxyamide; (17) $N^2$-[4-(diisopropylamino)butyl]-$N^5$,$N^5$-bis(1H-imidazol-2-ylmethyl)thiophene-2,5-dicarboxyamide; (18) $N^2$-[4-(diisopropylamino)butyl]-$N^5$,$N^5$-bis(1H-imidazol-2-ylmethyl)furan-2,5-dicarboxyamide;

(19) N²-[4-(diisopropylamino)butyl]-N⁵,N⁵-bis(1H-imidazol-2-ylmethyl)-1,3,4-oxadiazole-2,5-dicarboxyamide; (20) N³-[4-(diisopropylamino)butyl]-N⁵,N⁵-bis(1H-imidazol-2-ylmethyl)-1,2,4-oxadiazole-3,5-dicarboxyamide; (21) N³-[4-(diisopropylamino)butyl]-N⁵,N⁵-bis(1H-imidazol-2-ylmethyl)-1,2,4-thiadiazole-3,5-dicarboxyamide; (22) N⁵-[4-(diisopropylamino)butyl]-N³,N³-bis(1H-imidazol-2-ylmethyl)-1,2,4-oxadiazole-3,5-dicarboxyamide; (23) N⁵-[4-(diisopropylamino)butyl]-N³,N³-bis(1H-imidazol-2-ylmethyl)-1,2,4-thiadiazole-3,5-dicarboxyamide; (24) N²-[4-(diisopropylamino)butyl]-N⁵,N⁵-bis(1H-imidazol-2-ylmethyl)-1,3,4-thiadiazole-2,5-dicarboxyamide; (25) 4-({[4-(diisopropylamino)butyl]amino}sulfonyl)-N,N-bis(1H-imidazol-2-ylmethyl)benzamide; (26) 4-{[5-(diisopropylamino)pentyl]sulfanyl}-N,N-bis(1H-imidazol-2-ylmethyl)benzamide; (27) 4-{[5-(diisopropylamino)pentyl]oxy}-N,N-bis(1H-imidazol-2-ylmethyl)benzamide; (28) 4-{[5-(diisopropylamino)pentyl]amino}-N,N-bis(1H-imidazol-2-ylmethyl)benzamide; (29) 4-[(1E)-6-(diisopropylamino)hexa-1-enyl]-N,N-bis(1H-imidazol-2-ylmethyl)benzamide; (30) 4-{[5-(diisopropylamino)pentanoyl]amino}-N,N-bis(1H-imidazol-2-ylmethyl)benzamide; (31) 4-({[4-(diisopropylamino)butyl]sulfonyl}amino)-N,N-bis(1H-imidazol-2-ylmethyl)benzamide; (32) 4-({[4-(diisopropylamino)butyl]sulfanyl}methyl)-N,N-bis(1H-imidazol-2-ylmethyl)benzamide; (33) 4-{[4-(diisopropylamino)butoxy]methyl}-N,N-bis(1H-imidazol-2-ylmethyl)benzamide; (34) 4-{[5-(diisopropylamino)pentyl]sulfonyl}-N,N-bis(1H-imidazol-2-ylmethyl)benzamide; (35) 4-({[4-(diisopropylamino)butyl]sulfonyl}methyl)-N,N-bis(1H-imidazol-2-ylmethyl)benzamide; (36) 4-[6-(diisopropylamino)-2-oxohexyl]-N,N-bis(1H-imidazol-2-ylmethyl)benzamide; (37) 4-[6-(diisopropylamino)hexa-1-ynyl]-N,N-bis(1H-imidazol-2-ylmethyl)benzamide; (38) N-[4-(diisopropylamino)butyl]-4-[3-(1H-imidazol-2-yl)-2-(1H-imidazol-2-ylmethyl)propanoyl]benzamide; (39) N-[4-(diisopropylamino)butyl]-4-[3-(1H-imidazol-2-yl)-2-(1H-imidazol-2-ylmethyl)propyl]benzamide; (40) N-[4-(diisopropylamino)butyl]-4-{[2-(1H-imidazol-2-yl)-1-(1H-imidazol-2-ylmethyl)ethyl]sulfonyl}benzamide; (41) N-[4-(diisopropylamino)butyl]-4-[2-(1H-imidazol-2-yl)-1-(1H-imidazol-2-ylmethyl)ethoxy]benzamide; (42) N-[4-(diisopropylamino)butyl]-4-{[2-(1H-imidazol-2-yl)-1-(1H-imidazol-2-ylmethyl)ethyl]sulfanyl}benzamide; (43) N-[4-(diisopropylamino)butyl]-4-{[2-(1H-imidazol-2-yl)-1-(1H-imidazol-2-ylmethyl)ethyl]amino}benzamide; (44) N-[4-(diisopropylamino)butyl]-4-[3-(1H-imidazol-2-yl)-2-(1H-imidazol-2-ylmethyl)propa-1-enyl]benzamide; (45) N¹-[4-(diisopropylamino)butyl]-N⁴,N⁴-bis(1H-imidazol-2-ylmethyl)cyclohexane-1,4-dicarboxyamide; (46) N¹-[4-(diisopropylamino)butyl]-N³,N³-bis(1H-imidazol-2-ylmethyl)isophthalamide; (47) N-[4-({[4-(diisopropylamino)butyl]amino}methyl)benzyl]-N-(1H-imidazol-2-ylmethyl)-1H-imidazole-2-carboxyamide; (48) N¹,N¹-bis(1H-benzoimidazol-2-ylmethyl)-N⁴-[4-(diisopropylamino)butyl]terephthalamide; (49) N¹-[4-(diisopropylamino)butyl]-N⁴-(1H-imidazol-2-ylmethyl)-N⁴-[(1-methyl-1H-imidazol-2-yl)methyl]terephthalamide; (50) N¹-[4-(diisopropylamino)butyl]-N⁴,N⁴-bis[(1-methyl-1H-imidazol-2-yl)methyl]terephthalamide; (51) N¹-[4-(diisopropylamino)butyl]-N⁴-(1H-imidazol-2-ylmethyl)-N⁴-(pyridine-2-ylmethyl)terephthalamide; (52) N¹-[4-(diisopropylamino)butyl]-N⁴,N⁴-bis(pyridine-2-ylmethyl)terephthalamide; (53) N¹-[4-(diisopropylamino)butyl]-N⁴-(1H-imidazol-2-ylmethyl)-N⁴-(5,6,7,8-tetrahydroquinoline-8-yl)terephthalamide; (54) N¹-(1H-benzoimidazol-2-ylmethyl)-N⁴-(diisopropylamino)butyl]-N¹-(5,6,7,8-tetrahydroquinoline-8-yl)terephthalamide; (55) N¹-{3-[(diisopropylamino)methyl]phenyl}-N⁴,N⁴-bis(1H-imidazol-2-ylmethyl)terephthalamide; (56) N¹-[3-(diisopropylamino)benzyl]-N⁴,N⁴-bis(1H-imidazol-2-ylmethyl)terephthalamide; (57) N¹-{3-[(diisopropylamino)methyl]cyclohexyl}-N⁴,N⁴-bis(1H-imidazol-2-ylmethyl)terephthalamide; (58) N¹-{[3-(diisopropylamino)cyclohexyl]methyl}-N⁴,N⁴-bis(1H-imidazol-2-ylmethyl)terephthalamide; (59) N¹-[4-(dimethylamino)butyl]-N⁴,N⁴-bis(1H-imidazol-2-ylmethyl)terephthalamide; (60) N¹-[4-(diethylamino)butyl]-N⁴,N⁴-bis(1H-imidazol-2-ylmethyl)terephthalamide; (61) N¹,N¹-bis(1H-imidazol-2-ylmethyl)-N⁴-(4-pyrrolidine-1-ylbutyl)terephthalamide; (62) N¹,N¹-bis(1H-imidazol-2-ylmethyl)-N⁴-(4-piperidine-1-ylbutyl)terephthalamide; (63) 4-{[[4-(diisopropylamino)butyl](methyl)amino]methyl}-N,N-bis(1H-imidazol-2-ylmethyl)benzamide; (64) N-[4-({[4-(diisopropylamino)butyl]amino}carbonyl)benzyl]-N-(1H-imidazol-2-ylmethyl)pyridine-2-carboxyamide, salts thereof, N-oxides thereof or solvates thereof or prodrugs thereof.

Examples of more preferable compound include compounds described in Examples, salts thereof, N-oxides thereof or solvates thereof or prodrugs thereof.

Examples of particularly preferable compound include (1) 4-[({trans-4-[cyclohexyl(propyl)amino]cyclohexyl}amino)methyl]-N,N-bis(1H-imidazol-2-ylmethyl)benzamide; (2) 4-[(2-cyclohexyl-2,8-diazaspiro[4.5]dec-8-yl)methyl]-N,N-bis(1H-imidazol-2-ylmethyl)benzamide; (3) 4-[(8-cyclohexyl-2,8-diazaspiro[4.5]dec-2-yl)methyl]-N,N-bis(1H-imidazol-2-ylmethyl)benzamide; (4) 4-[(2-cyclohexyl-2,8-diazaspiro[4.5]dec-8-yl)methyl]-N,N-bis(1H-imidazol-2-ylmethyl)benzamide; (5) 4-[8-cyclohexyl-2,8-diazaspiro[4.5]dec-2-yl)methyl]-N,N-bis(1H-imidazol-2-ylmethyl)benzamide; (6) 4-[(7-cyclohexyl-2,7-diazaspiro[4.5]dec-2-yl)methyl]-N,N-bis(1H-imidazol-2-ylmethyl)benzamide; (7) 4-[(7-cyclohexyl-2,7-diazaspiro[4.4]nona-2-yl)methyl]-N,N-bis(1H-imidazol-2-ylmethyl)benzamide; (8) 4-[(9-cyclohexyl-3,9-diazaspiro[5.5]undec-3-yl)methyl]-N,N-bis(1H-imidazol-2-ylmethyl)benzamide; (9) 4-{[8-(cyclohexylmethyl)-2,8-diazaspiro[4.5]dec-2-yl]methyl}-N,N-bis(1H-imidazol-2-ylmethyl)benzamide; (10) 4-{[8-(cyclopropylmethyl)-2,8-diazaspiro[4.5]dec-2-yl]methyl}-N,N-bis(1H-imidazol-2-ylmethyl)benzamide; (11) 4-{[8-(cyclopentylmethyl)-2,8-diazaspiro[4.5]dec-2-yl]methyl}-N,N-bis(1H-imidazol-2-ylmethyl)benzamide; (12) N,N-bis(1H-imidazol-2-ylmethyl)-4-{[8-(2-thienylmethyl)-2,8-diazaspiro[4.5]dec-2-yl]methyl}benzamide; (13) N,N-bis(1H-imidazol-2-ylmethyl)-4-{[8-(3-thienylmethyl)-2,8-diazaspiro[4.5]dec-2-yl]methyl}benzamide; (14) 4-{[8-(3-fluorobenzyl)-2,8-diazaspiro[4.5]dec-2-yl]methyl}-N,N-bis(1H-imidazol-2-ylmethyl)benzamide; (15) 4-{[8-(4-fluorobenzyl)-2,8-diazaspiro[4.5]dec-2-yl]methyl}-N,N-bis(1H-imidazol-2-ylmethyl)benzamide; (16) N-(1H-benzoimidazol-2-ylmethyl)-4-[(8-cyclohexyl-2,8-diazaspiro[4.5]dec-2-yl)methyl]-N-(1H-imidazol-2-ylmethyl)benzamide; (17) N-(1H-benzoimidazol-2-ylmethyl)-N-{4-[(8-cyclohexyl-2,8-diazaspiro[4.5]dec-2-yl)methyl]benzyl}-1H-imidazole-2-carboxamide; (18) 4-[(8-cyclopentyl-2,8-diazaspiro[4.5]dec-2-yl)methyl]-N,N-bis(1H-imidazol-2-ylmethyl)benzamide; (19) N,N-bis(1H-imidazol-2-ylmethyl)-4-{[8-(2-naphthylmethyl)-2,8-diazaspiro[4.5]dec-2-yl]methyl}benzamide; (20) 4-[(8-cycloheptyl-2,8-diazaspiro[4.5]dec-2-yl)methyl]-N,N-bis(1H-imidazol-2-ylmethyl)benzamide; (21) 4-{[8-(2,3-dihydro-1H-inden-2-yl)-2,8-diazaspiro[4.5]dec-2-yl]methyl}-N,N-bis(1H-imidazol-2-ylmethyl)benzamide; (22) 4-[(8-cyclobutyl-2,8-diazaspiro[4.5]dec-2-yl)methyl]-N,N-bis(1H-imidazol-2-ylmethyl)benzamide; (23) N,N-bis(1H- imidazol-2-ylmethyl)-4-[(8-isobutyl-2,8-diazaspiro[4.5]dec-2-yl)methyl]benzamide; (24) 4-[(2-cyclohexyl-2,8-diazaspiro[4.5]dec-8-yl)methyl]-N,N-bis(1H-imidazol-2-ylmethyl)-2-methylbenzamide; (25) N,N-bis(1H-imidazol-2-ylmethyl)-4-{[8-(3-methyl-2-butene-1-yl)-2,8-diazaspiro[4.5]dec-2-yl]methyl}benzamide; (26) 4-{[8-(2-ethylbutyl)-2,8-diazaspiro[4.5]dec-2-yl]methyl}-N,N-bis(1H-imidazol-2-ylmethyl)benzamide; (27) N,N-bis(1H-imidazol-2-ylmethyl)-4-({8-[(3-methyl-2-thienyl)methyl]-2,8-diazaspiro[4.5]dec-2-yl}methyl)benzamide; (28) 4-{[8-(1-ethylpropyl)-2,8-diazaspiro[4.5]dec-2-yl]methyl}-N,N-bis(1H-imidazol-2-ylmethyl)benzamide; (29) N,N-bis(1H-imidazol-2-ylmethyl)-4-({8-[(5-methyl-2-thienyl)methyl]-2,8-diazaspiro[4.5]dec-2-yl}methyl)benzamide; (30) 4-({8-[(5-chloro-2-thienyl)methyl]-2,8-diazaspiro[4.5]dec-2-yl}methyl)-N,N-bis(1H-imidazol-2-ylmethyl)benzamide; (31) 4-[(8-cyclohexyl-2,8-diazaspiro[4.5]dec-2-yl)methyl]-N,N-bis(1H-imidazol-2-ylmethyl)-2-methoxybenzamide; (32) 1-{4-[(8-cyclohexyl-2,8-diazaspiro[4.5]dec-2-yl)methyl]phenyl}-N,N-bis(1H-imidazol-2-ylmethyl)methaneamine; (33) 3-chloro-4-[(8-cyclohexyl-2,8-diazaspiro[4.5]dec-2-yl)methyl]-N,N-bis(1H-imidazol-2-ylmethyl)benzamide; (34) 4-[(8-cyclooctyl-2,8-diazaspiro[4.5]dec-2-yl)methyl]-N,N-bis(1H-imidazol-2-ylmethyl)benzamide; (35) 1-{4-[(8-cyclohexyl-2,8-diazaspiro[4.5]dec-2-yl)carbonyl]phenyl}-N,N-bis(1H-imidazol-2-ylmethyl)methaneamine; (36) 4-[(7-cycloheptyl-2,7-diazaspiro[3.5]nona-2-yl)methyl]N,N-bis(1H-imidazol-2-ylmethyl)benzamide; (37) (2E)-3-{4-[(8-cyclohexyl-2,8-diazaspiro[4.5]dec-2-yl)methyl]phenyl}-N,N-bis(1H-imidazol-2-ylmethyl)acrylamide; (38) 3-{4-[(8-cyclohexyl-2,8-diazaspiro[4.5]dec-2-yl)methyl]phenyl}-N,N-bis(1H-imidazol-2-ylmethyl)propaneamide; (39) 4-{[8-(cyclobutylmethyl)-2,8-diazaspiro[4.5]dec-2-yl]methyl}-N,N-bis(1H-imidazol-2-ylmethyl)benzamide; (40) 4-[({trans-4-[benzyl(propyl)amino]cyclohexyl}amino)methyl]-N,N-bis(1H-imidazol-2-ylmethyl)benzamide; (41) 4-[({trans-4-[cyclohexyl(ethyl)amino]cyclohexyl}amino)methyl]-N,N-bis(1H-imidazol-2-ylmethyl)benzamide; (42) 4-({[4-(3,4-dihydro-2(1H)-isoquinolinyl)cyclohexyl]amino}methyl)-N,N-bis(1H-imidazol-2-ylmethyl)benzamide; (43) N,N-bis(1H-imidazol-2-ylmethyl)-4-({[4-(1-piperidinyl)cyclohexyl]amino}methyl)benzamide; (44) 4-({4-(1-azepanyl)cyclohexyl]amino methyl)-N,N-bis(1H-imidazol-2-ylmethyl)benzamide; (45) 4-({[trans-4-(cyclohexylamino)cyclohexyl]amino}methyl)-N,N-bis(1H-imidazol-2-ylmethyl)benzamide; (46) N-(1H-benzoimidazol-2-ylmethyl)-4-[({trans-4-[cyclohexyl(propyl)amino]cyclohexyl}amino)methyl]-N-(1H-imidazol-2-ylmethyl)benzamide; (47) 4-[({trans-4-[(1-ethylpropyl)(propyl)amino]cyclohexyl}amino)methyl]-N,N-bis(1H-imidazol-2-ylmethyl)benzamide; (48) 4-{[{trans-4-[cyclohexyl(propyl)amino]cyclohexyl}(methyl)amino]methyl}-N,N-bis(1H-imidazol-2-ylmethyl)benzamide; (49) 4-{[{trans-4-[cyclohexyl(propyl)amino]cyclohexyl}(ethyl)amino]methyl}-N,N-bis(1H-imidazol-2-ylmethyl)benzamide; (50) 4-{[{trans-4-[cyclohexyl(propyl)amino]cyclohexyl}(propyl)amino]methyl}-N,N-bis(1H-imidazol-2-ylmethyl)benzamide; (51) 4-{[{trans-4-[cyclohexyl(propyl)amino]cyclohexyl}(2-hydroxyethyl)amino]methyl}-N,N-bis(1H-imidazol-2-ylmethyl)benzamide; (52) 4-[({trans-4-[(1-ethylpropyl)(2-hydroxyethyl)amino]cyclohexyl}amino)methyl]-N,N-bis(1H-imidazol-2-ylmethyl)benzamide; (53) 4-({[trans-4-(dipropylamino)cyclohexyl]amino}methyl)-N,N-bis(1H-imidazol-2-ylmethyl)-2-methoxybenzamide; (54)-3-chloro-4-({[trans-4-(dipropylamino)cyclohexyl]amino}methyl)-N,N-bis(1H-imidazol-2-ylmethyl)benzamide; (55) 4-({[4-(1-azocanyl)cyclohexyl]amino}methyl)-N,N-bis(1H-imidazol-2-ylmethyl)benzamide; (56) 4-({[4-(1-azocanyl)cyclohexyl]amino}methyl)-N,N-bis(1H-imidazol-2-ylmethyl)benzamide; (57) 4-({[(1-cyclohepty1-4-piperidinyl)methyl]amino}methyl)-N,N-bis(1H-imidazol-2-ylmethyl)benzamide; (58) 4-({[4-(dipropylamino)butyl]amino}methyl)-N,N-bis(1H-imidazol-2-ylmethyl)benzamide; (59) 4-({[3-(dibutylamino)propyl]amino}methyl)-N,N-bis(1H-imidazol-2-ylmethyl)benzamide; (60) 4-({[5-(dipropylamino)pentyl]amino}methyl)-N,N-bis(1H-imidazol-2-ylmethyl)benzamide; (61) 4-({4-[(dipropylamino)methyl]-1-piperidinyl}methyl)-N,N-bis(1H-imidazol-2-ylmethyl)benzamide; (62) 4-({[4-(dipropylamino)cyclohexyl]amino}methyl)-N,N-bis(1H-imidazol-2-ylmethyl)benzamide; (63) 4-({[3-(dipropylamino)propyl]amino}methyl)-N,N-bis(1H-imidazol-2-ylmethyl)benzamide; (64) 4-[(2-benzyl-2,9-diazaspiro[5.5]undec-9-yl)methyl]-N,N-bis(1H-imidazol-2-ylmethyl)benzamide; (65) 4-[(2-cyclohexyl-2,9-diazaspiro[5.5]undec-9-yl)methyl]-N,N-bis(1H-imidazol-2-ylmethyl)benzamide; (66)₂-[4-(dipropylamino)butyl]-N,N-bis(1H-imidazol-2-ylmethyl)-1,2,3,4-tetrahydro-6-isoquinolinecarboxamide; (67) N-[4-({[4-(dipropylamino)butyl]amino}methyl)benzyl]-N-(1H-imidazol-2-ylmethyl)-1H-imidazole-2-carboxamide; (68) 4-({[4-(dipropylamino)butyl]amino}methyl)-N,N-bis(1H-imidazol-2-ylmethyl)benzene sulfonamide, salts thereof, N-oxides thereof or solvates thereof or prodrugs thereof.

Examples of the most preferable compound include 4-({[4-(dipropylamino)butyl]amino}methyl)-N,N-bis(1H-imidazol-2-ylmethyl)benzamide (compound 10), 4-({[3-(dibutylamino)propyl]amino}methyl)-N,N-bis(1H-imidazol-2-ylmethyl)benzamide (compound 11), 4-({[5-(dipropylamino)pentyl]amino}methyl)-N,N-bis(1H-imidazol-2-ylmethyl)benzamide (compound 11-2), 4-({4-[(dipropylamino)methyl]-1-piperidinyl}methyl)-N,N-bis(1H-imidazol-2-ylmethyl)benzamide (compound 11-3), 4-({[4-(dipropylamino)cyclohexyl]amino}methyl)-N,N-bis(1H-imidazol-2-ylmethyl)benzamide (compound 11-4), 4-({[3-(dipropylamino)propyl]amino}methyl)-N,N-bis(1H-imidazol-2-ylmethyl)benzamide (compound 11-10), 4-[(2-benzyl-2,9-diazaspiro[5.5]undec-9-yl)methyl]-N,N-bis(1H-imidazol-2-ylmethyl)benzamide (compound 11-17), 4-[(2-cyclohexyl-2,9-diazaspiro[5.5]undec-9-yl)methyl]-N,N-bis(1H-imidazol-2-ylmethyl)benzamide (compound 11-18), 2-[4-(dipropylamino)butyl]-N,N-bis(1H-imidazol-2-ylmethyl)-1,2,3,4-tetrahydro-6-isoquinolinecarboxamide (compound 15), N-[4-({[4-(dipropylamino)butyl]amino}methyl)benzyl]-N-(1H-imidazol-2-ylmethyl)-1H-imidazole-2-carboxamide (compound 19), 4-({[4-(dipropylamino)butyl]amino}methyl)-N,N-bis(1H-imidazol-2-ylmethyl)benzene sulfonamide (compound 38), 4-[({trans-4-[cyclohexyl(propyl)amino]cyclohexyl}amino)methyl]-N,N-bis(1H-imidazol-2-ylmethyl)benzamide (compound 43-4), 4-[(2-cyclohexyl-2,8-diazaspiro[4.5]dec-8-yl)methyl]-N,N-bis(1H-imidazol-2-ylmethyl)benzamide (compound 49-1), 4-[(8-cyclohexyl-2,8-diazaspiro[4.5]dec-2-yl)methyl]-N,N-bis(1H-imidazol-2-ylmethyl)benzamide (compound 49-2), 4-[(2-cyclohexyl-2,8-diazaspiro[4.5]dec-8-yl)methyl]-N,N-bis(1H-imidazol-2-ylmethyl)benzamide (compound 50-92), 4-[(8-cyclohexyl-2,8-diazaspiro[4.5]dec-2-yl)methyl]-N,N-bis(1H-imidazol-2-ylmethyl)benzamide (compound 50-95), N,N-bis(1H-imidazol-2-ylmethyl)-4-{[8-(2-thienylmethyl)-2,8-diazaspiro[4.5]dec-2-yl]methyl}benzamide (compound 50-29), N-(1H-benzoimidazol-2-ylmethyl)-4-[(8-cyclohexyl-2,8-diazaspiro[4.5]dec-2-yl)methyl]-N-(1H-imidazol-2-ylmethyl)benzamide (compound 50-38), 4-[(8-cycloheptyl-2,8-diazaspiro[4.5]dec-2-yl)methyl]-N,N-bis(1H-imidazol-2-ylmethyl)benzamide (compound 50-49), N,N-bis(1H-imidazol-2-ylmethyl)-4-({8-[(3-methyl-2-thienyl)methyl]-2,8-diazaspiro[4.5]dec-2-yl}methyl)benzamide (compound 50-78), 4-{[8-(1-ethylpropyl)-2,8-diazaspiro[4.5]dec-2-yl]methyl}-N,N-bis(1H-imidazol-2-ylmethyl)benzamide (compound 50-81), 4-[({trans-4-[benzyl(propyl)amino]cyclohexyl}amino)methyl]-N,N-bis(1H-imidazol-2-ylmethyl)benzamide (compound 50-1), 4-({[4-(1-azepanyl)cyclohexyl]amino}methyl)-N,N-bis(1H-imidazol-2-ylmethyl)benzamide (compound 50-19, compound 50-20), N-(1H-benzoimidazol-2-ylmethyl)-4-[({trans-4-[cyclohexyl(propyl)amino]cyclohexyl}amino)methyl]-N-(1H-imidazol-2-ylmethyl)benzamide (compound 50-39), 4-[({trans-4-[(1-ethylpropyl)(propyl)amino]cyclohexyl}amino)methyl]-N,N-bis(1H-imidazol-2-ylmethyl)benzamide (compound 50-41), 4-{[{trans-4-[cyclohexyl(propyl)amino]cyclohexyl}(methyl)amino]methyl}-N,N-bis(1H-imidazol-2-ylmethyl)benzamide (compound 50-67), 4-{[{trans-4-[cyclohexyl(propyl)amino]cyclohexyl}(2-hydroxyethyl)amino]methyl}-N,N-bis(1H-imidazol-2-ylmethyl)benzamide (compound 50-103), 4-[({trans-4-[(1-ethylpropyl)(2-hydroxyethyl)amino]cyclohexyl}amino)methyl]-N,N-bis(1H-imidazol-2-ylmethyl)benzamide (compound 50-105), salts thereof, N-oxides thereof or solvates thereof or prodrugs thereof.

[Method for Producing Compound of the Present Invention]

The compound of the present invention represented by formula (I-0) can be prepared by appropriately improving a known method, for example, methods shown below, methods described in Examples, and a method described in Comprehensive Organic Transformations: A Guide to Functional Group Preparations, Second edition (written by Richard C. Larock, John Wiley & Sons Inc, 1999) and using improved methods in combination. In the following production methods, starting compounds may be used in the form of a salt. As the salt, those described as a salt of the above described formula (I-0) are used.

Among the compound of the present invention represented by formula (I-0), a compound wherein ==== represents a single bond, D represents a nitrogen atom, and G represents a carbonyl group, namely, a compound represented by formula (I-A):

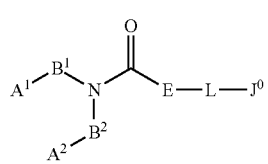

(I-A)

wherein all symbols have the same meanings as described above, can be prepared by subjecting a compound represented by formula (2):

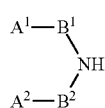

(2)

wherein all symbols have the same meanings as described above, and a compound represented by formula (3):

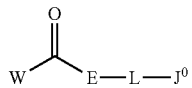

(3)

wherein W represents a hydroxyl group or a chlorine atom; and other symbols have the same meanings as described above, to the amidation reaction and if necessary to the deprotection reaction of a protective group and/or the cleavage reaction from a resin.

This amidation reaction is known and examples thereof include:

(1) a method using an acyl halide,
(2) a method using a mixed acid anhydride, and
(3) a method using a condensing agent.

These methods are described in detail below.

(1) The method using an acyl halide is carried out, for example, by reacting carboxylic acid with an acid halogenating agent (oxalyl chloride, thionyl chloride, etc.) in an organic solvent (chloroform, dichloromethane, diethylether, tetrahydrofuran, etc.) or in the absence of the solvent at −20° C. to reflux temperature. Then the obtained acyl halide derivative may be with amine in the presence of a base (pyridine, triethylamine, N,N-dimethylaniline, 4-dimethylaminopyridine, diisopropylethylamine, etc.) in an organic solvent (chloroform, dichloromethane, diethylether, tetrahydrofuran, etc.) at 0 to 40° C. Alternatively, the obtained acyl halide can be reacted with amine in an organic solvent (dioxane, tetrahydrofuran, etc.) at 0 to 40° C. using an aqueous alkali solution (sodium bicarbonate water or sodium hydroxide solution, etc.).

(2) The method using a mixed acid anhydride is carried out, for example, by reacting carboxylic acid with an acyl halide (pivaloyl chloride, tosyl chloride, mesyl chloride, etc.) or an acid derivative (ethyl chloroformate, butyl chloroformate, etc.) in the presence of a base (pyridine, triethylamine, N,N-dimethylaniline, 4-dimethylaminopyridine, diisopropylethylamine, etc.) in an organic solvent (chloroform, dichloromethane, diethylether, tetrahydrofuran, etc.) or in the absence of the solvent at 0 to 40° C., and reacting the resulting mixed acid anhydride with amine in an organic solvent (chloroform, dichloromethane, diethylether, tetrahydrofuran, etc.) at 0 to 40° C.

(3) The method using a condensing agent is carried out, for example, by reacting carboxylic acid with amine in an organic solvent (chloroform, dichloromethane, dimethyl formamide, diethylether, tetrahydrofuran, etc.) or in the absence of the solvent at 0 to 40° C. in the presence or absence of a base (pyridine, triethylamine, diisopropylethylamine, N,N-dimethylaniline, N-methylmorpholine, 4-dimethylaminopyridine, etc.), using a condensing agent (1,3-dicyclohexylcarbodiimide (DCC), 1-ethyl-3-[3-(dimethylamino)propyl]carbodiimide (EDC), 1,1'-carbonyldiimidazole (CDI), O-(7-azabenzotriazol-1-yl)N,N,N',N'-tetramethyluronium hexafluorophosphate (HATU), 2-chloro-1-methylpyridiniumiodine, 1-propylphosphonic acid cyclic anhydride (1-propanephosphonic acid cyclic anhydride, PPA), etc.) and using, or not using, 1-hydroxybenztriazole (HOBt) or 1-hydroxy-7-azabenzotriazole (HOAt).

The reactions described in (1), (2) and (3) are preferably carried out under an inert gas (argon, nitrogen, etc.) atmosphere on anhydrous condition.

The deprotection reaction of a protective group can be carried out by a known method, for example, a method described in Protective Groups in Organic Synthesis (written by T. W. Greene, John Wiley & Sons Inc, 1999). The protective group is not specifically limited as long as it is a group which is described in the above documents or other group that can be deprotected easily and selectively.

If the compound has a moiety to bind to a resin in the molecule and the resin is a polystyrene resin, the compound of the present invention can be cleaved from the resin by the following method. The reaction for cleavage from the resin is known and can be carried out, for example, by reacting in an organic solvent (dichloromethane, 1,2-dichloroethane, toluene, etc.) at 0 to 100° C. using an acid (acetic acid, trifluoroacetic acid, hydrochloric acid, etc.).

If necessary, the procedure of converting into the objective salt may be carried out by a known method after this reaction.

Among the compound of the present invention represented by formula (I-0), a compound wherein ---- represents a single bond, D represents a nitrogen atom, and G represents a —SO$_2$— group, namely, a compound represented by formula (I-B):

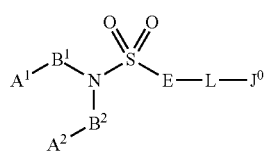

(I-B)

wherein all symbols have the same meanings as described above, can be prepared by subjecting a compound represented by formula (2) and a compound represented by formula (4):

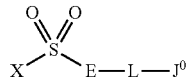

(4)

wherein X represents a halogen atom; and
other symbols have the same meanings as described above, to the sulfonamidation reaction, and if necessary to the deprotection reaction of a protective group and/or the cleavage reaction from a resin.

The sulfonamidation reaction is known and can be carried out by the following method. For example, a sulfonyl halide can be synthesized by reacting a sulfonic acid with an acyl halide (oxalyl chloride, thionyl chloride, phosphorous pentachloride, phosphorus trichloride or phosphorus oxychloride, or a mixture thereof, etc.) in an organic solvent (chloroform, dichloromethane, dichloroethane, diethylether, tetrahydrofuran, methyl t-butyl ether, etc.) or in the absence of the solvent at −20° C. to reflux temperature in the presence or absence of dimethyl formamide, or reacting a thiol with a chlorine gas in an aqueous acid solution (for example, hydrochloric acid, sulfuric acid, nitric acid, acetic acid, etc.) at 0° C. to reflux temperature. The sulfonyl halide thus synthesized can be reacted with amine in the presence of a base (diisopropylethylamine, pyridine, triethylamine, N,N-dimethylaniline, 4-dimethylaminopyridine, etc.) in an organic solvent (chloroform, dichloromethane, dichloroethane, diethylether, tetrahydrofuran, etc.) at 0 to 40° C. The deprotection reaction of a protective group or the cleavage reaction from the resin can be carried out by the same method as described above.

Among the compound of the present invention represented by formula (I-0), a compound wherein L represents an amide bond, namely, a compound represented by formula (I-C-1):

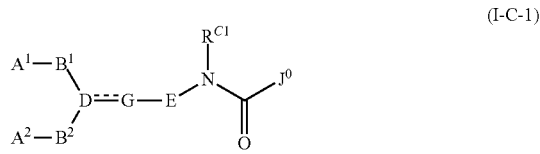

(I-C-1)

wherein $R^{C1}$ represents a hydrogen atom or a substituent in the "divalent nitrogen atom which may have a substituent" defined in L; and
other symbols have the same meanings as described above, or formula (I-C-2):

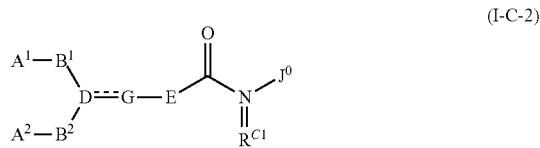

(I-C-2)

wherein all symbols have the same meanings as described above, can be prepared by subjecting a compound represented by formula (5):

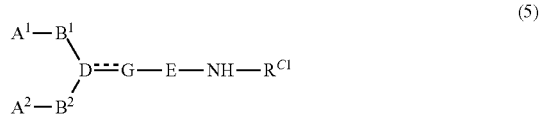

(5)

wherein all symbols have the same meanings as described above, and a compound represented by formula (6):

(6)

wherein all symbols have the same meanings as described above, to the amidation reaction, and if necessary to the deprotection reaction of a protective group and/or the cleavage reaction from a resin, or subjecting a compound represented by formula (7):

(7)

wherein all symbols have the same meanings as described above, and a compound represented by formula (8):

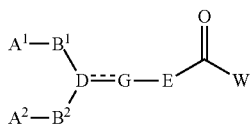
(8)

wherein all symbols have the same meanings as described above, to the amidation reaction, and if necessary to the deprotection reaction of a protective group and/or the cleavage reaction from a resin.

The amidation reaction, the deprotection reaction of a protective group, or the cleavage reaction from the resin can be carried out by the same method as described above.

Among the compound of the present invention represented by formula (I-0), a compound wherein L represents a sulfonamide bond, namely, a compound represented by formula (I-D-1):

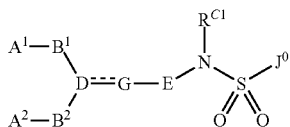
(I-D-1)

wherein all symbols have the same meanings as described above, or formula (I-D-2):

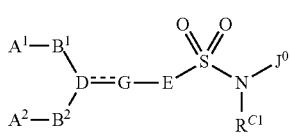
(I-D-2)

wherein all symbols have the same meanings as described above, can be prepared by subjecting a compound represented by formula (5) and a compound represented by formula (9):

(9)

wherein all symbols have the same meanings as described above, to the sulfonamidation reaction, and if necessary to the deprotection reaction of a protective group and/or the cleavage reaction from the resin, or subjecting a compound represented by formula (7) and a compound represented by formula (10):

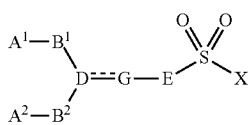
(10)

wherein all symbols have the same meanings as described above, to the sulfonamidation reaction, and if necessary to the deprotection reaction of a protective group and/or the cleavage reaction from the resin.

The sulfonamidation reaction, the deprotection reaction of a protective group, or the cleavage reaction from the resin can be carried out by the same method as described above.

Among the compound of the present invention represented by formula (I-0), a compound wherein L represents —CH(—$R^{E1}$)—NH— or —NH—CH(—$R^{E1}$)— (in the group, $R^{E1}$ represents a hydrogen atom or a substituent in the [divalent aliphatic hydrocarbon group having 1 to 4 carbon atom(s) which may have a substituent(s)] defined in L) which may have a substituent(s), namely, a compound represented by formula (I-E-1):

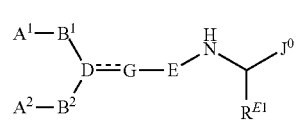
(I-E-1)

wherein all symbols have the same meanings as described above, or formula (I-E-2):

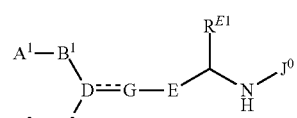
(I-E-2)

wherein all symbols have the same meanings as described above, can be prepared by subjecting a compound represented by formula (11):

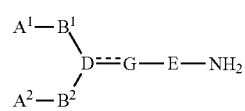
(11)

wherein all symbols have the same meanings as described above, and a compound represented by formula (12):

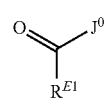
(12)

wherein all symbols have the same meanings as described above, to the reductive amination reaction, and if necessary to the deprotection reaction of a protective group and/or the cleavage reaction from the resin, or subjecting a compound represented by formula (13):

$H_2N-J^0$ (13)

wherein all symbols have the same meanings as described above, and a compound represented by formula (14):

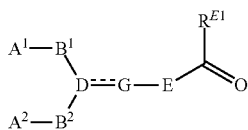
(14)

wherein all symbols have the same meanings as described above, to the reductive amination reaction, and if necessary to the deprotection reaction of a protective group and/or the cleavage reaction from the resin.

This reductive amination reaction is known and is carried out, for example, in an organic solvent (dichloroethane, dichloromethane, dimethyl formamide, acetic acid, a mixture thereof, etc.) at 0 to 40° C. in the presence of a reducing agent (sodium triacetoxyborohydride, sodium cyanoborohydride, sodium borohydride, etc.). The deprotection reaction of a protective group or the cleavage reaction from the resin can be carried out by the same method as described above.

Among the compound of the present invention represented by formula (I-0), a compound wherein a basic group in a $J^0$ group is a mono-substituted amino group, namely, a compound represented by formula (I-F):

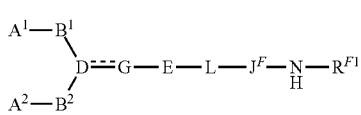
(I-F)

wherein $J^F$ represents a divalent aliphatic hydrocarbon group which may have a substituent(s), a divalent cyclic group which may have a substituent, an aliphatic hydrocarbon group substituted with a divalent cyclic group which may have a substituent(s), a cyclic group substituted with a divalent aliphatic hydrocarbon group which may have a substituent(s), divalent spiro-bound cyclic group which may have a substituent(s), or a divalent bridged cyclic group which may have a substituent(s);

$R^{F1}$ represents a substituent in the "mono-substituted amino group" defined in $J^0$; and other symbols have the same meanings as described above, can be prepared by subjecting the compound prepared by the above method, namely, a compound represented by formula (I-F-1):

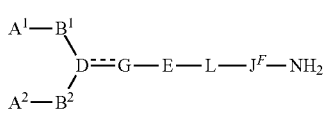
(I-F-1)

wherein all symbols have the same meanings as described above, and a compound represented by formula (15):

 —CHO (15)

wherein all symbols have the same meanings as described above, to the reductive amination reaction, and if necessary to the deprotection reaction of a protective group and/or the cleavage reaction from a resin.

The reductive amination reaction, the deprotection reaction of a protective group, or the cleavage reaction from the resin can be carried out by the same method as described above.

Among the compound of the present invention represented by formula (I-0), a compound wherein a basic group in a $J^0$ group is a di-substituted amino group, namely, a compound represented by formula (I-G):

(I-G)

wherein $R^{F2}$ represents a substituent in the "di-substituted amino group" defined in $J^0$; and other symbols have the same meanings as described above, can be prepared by subjecting the compound prepared by the above method, namely, a compound represented by formula (I-F) and a compound represented by formula (16):

—CHO (16)

wherein all symbols have the same meanings as described above, to the reductive amination reaction, and if necessary to the deprotection reaction of a protective group and/or the cleavage reaction from a resin.

The reductive amination reaction, the deprotection reaction of a protective group, or the cleavage reaction from the resin can be prepared by the same method as described above.

A compound represented by formula (I-G) wherein $R^{F1}$ and $R^{F2}$ represent the same substituent can be prepared by subjecting a compound represented by formula (I-F-1) and 2 or more equivalents of a compound represented by formula (15) or formula (16) to the reductive amination reaction, and if necessary to the deprotection reaction of a protective group and/or the cleavage reaction from a resin.

The reductive amination reaction, the deprotection reaction of a protective group, or the cleavage reaction from the resin can be prepared by the same method as described above.

Among the compound of the present invention represented by formula (I-0), a compound wherein $A^1$ and $A^2$ represent an imidazol-2-yl group, namely, a compound represented by formula (I-H):

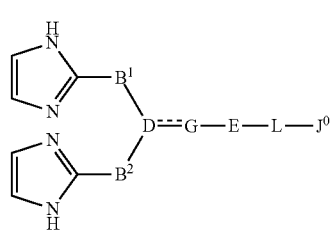
(I-H)

wherein all symbols have the same meanings as described above, can be prepared by subjecting a compound represented by formula (17):

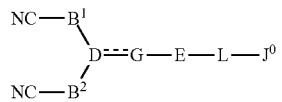
(17)

wherein all symbols have the same meanings as described above, to the cyclization reaction, using [2,2-bis(methyloxy)ethyl]amine or [2,2-bis(ethyloxy)ethyl]amine, and if necessary to the deprotection reaction of a protective group and/or the cleavage reaction from a resin.

This cyclization reaction is known and is carried out, for example, by improving a method described in *Synthesis*, 2001, (10), 1546-1550. For example, it is carried out by reacting a nitrile compound in an organic solvent (methanol, ethanol, etc.) at 0 to 40° C. in the presence of a base (sodium methoxide, sodium ethoxide, etc.), and reacting the solution at 40 to 150° C. in the presence of an acetal and a dehydrating agent (acetic acid, etc.). The deprotection reaction of a protective group or the cleavage reaction from the resin can be carried out by the same method as described above.

Among the compound of the present invention represented by formula (I-0), a compound wherein ---- represents a double bond, D represents a carbon atom, and G represents a nitrogen atom, namely, a compound represented by formula (I-J):

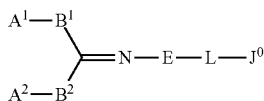   (I-J)

wherein all symbols have the same meanings as described above, can be prepared by subjecting a compound represented by formula (18):

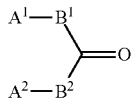   (18)

wherein all symbols have the same meanings as described above, and a compound represented by formula (19):

$H_2N\text{-}E\text{-}L\text{-}J^0$   (19)

wherein all symbols have the same meanings as described above, to the imination reaction, and if necessary to the deprotection reaction of a protective group and/or the cleavage reaction from a resin.

The imination reaction is known and is carried out, for example, in an organic solvent (methanol, ethanol, dichloromethane, chloroform, dichloroethane, benzene, toluene, etc.) at 20° C. to reflux temperature in the presence or absence of a dehydrating agent (anhydrous magnesium sulfate, Molecular Sieve (trade name), etc.) and an acid (hydrochloric acid, acetic acid, etc.).

Among the compound of the present invention represented by formula (I-0), a compound wherein D is a nitrogen atom and a divalent group adjacent to D in $B^1$ is —CO—, namely, a compound represented by formula (I-K):

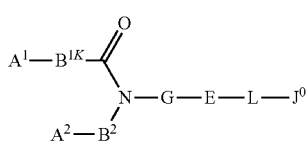   (I-K)

wherein $B^{1K}$ represents a bond or a spacer having 1 to 3 atom(s) in its main chain; and other symbols have the same meanings as described above, can be prepared by subjecting a compound represented by formula (20):

$A^2\text{-}B^2\text{—NH-G-E-L-}J^0$   (20)

wherein all symbols have the same meanings as described above, and a compound represented by formula (21):

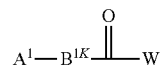   (21)

wherein all symbols have the same meanings as described above, to the amidation reaction, and if necessary to the deprotection reaction of a protective group and/or the cleavage reaction from a resin.

The amidation reaction, the deprotection reaction of a protective group, or the cleavage reaction from the resin can be carried out by the same method as described above.

Among the compound of the present invention represented by formula (I-0), a compound wherein D is a nitrogen atom and a divalent group adjacent to D in B' is —SO$_2$—, namely, a compound represented by formula (I-L):

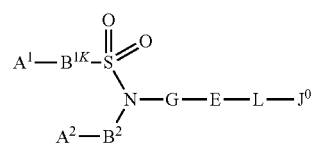   (I-L)

wherein $B^{1L}$ represents a bond or a spacer having 1 to 3 atom(s) in its main chain; and other symbols have the same meanings as described above, can be prepared by subjecting a compound represented by formula (20) and a compound represented by formula (22):

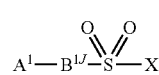   (22)

wherein all symbols have the same meanings as described above, to the sulfonamidation reaction, and if necessary to the deprotection reaction of a protective group and/or the cleavage reaction from a resin.

The sulfonamidation reaction, the deprotection reaction of a protective group, or the cleavage reaction from the resin can be carried out by the same method as described above.

Among the compound represented by formula (I-0), a compound wherein ---- represents a single bond;

D represents a nitrogen atom;

G represents one carbon atom which may have a substituent(s), and a divalent group adjacent to D in $B^1$; and $B^2$ is —CH$_2$—, namely, a compound represented by formula (I-M):

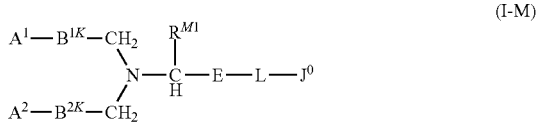

(I-M)

wherein $B^{K2}$ represents a bond or a spacer having 1 to 3 atom(s) in its main chain;

$R^{M1}$ represents a hydrogen atom or a substituent in the "carbon atom which may have a substituent(s)" defined in G; and other symbols have the same meanings as described above, can be prepared by subjecting a compound represented by formula (23):

(23)

wherein all symbols have the same meanings as described above, and a compound represented by formula (24):

(24)

wherein all symbols have the same meanings as described above, to the reductive amination reaction, and if necessary to the deprotection reaction of a protective group and/or the cleavage reaction from the resin.

The reductive amination reaction, the deprotection reaction of a protective group, or the method for cleavage from the resin can be carried out by the same reaction as described above.

A compound represented by formula (I-M) can be prepared by subjecting a compound represented by formula (25):

(25)

wherein all symbols have the same meanings as described above, and a compound represented by formula (26):

(26)

wherein all symbols have the same meanings as described above, to the reductive amination reaction, subjecting the obtained compound and a compound represented by formula (27):

(27)

wherein all symbols have the same meanings as described above, to the reductive amination reaction, and if necessary to the deprotection reaction of a protective group and/or the cleavage reaction from the resin.

The reductive amination reaction, the deprotection reaction of a protective group, or the cleavage reaction from the resin can be carried out by the same method as described above.

A compound represented by formula (I-M) wherein a $A^1$-$B^{1K}$—$CH_2$ group and a $A^2$-$B^{2K}$—$CH_2$ group represent the same substituent can be prepared by subjecting a compound represented by formula (25) and 2 or more equivalents of a compound represented by formula (26) or formula (27) to the reductive amination reaction, and if necessary to the deprotection reaction of a protective group and/or the cleavage reaction from the resin.

The reductive amination reaction, the deprotection reaction of a protective group, or the cleavage reaction from the resin can be carried out by the same method as described above.

The compounds represented by formulas (2) to (27) used as other starting materials or reagents can be easily prepared by using per se known methods or known methods, for example, methods described in Comprehensive Organic Transformations: A Guide to Functional Group Preparations, Second edition (written by Richard C. Larock, John Wiley & Sons Inc, 1999) in combination.

In the respective reactions in the present specification, as is apparent to those skilled in the art, the reaction with heating can be carried out using a water bath, an oil bath, a sand bath, or microwave.

In the respective reactions in the present specification, a solid phase supported reagent obtained by supporting on a polymer (for example, polystyrene, polyacrylamide, polypropylene, polyethylene glycol, etc.) may be used.

In the respective reactions in the present specification, the reaction product can be purified by conventional purification means, for example, distillation under normal pressure or reduced pressure, high performance liquid chromatography using a silica gel or magnesium silicate, thin layer chromatography, ion-exchange resin, scavenger resin or chromatography or washing, or recrystallization. The purification may be carried out for every reaction, or may be carried out after the completion of some reactions.

In the reaction using a polystyrene resin in the present specification, the reaction product can be purified by conventional purification methods, for example, washing plural times with a solvent (N,N-dimethyl formamide, dichloromethane, methanol, tetrahydrofuran, toluene, acetic acid/toluene, etc.).

[Toxicity]

The compound of the present invention has very low toxicity and is considered to be safe enough for pharmaceutical use.

[Application to Pharmaceuticals]

The compound of the present invention has CXCR4 antagonistic activity in an animal including human, particularly human, and is therefore effective, for example, for a preventive and/or therapeutic agent for inflammatory and immune diseases, allergic diseases, infections, particularly HIV infection, and diseases associated with the infection, psychoneurotic diseases, cerebral diseases, cardiovascular diseases, metabolic diseases, and cancerous diseases. Also, the compound is useful as an agent for regeneration therapy for the purpose of in vitro or in vivo amplification of stem cells for gene therapy as well as peripheral blood stem cells mobilization and tissue repair. The compound is particularly useful as an agent for transplantation medical treatment used in organ transplantation including bone marrow transplantation, peripheral blood stem cell transplantation and tissue repair among in the regeneration therapy. Furthermore, the compound is useful as an antiangiogenic agent which is effective for prevention and/or treatment of diseases associated with neoangiogenesis, such as retinopathy (diabetic retinopathy, aged macular degeneration, glaucoma, etc.) and cancer proliferation.

Examples of the inflammatory and immune disease include rheumatoid arthritis, arthritis, retinopathy, gout, replacement organ rejection, graft-versus-host disease (GVHD), nephritis, psoriasis, rhinitis, conjunctivitis, multiple sclerosis, ulcerative colitis, Crohn's disease, shock associated with bacterial infection, pulmonary fibrosis, systemic inflammatory response syndrome (SIRS), acute lung injury, and diabetes.

Examples of the allergic disease include asthma, atopic dermatitis, rhinitis, and conjunctivitis Examples of the disease associated with infection, particularly HIV infection, include acquired immunodeficiency syndrome (AIDS), candidiasis, *Pneumocystis carinii* pneumonia, Cytomegalovirus retinitis, Kaposi's sarcoma, malignant lymphoma, AIDS encephalopathy, and bacterial sepsis.

Examples of the psychoneurotic disease and cerebral disease include dementia including Alzheimer's disease, Parkinson's disease, stroke, cerebral infarction, cerebral hemorrhage, epilepsy, schizophrenia, and peripheral nerve disorder.

Examples of the cardiovascular disease include arteriosclerosis, ischemia reperfusion, hypertension, myocardial infarction, stenocardia, and heart failure.

Examples of the metabolic diseases include diabetes, osteoporosis, enlarged prostate, and frequent micturition.

Examples of the cancerous disease include malignant tumor such as breast cancer or malignant lymphoma, cancer metastasis, and myelosuppression or thrombocytopenia after radiation therapy/chemotherapy.

The compound of the present invention may be administered as a concomitant drug by using in combination with other drugs for the purpose of:
1) complementation and/or enhancement of the preventive and/or therapeutic effects of the compound,
2) improvement of pharmacokinetics and absorption of the compound and reduction of the dosage, and/or
3) reduction of side effects of the compound.

Also, the compound of the present invention may be administered as a concomitant drug by using in combination with other drugs the purpose of (1) complementation and/or enhancement of preventive and/or therapeutic effects, (2) improvement of pharmacokinetics and absorption of the compound and reduction of the dosage, and/or (3) reduction of side effects.

The concomitant drug of the compound of the present invention and other drugs may be administered in the form of a compounding agent(s) comprising both these components, or may be in the form of separately. In case of separately administering a preparation, simultaneous administration and administration with time-lag are included. In case of administration with time-lag, other drugs may be administered after the compound of the present invention is administered, or the compound of the present invention may be administered after other drugs may be administered. The administration method may be the same or different.

The disease, on which the preventive and/or therapeutic effects are exerted by the concomitant drug, is not specifically limited, and may be any disease which complements and/or enhances the preventive and/or therapeutic effects of the compound of the present invention.

A mass ratio of the compound of the present invention drug to other drugs is not specifically limited.

A combination of any two or more kinds other drugs may be administered.

The other drugs, which complements and/or enhances the preventive and/or therapeutic effects of the compound of the present invention, includes not only those which have ever been found based on the above described mechanism, but also those which may be found in future.

Examples of the preventive and/or therapeutic agents for HIV infection and acquired immunodeficiency syndrome, which is used in combination of the compound of the present invention, include reverse transcriptase inhibitors, protease inhibitors, chemokine (for example, CCR2, CCR3, CCR4, CCR5, CXCR4, etc.) antagonists, CD4 antagonists, antibody against surface antigen of HIV (for example, HIV-1, HIV-2, etc.) and vaccine of HIV (for example, HIV-1, HIV-2, etc.).

Examples of the reverse transcriptase inhibitors include (1) nucleoside reverse transcriptase inhibitors such as zidovudine (trade name: Retrovir), didanosine (trade name: Videx), zalcitabine (trade name: Hivid), stavudine (trade name: Zerit), lamivudine (trade name: Epivir), abacavir (trade name: Ziagen), didanosine (trade name: videx), adefovir, dipivoxil, emtricitabine (trade name: coviracil), tenofovir (trade name: viread), Combivir, Trizivir, truvada, or epzicom, (2) non-nucleoside reverse transcriptase inhibitors such as nevirapine (trade name: viramune), delavirdine (trade name: Rescriptor), efavirenz (trade name: Sustiva, Stocrin), or capravirine (AG1549).

Examples of the protease inhibitors include indinavir (trade name: Kurikisiban), ritonavir (trade name: norvir), nelfinavir (trade name: Viracept), saquinavir (trade name: Invirase, Fortovase), amprenavir (trade name: agenerase), lopinavir (trade name: Kaletra), atazanavir (trade name: Reyataz), fosamprenavir (trade name: lexiva), tipranavir and the like.

Examples of the chemokine antagonists include endogenous ligands of a chemokine receptor, or derivatives and nonpeptidic low molecular compounds thereof, or an antibody against a chemokine receptor.

Examples of the endogenous ligands of the chemokine receptor include MIP-1α, MIP-1β, RANTES, SDF-1α, SDF-1β, MCP-1, MCP-2, MCP-4, eotaxin, MDC and the like.

Examples of the derivative of the endogenous ligands include AOP-RANTES, Met-SDF-1α, Met-SDF-1β and the like.

Examples of the antibody of the chemokine receptor include Pro-140 and the like.

Examples of the CCR2 antagonists include compounds described in WO99/07351, WO99/40913, WO00/46195, WO00/46196, WO00/46197, WO00/46198, WO00/46199, WO00/69432, WO00/69815, and Bioorg. Med. Chem. Lett., 10, 1803 (2000), and the like.

Examples of the CCR3 antagonists include compounds described in DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/53172, WO00/53600, WO00/58305, WO00/59497, WO00/59498, WO00/59502, WO00/59503, WO00/62814, WO00/73327, and WO01/09088, and the like.

Examples of the CCR4 antagonists include compounds described in WO02/030357 and WO02/030358, and the like.

Examples of the CCR5 antagonists include compounds described in WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP2000-309598, WO00/51607, WO00/51608, WO00/51609, WO00/51610, WO00/56729, WO00/59497, WO00/59498, WO00/59502, WO00/59503, WO00/76933, WO98/25605, WO99/04794, WO99/38514 and Bioorg. Med. Chem. Lett., 10, 1803 (2000), TAK-779, SCH-351125 (SCH—C), SCH-417690 (SCH-D), UK-427857, GW 873140A (ONO-4128), TAK-220, TAK-652, and the like.

Examples of the CXCR4 antagonists include AMD-3100, AMD-070, T-22, KRH-1120, KRH-1636, KRH-2731, CS-3955, and compounds described in WO00/66112, WO2004/024697 and WO2004/052862, and the like.

Examples of the fusion inhibitors include T-20 (pentafuside) T-1249, and the like.

Examples of the HIV integrase inhibitors include Equisetin, Temacrazine, PL-2500, V-165, NSC-618929, L-870810, L-708906 analog, S-1360, 1838 and the like.

Examples of the Short Interfering RNA include Short Interfering RNA directed against HIV-1, HIV-1 constituent protein, genome HIV RNA, and the like.

The conventional clinical dosage of typical reverse transcriptase inhibitors and protease inhibitors is, for example, as described below, but is not limited thereto in the present invention.

Zidovudine: 100 mg capsule, three times per day in a diosage of 200 mg; 300 mg tablet, twice per day in a dosage of 300 mg;
Didanosine: 25 to 200 mg tablet, twice per day in a dosage of 125 to 200 mg;
Zalcitabine: 0.375 mg to 0.75 mg tablet, three times per day in a dosage of 0.75 mg;
Stavudine: 15 to 40 mg capsule, twice per day in a dosage of 30 to 40 mg;
Lamivudine: 150 mg tablet, twice per day in a dosage of 150 mg;
Abacavir: 300 mg tablet, twice per day in a dosage of 300 mg;
Nevirapine: 200 mg tablet, once per day for 14 days in a dosage of 200 mg, followed by twice per day;
Delavirdine: 100 mg tablet, three times per day in a dosage of 400 mg;
Efavirenz: 50 to 200 mg capsule, once per day in a dosage of 600 mg;
Indinavir: 200 to 400 mg capsule, three times per day in a dosage of 800 mg;
Ritonavir: 100 mg capsule, twice per day in a dosage of 600 mg;
Nelfinavir: 250 mg tablet, three times per day in a dosage of 750 mg;
Saquinavir: 200 mg capsule, three times per day in a dosage of 1,200 mg;
Amprenavir: 50 to 150 mg tablet, twice per day in a dosage of 1,200 mg.

Examples of the other drugs for complementation and/or enhancement of the preventive and/or therapeutic effects of the compound of the present invention against asthma include antihistaminic agents, antiallergic agents (chemical mediator release inhibitors, histamine antagonists, thromboxane synthetase inhibitors, thromboxane antagonists, Th2 cytokine inhibitors), steroids, bronchodilator agents (xanthine derivatives, sympathomimetic agents, parasympathomimetic agents), vaccinotherapeutic agents, gold preparations, Chinese medicines, basic nonsteroidal anti-inflammatory drugs, 5-lipoxygenase inhibitors, 5-lipoxygenase activation protein antagonists, leukotriene synthesis inhibitors, prostaglandins, cannabinoid-2 receptor stimulants, antitussive drugs, expectorants, and the like.

Examples of the antihistaminic agents include diphenhydramine, diphenylpyraline hydrochloride, diphenylpyraline chlorotheophyllinate, clemastine fumarate, dimenhydrinate, dl-chlorpheniramine maleate, d-chlorpheniramine maleate, triprolidine hydrochloride, promethazine hydrochloride, alimemazine tartrate, isothipendyl hydrochloride, homochlorcyclizine hydrochloride, hydroxyzine, cyproheptadine hydrochloride, levocabastine hydrochloride, astemizole, bepotastine, desloratadine, TAK-427, ZCR-2060, NIP-530, mometasone furoate, mizolastine, BP-294, andolast, auranofin, acrivastine and the like.

Examples of the chemical mediator release inhibitors include disodium cromoglycate, tranilast, amlexanox, repirinast, ibudilast, pemirolast potassium, tazanolast, nedocromil, cromoglicate, israpafant and the like.

Examples of the histamine antagonists include ketotifen fumarate, azelastine hydrochloride, oxatomide, mequitazine, terfenadine, emedastine fumarate, epinastine hydrochloride, ebastine, cetirizine hydrochloride, olopatadine hydrochloride, loratadine, fexofenadine and the like.

Examples of the thromboxane synthetase inhibitors include ozagrel hydrochloride imitrodast sodium and the like.

Examples of the thromboxane antagonists include seratrodast, ramatroban, domitroban calcium hydrate, KT-2-962 and the like.

Examples of the Th2 cytokine inhibitors include suplatast tosilate and the like.

Examples of the steroids include, for example, external medicine such as clobetasol propionate, diflorasone diacetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclometasone dipropionate, triamcinolone acetonide, flumetasone pivalate, alclometasone propionate, clobetasone butyrate, prednisolone, beclomethasone propionate, fludroxycortide, and the like.

Examples of drugs for internal use and injections include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methyl prednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone and the like.

Examples of the inhalations include beclometasone dipropionate, fluticasone propionate, budesonide, flunisolide, triamcinolone, ST-126P, ciclesonide, dexamethasone palmitate, mometasone furoate, prasterone sulfonate, deflazacort, methylprednisolone suleptanate, methylprednisolone sodium succinate and the like.

Examples of the xanthine derivative include aminophylline, theophylline, doxophylline, cipamfylline, diprophylline, proxyphylline, and choline theophylline.

Examples of the sympathomimetic agents include epinephrine, ephedrine hydrochloride, dl-methylephedrine hydrochloride, methoxyphenamine hydrochloride, isoproterenol sulfate, isoproterenol hydrochloride, orciprenaline sulfate, chloroprenaline hydrochloride, trimetoquinol hydrochloride, salbutamol sulfate, terbutaline sulfate, hexoprenaline sulfate, tulobuterol hydrochloride, procaterol hydrochloride, fenoterol hydrobromate, formoterol fumarate, clenbuterol hydrochloride, mabuterol hydrochloride, salmeterol xinafoate, R,R-formoterol, tulobuterol, pirbuterol hydrochloride, ritodrine hydrochloride, bambuterol, dopexamine hydrochloride, meluadrine tartrate, AR-C68397, levosalbutamol, KUR-1246, KUL-7211, AR-C89855, S-1319 and the like.

Examples of the parasympathomimetic agents include ipratropium bromide, flutropium bromide, oxitropium bromide, cimetropium bromide, temiverine, tiotropium bromide, revatropate (UK-112166) and the like.

Examples of the vaccinotherapeutic agents include paspat, asthremedin, Broncasma Berna, CS-560 and the like.

Examples of the gold preparations include gold sodium thiomalate and the like. Examples of the basic nonsteroidal anti-inflammatory drugs include tiaramide hydrochloride, tinoridine hydrochloride, epirizole, emorfazone and the like.

Examples of the 5-lipoxygenase inhibitors include zyleuton, docebenone, piriprost, SCH-40120, WY-50295, E-6700, ML-3000, TMK-688, ZD-2138, dalbufelone mesilate, R-68151, E-6080, DuP-654, SC-45662, CV-6504, NE-11740, CMI-977, NC-2000, E-3040, PD-136095, CMI-392, TZI-41078, Orf-20485, IDB-18024, BF-389, A-78773, TA-270, FLM-5011, CGS-23885, A-79175, ETH-615 and the like.

Examples of the 5-lipoxygenase activation protein antagonists include MK-591, MK-886 and the like.

Examples of the leukotriene synthesis inhibitors include auranofin, proglumetacin maleate, L-674636, A-81834, UPA-780, A-93178, MK-886, REV-5901A, SCH-40120, MK-591, Bay-x-1005, Bay-y-1015, DTI-0026, Amlexanox, E-6700 and the like.

Examples of the prostaglandins (hereinafter abbreviated to as PG) include PG receptor agonists, PG receptor antagonists and the like.

Examples of the PG receptor include PGE receptor (EP1, EP2, EP3, and EP4), PGD receptor (DP, CRTH2), PGF receptor (FP), PGI receptor (IP), TX receptor (TP) and the like.

Examples of the antitussive drugs include codeine phosphate, dihydrocodeine phosphate, oxymetebanol, dextromethorphan hydrobromate, pentoxyverine citrate, dimemorfan phosphate, oxeladin citrate, cloperastine, benproperine phosphate, clofedanol hydrochloride, fominoben hydrochloride, noscapine, tipepidine hibenzate, eprazinone hydrochloride, plantago herb extract and the like.

Examples of the expectorants include foeniculated ammonia spirit, sodium hydrogencarbonate, potassium iodide, bromhexine hydrochloride, cherry bark extract, carbocysteine, fudosteine, ambroxol hydrochloride, ambroxol hydrochloride sustained-release tablet, methylcysteine hydrochloride, acetylcysteine, L-ethylcysteine hydrochloride, tyloxapol and the like.

Examples of the other drugs for complementation and/or enhancement of the preventive and/or therapeutic effects against atopic dermatitis (urticaria, etc.) of the compound of the present invention include steroids, non-steroid anti-inflammatory drug (NSAID), immune inhibitor, prostaglandins, antiallergic agent, mediator release inhibitor, antihistaminic agent, forskolin preparation, phosphodiesterase inhibitor, and cannabinoid-2 receptor stimulant.

Examples of the other drugs for complementation and/or enhancement of the preventive and/or therapeutic effects against allergic diseases (allergic bronchopulmonary aspergillosis, allergic eoisinophilic gastroenteritis, etc.) of the compound of the present invention include antiasthmatic drug, inhaled steroid drug, inhaled β2 stimulant, methylxanthine-based stimulant, antiallergic agent, anti-inflammatory agent, anticholinergic agent, thromboxane antagonist, leukotriene antagonist, LTD4 antagonist, PAF antagonist, phosphodiesterase inhibitor, β2 agonist, steroid drug, mediator release inhibitor, eosinophile leukocytechemotaxis inhibitor, macrolide-based antibiotic, immune inhibitor, hyposensitization (allergen) injection and the like.

Examples of the antiasthmatic drug include theophylline, procaterol, ketotifen, azelastine and the like.

Examples of the inhaled steroid drug include beclomethasone, fluticasone, budesonide and the like.

Examples of the inhaled β2 stimulant include fenoterol, salbutamol, formoterol, salmeterol and the like.

Examples of the methylxanthine-based stimulant include theophylline and the like.

Examples of the antiallergic agent include ketotifen, terfenadine, azelastine, epinastine, suplatast, disodium cromoglycate and the like.

Examples of the anti-inflammatory agent include dichlofenac sodium, ibuprofen, indomethacin and the like.

Examples of the anticholinergic agent include ipratropium bromide, flutropium bromide, oxitropium bromide, tiotropium bromide and the like.

Examples of the thromboxane antagonist include ozagrel, seratrodast and the like.

Examples of the leukotriene antagonist include pranlukast, montelukast, z afirlukast, zyleuton and the like.

Examples of the macrolide-based antibiotic include erythromycin, roxithromycin and the like.

Examples of the immune inhibitor include cyclosporine, tacrolimus, FTY720, and the like.

Examples of the other drug for complementation and/or enhancement of the preventive and/or therapeutic effects against hepatitis of the compound of the present invention include liver hydrolysate preparation, polyenephosphatidylcholine, glycyrrhizin preparation, protoporphyrin sodium, ursodeoxycholic acid, steroids, anticholinergic agent, gastric antiacid, propagermanium, lipid peroxidase inhibitor, and mitochondrial benzodiazepine receptor antagonist.

Examples of the other drug for complementation and/or enhancement of the preventive and/or therapeutic effects against arthritis and rheumatoid arthritis of the compound of the present invention include metalloproteinase inhibitor, immune inhibitor, non-steroid anti-inflammatory drug (NSAID), steroid drug, prostaglandins, phosphodiesterase inhibitor, cannabinoid-2 receptor stimulant, disease modifying anti-rheumatic drug (slow-acting anti-rheumatic drug), anti-inflammatory enzyme preparation, cartilage protective agent, T cell inhibitor, TNFα inhibitor, prostaglandin synthetase inhibitor, IL-6 inhibitor, interferon γ agonist, IL-1 inhibitor and the like.

Examples of the other drug for complementation and/or enhancement of the preventive and/or therapeutic effects against psoriasis of the compound of the present invention include steroid drug, vitamin D derivative and the like.

Examples of the other drug for complementation and/or enhancement of the preventive and/or therapeutic effects against rhinitis of the compound of the present invention include antihistaminic agent, mediator release inhibitor, thromboxane synthetase inhibitor, thromboxane $A_2$ receptor antagonist, leukotriene receptor antagonist, steroids, α adrenalin receptor stimulant, xanthine derivative, anticholinergic agent, prostaglandins, nitrogen monoxide synthetase inhibitor, $β_2$ adrenalin receptor stimulant, phosphodiesterase inhibitor, cannabinoid-2 receptor stimulant and the like.

Examples of the other drug for complementation and/or enhancement of the preventive and/or therapeutic effects against conjunctivitis of the compound of the present invention include leukotriene receptor antagonist, antihistaminic agent, mediator release inhibitor, non-steroid anti-inflammatory drug, prostaglandins, steroid drug, nitrogen monoxide synthetase inhibitor, cannabinoid-2 receptor stimulant and the like.

Examples of the other drug for complementation and/or enhancement of the preventive and/or therapeutic effects against multiple sclerosis of the compound of the present invention include immune inhibitor, cannabinoid-2 receptor stimulant and the like.

Examples of the other drug for complementation and/or enhancement of the preventive and/or therapeutic effects against ulcerative colitis of the compound of the present invention include mesalazine, salazosulfapyridine, digestive tract ulcer therapeutic substance, anticholinergic agent, steroid drug, 5-lipoxygenase inhibitor, antioxidant, LTB4 antagonist, local anesthetic, immune inhibitor, protection factor enhancer, MMP inhibitor, and mitochondrial benzodiazepine receptor antagonist.

Examples of the other drug for complementation and/or enhancement of the preventive and/or therapeutic effects against diabetic complication of the compound of the present invention include sulfonyl urea-based hypoglycemic agent, biguanide-based drug, α-glucosidase inhibitor, ultrashort-acting insulinotropic agent, insulin drug, PPAR agonist, insulin sensitive enhancer having no PPAR antagonism, β3 adrenalin receptor agonist, aldose reductase inhibitor, dipeptidyl peptidase IV inhibitor and the like.

Examples of the sulfonyl urea-based hypoglycemic agent include acetohexamide, glibenclamide, gliclazide, glyclopyramide, chlorpropamide, tolazamide, tolbutamide, Glimepiride and the like.

Examples of the biguanide-based drug include buformin hydrochloride, metformin hydrochloride and the like.

Examples of the α-glucosidase inhibitor include acarbose, voglibose and the like.

Examples of the ultrashort-acting insulinotropic agent include nateglinide, repaglinide and the like.

Examples of the PPAR agonist include pioglitazone, troglitazone, rosiglitazone, JTT-501, and the like.

Examples of the insulin sensitive enhancer having no PPAR antagonism include ONO-5816, YM-440 and the like.

Examples of the β3 adrenalin receptor agonist include AJ9677, L750355, and CP331648.

Examples of the aldose reductase inhibitor include epalrestat, fidarestat, zenarestat and the like.

Examples of the other drug for complementation and/or enhancement of the preventive and/or therapeutic effects against cancer (malignant tumor) and cancer metastasis of the compound of the present invention include anticancer agent (for example, MMP inhibitor, alkylation agent (for example, cyclophosphamide, melphalan, thiotepa, mytomycin C, busulfan, procarbazine hydrochloride, etc.), antimetabolite (for example, methotrexate, mercaptpurine, azathiopurine, fluorouracil, tegafur, cytarabine, azaserine, etc.), antibiotic (for example, mytomycin C, bleomycin, Peplomycin, doxorubicin hydrochloride, aclarubicin, daunorubicin, actinomycin D, etc.), mitosis inhibitor, platinum complex (for example, Cisplatin), plant-derived antineoplastic agent (for example, vincristine sulfate, vinblastine sulfate, etc.), anti-cancerous hormone (for example, methyltestosterone, testosterone propionate, testosterone enanthate, mepitiostane, fosfestrol, chlormadinone acetate, etc.), immunopotentiator (for example, picibanil, krestin, etc.), and interferon (for example, IFNα, IFNα-2a, IFNα-2b, IFNβ, IFNγ-1a, etc.). Examples thereof include biologics capable of conducting T cell activation (for example, anti-CTLA-4 antibody, anti-PD-1 antibody, etc.), antiangiogenic agent (for example, bevacizumab, pegaptanib, SU-6668, vatalanib, ranibizumab, sorafenib, SU-11248, neovastat), etc.), and the like.

Examples of the other drug for complementation and/or enhancement of treatment including bone marrow transplantation, peripheral blood stem cell transplantation and tissue repair of the compound of the present invention include G-CSF, AMD3100 and the like.

Examples of the other drug for complementation and/or enhancement of the preventive and/or therapeutic effects against immune disease (for example, autoimmune disease, transplanted organ rejection, etc.) of the compound of the present invention include immune inhibitor (for example, cyclosporine, tacrolimus, FTY720, etc.).

Examples of the other drug for complementation and/or enhancement of the preventive and/or therapeutic effects against dementia such as Senile dementia with Alzheimer's type of the compound of the present invention include acetylcholine esterase inhibitor, nicotinic receptor modifier, cerebral ameliorator, monoamineoxidase inhibitor, vitamin E, aldose reductase inhibitor and the like.

Examples of the other drug for complementation and/or enhancement of the preventive and/or therapeutic effects against epilepsia of the compound of the present invention include phenyloin, trimethadione, ethosuximide, carbamazepine, phenobarbitone, primidone, acetazolamide, sultiame, sodium valproate, clonazepam, diazepam, nitrazepam and the like.

Examples of the other drug for complementation and/or enhancement of the preventive and/or therapeutic effects against arteriosclerosis of the compound of the present invention include HMG-CoA reductase inhibitor, fibrates, probucol preparation, anion-exchange resin, EPA preparation, nicotinic acid preparation, MTP inhibitor, other anti-high cholesterol agent, EDG-2 antagonist and the like.

Examples of the other drug for complementation and/or enhancement of the effects when the compound of the present invention is used in a regeneration therapy include cytokines and various growth factors, for example, various CSFs (for example, G-CSF, GM-CSF, etc.), various interleukins (for example, IL-3, 6, 7, 11, 12, etc.), EPO, TPO, SCF, FLT3 ligand, MIP-1α and the like.

Examples of the other drug for complementation and/or enhancement of the preventive and/or therapeutic effects against retinopathy of the compound of the present invention include antiangiogenic agent (for example, bevacizumab, pegaptanib, SU-6668, vatalanib, ranibizumab, sorafenib, SU-11248, neovastat, etc.) and the like.

The compound of the present invention is safe and has low toxicity and therefore can be administered to human and mammal other than human (for example, rat, mouse, rabbit, sheep, pig, cow, cat, dog, monkey, etc.).

In order to use a pharmaceutical composition comprising the compound of the present invention or a concomitant drug of the compound of the present invention and other drugs, it is commonly administered, systematically or locally, in an oral or parenteral dosage form.

The dosage of the pharmaceutical preparation varies depending on the age, body weight, symptom, the desired therapeutic effect, the route of administration and duration of treatment. For the human adult, the dosage per person is between 0.1 mg and 1000 mg, by oral administration, up to several times per day, between 0.01 mg and 100 mg, by parenteral administration, or continuous administration 1 hour to 24 hours per day from vein.

As a matter of course, since the dosage varies under various conditions as is described above, the dosage may be sometimes sufficient which is smaller than the above range, or sometimes the dosage must be more than the above range.

In case of administering a pharmaceutical composition comprising the compound of the present invention, or a concomitant drug of the compound of the present invention and other drugs, it is used as solid preparations for internal use and solutions for internal use for oral administration, and injections, external preparations, suppositories, ophthalmic solutions, nasal drops, inhalants and the like for parenteral administration.

Examples of the solid preparation for internal use for oral administration include tablets, pills, capsules, powders, and granules. Capsules include hard capsules and soft capsules.

In such a solid preparation for internal use, one or more active substances are used as they are, or used after mixing with excipients (lactose, mannitol, glucose, microcrystalline cellulose, starch, etc.), binders (hydroxypropyl cellulose, polyvinyl pyrrolidone, magnesium aluminometasilicate, etc.), disintegrants (calcium carboxymethyl cellulose, etc.), lubricants (magnesium stearate, etc.), stabilizers and solubilizing agents (glutamic acid, aspartic acid, etc.) and forming into a preparation according to a conventional method. If necessary, the preparation may be coated with a coating agent (saccharose, gelatin, hydroxypropyl cellulose, hydroxypropylmethyl cellulosephthalate, etc.) or may be coated with two or more layers. Furthermore, capsules made of an absorbable substance such as gelatin is included.

The solutions for internal use for oral administration include pharmaceutically acceptable water, suspensions, emulsions, syrups, and elixirs. In such a solution, one or more active substances are dissolved, suspended or emulsified in a diluent used commonly (purified water, ethanol, mixed solution thereof, etc.). Furthermore, this solution may contain humectants, suspending agents, emulsifiers, sweeteners, flavors, aromatics, preservatives, buffers, and the like.

The dosage form of the external preparation for parenteral administration includes, for example, ointment, gel, cream, fomentation, patch, liniment, propellant, inhalant, spray, aerosol, ophthalmic solution, and nasal drop. These products contain one or more active substances and are prepared according to the formulation which is known or commonly used.

An ointment is prepared in accordance with a well known formulation or a commonly employed formulation. For example, it is prepared by triturating or dissolving one or more active substances in a base. An ointment base is selected from well known ones or those commonly employed. For example, those selected from higher fatty acids or higher fatty acid esters (adipic acid, myristic acid, palmitic acid, stearic acid, oleic acid, adipate ester, myristate ester, palmitate ester, stearate ester, oleate ester, etc.), waxes (beeswax, whale wax, ceresin, etc.), surfactants (polyoxyethylene alkyl ether phosphate ester, etc.), higher alcohols (cetanol, stearyl alcohol, cetostearyl alcohol, etc.), silicone oils (dimethylpolysiloxane, etc.), hydrocarbons (hydrophilic petrolatum, white petrolatum, purified lanolin, liquid paraffin, etc.), glycols (ethylene glycol, diethylene glycol, propylene glycol, polyethylene glycol, macrogol, etc.), vegetable oils (castor oil, olive oil, sesame oil, turpentine oil, etc.), animal oils (mink oil, egg yolk oil, squalane, squalene, etc.), water, absorption accelerators, agents for preventing contact dermatitis are used alone or in combination. Furthermore, it may contain humectants, preservatives, stabilizers, antioxidizing agents, flavors, and the like.

A gel is prepared according to the formulation which is known or commonly used. For example, it is prepared by dissolving one or more active substances in a base. A gel base is selected from a base which is known or commonly used. For example, those selected from lower alcohols (ethanol, isopropyl alcohol, etc.), gelling agents (carboxymethyl cellulose, hydroxyethyl cellulose, hydroxypropyl cellulose, ethyl cellulose, etc.), neutralizers (triethanolamine, diisopropanolamine, etc.), surfactants (monostearic acid polyethylene glycol, etc.), gums, water, absorption accelerator, and agent for preventing contact dermatitis are used alone or in combination. Furthermore, it may contain preservatives, antioxidizing agents, and flavoring agent.

A cream is prepared according to the formulation which is known or commonly used. For example, it is prepared by dissolving or emulsifying one or more active substances in a base. A cream base is selected from a base which is known or commonly used. For example, those selected from higher fatty acid esters, lower alcohols, hydrocarbons, polyhydric alcohols (propylene glycol, 1,3-butylene glycol, etc.), higher alcohols (2-hexyl decanol, cetanol, etc.), emulsifiers (polyoxyethylene alkyl ethers, fatty acid esters, etc.), water, absorption accelerators, and agents for preventing contact dermatitis are used alone or in combination. Furthermore, it may contain preservatives, antioxidizing agents, and flavoring agents.

A fomentation is prepared according to the formulation which is known or commonly used. For example, it is prepared by dissolving one or more active substances in a base to obtain a kneaded mixture and spreading the kneaded mixture over a substrate. A fomentation base is selected from a base which is known or commonly used. For example, those selected from thickeners (polyacrylic acid, polyvinyl pyrrolidone, gum arabic, starch, gelatin, methyl cellulose, etc.), humectants (urea, glycerin, propylene glycol, etc.), fillers (kaolin, zinc oxide, talc, calcium, magnesium, etc.), water, solubilizing agents, tackifiers, and agents for preventing contact dermatitis are used alone or in combination. Furthermore, it may contain preservatives, antioxidizing agents, and flavoring agent.

A patch is prepared according to the formulation which is known or commonly used. For example, it is prepared by dissolving one or more active substances in a base, and spreading the solution over a substrate. A patch base is selected from a base which is known or commonly used. For example, those selected from polymer bases, fats and oils, higher fatty acids, tackifiers, and agents for preventing contact dermatitis are used alone or in combination. Furthermore, it may contain preservatives, antioxidizing agents, and flavoring agent.

A liniment is prepared according to the formulation which is known or commonly used. For example, it is prepared by dissolving, suspending or emulsifying one or more active substances in one or more kinds selected from water, alcohol (ethanol, polyethylene glycol, etc.), higher fatty acid, glycerin, soap, emulsifier, and suspending agent. Furthermore, it may contain preservatives, antioxidizing agents, and flavoring agent.

A propellant, an inhalant, and a spray may contain, in addition to a diluent used commonly, a stabilizer such as sodium hydrogensulfite and a buffer capable of imparting isotonicity, for example, an isotonicity such as sodium chloride, sodium citrate or citric acid. The method for producing a spray is described in detail in U.S. Pat. No. 2,868,691 and U.S. Pat. No. 3,095,355.

An injection for parenteral administration includes all injections and also includes a drop. For example, it includes intramuscular injection, subcutaneous injection, endodermic injection, intraarterial injection, intravenous injection, intraperitoneal injection, intraspinal injection, and intravenous drop.

The injection for parenteral administration includes solutions, suspensions, emulsions, and solid injections used by dissolving or suspending in a solvent before use. The injection is used after dissolving, suspending, or emulsifying one or more active substances in a solvent. As the solvent, for example, distilled water for injection, physiological saline, vegetable oil, and alcohols such as propylene glycol, polyethylene glycol or ethanol are used alone or in combination. Furthermore, the injection may contain stabilizers, solubilizing agents (glutamic acid, aspartic acid, polysolvate 80®, etc.), suspending agents, emulsifiers, soothing agents, buffers, and preservatives. These injections are prepared by sterilizing in the final process, or prepared by an aseptic treatment. Also, a sterile solid, for example, a freeze-dried product is prepared and can be used after dissolving in sterilized distilled water or distilled water for sterile injection, or the other solvent before use.

An ophthalmic solution for parenteral administration includes ophthalmic solution, suspension type ophthalmic solution, emulsion type ophthalmic solution, ophthalmic solution soluble when used, and eye ointment.

These ophthalmic solutions are prepared according to a known method. For example, one or more active substances are dissolved, suspended or emulsified in a solvent before use. As the solvent for ophthalmic solution, for example, sterilized purified water, physiological saline, and other aqueous solvent or non-aqueous agent for injection (for example, vegetable oil, etc.) are used alone or in combination. If necessary, the ophthalmic solution may contain appropriately selected isotonizing agents (sodium chloride, concentrated glycerin, etc.), buffering agents (sodium phosphoate, sodium acetate, etc.), surfactants (polysolvate 80 (trade name), polyoxyl 40 stearate, polyoxyethylene hardened castor oil, etc.), stabilizers (sodium citrate, sodium edetate, etc.), and antiseptics (benzalkonium chloride, paraben, etc.) These ophthalmic solutions are prepared by sterilizing in the final process, or prepared by an aseptic treatment. Also, a sterile solid, for example, a freeze-dried product is prepared and can be used after dissolving in sterilized distilled water or distilled water for sterile injection, or the other solvent before use.

An inhalants for parenteral administration includes aerozol, inhalation powder, and inhalation solution, and the inhalation solution may be such a configuration that it is used after dissolving in water or other suitable medium at the point of use.

These inhalants are prepared according to a known method.

For example, an inhalation solution is prepared by appropriately selecting antiseptics (benzalkonium chloride, paraben, etc.), colorants, buffering agents (sodium phosphate, sodium acetate, etc.), isotonizing agents (sodium chloride, concentrated glycerin, etc.), thickeners (carboxyvinyl polymer, etc.), and absorption accelerator, if necessary.

An inhalation powder is prepared by appropriately selecting lubricants (stearic acid and a salt thereof, etc.), binders (starch, dextrin, etc.), excipients (lactose, cellulose, etc.), colorants, antiseptics (benzalkonium chloride, paraben, etc.), and absorption accelerator if necessary.

In case of administering the inhalation solution, a spraying apparatus (atomizer, nebulizer) is commonly used. In case of administering the inhalation powder, an inhalation administration apparatus for powder is commonly used.

The other composition for parenteral administration includes suppositories for intrarectal injection and pessaries for vaginal administration, which contain one or more active substances and are formulate by a conventional method.

Designation of the compound of the present invention is described below.

The compounds used in the present invention were commonly designated using a computer program ACD/Name Batch® (manufactured by Advanced Chemistry Development Inc.) which designates according to the regulation of IUPAC, or commonly designated according to IUPAC Nomenclature. For example, a compound wherein $A^1$ and $A^2$ represent an imidazol-2-yl group, $B^1$ and $B^2$ represent a methylene group, D represents a nitrogen atom, G represents a carbonyl group, E represents a 1,4-phenylene group, L represents $-CH_2-NH-$, and J represents $-(CH_2)_4-N(CH_2CH_2CH_3)_2$, namely, a compound represented by the following formula:

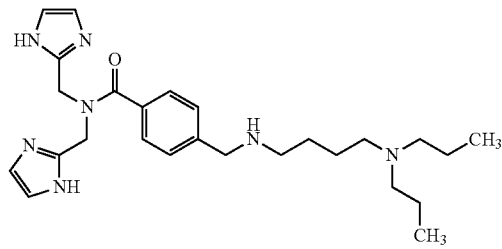 [SMILES: CCCN(CCC)CCCCNCc1ccc(C(=O)N(Cc2ncc[nH]2)Cc2ncc[nH]2)cc1]

is designated as 4-({[4-(dipropylamino)butyl]amino}methyl)-N,N-bis(1H-imidazol-2-ylmethyl)benzamide.

The compound of the present invention has an antagonistic activity against CXCR4 and is therefore useful as a preventive and/or therapeutic agent for diseases associated with CXCR4, namely, CXCR4-mediated diseases.

BEST MODE FOR CARRYING OUT THE INVENTION

The present invention is described in detail based on Examples, but the present invention is not limited thereto.

Crystallinity of the solid product was confirmed using a polarizing microscope.

The point of separation by chromatography and the solvent in the parentheses shown in TLC indicate a dissolution medium or an eluent used, and the proportion indicates a volume ratio.

NMR is a measured value of $^1$HNMR at 300 MHz and the solvent shown in the parentheses of NMR indicates a solvent used in the measurement.

Regarding MS, detection for only positive ions (pos.) was conducted using ESI (electron spray ion) method unless otherwise specified.

HPLC conditions are as follows.
Apparatus used: Waters LC/MS®
Column: Xterra MS $C_{18}$ 5 µM, 3×50 mm I.D.
Flow rate: 1.5 mL/min
Solvent:
Solution A: aqueous 0.1% trifluoroacetic acid solution
Solution B: 0.1% trifluoroacetic acid-acetonitrile solution For one minute after starting the measurement, the mixing ratio of the solution A to the solution B was fixed to 95:5. The mixing ratio of the solution A to the solution B was linearly changed to 5:95 over 3 minutes after fixation. Then, the mixing ratio of the solution A to the solution B was fixed to 5:95 for 0.5 minute. The mixing ratio of the solution A to the solution B was linearly changed to 95:5 for 0.01 minute after fixation.

Example 1

N-(4-methoxybenzyl)-N,N-bis[(1-{[2-(trimethylsilyl)ethoxy]methyl}-1H-imidazol-2-yl)methyl]amine (compound 1)

To a solution of 1-({[2-(trimethylsilyl)ethyloxy]methyl}-1H-imidazole-2-carboaldehyde (CAS Registry Number: 101226-42-0, 1.5 g) and {[4-(methyloxy)phenyl]methyl}amine (0.39 mL) in dichloromethane (containing 1% acetic acid) (10 mL), sodium triacetoxyborohydride (1.91 g) was added. The reaction mixture was stirred at room temperature for 16 hours. The reaction mixture was added by an aqueous 1 N sodium hydroxide solution and then extracted with dichloromethane. The extract thus obtained was washed with saturated brine, dried over anhydrous sodium sulfate and then concentrated. The obtained residue was purified by silica gel column chromatography (ethyl acetate:methanol:triethylamine=1:0:0→10:1:0→10:1:0.1) to obtain the title compound (1.71 g) having the following physical properties.

TLC: Rf 0.51 (chloroform:methanol:28% ammonia water=80:10:1)

NMR (CDCl$_3$): δ 7.20 (d, 2H), 6.97 (m, 4H), 6.83 (d, 2H), 5.11 (s, 4H), 3.82 (s, 4H), 3.78 (s, 3H), 3.60 (s, 2H), 3.24 (m, 4H), 0.77 (m, 4H), −0.05 (s, 18H)

Example 2

N,N-bis[(1-{[2-(trimethylsilyl)ethoxy]methyl}-1H-imidazol-2-yl)methyl]amine (compound 2)

To a solution of the compound 1 (665 mg) in ethanol (5 mL), 20% palladium hydroxide carbon (500 mg) was added under an argon atmosphere. The reaction mixture was stirred under a hydrogen gas atmosphere at 65° C. for 3 hours. The reaction mixture was filtered through Celite (trade name) and then concentrated. The obtained residue was purified by silica gel column chromatography (dichloromethane:methanol:28% ammonia water=10:1:0→80:10:1) to obtain the title compound (467 mg) having the following physical properties.

TLC: Rf 0.32 (chloroform:methanol:28% ammonia water=80:10:1)

NMR (CDCl$_3$): δ 6.97 (m, 4H), 5.35 (s, 4H), 3.47 (m, 4H), 3.18 (m, 4H), 0.88 (m, 4H), −0.03 (s, 18H)

Example 3

Methyl 4-[({4-[(tert-butoxycarbonyl)amino]butyl}amino)methyl]benzoate (compound 3)

The same procedure as a series of reactions of Example 1 was carried out, except that methyl 4-formylbenzoate was used in place of 1-({[2-(trimethylsilyl)ethyloxy]methyl}-1H-imidazole-2-carboaldehyde and 1,1-dimethylethyl(4-aminobutyl)carbamate was used in place of {[4-(methyloxy)phenyl]methyl}amine, to obtain the title compound having the following physical properties.

TLC: Rf 0.45 (chloroform:methanol=10:1)

NMR (CDCl$_3$): δ 7.99 (d, 2H), 7.39 (d, 2H), 4.77 (m, 1H), 3.91 (s, 3H), 3.84 (s, 2H), 3.13 (m, 2H), 2.64 (m, 2H), 1.54 (m, 4H), 1.44 (s, 9H)

Example 4

Methyl 4-[([(benzyloxy)carbonyl]{4-[(tert-butoxycarbonyl)amino]butyl}amino)methyl]benzoate (compound 4)

To a solution of the compound 3 (810 mg) and sodium carbonate (383 mg) in water (5 mL) and tetrahydrofuran (2 mL), benzyl chloroformate (413 μl) was added at 0° C. The reaction mixture was stirred at 0° C. for one hour. The reaction mixture was diluted with ethyl acetate. The organic layer was washed with water and saturated brine, dried over anhydrous sodium sulfate and then concentrated. The obtained residue was purified by silica gel column chromatography (hexane:ethyl acetate=4:1→3:1) to obtain the title compound (1.16 g) having the following physical properties.

TLC: Rf 0.27 (hexane:ethyl acetate=3:1)

NMR (CDCl$_3$): δ 7.97 (m, 2H), 7.27 (m, 7H), 5.17 (m, 2H), 4.53 (s, 2H), 4.41 (m, 1H), 3.91 (s, 3H), 3.26 (m, 2H), 3.09 (m, 2H), 1.47 (m, 4H), 1.43 (s, 9H)

Example 5

4-[([(benzyloxy)carbonyl]{4-[(tert-butoxycarbonyl)amino]butyl}amino)methyl]benzoic acid (compound 5)

To a solution of the compound 4 (1.13 g) in methanol (4 mL), an aqueous 2N sodium hydroxide solution (4 mL) was added. The reaction mixture was stirred at room temperature for 3 hours. The reaction mixture was concentrated. The obtained residue was added by 2N hydrochloric acid and then extracted with ethyl acetate. The extract was washed with saturated brine, dried over anhydrous sodium sulfate and then concentrated to obtain the title compound having the following physical properties.

TLC: Rf 0.51 (chloroform:methanol:acetic acid=90:10:5)

NMR (CDCl$_3$): δ 8.03 (m, 2H), 7.26 (m, 7H), 5.17 (m, 2H), 4.55 (s, 2H), 4.39 (m, 1H), 3.26 (m, 2H), 3.05 (m, 2H), 1.49 (m, 4H), 1.44 (s, 9H)

Example 6

Phenylmethyl({4-[(bis{[1-({[2-(trimethylsilyl)ethyl]oxy}methyl)-1H-imidazol-2-yl]methyl}amino)carbonyl]phenyl}methyl)[4-({[(1,1-dimethylethyl)oxy]carbonyl}amino)butyl]carbamate (compound 6)

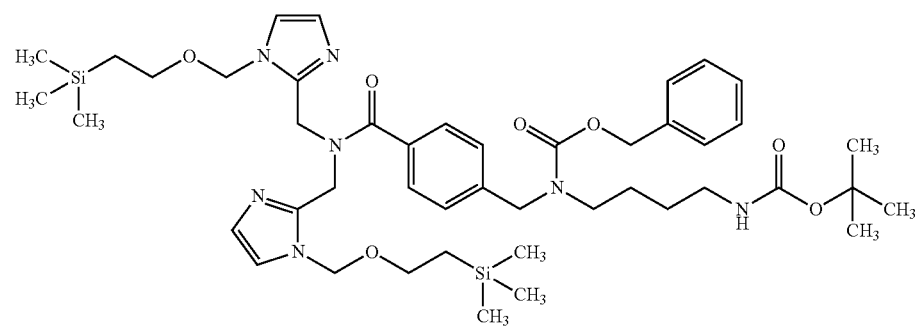 [SMILES: CC(C)(C)OC(=O)NCCCCN(Cc1ccc(C(=O)N(Cc2nccn2COCC[Si](C)(C)C)Cc2nccn2COCC[Si](C)(C)C)cc1)C(=O)OCc1ccccc1]

To a solution of the compound 5 (137 mg) in dichloromethane (3 mL), the compound 2 (131 mg), 1-hydroxybenzotriazole (69 mg), 1-ethyl-3-[3-(dimethylamino)propyl]carbodiimide hydrochloride (86 mg) and diisopropylethylamine (105 µl) were added. The reaction mixture was stirred at room temperature for 5 hours. The reaction mixture was added by water and then extracted with dichloromethane. The extract was washed with saturated brine, dried over anhydrous sodium sulfate and then concentrated. The obtained residue was purified by silica gel column chromatography (hexane: ethyl acetate=100:0→0:100→dichloromethane:methanol=10:1) to obtain the title compound (225 mg) having the following physical properties.

TLC: Rf 0.38 (chloroform:methanol:acetic acid=90:10:5)

NMR (CDCl$_3$): δ 7.33 (m, 9H), 7.16 (m, 4H), 5.55 (s, 2H), 5.15 (s, 4H), 4.89 (m, 2H), 4.47 (s, 2H), 4.41 (m, 1H), 3.60 (m, 4H), 3.22 (m, 6H), 1.58 (m, 4H), 1.44 (s, 9H), −0.92 (m, 4H), 0.05 (s, 18H)

Example 7

Benzyl 4-aminobutyl[4-({bis[(1-{[2-(trimethylsilyl)ethoxy]methyl}-1H-imidazol-2-yl)methyl]amino}carbonyl)benzyl]carbamate (compound 7)

To the compound 6 (225 mg), a solution of 25% trifluoroacetic acid in dichloromethane (6 mL) was added. The reaction mixture was stirred at room temperature for one hour. The reaction mixture was concentrated and the residue was added by 1N sodium hydroxide and then extracted with dichloromethane. The extract was washed with saturated brine, dried over anhydrous sodium sulfate and then concentrated. The obtained residue was purified by silica gel column chromatography (dichloromethane:methanol:28% ammonia water=80:10:1) to obtain the title compound (92 mg) having the following physical properties.

TLC: Rf 0.31 (chloroform:methanol:28% ammonia water=80:10:1)

NMR (CDCl$_3$): δ 7.32 (m, 9H), 7.14 (m, 4H), 5.51 (s, 2H), 5.16 (s, 4H), 4.88 (m, 2H), 4.47 (s, 2H), 3.53 (m, 4H), 3.25 (m, 6H), 1.58 (m, 4H), 0.92 (m, 4H), −0.04 (s, 18H).

Example 8

Benzyl 4-({bis[(1-{[2-(trimethylsilyl)ethoxy]methyl}-1H-imidazol-2-yl)methyl]amino}carbonyl)benzyl[4-(dipropylamino)butyl]carbamate (compound 8)

The same procedure as a series of reactions of Example 1 was carried out, except that 1-propanal was used in place of 1-({[2-(trimethylsilyl)ethyloxy]methyl}-1H-imidazole-2-carboaldehyde and the compound 7 was used in place of {[4-(methyloxy)phenyl]methyl}amine, to obtain the title compound having the following physical properties.

TLC: Rf 0.63 (chloroform:methanol:28% ammonia water=80:10:1)

NMR (CDCl$_3$): δ 7.63 (d, J=8.1 Hz, 2H), 7.29 (m, 7H), 7.02 (m, 4H), 5.51 (m, 2H), 5.17 (s, 4H), 4.84 (m, 2H), 4.66 (s, 2H), 4.47 (s, 2H), 3.53 (m, 2H), 3.35 (m, 2H), 3.24 (m, 2H), 2.58 (m, 6H), 1.55 (m, 8H), 0.92 (m, 6H), 0.76 (m, 4H), 0.03 (s, 18H).

Example 9

4-({[4-(dipropylamino)butyl]amino}methyl)-N,N-bis[(1-{[2-(trimethylsilyl)ethoxy]methyl}-1H-imidazol-2-yl)methyl]benzamide (compound 9)

The same procedure as a series of reactions of Example 2 was carried out, except that the compound 8 was used in place of the compound 1 and 10% palladium carbon was used in place of 20% palladium hydroxide carbon, to obtain the title compound having the following physical properties.

TLC: Rf 0.45 (chloroform:methanol:28% ammonia water=80:10:1)

Example 10

4-({[4-(dipropylamino)butyl]amino}methyl)-N,N-bis(1H-imidazol-2-ylmethyl)benzamide (compound 10)

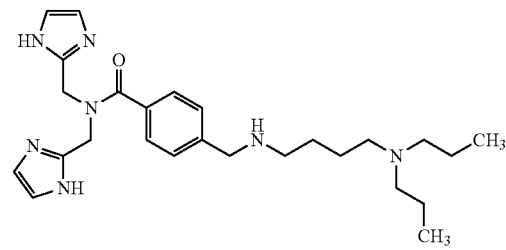 [SMILES: CCCN(CCC)CCCCNCc1ccc(C(=O)N(Cc2ncc[nH]2)Cc2ncc[nH]2)cc1]

To a solution of the compound 9 in methanol (2 mL), concentrated hydrochloric acid (2 mL) was added. The reaction mixture was stirred at 80° C. for 5 hours. The reaction mixture was added by an aqueous 5N sodium hydroxide solution and then extracted with dichloromethane. The extract was washed with saturated brine, dried over anhydrous sodium sulfate and then concentrated. The obtained residue was purified by silica gel column chromatography (dichloromethane:methanol:28% ammonia water=80:10:1→80:20:4) to obtain the title compound (21 mg) having the following physical properties.

TLC: Rf 0.67 (chloroform:methanol:28% ammonia water=80:20:4)

NMR (DMSO-d$_6$): δ 0.80 (t, J=7.20 Hz, 6H), 1.18-1.49 (m, 8H), 2.18-2.36 (m, 6H), 2.39-2.47 (m, 2H), 3.68 (s, 2H), 4.47-4.68 (m, 4H), 6.78-7.18 (m, 4H), 7.32 (d, J=7.80 Hz, 2H), 7.42 (d, J=7.80 Hz, 2H), 11.85-12.96 (m, 2H)

Example 11

4-({[3-(dibutylamino)propyl]amino}methyl)-N,N-bis(1H-imidazol-2-ylmethyl)benzamide (compound 11)

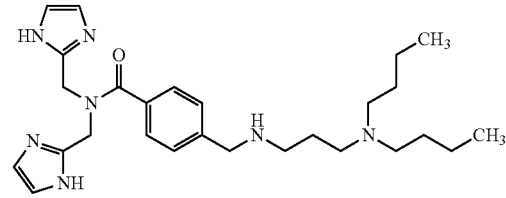 [SMILES: CCCCN(CCCC)CCCNCc1ccc(C(=O)N(Cc2ncc[nH]2)Cc2ncc[nH]2)cc1]

The same procedure as a series of reactions of Example 1 was carried out, except that methyl 4-formylbenzoate was used in place of 1-({[2-(trimethylsilyl)ethyloxy]methyl}-1H-imidazole-2-carboaldehyde and N,N-dibutyl-1,3-propanediamine was used in place of {[4-(methyloxy)phenyl]methyl}amine, to obtain methyl 4-({[3-(dibutylamino)propyl]amino}methyl)benzoate (compound 11-a). The same procedure as a series of reactions of Example 4→Example 5→Example 6→Example 9→Example 10 was carried out, except that the compound 11-a was used in place of the compound 3 in the process of Example 4, to obtain the title compound having the following physical properties.

Description: oily product
TLC: Rf 0.51 (dichloromethane:methanol:28% ammonia water=80:20:3)
NMR (CDCl$_3$): δ 0.89 (t, J=7.2 Hz, 6H), 1.16-1.46 (m, 8H), 1.55-1.72 (m, 2H), 2.31-2.50 (m, 6H), 2.64 (t, J=6.9 Hz, 2H), 3.78 (s, 2H), 4.51-4.77 (m, 4H), 6.89-7.11 (m, 4H), 7.35 (d, J=8.1 Hz, 2H), 7.55 (d, J=8.1 Hz, 2H)

Example 11(1) to Example 11(21)

The same procedure as a series of reactions of Example 11 was carried out, except that a corresponding amine compound was used in place of N,N-dibutyl-1,3-propanediamine, to obtain the following compound of the present invention.

Example 11(1)

4-({[4-(dipropylamino)-4-oxobutyl]amino}methyl)-N,N-bis(1H-imidazol-2-ylmethyl)benzamide (compound 11-1)

Description: amorphous
TLC: Rf 0.58 (dichloromethane:methanol:28% ammonia water=80:20:3);
NMR (CDCl$_3$): δ 0.77-0.98 (m, 6H), 1.40-1.64 (m, 4H), 1.72-1.91 (m, 2H), 2.36 (t, J=7.2 Hz, 2H), 2.68 (t, J=7.2 Hz, 2H), 3.08-3.32 (m, 4H), 3.81 (s, 2H), 4.45-4.80 (m, 4H), 6.92-7.10 (m, 4H), 7.33 (d, J=8.1 Hz, 2H), 7.48 (d, J=8.1 Hz, 2H).

Example 11(2)

4-({[5-(dipropylamino)pentyl]amino}methyl)-N,N-bis(1H-imidazol-2-ylmethyl)benzamide (compound 11-2)

Description: amorphous
TLC: Rf 0.52 (dichloromethane:methanol:28% ammonia water=80:20:3)
NMR (CDCl$_3$): δ 0.86 (t, J=7.5 Hz, 6H), 1.16-1.64 (m, 10H), 2.26-2.48 (m, 6H), 2.60 (t, J=7.2 Hz, 2H), 3.78 (s, 2H), 4.48-4.78 (m, 4H), 6.85-7.10 (m, 4H), 7.33 (d, J=8.1 Hz, 2H), 7.52 (d, J=8.1 Hz, 2H)

Example 11(3)

4-({4-[(dipropylamino)methyl]-1-piperidinyl}methyl)-N,N-bis(1H-imidazol-2-ylmethyl)benzamide (compound 11-3)

Description: amorphous
TLC: Rf 0.40 (methanol:28% ammonia water=99:1);
NMR (CDCl$_3$): δ 0.85 (t, J=7.5 Hz, 6H), 1.04-1.26 (m, 2H), 1.29-1.50 (m, 5H), 1.62-1.80 (m, 2H), 1.83-2.02 (m, 2H), 2.18 (d, J=6.9 Hz, 2H), 2.23-2.37 (m, 4H), 2.72-2.90 (m, 2H), 3.48 (s, 2H), 4.55-4.78 (m, 4H), 6.87-7.12 (m, 4H), 7.35 (d, J=8.1 Hz, 2H), 7.57 (d, J=8.1 Hz, 2H).

Example 11(4)

4-({[4-(dipropylamino)cyclohexyl]amino}methyl)-N,N-bis(1H-imidazol-2-ylmethyl)benzamide (compound 11-4)

Description: amorphous
TLC: Rf 0.22 (methanol:28% ammonia water=99:1)
NMR (CDCl$_3$): δ 0.77-0.92 (m, 6H), 0.99-2.06 (m, 12H), 2.28-2.56 (m, 6H), 3.69-3.89 (m, 2H), 4.52-4.78 (m, 4H), 6.91-7.15 (m, 4H), 7.29-7.45 (m, 2H), 7.48-7.64 (m, 2H)

Example 11(5)

N,N-bis(1H-imidazol-2-ylmethyl)-4-[(2-propyl-2,9-diazaspiro[5.5]undec-9-yl)methyl]benzamide (compound 11-5)

Description: amorphous
TLC: Rf 0.32 (methanol:28% ammonia water=99:1)
NMR (CDCl$_3$): δ 0.87 (t, J=7.5 Hz, 3H), 1.20-1.34 (m, 2H), 1.36-1.64 (m, 8H), 2.01-2.45 (m, 10H), 3.41-3.54 (m, 2H), 4.56-4.77 (m, 4H), 6.89-7.13 (m, 4H), 7.35 (d, J=8.1 Hz, 2H), 7.54 (d, J=8.1 Hz, 2H)

Example 11(6)

N,N-bis(1H-imidazol-2-ylmethyl)-4-[(2-propyl-2,8-diazaspiro[4.5]dec-8-yl)methyl]benzamide (compound 11-6)

Description: amorphous
TLC: Rf 0.13 (methanol:28% ammonia water=99:1);
NMR (CDCl$_3$): δ 0.89 (t, J=7.5 Hz, 3H), 1.40-1.69 (m, 8H), 2.23-2.44 (m, 8H), 2.57 (t, J=6.9 Hz, 2H), 3.46 (s, 2H), 4.55-4.77 (m, 4H), 6.86-7.14 (m, 4H), 7.35 (d, J=8.1 Hz, 2H), 7.56 (d, J=8.1 Hz, 2H)

Example 11(7)

N,N-bis(1H-imidazol-2-ylmethyl)-4-[(4-propyl-1,4-diazepan-1-yl)methyl]benzamide (compound 11-7)

Description: amorphous
TLC: Rf 0.22 (methanol:28% ammonia water=99:1);
NMR (CDCl$_3$): δ 0.87 (t, J=7.5 Hz, 2H), 1.32-1.60 (m, 3H), 1.68-1.85 (m, 2H), 2.34-2.50 (m, 2H), 2.56-2.80 (m, 8H), 3.62 (s, 2H), 4.52-4.80 (m, 4H), 6.85-7.13 (m, 4H), 7.37 (d, J=8.1 Hz, 2H), 7.54 (d, J=8.1 Hz, 2H)

Example 11(8)

4-{[(3S)-1-butyl-3-isobutyl-2,5-dioxo-1,4,9-triazaspiro[5.5]undec-9-yl]methyl}-N,N-bis(1H-imidazol-2-ylmethyl)benzamide (compound 11-8)

Description: amorphous
TLC: Rf 0.69 (methanol:28% ammonia water=99:1)
NMR (CDCl$_3$): δ 0.83-1.06 (m, 9H), 1.21-2.23 (m, 11H), 2.47-2.96 (m, 4H), 3.25-3.50 (m, 2H), 3.56 (s, 2H), 3.86-4.02 (m, 1H), 4.54-4.78 (m, 4H), 6.09-6.29 (m, 1H), 6.90-7.12 (m, 4H), 7.37 (d, J=8.1 Hz, 2H), 7.58 (d, J=8.1 Hz, 2H)

Example 11(9)

N,N-bis(1H-imidazol-2-ylmethyl)-4-(1-piperidinyl-methyl)benzamide (compound 11-9)

Description: amorphous
TLC: Rf 0.51 (methanol:28% ammonia water=99:1)
NMR (CDCl$_3$): δ 1.33-1.48 (m, 2H), 1.48-1.63 (m, 4H), 2.24-2.45 (m, 4H), 3.46 (s, 2H), 4.54-4.76 (m, 4H), 6.95-7.11 (m, 4H), 7.36 (d, J=8.1 Hz, 2H), 7.58 (d, J=8.1 Hz, 2H)

Example 11(10)

4-({[3-(dipropylamino)propyl]amino}methyl)-N,N-bis(1H-imidazol-2-ylmethyl)benzamide (compound 11-10)

Description: amorphous
TLC: Rf 0.28 (methanol:28% ammonia water=99:1);
NMR (CDCl$_3$): δ 0.84 (t, J=7.5 Hz, 6H), 1.31-1.52 (m, 4H), 1.53-1.74 (m, 2H), 2.26-2.39 (m, 4H), 2.45 (t, J=6.86 Hz, 2H), 2.64 (t, J=6.9 Hz, 2H), 3.77 (s, 2H), 4.50-4.79 (m, 4H), 6.84-7.13 (m, 4H), 7.32 (d, J=8.1 Hz, 2H), 7.51 (d, J=8.1 Hz, 2H)

Example 11(11)

4-({[2-(dipropylamino)ethyl]amino}methyl)-N,N-bis(1H-imidazol-2-ylmethyl)benzamide (compound 11-11)

Description: amorphous
TLC: Rf 0.42 (methanol:28% ammonia water=99:1)
NMR (CDCl$_3$): δ 0.84 (t, J=7.5 Hz, 6H), 1.30-1.53 (m, 4H), 2.25-2.41 (m, 4H), 2.48-2.58 (m, 2H), 2.59-2.70 (m, 2H), 3.80 (s, 2H), 4.50-4.79 (m, 4H), 6.86-7.14 (m, 4H), 7.34 (d, J=8.1 Hz, 2H), 7.56 (d, J=8.1 Hz, 2H)

Example 11(12)

4-{[7-(dipropylamino)-3,4-dihydro-2(1H)-isoquinolinyl]methyl}-N,N-bis(1H-imidazol-2-ylmethyl)benzamide (compound 11-12)

Description: amorphous
TLC: Rf 0.54 (methanol:28% ammonia water=99:1)
NMR (CDCl$_3$): δ 0.89 (t, J=7.5 Hz, 6H), 1.42-1.68 (m, 4H), 2.61-2.87 (m, 4H), 3.06-3.25 (m, 4H), 3.54 (s, 2H), 3.67 (s, 2H), 4.56-4.77 (m, 4H), 6.23 (d, J=2.7 Hz, 1H), 6.48 (dd, J=8.7, 2.4 Hz, 1H), 6.93 (d, J=8.7 Hz, 1H), 6.96-7.13 (m, 4H), 7.45 (d, J=8.1 Hz, 2H), 7.59 (d, J=8.1 Hz, 2H)

Example 11(13)

N,N-bis(1H-imidazol-2-ylmethyl)-4-[(9-propyl-3,9-diazaspiro[5.5]undec-3-yl)methyl]benzamide (compound 11-13)

Description: amorphous
TLC: Rf 0.61 (dichloromethane:methanol:28% ammonia water=80:20:3);
NMR (CDCl$_3$): δ 0.88 (t, J=7.5 Hz, 3H), 1.33-1.66 (m, 10H), 2.16-2.49 (m, 10H), 3.50 (s, 2H), 4.54-4.79 (m, 4H), 6.91-7.12 (m, 4H), 7.35 (d, J=8.1 Hz, 2H), 7.55 (d, J=8.1 Hz, 2H)

Example 11(14)

N,N-bis(1H-imidazol-2-ylmethyl)-4-[(9-propyl-2,9-diazaspiro[5.5]undec-2-yl)methyl]benzamide (compound 11-14)

Description: amorphous
TLC: Rf 0.64 (dichloromethane:methanol:28% ammonia water=80:20:3)
NMR (CDCl$_3$): δ 0.85 (t, J=7.5 Hz, 3H), 1.21-1.68 (m, 10H), 1.99-2.49 (m, 10H), 3.42 (s, 2H), 4.51-4.80 (m, 4H), 6.87-7.15 (m, 4H), 7.35 (d, J=8.1 Hz, 2H), 7.55 (d, J=8.1 Hz, 2H)

Example 11(15)

N,N-bis(1H-imidazol-2-ylmethyl)-4-({[(1-propyl-4-piperidinyl)methyl]amino}methyl)benzamide (compound 11-15)

Description: amorphous
TLC: Rf 0.15 (dichloromethane:methanol:28% ammonia water=80:20:3)
NMR (CDCl$_3$): δ 0.88 (t, J=7.32 Hz, 3H), 1.14-1.35 (m, 2H), 1.37-1.60 (m, 3H), 1.63-1.79 (m, 2H), 1.81-1.98 (m, 2H), 2.19-2.34 (m, 2H), 2.48 (d, J=6.77 Hz, 2H), 2.84-3.02 (m, 2H), 3.79 (s, 2H), 4.51-4.76 (m, 4H), 6.91-7.16 (m, 4H), 7.37 (d, J=8.1 Hz, 2H), 7.63 (d, J=8.1 Hz, 2H)

Example 11(16)

4-({[4-(dipropylamino)phenyl]amino}methyl)-N,N-bis(1H-imidazol-2-ylmethyl)benzamide (compound 11-16)

Description: dark green amorphous
TLC: Rf 0.64 (dichloromethane:methanol:28% ammonia water=80:20:3)
NMR (CDCl$_3$): δ 0.70-1.06 (m, 6H), 1.31-1.74 (m, 4H), 2.68-3.50 (m, 4H), 4.01-4.57 (m, 2H), 4.57-4.84 (m, 4H), 6.22-6.89 (m, 4H), 6.90-7.14 (m, 4H), 7.41 (d, J=8.1 Hz, 2H), 7.60 (d, J=8.1 Hz, 2H)

Example 11(17)

4-[(2-benzyl-2,9-diazaspiro[5.5]undec-9-yl)methyl]-N,N-bis(1H-imidazol-2-ylmethyl)benzamide (compound 11-17)

Description: amorphous
TLC: Rf 0.67 (dichloromethane:methanol:28% ammonia water=80:20:1)
NMR (CDCl$_3$): δ 1.21-1.38 (m, 2H), 1.40-1.66 (m, 6H), 1.99-2.44 (m, 8H), 3.34-3.47 (m, 4H), 4.53-4.81 (m, 4H), 6.92-7.12 (m, 4H), 7.19-7.30 (m, 5H), 7.32 (d, J=8.1 Hz, 2H), 7.52 (d, J=8.1 Hz, 2H)

Example 11(18)

4-[(2-cyclohexyl-2,9-diazaspiro[5.5]undec-9-yl)methyl]-N,N-bis(1H-imidazol-2-ylmethyl)benzamide (compound 11-18)

Description: amorphous
TLC: Rf 0.40 (dichloromethane:methanol:28% ammonia water=80:20:1)

NMR (CDCl$_3$): δ 1.08-1.84 (m, 18H), 2.13-2.54 (m, 9H), 3.48 (s, 2H), 4.57-4.77 (m, 4H), 6.93-7.13 (m, 4H), 7.36 (d, J=8.1 Hz, 2H), 7.53 (d, J=8.1 Hz, 2H)

Example 11(19)

4-{[(3S)-1-butyl-3-isobutyl-5-oxo-1,4,9-triazaspiro[5.5]undec-9-yl]methyl}-N,N-bis(1H-imidazol-2-ylmethyl)benzamide (compound 11-19)

Description: amorphous
TLC: Rf 0.60 (dichloromethane:methanol:28% ammonia water=80:20:1)
NMR (CDCl$_3$): δ 0.81-1.03 (m, 9H), 1.13-1.53 (m, 6H), 1.56-1.73 (m, 1H), 1.75-3.06 (m, 12H), 3.56 (s, 2H), 3.59-3.73 (m, 1H), 4.51-4.84 (m, 4H), 5.66 (s, 1H), 6.91-7.10 (m, 4H), 7.36 (d, J=8.1 Hz, 2H), 7.49 (d, J=8.1 Hz, 2H)

Example 11(20)

4-{[(3S)-1-butyl-3-isobutyl-2-oxo-4-propyl-1,4,9-triazaspiro[5.5]undec-9-yl]methyl}-N,N-bis(1H-imidazol-2-ylmethyl)benzamide (compound 11-20)

Description: amorphous
TLC: Rf 0.69 (dichloromethane:methanol:28% ammonia water=80:20:1)
NMR (CDCl$_3$): δ 0.75-1.02 (m, 12H), 1.19-2.22 (m, 17H), 2.45-2.67 (m, 1H), 2.67-2.84 (m, 2H), 2.86-2.98 (m, 1H), 2.98-3.16 (m, 1H), 3.16-3.27 (m, 1H), 3.28-3.43 (m, 1H), 3.50 (s, 2H), 4.54-4.81 (m, 4H), 6.93-7.12 (m, 4H), 7.37 (d, J=8.1 Hz, 2H), 7.58 (d, J=8.1 Hz, 2H)

Example 11(21)

4-{[(3S)-1-butyl-3-isobutyl-4-propyl-1,4,9-triazaspiro[5.5]undec-9-yl]methyl}-N,N-bis(1H-imidazol-2-ylmethyl)benzamide (compound 11-21)

Description: amorphous
TLC: Rf 0.67 (dichloromethane:methanol:28% ammonia water=80:20:1)
NMR (CDCl$_3$): δ 0.78-1.00 (m, 12H), 1.10-1.69 (m, 11H), 1.78-2.35 (m, 9H), 2.49-2.82 (m, 5H), 2.93-3.09 (m, 1H), 3.37-3.58 (m, 2H), 4.51-4.82 (m, 4H), 6.91-7.14 (m, 4H), 7.36 (d, J=8.1 Hz, 2H), 7.55 (d, J=8.1 Hz, 2H)

Example 12

Benzyl 6-({bis[(1-{[2-(trimethylsilyl)ethoxy]methyl}-1H-imidazol-2-yl)methyl]amino}carbonyl)-3,4-dihydro-2(1H)-isoquinolinecarboxylate (compound 12)

The same procedure as a series of reactions of Example 6 was carried out, except that 2-[(benzyloxy)carbonyl]-1,2,3,4-tetrahydro-6-isoquinolinecarboxylic acid was use in place of the compound 2 and the compound 5, to obtain the title compound having the following physical properties.
TLC: Rf 0.34 (chloroform:methanol=10:1)
NMR (CDCl$_3$): δ 7.37 (m, 6H), 7.00 (m, 6H), 5.55 (m, 2H), 5.21 (m, 2H), 5.17 (s, 2H), 4.87 (m, 4H), 4.62 (s, 2H), 3.69 (t, J=5.7 Hz, 2H), 3.53 (m, 4H), 3.33 (m, 2H), 0.88 (m, 2H), 0.74 (m, 2H), −0.05 (s, 18H)

Example 13

N,N-bis[(1-{[2-(trimethylsilyl)ethoxy]methyl}-1H-imidazol-2-yl)methyl]-1,2,3,4-tetrahydro-6-isoquinolinecarboxamide (compound 13)

The same procedure as a series of reactions of Example 2 was carried out, except that the compound 12 was used in place of the compound 1 and 10% palladium carbon was used in place of 20% palladium hydroxide carbon, to obtain the title compound having the following physical properties.
TLC: Rf 0.50 (chloroform:methanol:28% ammonia water=80:10:1)
NMR (CDCl$_3$): δ 7.43 (d, J=6.0 Hz, 1H), 7.36 (s, 1H), 6.99 (m, 5H), 5.50 (m, 2H), 5.15 (m, 2H), 4.84 (m, 2H), 4.69 (m, 2H), 4.04 (s, 2H), 3.53 (m, 2H), 3.52 (m, 2H), 3.15 (t, J=5.7 Hz, 2H), 2.81 (m, 2H), 0.77 (m, 2H), −0.05 (s, 18H)

Example 14

2-[4-(dipropylamino)butyl]-N,N-bis[(1-{[2-(trimethylsilyl)ethoxy]methyl}-1H-imidazol-2-yl)methyl]-1,2,3,4-tetrahydro-6-isoquinolinecarboxamide (compound 14)

The same procedure as a series of reactions of Example 1 was carried out, except that 4-(dipropylamino)butanal was used in place of 1-({[2-(trimethylsilyl)ethyloxy]methyl}-1H-imidazole-2-carboaldehyde and the compound 13 was used in place of {[4-(methyloxy)phenyl]methyl}amine, to obtain the title compound having the following physical properties.
TLC: Rf 0.39 (chloroform:methanol:28% ammonia water=80:10:1)
NMR (CDCl$_3$): δ 7.38 (m, 2H), 6.99 (m, 5H), 5.50 (s, 2H), 5.15 (sm, 2H), 4.84 (s, 2H), 4.68 (s, 2H), 3.58 (m, 4H), 3.33 (m, 2H), 2.84 (t, J=5.7 Hz, 2H), 2.70 (t, J=5.7 Hz, 2H), 2.51 (m, 4H), 1.60 (m, 12H), 0.90 (m, 10H), −0.05 (s, 18H)

Example 15

2-[4-(dipropylamino)butyl]-N,N-bis(1H-imidazol-2-ylmethyl)-1,2,3,4-tetrahydro-6-isoquinolinecarboxamide (compound 15)

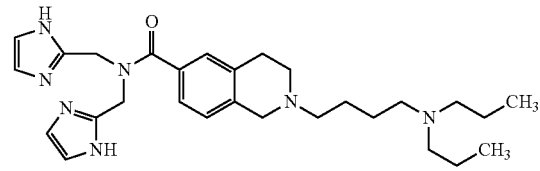 [SMILES: CCCN(CCC)CCCCN1CCc2cc(C(=O)N(Cc3ncc[nH]3)Cc3ncc[nH]3)ccc2C1]

The same procedure as a series of reactions of Example 10 was carried out, except that the compound 14 was used in place of the compound 9, to obtain the title compound having the following physical properties.
Description: amorphous
TLC: Rf 0.67 (chloroform:methanol:28% ammonia water=80:20:4)
NMR (DMSO-d$_6$): δ 0.81 (t, J=7.20 Hz, 6H), 1.27-1.43 (m, 6H), 1.43-1.59 (m, 2H), 2.22-2.31 (m, 4H), 2.34 (t, J=6.9 Hz, 2H), 2.41 (t, J=7.20 Hz, 2H), 2.59 (t, J=6.3 Hz, 2H), 2.72 (t, J=6.30 Hz, 2H), 3.50 (s, 2H), 4.43-4.57 (m, 2H), 4.57-4.71 (m, 2H), 6.75-6.98 (m, 2H), 6.99-7.16 (m, 4H), 7.20 (dd, J=7.8, 1.5 Hz, 1H), 12.03-12.57 (m, 2H)

Example 15(1) to Example 15(3)

The same procedure as a series of reactions of Example 12→Example 13→Example 14 and, if necessary, Example 15 was carried out, except that the compound 2 was used or bis[(1-methyl-1H-imidazol-2-yl)methyl]amine or bis(2-pyridinylmethyl)amine was used in place of it, and 2-[(benzyloxy)carbonyl]-1,2,3,4-tetrahydro-6-isoquinolinecarboxylic acid was used or 2-[(benzyloxy)carbonyl]-1,2,3,4-tetrahydro-7-isoquinolinecarboxylic acid was used in place of it in the process of Example 12, to obtain the following compound of the present invention.

Example 15(1)

2-[4-(dipropylamino)butyl]-N,N-bis(1H-imidazol-2-ylmethyl)-1,2,3,4-tetrahydro-7-isoquinolinecarboxamide (compound 15-1)

Description: amorphous;
TLC: Rf 0.30 (chloroform:methanol:28% ammonia water=80:10:1);
NMR (DMSO-$d_6$): δ 0.81 (t, J=7.2 Hz, 6H), 1.27-1.45 (m, 6H), 1.45-1.58 (m, 2H), 2.22-2.31 (m, 4H), 2.32-2.37 (m, 2H), 2.37-2.45 (m, 2H), 2.60 (t, J=5.4 Hz, 2H), 2.78 (t, J=5.4 Hz, 2H), 3.43 (s, 2H), 4.45-4.70 (m, 4H), 6.72-6.99 (m, 2H), 6.99-7.15 (m, 3H), 7.16-7.31 (m, 2H), 11.94-12.28 (m, 1H), 12.28-12.63 (m, 1H)

Example 15(2)

2-[4-(dipropylamino)butyl]-N,N-bis[(1-methyl-1H-imidazol-2-yl)methyl]-1,2,3,4-tetrahydro-6-isoquinolinecarboxamide (compound 15-2)

Description: oily product;
TLC: Rf 0.33 (chloroform:methanol:28% ammonia water=80:10:1);
NMR (DMSO-$d_6$): δ 0.81 (t, J=7.5 Hz, 6H), 1.25-1.43 (m, 6H), 1.44-1.59 (m, 2H), 2.22-2.31 (m, 4H), 2.34 (t, J=6.0 Hz, 2H), 2.38-2.46 (m, 2H), 2.59 (t, J=5.7 Hz, 2H), 2.67-2.82 (m, 2H), 3.14-3.43 (m, 3H), 3.50 (s, 2H), 3.53-3.75 (m, 3H), 4.30-4.51 (m, 2H), 4.52-4.75 (m, 2H), 6.74-6.91 (m, 2H), 6.97-7.13 (m, 3H), 7.15-7.23 (m, 1H), 7.28 (d, J=8.1 Hz, 1H)

Example 15(3)

2-[4-(dipropylamino)butyl]-N,N-bis(2-pyridinylmethyl)-1,2,3,4-tetrahydro-6-isoquinolinecarboxamide (compound 15-3)

Description: oily product;
TLC: Rf 0.48 (chloroform:methanol:28% ammonia water=80:10:1);
NMR (DMSO-$d_6$): δ 0.70-0.91 (m, 6H), 1.21-1.42 (m, 6H), 1.43-1.59 (m, 2H), 2.17-2.45 (m, 8H), 2.55-2.66 (m, 2H), 2.68-2.80 (m, 2H), 3.43-3.59 (m, 2H), 4.60 (s, 2H), 4.67 (s, 2H), 6.99-7.09 (m, 1H), 7.16-7.25 (m, 3H), 7.25-7.32 (m, 2H), 7.36 (d, J=8.4 Hz, 1H), 7.65-7.93 (m, 1H), 8.42-8.72 (m, 2H)

Example 16

1-[4-(diethoxymethyl)phenyl]-N-[(1-{[2-(trimethylsilyl)ethoxy]methyl}-1H-imidazol-2-yl)methyl] methaneamine (compound 16)

The same procedure as a series of reactions of Example 1, except that 4-(diethoxymethyl)benzaldehyde was used in place of 1-({[2-(trimethylsilyl)ethyloxy]methyl}-1H-imidazole-2-carboaldehyde and 1-(1-{[2-(trimethylsilyl)ethoxy]methyl}-1H-imidazol-2-yl)methaneamine was used in place of {[4-(methyloxy)phenyl]methyl}amine, to obtain the title compound having the following physical properties.

TLC: Rf 0.63 (chloroform:methanol:28% ammonia water=80:10:1)
NMR (CDCl$_3$): δ 7.43 (d, J=7.8 Hz, 2H), 7.33 (J=7.8 Hz, 2H), 6.97 (m, 2H), 5.49 (s, 1H), 5.32 (s, 2H), 3.94 (s, 2H), 3.84 (s, 2H), 3.52 (m, 6H), 1.24 (m, 6H), 0.88 (m, 2H), −0.03 (s, 9H)

Example 17

N-[4-(diethoxymethyl)benzyl]-N-[(1-{[2-(trimethylsilyl)ethoxy]methyl}-1H-imidazol-2-yl)methyl]-1H-imidazole-2-carboxamide (compound 17)

To a solution of the compound 16 (1.93 g), 1H-imidazole-2-carboxylic acid (773 mg) and diisopropylethylamine (2.97 g) in dichloromethane (15 mL), O-(7-azabenzotriazol-1-yl) N,N,N',N'-tetramethyluronium hexafluorophosphate (HATU) (2.62 g) was added under ice cooling. The reaction mixture was stirred at room temperature for 4 hours. To the reaction mixture, an aqueous 1N sodium hydroxide solution (30 mL) was added. The aqueous layer was extracted twice with dichloromethane (50 mL). The combined organic layer was washed with saturated brine, dried over anhydrous magnesium sulfate and then concentrated. The residue was purified by silica gel chromatography (ethyl acetate:methanol=1:0→10:1) to obtain the title compound (977 mg) having the following physical properties.

TLC: Rf 0.44 (chloroform:methanol:28% ammonia water=80:10:1);
NMR (CDCl$_3$): δ 7.41 (m, 4H), 7.15 (s, 2H), 7.04 (s, 1H), 6.96 (m, 1H), 5.82 (s, 1H) 5.77 (s, 1H), 5.46 (s, 1H), 5.37 (s, 1H), 5.23 (s, 1H), 4.83 (s, 1H), 4.76 (s, 1H), 3.51 (m, 6H), 1.25 (m, 6H), 0.82 (t, J=8.1 Hz, 2H), −0.06 (s, 9H)

Example 18

N-(4-formylbenzyl)-N-(1H-imidazol-2-ylmethyl)-1H-imidazole-2-carboxamide (compound 18)

To the compound 17 (970 mg), a 50% trifluoroacetic acid-dichloromethane solution (10 mL) was added under ice cooling. The reaction mixture was stirred at room temperature for 3 hours. The reaction mixture was concentrated and an aqueous 2N sodium hydroxide solution (20 mL) was added to the residue. The aqueous layer was extracted twice with dichloromethane (50 mL). The combined organic layer was washed with saturated brine, dried over anhydrous magnesium sulfate and then concentrated to obtain the title compound having the following physical properties. The obtained compound was used in the following reaction without being purified.

TLC: Rf 0.50 (chloroform:methanol:28% ammonia water=80:10:1);
NMR (CDCl$_3$): δ 9.98 (s, 1H), 7.81 (d, J=8.1 Hz, 2H), 7.49 (d, J=8.1 Hz, 2H), 7.23 (s, 2H), 7.08 (s, 2H), 5.04 (s, 2H), 4.87 (s, 2H)

Example 19

N-[4-({[4-(dipropylamino)butyl]amino}methyl)benzyl]-N-(1H-imidazol-2-ylmethyl)-1H-imidazole-2-carboxamide (compound 19)

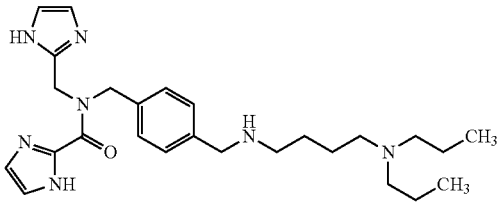 [SMILES: CCCN(CCC)CCCCNCc1ccc(CN(Cc2ncc[nH]2)C(=O)c2ncc[nH]2)cc1]

The same procedure as a series of reactions of Example 1 was carried out, except that the compound 18 was used in place of 1-({[2-(trimethylsilyl)ethyloxy]methyl}-1H-imidazole-2-carboaldehyde and N,N-dipropyl-1,4-butanediamine was used in place of {[4-(methyloxy)phenyl]methyl}amine, to obtain the title compound having the following physical properties.

Description: semisolid;
TLC: Rf 0.64 (chloroform:methanol:28% ammonia water=80:20:4);
NMR (DMSO-d$_6$): δ 0.80 (t, J=7.5 Hz, 6H), 1.22-1.51 (m, 8H), 2.16-2.35 (m, 6H), 2.44 (t, J=6.3 Hz, 2H), 3.63 (s, 2H), 4.48 (s, 1H), 4.54 (s, 1H), 5.25 (s, 1H), 5.53 (s, 1H), 6.72-6.92 (m, 1H), 6.92-7.10 (m, 1H), 7.11-7.22 (m, 3H), 7.22-7.36 (m, 3H), 11.70-12.25 (m, 2H)

Example 19(1) to Example 19(19)

The same procedure as a series of reactions of Example 16→Example 17→Example 18→Example 19 was carried out, except that 1-(1-{[2-(trimethylsilyl)ethoxy]methyl}-1H-imidazol-2-yl)methaneamine was used or a corresponding amine compound was used in place of it in the process of Example 16, 1H-imidazole-2-carboxylic acid was used or a corresponding carboxylic acid was used in place of it the process of Example 17, and N,N-dipropyl-1,4-butanediamine was used or a corresponding amine was used in place of it in the process of Example 19, to obtain the following compound of the present invention.

Example 19(1)

N-[4-({[4-(dipropylamino)butyl]amino}methyl)benzyl]-N-[(5-methyl-2-pyridinyl)methyl]-1H-imidazole-2-carboxamide (compound 19-1)

Description: oily product;
TLC: Rf 0.27 (chloroform:methanol:28% ammonia water=80:10:1);
NMR (DMSO-d$_6$): δ 0.80 (t, J=7.5 Hz, 6H), 1.25-1.46 (m, 8H), 2.18-2.34 (m, 9H), 2.37-2.47 (m, 2H), 3.62 (s, 2H), 4.53 (s, 1H), 4.57 (s, 1H), 5.48 (s, 1H), 5.52 (s, 1H), 6.86-7.41 (m, 7H), 7.47-7.61 (m, 1H), 8.24-8.40 (m, 1H), 12.50-13.44 (m, 1H)

Example 19(2)

N-[4-({[4-(dipropylamino)butyl]amino}methyl)benzyl]-N-(1H-imidazol-2-ylmethyl)-4-methyl-1H-imidazole-2-carboxamide (compound 19-2)

TLC: Rf 0.47 (dichloromethane:methanol:28% ammonia water=90:10:2);
NMR (CDCl$_3$): δ 0.86 (m, 6H), 1.38-1.60 (m, 8H), 2.15-2.50 (m, 9H), 2.58-2.68 (m, 2H), 3.78 (m, 2H), 4.45-4.98 (m, 4H), 6.92-7.42 (m, 7H)

Example 19(3)

N-[4-({[4-(dipropylamino)butyl]amino}methyl)benzyl]-N-(1H-imidazol-2-ylmethyl)-2-pyridinecarboxamide (compound 19-3)

Description: oily product;
TLC: Rf 0.20 (chloroform:methanol:28% ammonia water=80:10:1);
NMR (DMSO-d$_6$): δ 0.75-0.90 (m, 6H), 1.26-1.47 (m, 8H), 2.16-2.37 (m, 6H), 2.38-2.47 (m, 2H), 3.63 (s, 1H), 3.66 (s, 1H), 4.47 (s, 1H), 4.52 (s, 1H), 4.57 (s, 1H), 4.59 (s, 1H), 6.77-6.91 (m, 1H), 7.05 (s, 1H), 7.15 (d, J=7.8 Hz, 1H), 7.19-7.35 (m, 3H), 7.42-7.55 (m, 1H), 7.59-7.76 (m, 1H), 7.84-8.02 (m, 1H), 8.50-8.72 (m, 1H), 11.71-12.10 (m, 1H)

Example 19(4)

N-[4-({[4-(dipropylamino)butyl]amino}methyl)benzyl]-N-(2-pyridinylmethyl)-1H-imidazole-2-carboxamide (compound 19-4)

Description: oily product
TLC: Rf 0.31 (chloroform:methanol:28% ammonia water=80:10:1);
NMR (DMSO-d$_6$): δ 0.80 (t, J=7.5 Hz, 6H), 1.24-1.48 (m, 8H), 2.17-2.36 (m, 6H), 2.37-2.46 (m, 2H), 3.63 (s, 2H), 4.51-4.68 (m, 2H), 5.47-5.64 (m, 2H), 6.91-7.14 (m, 1H), 7.24 (t, 7H), 7.73 (t, J=7.5 Hz, 1H), 8.38-8.63 (m, 1H)

Example 19(5)

N-[4-({[4-(dipropylamino)butyl]amino}methyl)benzyl]-N-(2-pyridinylmethyl)-2-pyridinecarboxamide (compound 19-5)

Description: oily product;
TLC: Rf 0.29 (chloroform:methanol:28% ammonia water=80:10:1);
NMR (DMSO-d$_6$): δ 0.70-0.89 (m, 6H), 1.24-1.48 (m, 8H), 2.16-2.36 (m, 6H), 2.36-2.47 (m, 2H), 3.57-3.72 (m, 2H), 4.51-4.73 (m, 4H), 7.11-7.18 (m, 1H), 7.19-7.38 (m, 5H), 7.39-7.51 (m, 1H), 7.56-7.67 (m, 1H), 7.67-7.97 (m, 2H), 8.41-8.68 (m, 2H)

Example 19(6)

N-[4-({[4-(dipropylamino)butyl]amino}methyl)benzyl]-N-(1H-imidazol-2-ylmethyl)-1H-pyrrole-2-carboxamide (compound 19-6)

Description: oily product;
TLC: Rf 0.27 (chloroform:methanol:28% ammonia water=80:10:1);
NMR (DMSO-d$_6$): δ 0.81 (t, J=7.50 Hz, 6H), 1.18-1.51 (m, 8H), 2.15-2.40 (m, 8H), 3.72 (s, 2H), 4.31-4.48 (m, 2H), 4.51-4.72 (m, 2H), 5.97-6.14 (m, 1H), 6.73-7.47 (m, 9H), 11.58-12.28 (m, 1H)

Example 19(7)

N-[4-({[4-(dipropylamino)butyl]amino}methyl)benzyl]-N-(5,6,7,8-tetrahydro-8-quinolinyl)-1H-imidazole-2-carboxamide (compound 19-7)

Description: oily product;
TLC: Rf 0.43 (chloroform:methanol:28% ammonia water=80:10:1);

NMR (DMSO-d$_6$): δ 0.80 (t, J=7.2 Hz, 6H), 1.22-1.51 (m, 8H), 1.61-2.08 (m, 2H), 2.17-2.35 (m, 8H), 2.36-2.47 (m, 2H), 2.58-2.96 (m, 2H), 3.51-3.71 (m, 3H), 4.73-5.11 (m, 1H), 5.34-5.67 (m, 1H), 6.92-7.36 (m, 7H), 7.39-7.59 (m, 1H), 8.19-8.43 (m, 1H), 12.43-13.40 (m, 1H)

Example 19(8)

N-[4-({[4-(dipropylamino)butyl]amino}methyl)benzyl]-N-(1H-imidazol-2-ylmethyl)-1H-pyrazole-4-carboxamide (compound 19-8)

Description: oily product;
TLC: Rf 0.15 (ethyl acetate:methanol:28% ammonia water=80:20:3);
NMR (DMSO-d$_6$): δ 7.40-6.70 (m, 8H), 4.60-4.38 (m, 4H), 3.76 (m, 2H), 2.57 (m, 2H), 2.40-2.22 (m, 6H), 1.60-1.28 (m, 8H), 0.82 (t, J=7.2 Hz, 6H)

Example 19(9)

N-[4-({[4-(dipropylamino)butyl]amino}methyl)benzyl]-N-(1H-imidazol-2-ylmethyl)-1H-imidazole-4-carboxamide (compound 19-9)

Description: oily product;
TLC: Rf 0.12 (ethyl acetate:methanol:28% ammonia water=80:20:3);
NMR (DMSO-d$_6$): δ 7.88-7.65 (m, 2H), 7.35-7.18 (m, 4H), 7.18-6.75 (m, 2H), 5.42-4.85 (m, 2H), 4.60-4.35 (m, 2H), 3.63 (m, 2H), 2.55-2.38 (m, 2H), 2.38-2.00 (m, 6H), 1.48-1.24 (m, 8H), 0.80 (t, J=7.2 Hz, 6H)

Example 19(10)

N-(1H-imidazol-2-ylmethyl)-N-[4-({[4-(1-piperidinyl)butyl]amino}methyl)benzyl]-1H-imidazole-2-carboxamide (compound 19-10)

Description: amorphous;
TLC: Rf 0.55 (chloroform:methanol:28% ammonia water=80:20:4);
NMR (DMSO-d$_6$): δ 1.21-1.56 (m, 10H), 2.07-2.20 (m, 2H), 2.19-2.35 (m, 4H), 2.36-2.47 (m, 2H), 3.63 (s, 2H), 4.48 (s, 1H), 4.54 (s, 1H), 5.25 (s, 1H), 5.53 (s, 1H), 6.72-7.10 (m, 3H), 7.10-7.36 (m, 5H), 11.68-12.15 (m, 2H)

Example 19(11)

N-(1H-imidazol-2-ylmethyl)-N-[4-({[4-(4-morpholinyl)butyl]amino}methyl)benzyl]-1H-imidazole-2-carboxamide (compound 19-11)

Description: amorphous;
TLC: Rf 0.58 (chloroform:methanol:28% ammonia water=80:10:1);
NMR (DMSO-d$_6$): δ 1.34-1.48 (m, 4H), 2.14-2.25 (m, 2H), 2.24-2.36 (m, 4H), 2.38-2.48 (m, 2H), 3.46-3.58 (m, 4H), 3.65 (s, 2H), 4.48 (s, 1H), 4.55 (s, 1H), 5.26 (s, 1H), 5.53 (s, 1H), 6.70-6.92 (m, 1H), 6.93-7.12 (m, 1H), 7.13-7.24 (m, 3H), 7.24-7.45 (m, 3H), 11.65-12.34 (m, 2H)

Example 19(12)

N-(1H-benzoimidazol-2-ylmethyl)-N-[4-({[4-(dipropylamino)butyl]amino}methyl)benzyl]-1H-imidazole-2-carboxamide (compound 19-12)

Description: amorphous;
TLC: Rf 0.26 (chloroform:methanol:28% ammonia water=80:10:1);
NMR (DMSO-d$_6$): δ 0.80 (t, J=7.5 Hz, 6H), 1.24-1.50 (m, 8H), 2.19-2.38 (m, 8H), 3.67 (s, 2H), 4.68 (s, 2H), 5.61 (s, 1H), 5.65 (s, 1H), 6.99-7.19 (m, 3H), 7.19-7.37 (m, 5H), 7.37-7.50 (m, 1H), 7.50-7.65 (m, 1H), 12.10-12.70 (m, 2H)

Example 19(13)

N-[4-({[4-(3,4-dihydro-2(1H)-isoquinolinyl)butyl]amino}methyl)benzyl]-N-(1H-imidazol-2-ylmethyl)-1H-imidazole-2-carboxamide (compound 19-13)

Description: amorphous;
TLC: Rf 0.36 (chloroform:methanol:28% ammonia water=80:10:1);
NMR (DMSO-d$_6$): δ 1.34-1.66 (m, 4H), 2.39 (t, J=6.9 Hz, 2H), 2.44-2.56 (m, 2H), 2.59 (t, J=6.0 Hz, 2H), 2.76 (t, J=6.0 Hz, 2H), 3.48 (s, 2H), 3.64 (s, 2H), 4.48 (s, 1H), 4.54 (s, 1H), 5.25 (s, 1H), 5.53 (s, 1H), 6.73-6.91 (m, 1H), 6.92-7.13 (m, 5H), 7.12-7.43 (m, 6H), 11.70-12.33 (m, 2H)

Example 19(14)

N-[4-({[4-(dipropylamino)butyl]amino}methyl)benzyl]-2-(1H-imidazole-4-yl)-N-(1H-imidazol-2-ylmethyl)acetamide (compound 19-14)

Description: oily product;
TLC: Rf 0.36 (ethyl acetate:methanol:28% ammonia water=20:2:1);
NMR (DMSO-d$_6$): δ 0.81 (t, J=7.5 Hz, 6H), 1.20-1.50 (m, 8H), 2.20-2.40 (m, 8H), 3.60-3.95 (m, 4H), 4.38-4.68 (m, 4H), 6.78-7.35 (m, 7H), 7.60 (m, 1H)

Example 19(15)

N-[4-({[4-(dipropylamino)butyl]amino}methyl)benzyl]-N-(1H-imidazol-2-ylmethyl)-1H-pyrazole-3-carboxamide (compound 19-15)

Description: oily product;
TLC: Rf 0.35 (dichloromethane:methanol:28% ammonia water=90:10:3);
NMR (CDCl$_3$): δ 0.86 (t, J=7.5 Hz, 6H), 1.39-1.60 (m, 8H), 2.30-2.52 (m, 6H), 2.58-2.72 (m, 2H), 3.72-3.84 (m, 2H), 4.56-5.05 (m, 4H), 6.70-6.94 (m, 1H), 6.95-7.05 (m, 2H), 7.18-7.40 (m, 4H), 7.55-7.68 (m, 1H)

Example 19(16)

N-[4-({[4-(dipropylamino)butyl]amino}methyl)benzyl]-N-(1H-imidazol-2-ylmethyl)-4-methyl-1H-imidazole-2-carboxamide (compound 19-16)

Description: oily product;
TLC: Rf 0.47 (dichloromethane:methanol:28% ammonia water=90:10:2);

NMR (CDCl₃): δ d 0.86 (m, 6H), 1.38-1.60 (m, 8H), 2.15-2.50 (m, 9H), 2.58-2.68 (m, 2H), 3.78 (m, 2H), 4.45-4.98 (m, 4H), 6.92-7.42 (m, 7H), 8.40-8.50 (m, 1H)

Example 19(17)

N-[4-({[4-(dipropylamino)butyl]amino}methyl)benzyl]-N-(1H-imidazol-2-ylmethyl)-5-methyl-2-pyridinecarboxamide (compound 19-17)

Description: oily product;
TLC: Rf 0.16 (ethyl acetate:methanol:28% ammonia water=90:10:2);
NMR (CDCl₃): δ d 0.87 (t, J=7.5 Hz, 6H), 1.38-1.60 (m, 8H), 2.30-2.55 (m, 6H), 2.43 (s, 3H), 2.64 (t, J=6.0 Hz, 2H), 3.78 (s, 2H), 4.40-4.78 (m, 4H), 7.00-7.18 (m, 2H), 7.29 (d, J=8.1 Hz, 2H), 7.39 (d, J=8.1 Hz, 2H), 7.59-7.82 (m, 2H), 8.40-8.50 (m, 1H)

Example 19(18)

N-[4-({[4-(dipropylamino)butyl]amino}methyl)benzyl]-N-(1H-imidazol-2-ylmethyl)-1H-1,2,4-triazole-5-carboxamide (compound 19-18)

Description: amorphous;
TLC: Rf 0.33 (dichloromethane:methanol:28% ammonia water=80:20:3);
NMR (CDCl₃): δ d 0.78-0.95 (m, 6H), 135-1.78 (m, 8H), 2.40-2.68 (m, 6H), 2.70-2.85 (m, 2H), 3.80-4.00 (m, 2H), 4.52-5.12 (m, 4H), 6.95-7.12 (m, 2H), 7.08-7.40 (m, 4H), 8.10-8.21 (m, 1H)

Example 19(19)

N-(4-{[{4-[(dipropylamino)methyl]benzyl}(methyl)amino]methyl}benzyl)-N-(1H-imidazol-2-ylmethyl)-1H-imidazole-2-carboxamide Description: amorphous;
TLC: Rf 0.44 (dichloromethane:methanol:28% ammonia water=90:10:1);
NMR (CDCl₃): δ 0.84 (t, J=7.2 Hz, 6H), 1.41-1.53 (m, 4H), 2.16 (s, 3H), 2.33-2.38 (m, 4H), 3.48 (s, 2H), 3.49 (s, 2H), 3.53 (s, 2H), 4.77 (s, 2H), 4.97 (s, 2H), 6.94-7.38 (m, 12H)

Example 20

Methyl 2-[4-(dipropylamino)butyl]-1,2,3,4-tetrahydro-6-isoquinolinecarboxylate (compound 20)

The same procedure as a series of reactions of Example 1 was carried out, except that 4-(dipropylamino)butanal was used in place of 1-({[2-(trimethylsilyl)ethyloxy]methyl}-1H-imidazole-2-carboaldehyde and methyl 1,2,3,4-tetrahydro-6-isoquinolinecarboxylate hydrochloride was used in place of {[4-(methyloxy)phenyl]methyl}amine, to obtain the title compound having the following physical properties.
TLC: Rf 0.30 (chloroform:methanol:28% ammonia water=80:10:1);
NMR (CDCl₃): δ 7.77 (m, 2H), 7.08 (d, J=7.8 Hz, 1H), 3.890 (s, 3H), 3.66 (s, 2H), 2.94 (t, J=6.3 Hz, 2H), 2.74 (t, J=6.0 Hz, 2H), 2.47 (m, 2H), 2.42 (m, 2H), 2.36 (m, 4H), 1.28 (m, 6H), 0.86 (m, 8H)

Example 21

{2-[4-(dipropylamino)butyl]-1,2,3,4-tetrahydro-6-isoquinolinyl}methanol (compound 21)

To a solution of the compound 20 (3.02 g) in tetrahydrofuran (25 mL), lithium aluminum hydride (330 mg) was added at −78° C. The reaction mixture was stirred at −78° C. for 30 minutes. To the reaction mixture, sodium sulfate decahydrate (2.8 g) and diethylether (100 mL) were added and the temperature of the reaction mixture was raised to room temperature. The reaction mixture was filtered through Celite (trade name) and then concentrated. The residue was purified by silica gel column chromatography (ethyl acetate:methanol:triethylamine=10:1:0→10:1:0.5) to obtain the title compound (2.28 g) having the following physical properties.
TLC: Rf 0.57 (chloroform:methanol:28% ammonia water=80:10:1);
NMR (CDCl₃): δ 7.10 (m, 2H), 7.00 (d, J=8.4 Hz, 1H), 4.62 (s, 2H), 3.61 (s, 2H), 2.89 (t, J=5.7 Hz, 2H), 2.72 (t, J=5.7 Hz, 2H), 2.51 (m, 2H), 2.45 (m, 2H), 2.37 (m, 4H), 1.46 (m, 8H), 0.83 (m, 6H)

Example 22

2-[4-(dipropylamino)butyl]-1,2,3,4-tetrahydro-6-isoquinolinecarboaldehyde (compound 22)

To a solution of the compound 21 (2.28 g) and triethylamine (4.99 mL) in dimethyl sulfoxide (30 mL), a sulfur trioxide-pyridine complex (2.28 g) was slowly added. The reaction mixture was stirred at room temperature for one hour. To the reaction solution, water (100 mL) was added. The aqueous layer was extracted twice with dichloromethane (50 mL). The combined organic layer was washed with saturated brine, dried over anhydrous magnesium sulfate and then concentrated. The residue was purified by silica gel chromatography (ethyl acetate:methanol:triethylamine=10:1:0→10:1:0.5) to obtain the title compound (2.26 g) having the following physical properties.
TLC: Rf 0.40 (chloroform:methanol:28% ammonia water=80:10:1);
NMR (CDCl₃): δ 9.94 (s, 1H), 7.62 (m, 2H), 7.18 (d, 8.4 Hz, 1H), 3.69 (s, 2H), 2.98 (t, J=5.7 Hz, 2H), 2.75 (t, J=6.3 Hz, 2H), 2.54 (m, 2H), 2.42 (m, 2H), 2.34 (m, 4H), 1.46 (m, 8H), 0.87 (m, 6H)

Example 23

N-({2-[4-(dipropylamino)butyl]-1,2,3,4-tetrahydro-6-isoquinolinyl}methyl)-N-[(1-methyl-1H-imidazol-2-yl)methyl]-1H-imidazole-2-carboxamide (compound 23)

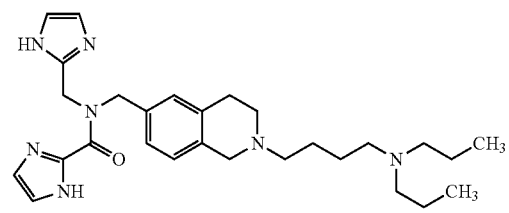 [SMILES: CCCN(CCC)CCCCN1CCc2cc(CN(Cc3ncc[nH]3)C(=O)c3ncc[nH]3)ccc2C1]

The same procedure as a series of reactions of Example 1 was carried out, except that the compound 22 was used in place of 1-({[2-(trimethylsilyl)ethyloxy]methyl}-1H-imidazole-2-carboaldehyde and [(1-methyl-1H-imidazol-2-yl)methyl]amine was used in place of {[4-(methyloxy)phenyl]methyl}amine to obtain ({2-[4-(dipropylamino)butyl]-1,2,3,4-tetrahydro-6-isoquinolinyl}methyl)[(1-methyl-1H-imidazol-2-yl)methyl]amine (compound 23-a). The same procedure as a series of reactions of Example 17 was carried out, except that the obtained compound 23-a was used in place of the compound 16, to obtain the title compound having the following physical properties.

Description: oily product;
TLC: Rf 0.28 (chloroform:methanol:28% ammonia water=80:10:1);
NMR (DMSO-$d_6$): δ 0.81 (t, J=7.50 Hz, 6H), 1.26-1.44 (m, 6H), 1.44-1.59 (m, 2H), 2.21-2.32 (m, 4H), 2.32-2.37 (m, 2H), 2.37-2.46 (m, 2H), 2.55-2.66 (m, 2H), 2.67-2.83 (m, 2H), 3.43-3.53 (m, 3H), 3.57 (s, 1H), 3.62 (s, 1H), 4.34-4.51 (m, 2H), 4.51-4.66 (m, 1H), 5.46-5.62 (m, 1H), 6.75-6.80 (m, 1H), 6.80-6.84 (m, 1H), 6.87-7.01 (m, 2H), 7.01-7.15 (m, 2H), 7.28 (s, 1H), 13.04 (s, 1H)

Example 23(1) to Example 23(2)

The same procedure as a series of reactions of Example 17 was carried out, except that the compound 23-a was used in place of the compound 16 and 2-pyridinecarboxylic acid or 3-pyridinecarboxylic acid was used in place of 1H-imidazole-2-carboxylic acid, to obtain the title compound having the following physical properties.

Example 23(1)

N-({2-[4-(dipropylamino)butyl]-1,2,3,4-tetrahydro-6-isoquinolinyl}methyl)-N-[(1-methyl-1H-imidazol-2-yl)methyl]-2-pyridinecarboxamide (compound 23-1)

Description: oily product;
TLC: Rf 0.60 (chloroform:methanol:28% ammonia water=80:20:4);
NMR (DMSO-$d_6$): δ 0.82 (t, J=7.2 Hz, 6H), 1.22-1.44 (m, 6H), 1.44-1.61 (m, 2H), 2.19-2.45 (m, 8H), 2.54-2.66 (m, 2H), 2.67-2.82 (m, 2H), 3.40-3.56 (m, 2H), 3.64 (s, 2H), 4.50 (s, 2H), 4.54-4.71 (m, 3H), 6.70-7.07 (m, 4H), 7.12 (s, 1H), 7.39-7.52 (m, 1H), 7.58 (t, J=7.5 Hz, 1H), 7.89 (td, J=7.5, 1.8 Hz, 1H), 8.56 (t, J=4.8 Hz, 1H)

Example 23(2)

N-({2-[4-(dipropylamino)butyl]-1,2,3,4-tetrahydro-6-isoquinolinyl}methyl)-N-[(1-methyl-1H-imidazol-2-yl)methyl]nicotinamide (compound 23-2)

Description: oily product;
TLC: Rf 0.60 (chloroform:methanol:28% ammonia water=80:20:4);
NMR (DMSO-$d_6$): δ 0.82 (t, J=7.2 Hz, 6H), 1.25-1.45 (m, 6H), 1.45-1.61 (m, 2H), 2.18-2.46 (m, 8H), 2.54-2.66 (m, 2H), 2.67-2.86 (m, 2H), 3.48 (s, 2H), 3.64 (s, 2H), 4.27-4.38 (m, 1H), 4.39-4.45 (m, 1H), 4.45-4.51 (m, 1H), 4.51-4.59 (m, 1H), 4.59-4.72 (m, 1H), 6.69-7.22 (m, 5H), 7.42 (dd, J=7.8, 4.8 Hz, 1H), 7.71-8.06 (m, 1H), 8.52-8.82 (m, 2H)

Example 24

Methyl 4-[(5-hydroxypentyl)oxy]benzoate (compound 24)

To a solution of methyl p-hydroxybenzoate (3.38 g), 1,5-pentanediol (2.30 g) and triphenylphosphine (5.96 g) in tetrahydrofuran (100 mL), diethylazodicarboxylate (2.2N toluene solution, 10 mL) was slowly added under ice cooling. The reaction mixture was stirred under ice cooling for 16 hours. The reaction mixture was concentrated and the residue was washed with n-hexane-ethyl acetate solution (n-hexane:ethyl acetate=1:1). The reaction mixture was concentrated and then purified by silica gel chromatography (n-hexane:ethyl acetate=64:36→45:55) to obtain the title compound (3.58 g) having the following physical properties.

TLC: Rf 0.36 (n-hexane:ethyl acetate=1:1);
NMR (CDCl$_3$): δ 1.47-1.73 (m, 4H), 1.76-1.92 (m, 2H), 3.69 (t, J=6.3 Hz, 2H), 3.88 (s, 3H), 4.02 (t, J=6.3 Hz, 2H), 6.90 (d, J=9.0 Hz, 2H), 7.97 (d, J=9.0 Hz, 2H)

Example 25

Methyl 4-({5-[(methylsulfonyl)oxy]pentyl}oxy)benzoate (compound 25)

To a solution of the compound 24 (3.58 g) and triethylamine (2.76 mL) in ethyl acetate (50 mL), methanesulfonyl chloride (0.78 mL) was slowly added under ice cooling. The reaction mixture was stirred under ice cooling for 2 hours. The reaction mixture was diluted with ethyl acetate (100 mL). The diluted solution was washed in turn with water and saturated brine, dried over anhydrous magnesium sulfate and then concentrated. The residue was purified by silica gel chromatography (ethyl acetate:methanol=1:0→10:1) to obtain the title compound (3.70 g) having the following physical properties.

TLC: Rf 0.39 (n-hexane:ethyl acetate=1:1);
NMR (CDCl$_3$): δ 1.56-1.69 (m, 2H), 1.76-1.93 (m, 4H), 3.01 (s, 3H), 3.89 (s, 3H), 4.03 (t, J=6.3 Hz, 2H), 4.27 (t, J=6.3 Hz, 2H), 6.90 (d, J=9.0 Hz, 2H), 7.98 (d, J=9.0 Hz, 2H)

Example 26

Methyl 4-{[5-(dipropylamino)pentyl]oxy}benzoate (compound 26)

A solution of the compound 25 (3.70 g) and dipropylamine (3.00 mL) in isopropyl alcohol (40 mL) was stirred at 60° C. for 16 hours. The reaction mixture was cooled to room temperature and saturated sodium bicarbonate water (40 mL) was added. The aqueous layer was extracted twice with ethyl acetate (50 mL). The combined organic layer was washed with saturated brine, dried over anhydrous magnesium sulfate and then concentrated. The residue was purified by silica gel chromatography (ethyl acetate:methanol=10:90→0:100) to obtain the title compound (1.94 g) having the following physical properties.

TLC: Rf 0.30 (ethyl acetate:methanol=10:90);
NMR (CDCl$_3$): δ 0.87 (t, J=7.5 Hz, 6H), 1.33-1.59 (m, 8H), 1.73-1.91 (m, 2H), 2.29-2.39 (m, 4H), 2.39-2.48 (m, 2H), 3.88 (s, 3H), 4.01 (t, J=6.6 Hz, 2H), 6.89 (d, J=9.0 Hz, 2H), 7.97 (d, J=9.0 Hz, 2H)

Example 27

4-{[5-(dipropylamino)pentyl]oxy}-N,N-bis(1H-imidazol-2-ylmethyl)benzamide (compound 27)

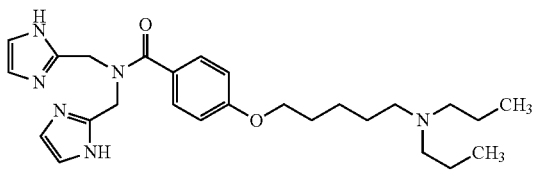

The same procedure as a series of reactions of Example 5→Example 6→Example 10 was carried out, except that the compound 26 was used in place of the compound 4 in the process of Example 5, to obtain the title compound having the following physical properties.

Description: amorphous;

TLC: Rf 0.66 (dichloromethane:methanol:28% ammonia water=16:4:1);

NMR (CDCl$_3$): δ 0.86 (t, J=7.5 Hz, 6H), 1.31-1.57 (m, 8H), 1.69-1.87 (m, 2H), 2.28-2.49 (m, 6H), 3.96 (t, J=6.6 Hz, 2H), 4.65 (s, 4H), 6.89 (d, J=8.7 Hz, 2H), 6.93-7.12 (m, 4H), 7.66 (d, J=8.7 Hz, 2H)

Example 28

(5E)-6-[4-(methoxycarbonyl)phenyl]-5-hexanoic acid (compound 28)

A solution of 5-(triphenylphosphonium)pentanoic acid bromide (26.8 g) in toluene (200 mL), t-butoxy potassium (13.5 g) was added. The reaction mixture was stirred at 80° C. for one hour. The reaction mixture was cooled to 0° C. and 4-methyl formylbenzoate (3.41 g) was added to the reaction mixture. The reaction mixture was stirred at 0° C. for 2 hours and then stirred at room temperature for 30 minutes. To the reaction mixture, water (150 mL) was added. The aqueous layer was acidified by adding 5N hydrochloric acid (15 mL) and the aqueous layer was extracted twice with ethyl acetate (100 mL). The combined organic layer was washed with saturated brine, dried over anhydrous magnesium sulfate and then concentrated. The residue was purified by silica gel chromatography (n-hexane:ethyl acetate=3:1→2:1) to obtain the title compound (3.10 g) having the following physical properties.

TLC: Rf 0.50 (n-hexane:ethyl acetate=1:9);

NMR (CDCl$_3$): δ 1.71-1.94 (m, 2H), 2.23-2.50 (m, 4H), 3.84-3.96 (m, 3H), 5.66-6.39 (m, 1H), 6.40-6.56 (m, 1H), 7.28-7.44 (m, 2H), 7.90-8.06 (m, 2H)

Example 29

Methyl 4-[(1E)-6-hydroxy-1-hexene-1-yl]benzoate (compound 29)

To a solution of the compound 28 (3.10 g) in tetrahydrofuran (40 mL), a borane-tetrahydrofuran complex (0.98 N/THF, 13 mL) was slowly added under ice cooling. The reaction mixture was stirred at 0° C. for 20 minutes. To the reaction mixture, water (10 mL) was slowly added and furthermore potassium carbonate (3 g) was added. This solution was diluted with water (100 mL) and the aqueous layer was extracted twice with ethyl acetate (100 mL). The combined organic layer was washed with saturated brine, dried over anhydrous magnesium sulfate and then concentrated. The residue was purified by silica gel chromatography (n-hexane:ethyl acetate=7:3→3:7) to obtain the title compound (2.50 g) having the following physical properties.

TLC: Rf 0.45 (n-hexane:ethyl acetate=1:1);

NMR (CDCl$_3$): δ 1.47-1.74 (m, 4H), 2.21-2.72 (m, 2H), 3.55-3.76 (m, 2H), 3.82-3.97 (m, 3H), 5.68-6.54 (m, 2H), 7.28-7.44 (m, 2H), 7.88-8.06 (m, 2H)

Example 30

Methyl 4-{6-[(methylsulfonyl)oxy]hexyl}benzoate (compound 30)

In a solution of the compound 29 (2.50 g) in methanol (30 mL), 10% palladium carbon (250 mg) was added under an argon atmosphere. The reaction mixture was stirred under a hydrogen atmosphere at room temperature for 3 hours. The reaction mixture was filtered with Celite (trade name) and the filtrate was concentrated. The residue was purified by silica gel chromatography (n-hexane:ethyl acetate=7:3→3:7) to obtain methyl 4-(6-hydroxyhexyl)benzoate (2.22 g). The same procedure as a series of reactions of Example 25 was carried out, except that methyl 4-(6-hydroxyhexyl)benzoate was used in place of the compound 24, to obtain the title compound having the following physical properties.

TLC: Rf 0.56 (n-hexane:ethyl acetate=1:1);

NMR (CDCl$_3$): δ1.29-1.52 (m, 4H), 1.58-1.83 (m, 4H), 2.59-2.73 (m, 2H), 2.99 (s, 3H), 3.90 (s, 3H), 4.21 (t, J=6.6 Hz, 2H), 7.24 (d, J=8.4 Hz, 2H), 7.95 (d, J=8.4 Hz, 2H)

Example 31

4-[6-(dipropylamino)hexyl]-N,N-bis(1H-imidazol-2-ylmethyl)benzamide (compound 31)

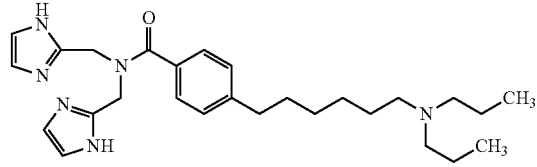 [SMILES: CCCN(CCC)CCCCCOc1ccc(C(=O)N(Cc2ncc[nH]2)Cc2ncc[nH]2)cc1]

The same procedure as a series of reactions of Example 26 was carried out, except that the compound 30 was used in place of the compound 25, to obtain methyl 4-[6-(dipropylamino)hexyl]benzoate. The same procedure as a series of reactions of Example 5→Example 6→Example 10 was carried out, except that methyl 4-[6-(dipropylamino)hexyl]benzoate was used in place of the compound 4 in the process of Example 5, to obtain the title compound having the following physical properties.

Description: oily product;

TLC: Rf 0.37 (dichloromethane:methanol:28% ammonia water=90:10:1);

NMR (CDCl$_3$): δ 0.87 (t, J=7.5 Hz, 6H), 1.14-1.71 (m, 12H), 2.30-2.49 (m, 6H), 2.60 (t, J=7.5 Hz, 2H), 4.68 (m, 4H), 6.90-7.09 (m, 4H), 7.19 (d, J=8.1 Hz, 2H), 7.51 (d, J=8.1 Hz, 2H)

Example 32

Methyl 4-[(5-bromopentyl)thio]benzoate (compound 32)

To a solution of methyl 4-mercaptobenzoate (3.39 g) and 1,5-dibromopentane (9.31 g) in dimethyl formamide (100 mL), potassium carbonate (3.07 g) was added. The reaction mixture was stirred at room temperature for 3 hours. To the reaction mixture, water (300 mL) was added and the aqueous layer was extracted twice with an n-hexane-ethyl acetate solution (n-hexane:ethyl acetate=1:1) (150 mL). The combined organic layer was washed with saturated brine, dried over anhydrous magnesium sulfate and then concentrated. The residue was purified by silica gel chromatography (n-hexane:ethyl acetate=1:0→8:2) to obtain the title compound (4.69 g) having the following physical properties.

TLC: Rf 0.68 (n-hexane:ethyl acetate=4:1);
NMR (CDCl$_3$): δ 1.54-1.80 (m, 4H), 1.80-1.98 (m, 2H), 3.00 (t, J=6.9 Hz, 2H), 3.41 (t, J=6.6 Hz, 2H), 3.90 (s, 3H), 7.28 (d, J=8.7 Hz, 2H), 7.92 (d, J=8.7 Hz, 2H)

Example 33

4-{[5-(dipropylamino)pentyl]sulfanyl}-N,N-bis(1H-imidazol-2-ylmethyl)benzamide (compound 33)

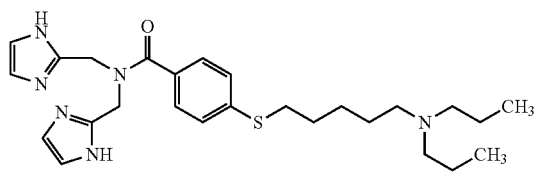

The same procedure as a series of reactions of Example 26 was carried out, except that the compound 32 was used in place of the compound 25, to obtain methyl 4-{[5-(dipropylamino)pentyl]thio}benzoate. The same procedure as a series of reactions of Example 5→Example 6→Example 10 was carried out, except that methyl 4-{[5-(dipropylamino)pentyl]thio}benzoate was used in place of the compound 4 in the process of Example 5, to obtain the title compound having the following physical properties.

Description: amorphous;
TLC: Rf 0.24 (dichloromethane:methanol:28% ammonia water=80:20:1);
NMR (DMSO-d$_6$): δ 0.81 (t, J=7.5 Hz, 6H), 1.25-1.46 (m, 8H), 1.49-1.67 (m, 2H), 2.19-2.45 (m, 6H), 2.97 (t, J=7.2 Hz, 2H), 4.56 (s, 4H), 6.79-7.13 (m, 4H), 7.27 (d, J=8.4 Hz, 2H), 7.44 (d, J=8.4 Hz, 2H), 10.97-13.23 (m, 2H)

Example 34

Methyl 4-{[(4-hydroxybutyl)amino]carbonyl}benzoate (compound 34)

The same procedure as a series of reactions of Example 17 was carried out, except that 4-amino-1-butanol was used in place of the compound 16 and 4-(methoxycarbonyl)benzoic acid was used in place of 1H-imidazole-2-carboxylic acid, to obtain the title compound having the following physical properties.

TLC: Rf 0.31 (ethyl acetate)

Example 35

N$^1$-[4-(dipropylamino)butyl]-N$^4$,N$^4$-bis(1H-imidazol-2-ylmethyl)terephthalamide (compound 35)

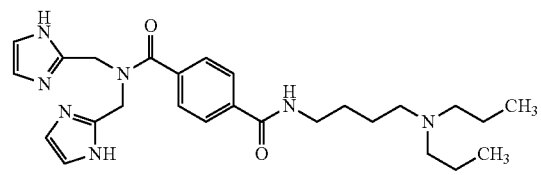 [SMILES: CCCN(CCC)CCCCNC(=O)c1ccc(C(=O)N(Cc2ncc[nH]2)Cc2ncc[nH]2)cc1]

The same procedure as a series of reactions of Example 25→Example 26 was carried out, except that the compound 34 was used in place of the compound 24 in the process of Example 25, to obtain methyl 4-({[4-(dipropylamino)butyl]amino}carbonyl)benzoate. The same procedure as a series of reactions of Example 5→Example 6→Example 10 was carried out, except that methyl 4-({[4-(dipropylamino)butyl]amino}carbonyl)benzoate was used in place of the compound 4 in the process of Example 5, to obtain the title compound having the following physical properties.

Description: amorphous;
TLC: Rf 0.58 (dichloromethane:methanol:28% ammonia water=16:4:1);
NMR (CDCl$_3$): δ 0.86 (t, J=7.5 Hz, 6H), 1.34-1.54 (m, 4H), 1.54-1.74 (m, 4H), 2.33-2.48 (m, 4H), 2.51 (t, J=6.6 Hz, 2H), 3.31-3.56 (m, 2H), 4.55 (s, 2H), 4.66 (s, 2H), 6.85-7.03 (m, 2H), 7.08 (s, 2H), 7.18-7.37 (m, 1H), 7.43-7.79 (m, 4H)

Example 35(1)

4-({[4-(dipropylamino)butyl]amino}methyl)-N- (compound 35-1)

The same operation as a series of reactions of Example 35 was carried out, except that 1-(1H-imidazol-2-yl)-N-(pyridin-3-ylmethyl)methaneamine was used in place of the compound 2 in the process of Example 6, to obtain the title compound having the following physical properties.

Description: oily product;
TLC: Rf 0.83 (chloroform:methanol:28% ammonia water=40:10:2);
NMR (CDCl$_3$): δ 0.85 (t, J=7.2 Hz, 6H), 1.22-1.70 (m, 8H), 2.24-2.48 (m, 6H), 2.54-2.66 (m, 2H), 3.4.9 (s, 2H), 3.79 (s, 2H), 4.63 (s, 2H), 6:82-7.11 (m, 2H), 7.19-7.44 (m, 5H), 7.45-7.64 (m, 1H), 8.46 (s, 1H), 8.55 (d, J=1.5 Hz, 1H)

Example 36

1H-imidazole-2-sulfonyl chloride hydrochloride (compound 36)

Under ice cooling, a chlorine gas was bubbled into a solution of 2-mercaptoimidazole (3.0 g) in 1N hydrochloric acid (30 mL) for one hour. The reaction mixture was stirred under ice cooling for 2 hours. The reaction mixture was filtered and the solid collected after filtration was washed with ice water and then dried to obtain the title compound (1.76 g) having the following physical properties.

NMR (DMSO-d$_6$): δ 14.82 (m, 2H), 7.58 (s, 2H)

Example 37

N-({2-[4-(dipropylamino)butyl]-1,2,3,4-tetrahydro-6-isoquinolinyl}methyl)-N-[(1-methyl-1H-imidazol-2-yl)methyl]-1H-imidazole-2-sulfonamide (compound 37)

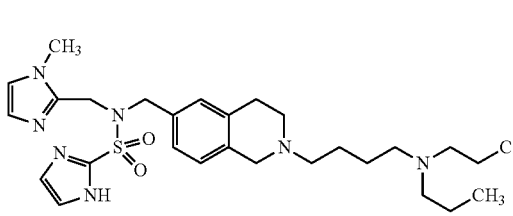

In a solution of the compound 23-a (100 mg) and pyridine (59 mL) in dichloromethane (3 mL), the compound 36 (74 mg) was added. The reaction mixture was stirred at room temperature for 30 minutes. To the reaction mixture, an aqueous 1N sodium hydroxide solution (15 mL) was added. The aqueous layer was extracted twice with dichloromethane (30 mL). The combined organic layer was washed with saturated brine, dried over anhydrous magnesium sulfate and then concentrated. The residue was purified by silica gel chromatography (ethyl acetate:methanol:triethylamine=10:1:0→10:1:0.5) to obtain the title compound (119 mg) having the following physical properties.

Description: semisolid;

TLC: Rf 0.71 (chloroform:methanol:28% ammonia water=80:20:4);

NMR (DMSO-$d_6$): δ 0.82 (t, J=7.5 Hz, 6H), 1.27-1.44 (m, 6H), 1.45-1.57 (m, 2H), 2.22-2.32 (m, 4H), 2.32-2.45 (m, 4H), 2.53-2.62 (m, 2H), 2.62-2.70 (m, 2H), 3.41-3.49 (m, 5H), 4.26 (s, 2H), 4.41 (s, 2H), 6.59 (s, 1H), 6.79 (s, 1H), 6.80-6.86 (m, 1H), 6.87-6.94 (m, 1H), 7.00 (s, 1H), 7.25 (s, 2H)

Example 37(1)

N-[4-({[4-(dipropylamino)butyl]amino}methyl)benzyl]-N-(1H-imidazol-2-ylmethyl)-1H-imidazole-2-sulfonamide (compound 37-1)

The same procedure as a series of reactions of Example 20→Example 21→Example 22→Example 23 was carried out, except that 4-(aminomethyl)benzoic acid was used in place of methyl 1,2,3,4-tetrahydro-6-isoquinolinecarboxylate hydrochloride. The same procedure as a series of reactions of Example 35 was carried out, except that the obtained N'-(4-{[(cyclopenta-1,3-dien-1-ylmethyl)amino]methyl}benzyl)-N,N-dipropylpropane-1,3-diamine was used in place of the compound 23-a, to obtain the title compound having the following physical properties.

Description: amorphous;

TLC: Rf 0.26 (ethyl acetate:methanol:28% ammonia water=90:10:2);

NMR (CDCl$_3$): δ d 0.88 (t, J=7.2 Hz, 6H); 1.38-1.68 (m, 8H), 2.30-2.60 (m, 6H), 2.74 (m, 2H), 3.70 (m, 2H), 3.77 (s, 2H), 4.56 (m, 2H), 6.98-7.30 (m, 8H)

Example 38

4-({[4-(dipropylamino)butyl]amino}methyl)-N,N-bis(1H-imidazol-2-ylmethyl)benzenesulfonamide (compound 38)

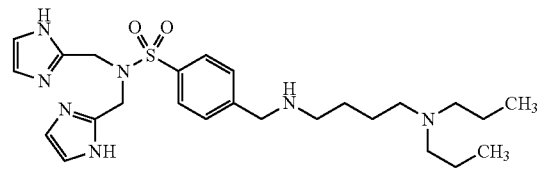 [SMILES: CCCN(CCC)CCCCNCc1ccc(S(=O)(=O)N(Cc2ncc[nH]2)Cc2ncc[nH]2)cc1]

The same procedure as a series of reactions of Example 37 was carried out, except that the compound 2 was used in place of the compound 23-a and 4-formylbenzenesulfonyl chloride was used in place of the compound 36, to obtain a 4-formyl-N,N-bis[(1-{[2-(trimethylsilyl)ethoxy]methyl}-1H-imidazol-2-yl)methyl]benzamide (compound 38-a). The same procedure as a series of reactions of Example 1→Example 10 was carried out, except that the compound 38-a was used in place of 1-({[2-(trimethylsilyl)ethyloxy]methyl}-1H-imidazole-2-carboaldehyde and N,N-dipropyl-1,4-butanediamine was used in place of {[4-(methyloxy)phenyl]methyl}amine in the process of Example 1, to obtain the title compound having the following physical properties.

Description: amorphous;

TLC: Rf 0.66 (chloroform:methanol:28% ammonia water=80:20:4);

NMR (DMSO-$d_6$): δ 0.81 (t, J=7.5 Hz, 6H), 1.24-1.48 (m, 8H), 2.18-2.37 (m, 6H), 2.42 (t, J=6.3 Hz, 2H), 3.70 (s, 2H), 4.49 (s, 4H), 6.68-6.91 (m, 2H), 6.91-7.16 (m, 2H), 7.40 (d, J=8.1 Hz, 2H), 7.54 (d, J=8.1 Hz, 2H), 12.19-12.64 (m, 2H)

Example 39

N-[4-({[4-(dimethylamino)butyl]amino}carbonyl)benzyl]-N-(1H-imidazol-2-ylmethyl)-1H-imidazole-2-carboxamide (compound 39)

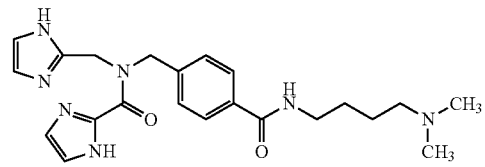 [SMILES: CN(C)CCCCNC(=O)c1ccc(CN(Cc2ncc[nH]2)C(=O)c2ncc[nH]2)cc1]

The same procedure as a series of reactions of Example 16→Example 17 was carried out, except that methyl 4-formylbenzoate was used in place of 4-(diethoxymethyl)benzaldehyde, to obtain methyl 4-({(1H-imidazol-2-ylcarbonyl)[(1-{[2-(trimethylsilyl)ethoxy]methyl}-1H-imidazol-2-yl)methyl]amino}methyl)benzoate (compound 39-a). The same procedure as a series of reactions of Example 5→Example 6→Example 10 was carried out, except that the compound 39-a was used in place of the compound 4 in the process of Example 5 and N,N-dimethyl-1,4-butaneamine was used in place of the compound 2 in the process of Example 6, to obtain the title compound having the following physical properties.

Description: amorphous;

TLC: Rf 0.24 (chloroform:methanol:28% ammonia water=80:20:4);

NMR (DMSO-d$_6$): δ 1.32-1.64 (m, 4H), 2.09 (s, 6H), 2.13-2.27 (m, 2H), 3.14-3.29 (m, 2H), 3.65 (s, 1H), 3.71 (s, 1H), 4.52 (s, 0.5H), 4.62 (s, 0.5H), 5.31 (s, 0.5H), 5.60 (s, 0.5H), 6.71-6.89 (m, 1H), 6.94-7.11 (m, 1H), 7.24-7.35 (m, 1H), 7.41 (d, J=8.1 Hz, 1H), 7.77 (d, J=8.1 Hz, 2H), 7.92-8.08 (m, 2H), 8.35-8.50 (m, 1H), 8.62-8.78 (m, 1H), 10.06 (s, 1H)

Example 39(1)

N-[4-({[4-(dipropylamino)butyl]amino}carbonyl)benzyl]-N-(1H-imidazol-2-ylmethyl)-1H-imidazole-2-carboxamide (compound 39-1)

The same procedure as a series of reactions of Example 39 was carried out, except that N,N-dipropyl-1,4-butaneamine was used in place of N,N-dimethyl-1,4-butaneamine, to obtain the title compound having the following physical properties.

Description: amorphous;

TLC: Rf 0.32 (chloroform:methanol:28% ammonia water=80:20:4);

NMR (DMSO-d$_6$): δ 0.80 (t, J=7.5 Hz, 6H), 1.20-1.44 (m, 6H), 1.44-1.65 (m, 2H), 2.14-2.42 (m, 6H), 3.14-3.28 (m, 2H), 4.51 (s, 1H), 4.62 (s, 1H), 5.30 (s, 1H), 5.60 (s, 1H), 6.82 (s, 1H), 6.96-7.19 (m, 2H), 7.22-7.44 (m, 3H), 7.77 (d, J=8.4 Hz, 2H), 8.27-8.55 (m, 1H), 11.77-12.18 (m, 1H), 12.90-13.27 (m, 1H)

Example 40

4-formyl-N,N-bis[(1-{[2-(trimethylsilyl)ethoxy]methyl}-1H-imidazol-2-yl)methyl]benzamide (compound 40)

The same procedure as a series of reactions of Example 17 was carried out, except that the compound 2 was used in place of the compound 16 and 4-formylbenzoic acid was used in place of 1H-imidazole-2-carboxylic acid, to obtain the title compound having the following physical properties.

TLC: Rf 0.47 (chloroform:methanol=10:1);

NMR (CDCl$_3$): δ 10.01 (s, 1H), 7.85 (m, 2H), 7.77 (m, 2H), 7.04 (m, 4H), 5.51 (s, 2H), 5.15 (s, 2H), 4.93 (s, 2H), 4.67 (s, 2H), 3.59 (t, J=8.1 Hz, 2H), 3.30 (t, J=8.1 Hz, 2H), 0.94 (t, J=8.1 Hz, 2H), 0.70 (t, J=8.1 Hz, 2H), 0.00 (s, 9H), −0.09 (s, 9H)

Example 41

4-formyl-N,N-bis(1H-imidazol-2-ylmethyl)benzamide (Example 41)

To the compound 40 (1.7 g), a 50% trifluoroacetic acid-dichloromethane solution (10 mL) was added. The reaction mixture was stirred at room temperature for 3 hours. The reaction mixture was concentrated and an aqueous 5N sodium hydroxide solution (15 mL) was added to the residue. The aqueous layer was extracted three times with 50 mL of dichloromethane. The combined organic layer was washed with saturated brine and then dried over anhydrous magnesium sulfate. The solvent was concentrated to obtain the title compound (compound B) (922 mg) having the following physical properties.

TLC: Rf 0.60 (chloroform:methanol:28% ammonia water=80:10:1);

NMR (CDCl$_3$): δ 10.03 (s, 1H), 7.92 (d, J=8.1 Hz, 2H), 7.74 (d, J=8.1 Hz, 2H), 7.12-6.94 (m, 4H), 4.73 (s, 2H), 4.58 (s, 2H)

Example 42

Cis-N,N-dipropylcyclohexane-1,4-diamine (compound 42)

The same procedure as a series of reactions of Example 8 was carried out, except that tert-butyl 4-aminocyclohexylcarbamate was used in place of the compound 7 in the process of Example 8, and a 10% hydrogen chloride-methanol solution (10 mL) was added to the obtained compound. The reaction mixture was stirred at room temperature for 2 hours. The solvent was concentrated and the residue was dissolved in methanol (30 mL). To this solution, a carbonate resin (trade name: MP-Carbonate, manufactured by Argonaut Technologies Inc., product number: 800267, 3 g) was added, followed by stirring at room temperature for 2 hours. The reaction mixture was filtered and then the filtrate was concentrated. The title compound (467 mg) having the following physical properties was obtained without purifying the residue.

TLC: Rf 0.26 (dichloromethane:methanol:28% ammonia water=80:20:3);

NMR (CDCl$_3$): δ 3.35-3.29 (m, 1H), 2.85-2.73 (m, 1H), 2.72-2.64 (m, 4H), 1.95-1.56 (m, 12H), 0.92 (t, J=7.2 Hz, 6H)

Example 43

4-({[cis-4-(dipropylamino)cyclohexyl]amino}methyl)-N,N-bis(1H-imidazol-2-ylmethyl)benzamide (compound 43)

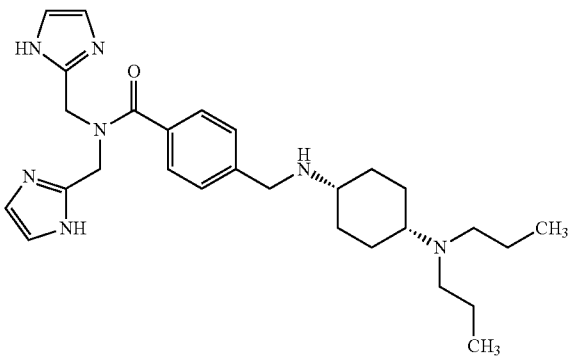 [SMILES: CCCN(CCC)[C@H]1CC[C@@H](NCc2ccc(C(=O)N(Cc3ncc[nH]3)Cc3ncc[nH]3)cc2)CC1]

To a solution of the compound 41 (116 mg) and the compound 42 (203 mg) in a 1% acetic acid-dichloromethane solution (5 mL), an anhydrous sodium sulfate (220 mg) was added. The mixture was stirred at room temperature for 30 minutes. To the reaction mixture, sodium triacetoxyborohydride (225 mg) was added. The mixture was stirred at room temperature for 6 hours. To the reaction mixture, an aqueous saturated sodium hydrogen carbonate solution (10 mL) was added. The aqueous layer was extracted twice with a mixture of dichloromethane:methanol=3:1 (50 mL). The combined organic layer was washed with saturated brine and then dried over anhydrous magnesium sulfate. The solvent was concentrated and then purified by silica gel chromatography to obtain the title compound (149 mg) having the following physical properties.

Description: amorphous;
TLC: Rf 0.64 (dichloromethane:methanol:28% ammonia water=80:20:3);
NMR (CDCl₃): δ 0.86 (t, J=7.2 Hz, 6H), 1.30-1.69 (m, 10H), 1.70-1.86 (m, 2H), 2.34-2.57 (m, 5H), 2.71-2.83 (m, 1H), 3.76 (s, 2H), 4.53-4.81 (m, 4H), 6.91-7.14 (m, 4H), 7.38 (d, J=8.1 Hz, 2H), 7.55 (d, J=8.1 Hz, 2H)

Example 43(1) to Example 43(11)

The same procedure as a series of reactions of Example 42→Example 43, except that a corresponding aldehyde or ketone was used in place of tert-butyl 4-aminocyclohexylcarbamate and a corresponding carbonyl compound was used in place of 1-propanal in the process of conducting the same procedure as a series of reactions of Example 8 of Example 42, to obtain the title compound having the following physical properties Example 43(1)

N,N-bis(1H-imidazol-2-ylmethyl)-4-[(2-propyl-2,7-diazaspiro[3.5]non-7-yl)methyl]benzamide (compound 43-1)

Description: amorphous;
TLC: Rf 0.23 (dichloromethane:methanol:28% ammonia water=80:20:1);
NMR (CDCl₃): δ 0.87 (t, J=7.5 Hz, 3H), 1.23-1.44 (m, 2H), 1.72 (t, J=5.40 Hz, 4H), 2.19-2.45 (m, 6H), 2.95 (s, 4H), 3.44 (s, 2H), 4.52-4.77 (m, 4H), 6.89-7.17 (m, 4H), 7.35 (d, J=8.1 Hz, 2H,), 7.59 (d, J=8.1 Hz, 2H)

Example 43(2)

4-{[4-(dipropylamino)-1-piperidinyl]methyl}-N,N-bis(1H-imidazol-2-ylmethyl)benzamide (compound 43-2)

Description: amorphous;
TLC: Rf 0.49 (dichloromethane:methanol:28% ammonia water=80:20:1);
NMR (CDCl₃): δ 0.85 (t, J=7.2 Hz, 6H), 1.29-1.76 (m, 8H), 1.84-2.05 (m, 2H), 2.33-2.54 (m, 5H), 2.80-2.97 (m, 2H), 3.49 (s, 2H), 4.52-4.79 (m, 4H), 6.91-7.15 (m, 4H), 7.36 (d, J=7.8 Hz, 2H), 7.61 (d, J=7.8 Hz, 2H)

Example 43(3)

4-({[trans-4-(dipropylamino)cyclohexyl]amino}methyl)-N,N-bis(1H-imidazol-2-ylmethyl)benzamide (compound 43-3)

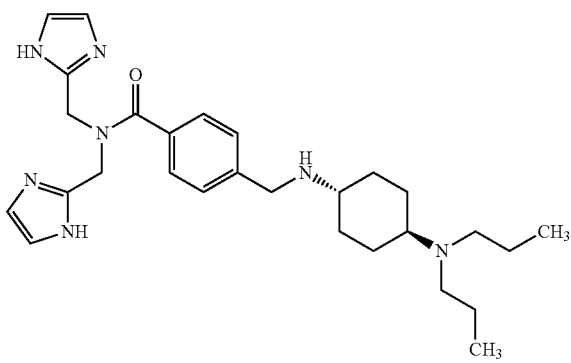 [SMILES: CCCN(CCC)[C@H]1CC[C@H](NCc2ccc(C(=O)N(Cc3ncc[nH]3)Cc3ncc[nH]3)cc2)CC1]

Description: amorphous;
TLC: Rf 0.57 (dichloromethane:methanol:28% ammonia water=80:20:3);
NMR (CDCl₃): δ 0.85 (t, J=7.2 Hz, 6H), 0.98-1.33 (m, 4H), 1.33-1.51 (m, 4H), 1.71-1.86 (m, 2H), 1.91-2.07 (m, 2H), 2.28-2.56 (m, 6H), 3.81 (s, 2H), 4.53-4.77 (m, 4H), 6.91-7.13 (m, 4H), 7.34 (d, J=8.1 Hz, 2H), 7.54 (d, J=8.1 Hz, 2H)

Example 43(4)

4-[({trans-4-[cyclohexyl(propyl)amino]cyclohexyl}amino)methyl]-N,N-bis(1H-imidazol-2-ylmethyl)benzamide (compound 43-4)

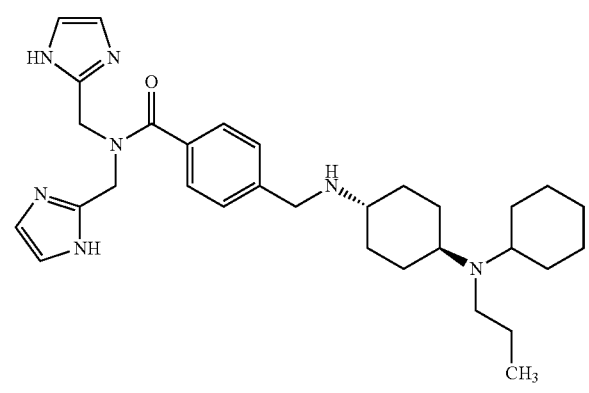 [SMILES: CCCN(C1CCCCC1)[C@H]1CC[C@H](NCc2ccc(C(=O)N(Cc3ncc[nH]3)Cc3ncc[nH]3)cc2)CC1]

Description: amorphous;
TLC: Rf 0.60 (dichloromethane:methanol:28% ammonia water=80:20:3);
NMR (CDCl₃): δ 0.81 (t, J=7.2 Hz, 3H), 0.96-1.46 (m, 11H), 1.51-1.65 (m, 1H), 1.65-1.82 (m, 6H), 1.88-2.04 (m, 2H), 2.28-2.68 (m, 5H), 3.81 (s, 2H), 4.51-4.80 (m, 4H), 6.89-7.16 (m, 4H), 7.34 (d, J=8.1 Hz, 2H), 7.55 (d, J=8.1 Hz, 2H)

Example 43(5)

4-[(7-cyclohexyl-2,7-diazaspiro[3.5]non-2-yl)methyl]-N,N-bis(1H-imidazol-2-ylmethyl)benzamide (compound 43-5)

Description: amorphous;
TLC: Rf 0.37 (dichloromethane:methanol:28% ammonia water=80:20:3);
NMR (CDCl₃): δ 0.98-1.33 (m, 5H), 1.52-1.96 (m, 9H), 2.20-2.62 (m, 5H), 2.99 (s, 4H), 3.63 (s, 2H), 4.52-4.81 (m, 4H), 6.92-7.14 (m, 4H), 7.29 (d, J=8.1 Hz, 2H), 7.48 (d, J=8.1 Hz, 2H)

Example 43(6)

4-({[3-(dipropylamino)cyclohexyl]amino}methyl)-N,N-bis(1H-imidazol-2-ylmethyl)benzamide (compound 43-6)

Description: amorphous;
TLC: Rf 0.32 (chloroform:methanol:28% ammonia water=80:10:1);
NMR (DMSO-D₆): δ d 0.78 (t, J=7.5 Hz, 6H), 1.28 (m, 7H), 1.61 (m, 4H), 1.94 (m, 1H), 2.28 (m, 4H), 2.86 (m, 2H), 3.65 (m, 2H), 4.58 (m, 4H), 6.88 (m, 2H), 7.08 (m, 2H), 7.33 (d, J=8.1 Hz, 2H), 7.43 (d, J=8.10 Hz, 2H), 12.14 (m, 1H), 12.36 (m, 1H)

Example 43(7)

4-({[3-(dipropylamino)cyclohexyl]amino}methyl)-N,N-bis(1H-imidazol-2-ylmethyl)benzamide (compound 43-7)

Description: amorphous;
TLC: Rf 0.26 (chloroform:methanol:28% ammonia water=80:10:1);
NMR (DMSO-$D_6$): δ d 0.80 (m, 6H), 1.32 (m, 6H), 1.66 (m, 3H), 1.94 (m, 2H), 2.32 (m, 6H), 2.89 (m, 1H), 3.66 (m, 1H), 3.75 (m, 1H), 4.56 (m, 4H), 6.97 (m, 4H), 7.33 (m, 2H), 7.42 (m, 2H), 12.21 (m, 2H)

Example 43(8)

4-{[{3-[(dipropylamino)methyl]benzyl}(methyl)amino]methyl}-N,N-bis(1H-imidazol-2-ylmethyl)benzamide (compound 43-8)

Description: amorphous;
TLC: Rf 0.32 (dichloromethane:methanol:28% ammonia water=90:10:1);
NMR (CDCl$_3$): δ 0.85 (t, J=7.5 Hz, 6H), 1.41-1.53 (m, 4H), 2.16 (s, 3H), 2.33-2.38 (m, 4H), 3.51 (s, 4H), 3.55 (s, 2H), 4.64 (s, 2H), 4.68 (s, 2H), 6.96-7.04 (m, 4H), 7.22-7.30 (m, 4H), 7.40 (d, J=7.8 Hz, 2H), 7.59 (d, J=7.8 Hz, 2H)

Example 43(9)

N,N-bis(1H-imidazol-2-ylmethyl)-4-({[4-(1-pyrrolidinyl)cyclohexyl]amino}methyl)benzamide (compound 43-9)

Description: amorphous;
TLC: Rf 0.25 (dichloromethane:methanol:28% ammonia water=90:10:1);
NMR (CDCl$_3$): δ d 1.10-2.10 (m, 12H), 2.20 (m, 1H), 2.50 (m, 1H), 2.65-2.88 (m, 4H), 3.82 (s, 2H), 4.55-4.80 (m, 4H), 6.98-7.12 (m, 4H), 7.32-7.42 (m, 2H), 7.52-7.64 (m, 2H)

Example 43(10)

4-({[2-(dipropylamino)cyclohexyl]amino}methyl)-N,N-bis(1H-imidazol-2-ylmethyl)benzamide (compound 43-10)

Description: amorphous;
TLC: Rf 0.70 (chloroform:methanol:28% ammonia water=40:10:2);
NMR (CDCl$_3$): δ 0.80 (t, J=7.2 Hz, 3H), 0.87 (t, J=7.2 Hz, 3H), 1.00-1.56 (m, 8H), 1.55-1.87 (m, 4H), 1.98-2.56 (m, 6H), 3.65 (d, J=13.5 Hz, 1H), 3.88 (d, J=13.5 Hz, 1H), 4.48-4.80 (m, 4H), 6.85-7.12 (m, 4H), 7.33 (d, J=8.1 Hz, 2H), 7.57 (d, J=8.1 Hz, 2H)

Example 43(11)

4-({[5-(dipropylamino)octahydro-2-pentalenyl]amino}methyl)-N,N-bis(1H-imidazol-2-ylmethyl)benzamide (compound 43-11)

Description: amorphous;
TLC: Rf 0.35 (chloroform:methanol:28% ammonia water=40:10:2);
NMR (CDCl$_3$): δ 0.87 (t, J=7.2 Hz, 6H), 1.07-1.63 (m, 8H), 1.96-2.41 (m, 6H), 2.44-2.63 (m, 4H), 2.87-3.19 (m, 2H), 3.79 (s, 2H), 4.49-4.79 (m, 4H), 6.86-7.15 (m, 4H), 7.36 (d, J=8.1 Hz, 2H), 7.58 (d, J=8.1 Hz, 2H)

Example 44 tert-butyl 4-(2-{bis[(1-{[2-(trimethylsilyl)ethoxy]methyl}-1H-imidazol-2-yl)methyl]amino}-2-oxoethyl)-1-piperidine carboxylate (compound 44)

Under an argon atmosphere at room temperature, [1-(tert-butoxycarbonyl)-4-piperidinyl]acetic acid (500 mg) and the compound 2 (899 mg) were dissolved in anhydrous dimethyl formamide (12 mL), and 1-ethyl-3-[3-(dimethylamino)propyl]carbodiimide (590 mg), 1-hydroxybenztriazole (417 mg) and 4-dimethylaminopyridine (377 mg) were added, followed by stirring at room temperature for 16 hours. After the addition of city water and stirring, the obtained solution was extracted three times with ethyl acetate. The organic layer was collected and then washed with saturated brine. After drying over anhydrous sodium sulfate, the solvent was distilled off. The residue was purified by silica gel column chromatography to obtain the title compound (216 mg) having the following physical properties.
TLC: Rf 0.85 (chloroform:methanol:28% ammonia water=90:10:1);
NMR (CDCl$_3$): δ 7.00-6.91 (m, 4H), 5.36 (s, 2H), 5.33 (s, 2H), 4.77 (s, 4H), 4.68 (s, 2H), 4.08 (m, 2H), 3.50 (m, 2H), 2.75 (m, 2H), 2.46 (d, J=6.6 Hz, 2H), 2.12 (m, 1H), 1.76 (m, 2H), 1.65 (s, 9H), 1.14 (m, 2H), 0.90 (m, 2H), 0.00 (m, 18H)

Example 45

N,N-bis(1H-imidazol-2-ylmethyl)-2-(4-piperidinyl)acetamide trihydrochloride (compound 45)

To the compound (216 mg) prepared in Example 44, 4N hydrogen chloride/dioxane (8 mL) was added, followed by stirring at room temperature for 3 hours and further stirring at 70° C. for 3 hours. The solvent was distilled off to obtain the title compound without purifying the residue.
TLC: Rf 0.11 (chloroform:methanol:28% ammonia water=40:10:2)

Example 46

2-{1-[4-(dipropylamino)butyl]-4-piperidinyl}-N,N-bis(1H-imidazol-2-ylmethyl)acetamide (compound 46)

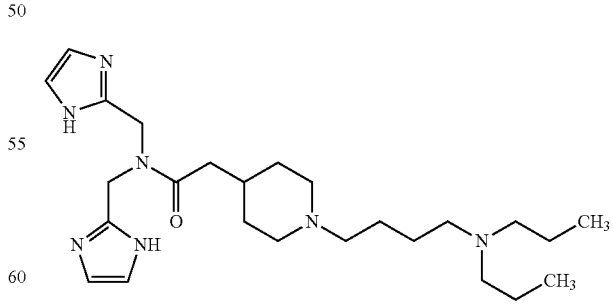

The compound 45 and 4-(dipropylamino)butanal (55.6 mg) were added and a 10% acetic acid-anhydrous dimethyl formamide solution (3 mL) was stirred under an argon atmosphere for 5 minutes. To the reaction solution, sodium triacetoxyborohydride (103 mg) was added, followed by stirring at room temperature for 15 hours. To the reaction solution, an aqueous 2N sodium hydroxide solution (10 mL) was added and the aqueous layer was extracted three times with ethyl acetate. The organic layer was collected, washed with saturated brine, dried over anhydrous sodium sulfate, and then the solvent was distilled off. The residue was purified by silica gel column chromatography to obtain the title compound (86.4 mg) having the following physical properties.

Description: oily product;
TLC: Rf 0.78 (chloroform:methanol:28% ammonia water=40:10:2);
NMR (CDCl$_3$): δ 0.86 (t, J=7.2 Hz, 6H), 1.10-1.29 (m, 2H), 1.34-1.52 (m, 8H), 1.53-1.77 (m, 3H), 1.77-1.95 (m, 2H), 2.19-2.51 (m, 10H), 2.70-2.94 (m, 2H), 4.66 (s, 2H), 4.75 (s, 2H), 6.90-7.06 (m, 4H)

Example 46(1) to Example 46(2)

The same procedure as a series of reactions of Example 44→Example 45→Example 46 was carried out, except that a corresponding carboxylic acid was used in place of [1-(tert-butoxycarbonyl)-4-piperidinyl]acetic acid and was optionally replaced by a salt, to obtain the following compound of the present invention

Example 46(1)

1-[4-(dipropylamino)butyl]-N,N-bis(1H-imidazol-2-ylmethyl)-4-piperidine carboxamide tetrahydrochloride (compound 46-1)

Description: amorphous;
TLC: Rf 0.68 (chloroform:methanol:28% ammonia water=40:10:2);
NMR (METHANOL-D$_4$): δ 1.02 (t, J=7.5 Hz, 6H), 1.54-1.90 (m, 7H), 1.94-2.21 (m, 5H), 2.88-3.25 (m, 12H), 3.50-3.74 (m, 1H), 4.81-5.01 (m, 2H), 5.42 (s, 2H), 7.50 (s, 2H), 7.61 (s, 2H)

Example 46(2)

3-{1-[4-(dipropylamino)butyl]-4-piperidinyl}-N,N-bis(1H-imidazol-2-ylmethyl)propaneamide (compound 46-2)

Description: oily product;
TLC: Rf 0.78 (chloroform:methanol:28% ammonia water=40:10:2);
NMR (CDCl$_3$): δ 0.86 (t, J=7.5 Hz, 6H), 1.09-1.28 (m, 2H), 1.32-1.62 (m, 11H), 1.73-1.84 (m, 2H), 2.17-2.48 (m, 12H), 2.80-2.89 (m, 2H), 4.65 (s, 2H), 4.74 (s, 2H), 6.92-7.03 (m, 4H)

Example 47

Ethyl 4-({bis[(1-{[2-(trimethylsilyl)ethoxy]methyl}-1H-imidazol-2-yl)methyl]amino}carbonylamino)benzoate (compound 47)

A solution of butyl 4-isocyanatebenzoate (250.4 mg) and the compound 2 (500 mg) in dichloromethane (3 mL) was stirred at room temperature for one hour. The reaction solution was concentrated under reduced pressure and the residue was purified by silica gel column chromatography to obtain the title compound (731.9 mg) having the following physical properties.
TLC: Rf 0.24 (n-hexane:methanol=3:1);

NMR (CDCl$_3$): δ 7.98 (d, J=9.0 Hz, 2H), 7.58 (d, J=9.0 Hz, 2H), 7.04 (s, 1H), 7.00 (s, 1H), 5.43 (s, 4H), 4.74 (s, 4H), 4.30 (t, J=6.6 Hz, 2H), 3.50 (m, 4H), 1.75 (m, 2H), 1.49 (m, 2H), 0.98 (t, J=7.5 Hz, 3H), 0.88 (m, 4H), −0.55 (s, 18H)

Example 48

4-({[bis(1H-imidazol-2-ylmethyl)amino]carbonyl}amino)-N-[4-(dipropylamino)butyl]benzamide (compound 48)

To a solution of the compound 47 (195 mg) in methanol (2 mL), 2 mL of concentrated hydrochloric acid was added. The reaction solution was stirred at 60° C. for 6 hours. After cooling to room temperature, the reaction solution was concentrated under reduced pressure. The same procedure as a series of reactions of Example 17 was carried out, using the obtained compound and N,N-dipropyl-1,4-butanediamine, to obtain the title compound (76.6 mg) having the following physical properties.

Description: amorphous;
TLC: Rf 0.67 (chloroform:methanol:28% ammonia water=80:20:4);
NMR (DMSO-D$_6$): δ d 0.81 (t, J=7.5 Hz, 6H), 1.22-1.60 (m, 8H), 2.13-2.43 (m, 6H), 3.22 (q, J=6.6 Hz, 2H), 4.59 (s, 4H), 6.73-6.98 (m, 2H), 6.98-7.24 (m, 2H), 7.50 (d, J=9.0 Hz, 2H), 7.74 (d, J=9.0 Hz, 2H), 8.25 (t, J=5.7 Hz, 1H), 9.57 (s, 1H), 11.99-12.39 (m, 2H)

Example 49

4-[(2-cyclohexyl-2,7-diazaspiro[3.5]nona-7-yl)methyl]-N,N-bis(1H-imidazol-2-ylmethyl)benzamide (compound 49)

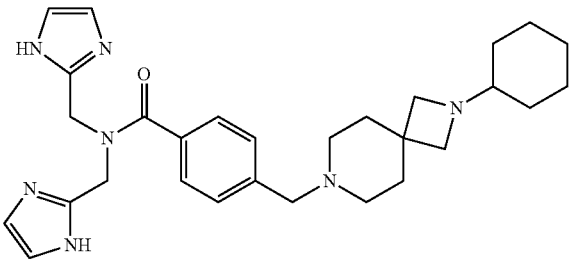 [SMILES: O=C(c1ccc(CN2CCC3(CC2)CN(C2CCCCC2)C3)cc1)N(Cc1ncc[nH]1)Cc1ncc[nH]1]

The same procedure as a series of reactions of Example 43 was carried out, using the compound 41 and 2-cyclohexyl-2,7-diazaspiro[3.5]nonane, to obtain the title compound having the following physical properties.
MS: 502 (M+H)$^+$; HPLC retention time: 2.74 minutes.

Example 49(1) to Example 49(20)

The same operation as a series of reactions of Example 49 was carried out, except that a corresponding amine compound was used in place of 2-cyclohexyl-2,7-diazaspiro[3.5]nonane, to obtain the title compound having the following physical properties.

Example 49(1)

4-[(2-cyclohexyl-2,8-diazaspiro[4.5]dec-8-yl)methyl]-N,N-bis(1H-imidazol-2-ylmethyl)benzamide (compound 49-1)

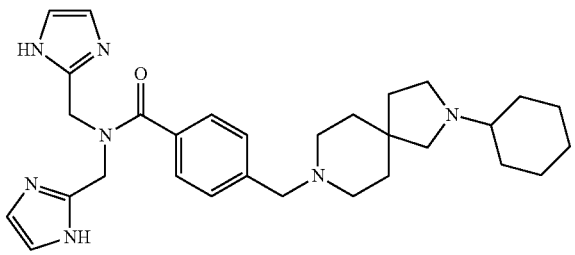 [SMILES: O=C(c1ccc(CN2CCC3(CC2)CCN(C2CCCCC2)C3)cc1)N(Cc1ncc[nH]1)Cc1ncc[nH]1]

MS: 516 (M+H)⁺; HPLC retention time: 2.40 minutes.

Example 49(2)

4-[(8-cyclohexyl-2,8-diazaspiro[4.5]dec-2-yl)methyl]-N,N-bis(1H-imidazol-2-ylmethyl)benzamide (compound 49-2)

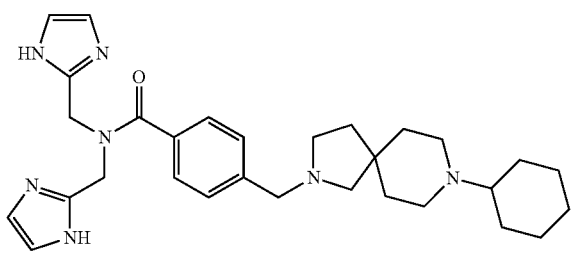 [SMILES: O=C(c1ccc(CN2CCC3(CCN(C4CCCCC4)CC3)C2)cc1)N(Cc1ncc[nH]1)Cc1ncc[nH]1]

MS: 516 (M+H)⁺; HPLC retention time: 2.41 minutes

Example 49(3)

4-[(9-cyclohexyl-2,9-diazaspiro[5.5]undec-2-yl)methyl]-N,N-bis(1H-imidazol-2-ylmethyl)benzamide (compound 49-3)

MS: 530 (M+H)⁺; HPLC retention time: 2.46 minutes

Example 49(4)

4-[(7-cyclohexyl-2,7-diazaspiro[4.5]dec-2-yl)methyl]-N,N-bis(1H-imidazol-2-ylmethyl)benzamide (compound 49-4)

MS: 516 (M+H)⁺; HPLC retention time: 2.43 minutes

Example 49(5)

4-[(8-cyclohexyl-2,8-diazaspiro[5.5]undec-2-yl)methyl]-N,N-bis(1H-imidazol-2-ylmethyl)benzamide (compound 49-5)

MS: 530 (M+H)⁺; HPLC retention time: 2.46 minutes

Example 49(6)

4-[(1'-cyclohexylspiro[indole-3,4'-piperidine]-1(2H)-yl)methyl]-N,N-bis(1H-imidazol-2-ylmethyl)benzamide (compound 49-6)

MS: 564 (M+H)⁺; HPLC retention time: 2.80 minutes

Example 49(7)

4-[(1'-cyclohexyl-5-methylspiro[indole-3,4'-piperidine]-1(2H)-yl)methyl]-N,N-bis(1H-imidazol-2-ylmethyl)benzamide (compound 49-7)

MS: 578 (M+H)⁺; HPLC retention time: 2.88 minutes

Example 49(8)

4-[(1'-cyclohexyl-5-fluorospiro[indole-3,4'-piperidine]-1(2H)-yl)methyl]-N,N-bis(1H-imidazol-2-ylmethyl)benzamide (compound 49-8)

MS: 582 (M+H)⁺; HPLC retention time: 2.84 minutes.

Example 49(9)

4-[(5-chloro1'-cyclohexylspiro[indole-3,4'-piperidine]-1(2H)-yl)methyl]-N,N-bis(1H-imidazol-2-ylmethyl)benzamide (compound 49-9)

MS: 598 (M+H)⁺; HPLC retention time: 2.93 minutes

Example 49(10)

4-[(1-cyclohexyl-1,2-dihydro-1'H-spiro[indole-3,4'-piperidine]-1'-yl)methyl]-N,N-bis(1H-imidazol-2-ylmethyl)benzamide (compound 49-10)

MS: 564 (M+H)⁺; HPLC retention time: 2.95 minutes

Example 49(11)

4-{[3-(dipropylamino)-2,3-dihydro-1'H-spiro[indene-1,4'-piperidine]-1'-yl]methyl}-N,N-bis(1H-imidazol-2-ylmethyl)benzamide (compound 49-11)

MS: 580 (M+H)⁺; HPLC retention time: 2.59 minutes

Example 49(12)

4-[(1-cyclohexyl-5-methyl-1,2-dihydro-1'H-spiro[indole-3,4'-piperidine]-1'-yl)methyl]-N,N-bis(1H-imidazol-2-ylmethyl)benzamide (compound 49-12)

MS: 576 (M+H)⁺; HPLC retention time: 2.76 minutes

Example 49(13)

4-[(4-cyclohexyl-1-oxa-4,9-diazaspiro[5.5]undec-9-yl)methyl]-N,N-bis(1H-imidazol-2-ylmethyl)benzamide (compound 49-13)

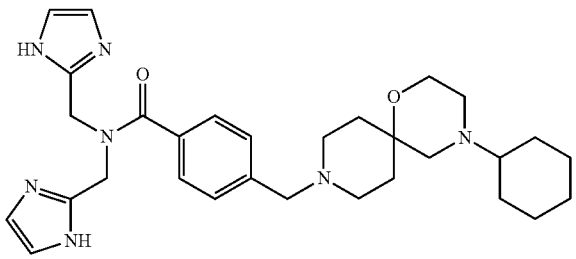 [SMILES: O=C(c1ccc(CN2CCC3(CC2)CN(C2CCCCC2)CCO3)cc1)N(Cc1ncc[nH]1)Cc1ncc[nH]1]

MS: 532 (M+H)+; HPLC retention time: 2.39 minutes

Example 49(14)

4-[(9-cyclohexyl-1-oxa-4,9-diazaspiro[5.5]undec-4-yl)methyl]-N,N-bis(1H-imidazol-2-ylmethyl)benzamide (compound 49-14)

MS: 532 (M+H)+; HPLC retention time: 2.47 minutes

Example 49(15)

4-[(4-cyclohexyl-1-oxa-4,8-diazaspiro[5.5]undec-8-yl)methyl]-N,N-bis(1H-imidazol-2-ylmethyl)benzamide (compound 49-15)

MS: 532 (M+H)+; HPLC retention time: 2.41 minutes

Example 49(16)

4-[(8-cyclohexyl-1-oxa-4,8-diazaspiro[5.5]undec-4-yl)methyl]-N,N-bis(1H-imidazol-2-ylmethyl)benzamide (compound 49-16)

MS: 532 (M+H)+; HPLC retention time: 2.41 minutes

Example 49(17)

4-[(2-cyclohexyl-2,3-dihydro-1H,1'H-spiro[isoquinoline-4,4'-piperidine]-1'-yl)methyl]-N,N-bis(1H-imidazol-2-ylmethyl)benzamide (compound 49-17)

MS: 578 (M+H)+; HPLC retention time: 2.60 minutes

Example 49(18)

4-[(1'-cyclohexyl-1H-spiro[isoquinoline-4,4'-piperidine]-2(3H)-yl)methyl]-N,N-bis(1H-imidazol-2-ylmethyl)benzamide (compound 49-18)

MS: 578 (M+H)+; HPLC retention time: 2.54 minutes

Example 49(19)

ethyl 8-(4-{[bis(1H-imidazol-2-ylmethyl)amino]carbonyl}benzyl)-2-cyclohexyl-2,8-diazaspiro[4.5]decane-3-carboxylate (compound 49-19)

MS: 588 (M+H)+; HPLC retention time: 2.57 minutes

Example 49(20)

4-{[4-(dipropylamino)-3,4-dihydro-1'H-spiro[chromene-2,4'-piperidine]-1'-yl]methyl}-N,N-bis(1H-imidazol-2-ylmethyl)benzamide (compound 49-20)

MS: 596 (M+H)+; HPLC retention time: 2.61 minutes

Example 50(1) to Example 50(147)

The same procedure as a series of reactions of Example 43 was carried out, except that a corresponding aldehyde was used in place of the compound 41 and a corresponding amine was used in place of the compound 42, to obtain the title compound having the following physical properties.

Example 50(1)

4-[({trans-4-[benzyl(propyl)amino]cyclohexyl}amino)methyl]-N,N-bis(1H-imidazol-2-ylmethyl)benzamide

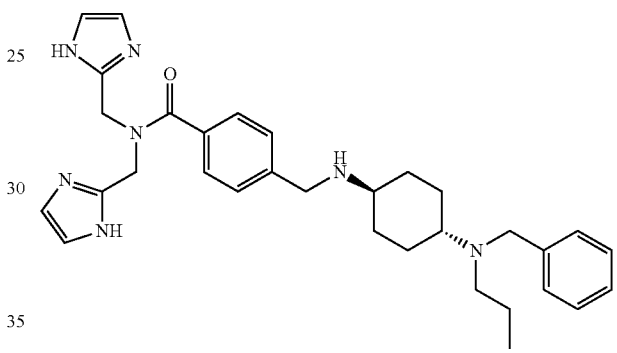

Description: amorphous;
TLC: Rf 0.48 (ethyl acetate:methanol:28% ammonia water=90:10:2);
NMR (CDCl3): δ d 0.81 (t, J=7.2 Hz, 3H), 1.02-1.42 (m, 6H), 1.78-1.90 (m, 2H), 1.95-2.06 (m, 2H), 2.40 (t, J=7.2 Hz, 2H), 2.40-2.60 (m, 2H), 3.59 (s, 2H), 3.81 (s, 2H), 4.50-4.75 (m, 4H), 6.96-7.10 (m, 4H), 7.15-7.40 (m, 7H), 7.50-7.60 (m, 2H)

Example 50(2)

4-[({trans-4-[cyclohexyl(ethyl)amino]cyclohexyl}amino)methyl]-N,N-bis(1H-imidazol-2-ylmethyl)benzamide (compound 50-2)

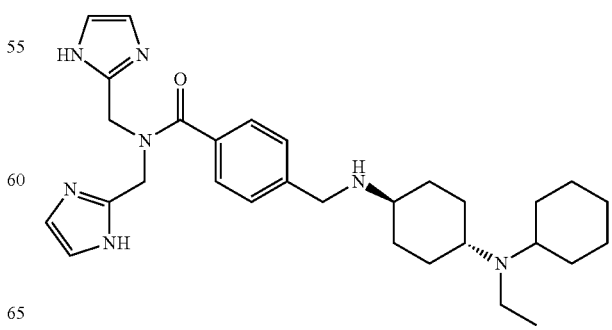

Description: amorphous;

TLC: Rf 0.21 (ethyl acetate:methanol:28% ammonia water=90:10:2)

NMR (CDCl$_3$): δ d 0.98-2.05 (m, 21H), 2.40 (m, 1H), 2.50-2.75 (m, 4H), 3.81 (s, 2H), 4.58-4.75 (m, 4H), 6.98-7.10 (m, 4H), 7.35 (d, J=8.1 Hz, 2H), 7.59 (d, J=8.1 Hz, 2H)

Example 50(3)

4-[(7-cyclohexyl-2,7-diazaspiro[4.4]nona-2-yl)methyl]-N,N-bis(1H-imidazol-2-ylmethyl)benzamide (compound 50-3)

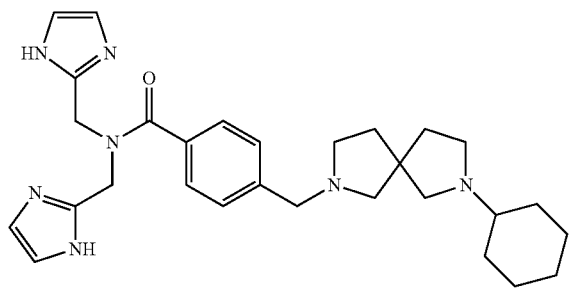 [SMILES: O=C(c1ccc(CN2CCC3(CCN(C4CCCCC4)C3)C2)cc1)N(Cc1ncc[nH]1)Cc1ncc[nH]1]

Description: amorphous;

TLC: Rf 0.65 (chloroform:methanol:28% ammonia water=40:10:2);

NMR (CDCl$_3$): δ 1.00-1.45 (m, 6H), 1.53-2.10 (m, 8H), 2.19-2.41 (m, 2H), 2.47-3.00 (m, 7H), 3.53-3.68 (m, 2H), 4.48-4.88 (m, 4H), 6.95-7.09 (m, 4H), 7.33 (d, J=8.1 Hz, 2H), 7.53 (d, J=8.1 Hz, 2H)

Example 50(4)

4-[(2-cyclohexyl-2,7-diazaspiro[4.5]dec-7-yl)methyl]-N,N-bis(1H-imidazol-2-ylmethyl)benzamide (compound 50-4)

Description: amorphous;

TLC: Rf 0.72 (chloroform:methanol:28% ammonia water=40:10:2);

NMR (CDCl$_3$): δ 0.94-1.30 (m, 4H), 1.30-2.57 (m, 19H), 2.56-2.91 (m, 2H), 3.24-3.51 (m, 2H), 4.40-4.92 (m, 4H), 7.01 (s, 4H), 7.33 (d, J=8.1 Hz, 2H), 7.50 (d, J=8.1 Hz, 2H)

Example 50(5)

4-({[4-(3,4-dihydroisoquinoline-2(1H)-yl)cyclohexyl]amino}methyl)-N,N-bis(1H-imidazol-2-ylmethyl)benzamide (low polar compound) (compound 50-5)

Description: amorphous;

TLC: Rf 0.55 (ethyl acetate:methanol:28% ammonia water=90:10:2);

NMR (CDCl$_3$): δ d 1.44-1.92 (m, 8H), 2.48 (m, 1H), 2.75-2.95 (m, 5H), 3.78 (s, 2H), 3.79 (s, 2H), 4.55-4.72 (m, 4H), 6.98-7.18 (m, 8H), 7.40 (d, J=7.8 Hz, 2H), 7.63 (d, J=7.8 Hz, 2H)

Example 50(6)

4-({[4-(3,4-dihydro-2(1H)-isoquinolinyl)cyclohexyl]amino}methyl)-N,N-bis(1H-imidazol-2-ylmethyl)benzamide (high polar compound) (compound 50-6)

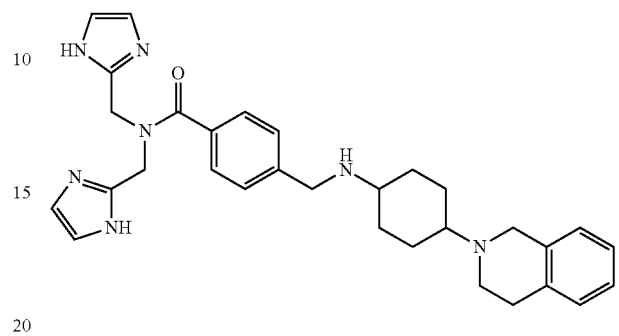

Description: amorphous;

TLC: Rf 0.41 (ethyl acetate:methanol:28% ammonia water=90:10:2);

NMR (CDCl$_3$): δ d 1.15-2.60 (m, 10H), 2.80-2.98 (m, 4H), 3.79 (s, 2H), 3.86 (s, 2H), 4.55-4.75 (m, 4H), 6.98-7.15 (m, 8H), 7.39 (d, J=8.4 Hz, 2H), 7.63 (d, J=8.4 Hz, 2H)

Example 50(7)

N,N-bis(1H-imidazol-2-ylmethyl)-4-[({4-[(4aS,8aR)-octahydroisoquinoline-2(1H)-yl]cyclohexyl}amino)methyl]benzamide (low polar compound) (compound 50-7)

Description: amorphous;

TLC: Rf 0.50 (ethyl acetate:methanol:28% ammonia water=90:10:2);

NMR (CDCl$_3$): δ d 0.80-2.82 (m, 24H), 2.94 (m, 1H), 3.12 (m, 1H), 3.75 (s, 2H), 4.52-4.72 (m, 4H), 6.98-7.18 (m, 4H), 7.39 (d, J=8.4 Hz, 2H), 7.63 (d, J=8.4 Hz, 2H)

Example 50(8)

4-[({4-[(4aS,8aR)-octahydro-2(1H)-isoquinolinyl]cyclohexyl}amino)methyl]-N,N-bis(1H-imidazol-2-ylmethyl)benzamide (high polar compound) (compound 50-8)

Description: amorphous;

TLC: Rf 0.37 (ethyl acetate:methanol:28% ammonia water=90:10:2);

NMR (CDCl$_3$): δ d 0.80-2.50 (m, 24H), 2.90 (m, 1H), 2.98 (m, 1H), 3.81 (s, 2H), 4.52-4.75 (m, 4H), 6.98-7.18 (m, 4H), 7.36 (d, J=8.4 Hz, 2H), 7.63 (d, J=8.4 Hz, 2H)

Example 50(9)

4-[({trans-4-[benzyl(cyclohexyl)amino]cyclohexyl}amino)methyl]-N,N-bis(1H-imidazol-2-ylmethyl)benzamide (compound 50-9)

Description: amorphous;

TLC: Rf 0.54 (ethyl acetate:methanol:28% ammonia water=90:10:2);

NMR (CDCl$_3$): δ d 0.95-2.65 (m, 21H), 3.72 (s, 2H), 3.80 (s, 2H), 4.52-4.75 (m, 4H), 6.98-7.15 (m, 4H), 7.18-7.40 (m, 7H), 7.59 (d, J=8.1 Hz, 2H)

Example 50(10)

N,N-bis(1H-imidazol-2-ylmethyl)-4-{[(cis-4-morpholine-4-ylcyclohexyl)amino]methyl}benzamide (compound 50-10)

Description: amorphous;
TLC: Rf 0.62 (chloroform:methanol:28% ammonia water=80:20:4);
NMR (DMSO-$D_6$): δ d 1.26-1.47 (m, 4H), 1.53-1.75 (m, 4H), 2.00-2.15 (m, 1H), 2.32-2.45 (m, 4H), 2.54-2.64 (m, 1H), 3.48-3.61 (m, 4H), 3.67 (s, 2H), 4.47-4.68 (m, 4H), 6.76-7.00 (m, 2H), 7.00-7.15 (m, 2H), 7.33 (d, J=8.4 Hz, 2H), 7.42 (d, J=8.4 Hz, 2H), 11.95-12.24 (m, 1H), 12.25-12.56 (m, 1H)

Example 50(11)

N,N-bis(1H-imidazol-2-ylmethyl)-4-[(trans-4-morpholine-4-ylcyclohexyl)amino]methyl benzamide (compound 50-11)

Description: amorphous;
TLC: Rf 0.50 (chloroform:methanol:28% ammonia water=80:20:4);
NMR (DMSO-$D_6$): δ 0.86-1.26 (m, 4H), 1.66-1.82 (m, 2H), 1.84-1.99 (m, 2H), 2.04-2.18 (m, 1H), 2.19-2.33 (m, 1H), 2.34-2.45 (m, 4H), 3.44-3.58 (m, 4H), 3.70 (s, 2H), 4.42-4.69 (m, 4H), 6.76-6.98 (m, 2H), 6.98-7.17 (m, 2H), 7.31 (d, J=8.4 Hz, 2H), 7.41 (d, J=8.4 Hz, 2H), 11.99-1225 (m, 1H), 12.26-12.50 (m, 1H)

Example 50(12)

N,N-bis(1H-imidazol-2-ylmethyl)-4-{[(4-piperidine 1-ylcyclohexyl)amino]methyl}benzamide (low polar compound) (compound 50-12)

Description: amorphous;
TLC: Rf 0.21 (ethyl acetate:methanol:28% ammonia water=80:20:4);
NMR (CDCl$_3$): δ d 1.10-2.10 (m, 14H), 2.88-3.10 (m, 6H), 3.73 (s, 2H), 4.55-4.78 (m, 4H), 6.98-7.10 (m, 4H), 7.35 (d, J=8.1 Hz, 2H), 7.55 (d, J=8.1 Hz, 2H)

Example 50(13)

N,N-bis(1H-imidazol-2-ylmethyl)-4-({[4-(1-piperidinyl)cyclohexyl]amino}methyl)benzamide (high polar compound) (compound 50-13)

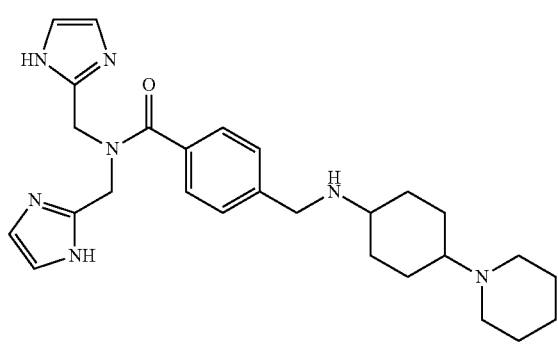 [SMILES: O=C(c1ccc(CNC2CCC(N3CCCCC3)CC2)cc1)N(Cc1ncc[nH]1)Cc1ncc[nH]1]

Description: amorphous;
TLC: Rf 0.15 (ethyl acetate:methanol:28% ammonia water=80:20:4);
NMR (CDCl$_3$): δ d 1.10-1.30 (m, 2H), 1.38-1.65 (m, 4H), 1.78-1.95 (m, 4H), 2.00-2.20 (m, 4H), 2.43 (m, 1H), 2.70-3.00 (m, 5H), 3.82 (s, 2H), 4.55-4.78 (m, 4H), 6.98-7.10 (m, 4H), 7.33 (d, J=8.1 Hz, 2H), 7.53 (d, J=8.1 Hz, 2H)

Example 50(14)

N,N-bis(1H-imidazol-2-ylmethyl)-4-({[4-(4-methylpiperazine-1-yl)cyclohexyl]amino}methyl)benzamide (low polar compound) (compound 50-14)

Description: amorphous;
TLC: Rf 0.22 (ethyl acetate:methanol:28% ammonia water=80:20:4);
NMR (CDCl$_3$): δ d 1.45-1.90 (m, 8H), 2.28-2.90 (m, 10H), 2.37 (s, 3H), 3.79 (s, 2H), 4.55-4.78 (m, 4H), 6.98-7.12 (m, 4H), 7.39 (d, J=7.8 Hz, 2H), 7.53 (d, J=7.8 Hz, 2H)

Example 50(15)

N,N-bis(1H-imidazol-2-ylmethyl)-4-({[4-(4-methyl-1-piperazinyl)cyclohexyl]amino}methyl)benzamide. (high polar compound) (compound 50-15)

Description: amorphous;
TLC: Rf 0.19 (ethyl acetate:methanol:28% ammonia water=80:20:4);
NMR (CDCl$_3$): δ d 1.20-1.48 (m, 4H), 1.99 (m, 2H), 2.15 (m, 2H), 2.34 (s, 3H), 2.38 (m, 1H), 2.45-2.80 (m, 9H), 3.88 (s, 2H), 4.50-4.78 (m, 4H), 7.03 (s, 4H), 7.40 (s, 4H)

Example 50(16)

4-({[4-(4,4-difluoropiperidine 1-yl)cyclohexyl]amino}methyl)-N,N-bis(1H-imidazol-2-ylmethyl) benzamide (low polar compound) (compound 50-16)

Description: amorphous;
TLC: Rf 0.69 (ethyl acetate:methanol:28% ammonia water=80:20:4);
NMR (CDCl$_3$): δ d 1.45-2.10 (m, 12H), 2.40 (m, 1H), 2.60-2.74 (m, 4H), 2.92 (m, 1H), 3.84 (s, 2H), 4.55-4.78 (m, 4H), 7.05 (s, 4H), 7.38-7.50 (m, 4H)

Example 50(17)

4-({[4-(4,4-difluoro-1-piperidinyl)cyclohexyl]amino}methyl)-N,N-bis(1H-imidazol-2-ylmethyl) benzamide (high polar compound) (compound 50-17)

Description: amorphous;
TLC: Rf 0.55 (ethyl acetate:methanol:28% ammonia water=80:20:4);
NMR (CDCl$_3$): δ d 1.23-1.42 (m, 4H), 1.82-2.20 (m, 8H), 2.42 (m, 1H), 2.60 (m, 1H), 2.60-2.70 (m, 4H), 3.87 (s, 2H), 4.52-4.76 (m, 4H), 7.04 (s, 4H), 7.35-7.48 (m, 4H)

Example 50(18)

4-{[(4-azepan-1-ylcyclohexyl)amino]methyl}-N,N-bis(1H-imidazol-2-ylmethyl)benzamide (low polar compound) (compound 50-18)

Description: amorphous;
TLC: Rf 0.52 (ethyl acetate:methanol:28% ammonia water=80:20:4);

NMR (CDCl$_3$): δ d 1.40-1.95 (m, 16H), 2.75-3.10 (m, 6H), 3.73 (s, 2H), 4.55-4.78 (m, 4H), 7.00-7.10 (m, 4H), 7.35 (d, J=8.4 Hz, 2H), 7.55 (d, J=8.4 Hz, 2H)

Example 50(19)

4-({[4-(1-azepanyl)cyclohexyl]amino}methyl)-N,N-bis(1H-imidazol-2-ylmethyl)benzamide (high polar compound) (compound 50-19)

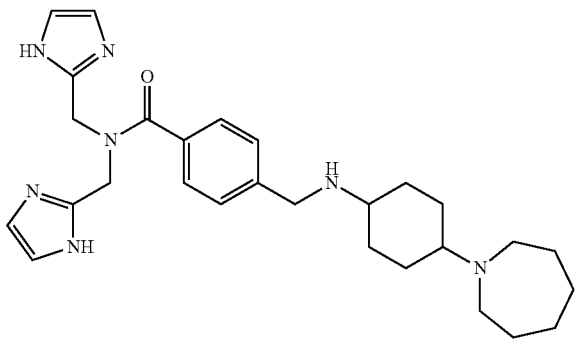 [SMILES: O=C(c1ccc(CNC2CCC(N3CCCCCC3)CC2)cc1)N(Cc1ncc[nH]1)Cc1ncc[nH]1]

Description: amorphous;
TLC: Rf 0.29 (ethyl acetate:methanol:28% ammonia water=80:20:4);
NMR (CDCl$_3$): δ d 1.10-1.25 (m, 2H), 1.32-1.52 (m, 2H), 1.60-2.20 (m, 12H), 2.41 (m, 1H), 2.70-3.22 (m, 5H), 3.81 (s, 2H), 4.55-4.78 (m, 4H), 6.98-7.10 (m, 4H), 7.33 (d, J=8.4 Hz, 2H), 7.56 (d, J=8.4 Hz, 2H)

Example 50(20)

4-({[4-(dibenzylamino)cyclohexyl]amino}methyl)-N,N-bis(1H-imidazol-2-ylmethyl)benzamide (low polar compound) (compound 50-20)

Description: amorphous;
TLC: Rf 0.52 (ethyl acetate:methanol:28% ammonia water=90:10:2);
NMR (CDCl$_3$): δ d 1.30-2.00 (m, 8H), 2.52 (m, 1H), 2.90 (m, 1H), 3.55-3.70 (m, 4H), 3.81 (s, 2H), 4.55-4.78 (m, 4H), 7.01 (s, 4H), 7.15-7.42 (m, 14H)

Example 50(21)

4-({[4-(dibenzylamino)cyclohexyl]amino}methyl)-N,N-bis(1H-imidazol-2-ylmethyl)benzamide (high polar compound) (compound 50-21)

Description: amorphous;
TLC: Rf 0.40 (ethyl acetate:methanol:28% ammonia water=90:10:2);
NMR (CDCl$_3$): δ d 1.00-1.20 (m, 2H), 1.30-1.50 (m, 2H), 1.82-1.98 (m, 2H), 1.98-2.10 (m, 2H), 2.40-2.60 (m, 2H), 3.60 (s, 4H), 3.81 (s, 2H), 4.50-4.76 (m, 4H), 6.90-7.08 (m, 4H), 7.18-7.40 (m, 12H), 7.47 (d, J=8.1 Hz, 2H)

Example 50(22)

4-({[trans-4-(cyclohexylamino)cyclohexyl]amino}methyl)-N,N-bis(1H-imidazol-2-ylmethyl)benzamide (compound 50-22)

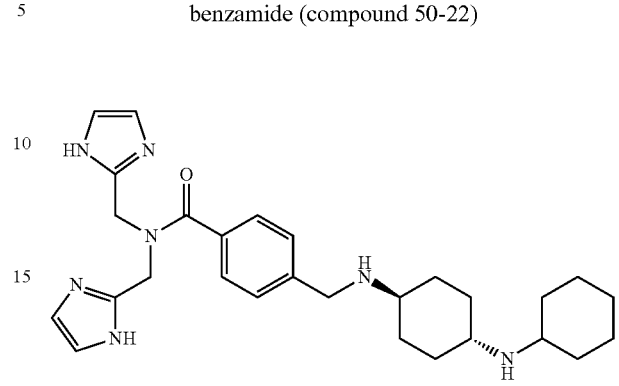

Description: amorphous;
TLC: Rf 0.41 (dichloromethane:methanol:28% ammonia water=90:10:2);
NMR (CDCl$_3$): δ d 1.02-2.12 (m, 18H), 2.44 (m, 1H), 2.65-2.82 (m, 2H), 3.81 (s, 2H), 4.56-4.80 (m, 4H), 6.95-7.10 (m, 4H), 7.33 (d, J=8.1 Hz, 2H), 7.53 (d, J=8.1 Hz, 2H)

Example 50(23)

3-({[4-(dipropylamino)butyl]amino}methyl)-N,N-bis(1H-imidazol-2-ylmethyl)benzamide (compound 50-23)

Description: oily product;
TLC: Rf 0.35 (dichloromethane:methanol:28% ammonia water=50:10:1);
NMR (CDCl$_3$): δ 0.85 (t, J=7.5 Hz, 6H), 1.39-1.49 (m, 8H), 2.33-2.43 (m, 6H), 2.61-2.66 (m, 2H), 3.79 (s, 2H), 4.51 (br-s, 2H), 4.73 (br-s, 2H), 7.05 (br, 4H), 7.36-7.38 (m, 2H), 7.54 (m, 1H), 7.62 (s, 1H)

Example 50(24)

4-[(9-cyclohexyl-3,9-diazaspiro[5.5]undec-3-yl)methyl]-N,N-bis(1H-imidazol-2-ylmethyl)benzamide (compound 50-24)

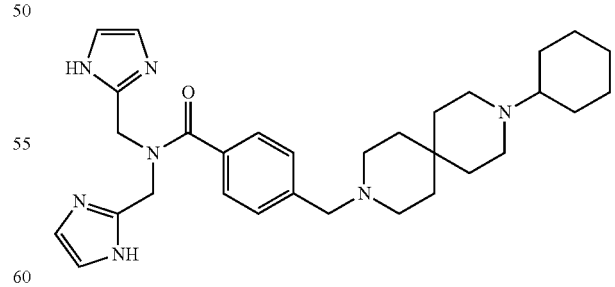

Description: amorphous;
TLC: Rf 0.37 (methanol:28% ammonia water=98:2);
NMR (CDCl$_3$): δ 0.97-1.34 (m, 5H), 1.37-1.69 (m, 9H), 1.71-1.98 (m, 4H), 2.24-2.42 (m, 5H), 2.45-2.64 (m, 4H), 3.48 (s, 2H), 4.53-4.85 (m, 4H), 6.86-7.13 (m, 4H), 7.33 (d, J=8.1 Hz, 2H), 7.48 (d, J=8.1 Hz, 2H)

Example 50(25)

4-{[8-(cyclohexylmethyl)-2,8-diazaspiro[4.5]dec-2-yl]methyl}-N,N-bis(1H-imidazol-2-ylmethyl)benzamide (compound 50-25)

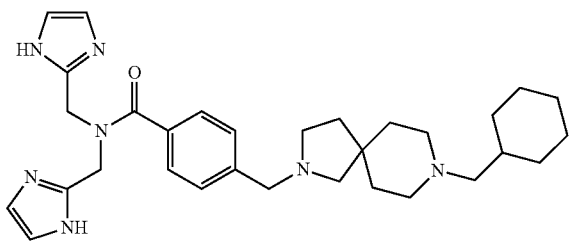 [SMILES: O=C(c1ccc(CN2CCC3(CCN(CC4CCCCC4)CC3)C2)cc1)N(Cc1ncc[nH]1)Cc1ncc[nH]1]

Description: amorphous;
TLC: Rf 0.73 (ethyl acetate:methanol:28% ammonia water=50:10:1);
NMR (CDCl$_3$): δ 0.78-0.92 (m, 2H), 1.10-1.30 (m, 3H), 1.40-1.79 (m, 12H), 2.07 (d, J=7.2 Hz, 2H), 2.22-2.36 (m, 6H), 2.54 (t, J=6.9 Hz, 2H), 3.58 (s, 2H), 4.59-4.68 (m, 4H), 6.95-7.10 (m, 4H), 7.38 (d, J=8.4 Hz, 2H), 7.64 (d, J=8.4 Hz, 2H)

Example 50(26)

4-[(8-benzyl-2,8-diazaspiro[4.5]dec-2-yl)methyl]-N,N-bis(1H-imidazol-2-ylmethyl)benzamide (compound 50-26)

Description: amorphous;
TLC: Rf 0.73 (ethyl acetate:methanol:28% ammonia water=50:10:1);
NMR (CDCl$_3$): δ 1.53-1.64 (m, 6H), 2.27-2.41 (m, 6H), 2.55 (t, J=6.9 Hz, 2H), 3.46 (s, 2H), 3.58 (s, 2H), 4.60-4.68 (m, 4H), 6.96-7.08 (m, 4H), 7.20-7.32 (m, 5H), 7.37 (d, J=8.4 Hz, 2H), 7.64 (d, J=8.4 Hz, 2H)

Example 50(27)

4-{[8-(cyclopropylmethyl)-2,8-diazaspiro[4.5]dec-2-yl]methyl}-N,N-bis(1H-imidazol-2-ylmethyl)benzamide (compound 50-27)

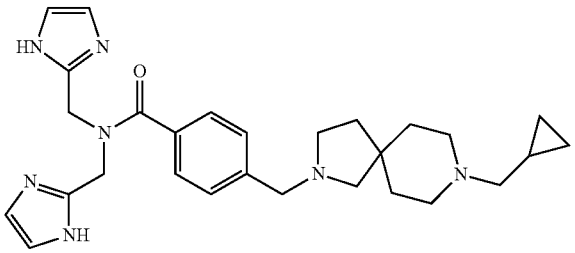 [SMILES: O=C(c1ccc(CN2CCC3(CCN(CC4CC4)CC3)C2)cc1)N(Cc1ncc[nH]1)Cc1ncc[nH]1]

Description: amorphous;
TLC: Rf 0.42 (ethyl acetate:methanol:28% ammonia water=50:10:1);
NMR (CDCl$_3$): δ 0.06-0.14 (m, 2H), 0.46-0.54 (m, 2H), 0.87 (m, 1H), 1.56-1.67 (m, 6H), 2.23 (d, J=6.6 Hz, 2H), 2.34 (s, 2H), 2.34-2.54 (m, 4H), 2.56 (t, J=6.9 Hz, 2H), 3.58 (s, 2H), 4.58-4.65 (m, 4H), 6.94-7.10 (m, 4H), 7.38 (d, J=8.4 Hz, 2H), 7.66 (d, J=8.4 Hz, 2H)

Example 50(28)

4-{[8-(cyclopentylmethyl)-2,8-diazaspiro[4.5]dec-2-yl]methyl}-N,N-bis(1H-imidazol-2-ylmethyl)benzamide (compound 50-28)

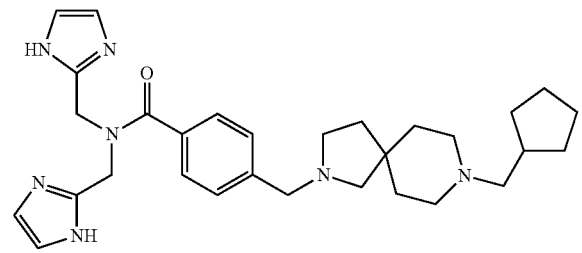 [SMILES: O=C(c1ccc(CN2CCC3(CCN(CC4CCCC4)CC3)C2)cc1)N(Cc1ncc[nH]1)Cc1ncc[nH]1]

Description: amorphous;
TLC: Rf 0.59 (ethyl acetate:methanol:28% ammonia water=50:10:1);
NMR (CDCl$_3$): δ 1.09-1.22 (m, 2H), 1.44-1.65 (m, 9H), 1.68-1.80 (m, 2H), 1.98-2.10 (m, 2H), 2.23 (d, J=7.2 Hz, 2H), 2.28-2.40 (m, 6H), 2.55 (t, J=6.9 Hz, 2H), 3.58 (s, 2H), 4.58-4.65 (m, 4H), 6.94-7.10 (m, 4H), 7.38 (d, J=8.4 Hz, 2H), 7.65 (d, J=8.4 Hz, 2H)

Example 50(29)

N,N-bis(1H-imidazol-2-ylmethyl)-4-{[8-(2-thienylmethyl)-2,8-diazaspiro[4.5]dec-2-yl]methyl}benzamide (compound 50-29)

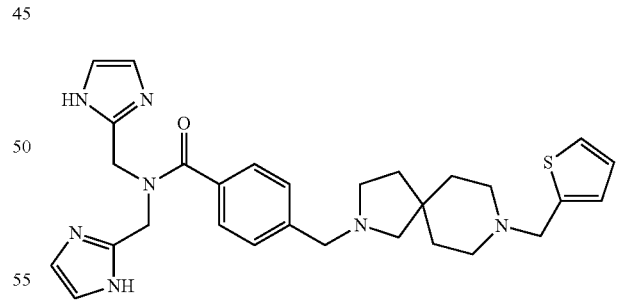

Description: amorphous;
TLC: Rf 0.60 (ethyl acetate:methanol:28% ammonia water=50:10:1);
NMR (CDCl$_3$): δ 1.53-1.65 (m, 6H), 2.32-2.47 (m, 6H), 2.55 (t, J=6.9 Hz, 2H), 3.58 (s, 2H), 3.67 (s, 2H), 4.58-4.65 (m, 4H), 6.88 (d, J=3.0 Hz, 1H), 6.93 (dd, J=4.5, 3.0 Hz, 1H), 6.98-7.10 (m, 4H), 7.20 (d, J=4.5 Hz, 1H), 7.38 (d, J=8.4 Hz, 2H), 7.68 (d, J=8.4 Hz, 2H)

Example 50(30)

N,N-bis(1H-imidazol-2-ylmethyl)-4-{[8-(3-thienyl-methyl)-2,8-diazaspiro[4.5]dec-2-yl]methyl}benzamide (compound 50-30)

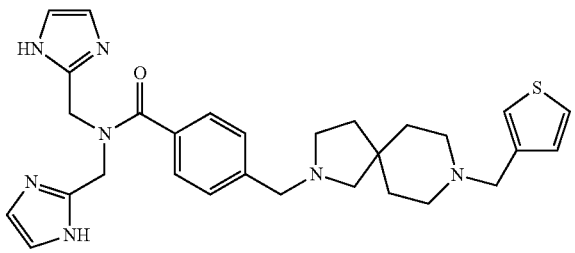 [SMILES: O=C(c1ccc(CN2CCC3(CCN(Cc4ccsc4)CC3)C2)cc1)N(Cc1ncc[nH]1)Cc1ncc[nH]1]

Description: amorphous;
TLC: Rf 0.60 (ethyl acetate:methanol:28% ammonia water=50:10:1);
NMR (CDCl₃): δ 1.53-1.65 (m, 6H), 2.28-2.42 (m, 6H), 2.55 (t, J=6.9 Hz, 2H), 3.49 (s, 2H), 3.58 (s, 2H), 4.58-4.65 (m, 4H), 6.96-7.14 (m, 6H), 7.25 (m, 1H), 7.38 (d, J=8.4 Hz, 2H), 7.68 (d, J=8.4 Hz, 2H)

Example 50(31)

4-(${[4-(3,4-dihydroquinoline-1(2H)-yl)cyclohexyl]amino}methyl)-N,N-bis(1H-imidazol-2-ylmethyl) benzamide (low polar compound) (compound 50-31)

Description: amorphous;
TLC: Rf 0.46 (ethyl acetate:methanol:28% ammonia water=90:10:2);
NMR (CDCl₃): δ d 1.50-1.75 (m, 4H), 1.82-2.10 (m, 6H), 2.71 (t, J=6.3 Hz, 2H), 3.00 (m, 1H), 3.24 (t, J=5.4 Hz, 2H), 3.60 (m, 1H), 3.83 (s, 2H), 4.58-4.80 (m, 4H), 6.53 (dd, J=7.8, 7.8 Hz, 1H), 6.62 (d, J=7.8 Hz, 1H), 6.93 (d, J=7.5 Hz, 1H), 6.99-7.12 (m, 5H), 7.45 (d, J=8.1 Hz, 2H), 7.54 (d, J=8.1 Hz, 2H)

Example 50(32)

4-({[4-(3,4-dihydro-1(2H)-quinolinyl)cyclohexyl]amino}methyl)-N,N-bis(1H-imidazol-2-ylmethyl) benzamide (high polar compound) (compound 50-32)

Description: amorphous;
TLC: Rf 0.30 (ethyl acetate:methanol:28% ammonia water=90:10:2);
NMR (CDCl₃): δ d 1.22-2.20 (m, 10H), 2.55 (m, 1H), 2.71 (t, J=6.0 Hz, 2H), 3.15 (t, J=5.7 Hz, 2H), 3.63 (m, 1H), 3.87 (s, 2H), 4.55-4.78 (m, 4H), 6.54 (dd, J=7.5, 7.5 Hz, 1H), 6.62 (d, J=7.5 Hz, 1H), 6.93 (d, J=7.5 Hz, 1H), 7.00-7.12 (m, 5H), 7.36-7.45 (m, 2H), 7.50-7.62 (m, 2H)

Example 50(33)

4-({8-[4-(diethylamino)benzyl]-2,8-diazaspiro[4.5]dec-2-yl}methyl)-N,N-bis(1H-imidazol-2-ylmethyl) benzamide (compound 50-33)

Description: amorphous;
TLC: Rf 0.44 (ethyl acetate:methanol:28% ammonia water=50:10:1);
NMR (CDCl₃): δ 1.14 (t, J=7.2 Hz, 6H), 1.51-1.64 (m, 6H), 2.25-2.42 (m, 6H), 2.53 (t, J=6.9 Hz, 2H), 3.28-3.38 (m, 6H), 3.56 (s, 2H), 4.60-4.67 (m, 4H), 6.61 (d, J=8.7 Hz, 2H), 6.94-7.08 (m, 4H), 7.12 (d, J=8.7 Hz, 2H), 7.36 (d, J=8.4 Hz, 2H), 7.59 (d, J=8.4 Hz, 2H)

Example 50(34)

4-{[8-(2-fluorobenzyl)-2,8-diazaspiro[4.5]dec-2-yl]methyl}-N,N-bis(1H-imidazol-2-ylmethyl)benzamide (compound 50-34)

Description: amorphous;
TLC: Rf 0.44 (ethyl acetate:methanol:28% ammonia water=50:10:1);
NMR (CDCl₃): δ 1.56-1.64 (m, 6H), 2.32-2.44 (m, 6H), 2.54 (t, J=6.9 Hz, 2H), 3.54 (s, 2H), 3.58 (s, 2H), 4.60-4.68 (m, 4H), 6.97-7.13 (m, 6H), 7.25 (m, 1H), 7.38-7.42 (m, 3H), 7.61 (d, J=8.4 Hz, 2H)

Example 50(35)

4-{[8-(3-fluorobenzyl)-2,8-diazaspiro[4.5]dec-2-yl]methyl}-N,N-bis(1H-imidazol-2-ylmethyl)benzamide (compound 50-35)

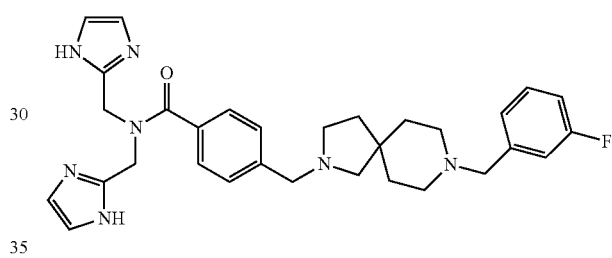

Description: amorphous;
TLC: Rf 0.44 (ethyl acetate:methanol:28% ammonia water=50:10:1);
NMR (CDCl₃): δ 1.50-1.66 (m, 6H); 2.24-2.41 (m, 6H), 2.56 (t, J=6.9 Hz, 2H), 3.43 (s, 2H), 3.59 (s, 2H), 4.60-4.68 (m, 4H), 6.90 (m, 1H), 6.95-7.09 (m, 6H), 7.23 (m, 1H), 7.36 (d, J=8.4 Hz, 2H), 7.60 (d, J=8.4 Hz, 2H)

Example 50(36)

4-{[8-(4-fluorobenzyl)-2,8-diazaspiro[4.5]dec-2-yl]methyl}-N,N-bis(1H-imidazol-2-ylmethyl)benzamide (compound 50-36)

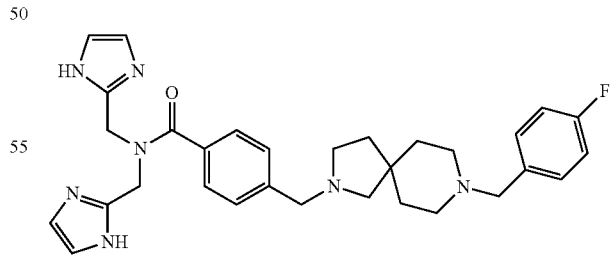

Description: amorphous;
TLC: Rf 0.44 (ethyl acetate:methanol:28% ammonia water=50:10:1);
NMR (CDCl₃): δ 1.52-1.62 (m, 6H), 2.24-2.41 (m, 6H), 2.55 (t, J=6.9 Hz, 2H), 3.41 (s, 2H), 3.58 (s, 2H), 4.60-4.68 (m, 4H), 6.93-7.09 (m, 6H), 7.20-7.28 (m, 2H), 7.35 (d, J=8.4 Hz, 2H), 7.60 (d, J=8.4 Hz, 2H)

Example 50(37)

4-[({trans-4-[acetyl(cyclohexyl)amino]cyclohexyl}amino)methyl]-N,N-bis(1H-imidazol-2-ylmethyl)benzamide (compound 50-37)

Description: amorphous;
TLC: Rf 0.50 (ethyl acetate:methanol:28% ammonia water=80:20:2);
NMR (CDCl$_3$): δ d 1.05-2.62 (m, 19H), 2.06 (s, 3H), 3.00 (brs, 1H), 3.39 (m, 1H), 3.82 (s, 2H), 4.50-4.80 (m, 4H), 6.95-7.12 (m, 4H), 7.30-7.40 (m, 2H), 7.45-7.60 (m, 2H)

Example 50(38)

N-(1H-benzoimidazol-2-ylmethyl)-4-[(8-cyclohexyl-2,8-diazaspiro[4.5]dec-2-yl)methyl]-N-(1H-imidazol-2-ylmethyl)benzamide (compound 50-38)

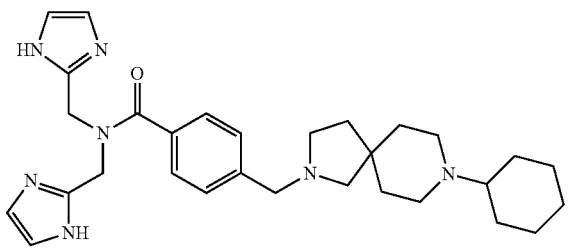 [SMILES: O=C(c1ccc(CN2CCC3(CCN(C4CCCCC4)CC3)C2)cc1)N(Cc1ncc[nH]1)Cc1ncc[nH]1]

Description: amorphous;
TLC: Rf 0.34 (methanol:28% ammonia water=98:2);
NMR (CDCl$_3$): δ 1.12-1.26 (m, 5H), 1.53-1.65 (m, 7H), 1.74-1.89 (m, 4H), 2.23-2.33 (m, 3H), 2.44-2.57 (m, 6H), 3.55 (s, 2H), 4.67-4.81 (m, 2H), 4.83-4.91 (m, 2H), 6.99-7.08 (m, 2H), 7.23-7.37 (m, 4H), 7.49-7.64 (m, 4H)

Example 50(39)

N-(1H-benzoimidazol-2-ylmethyl)-4-[({trans-4-[cyclohexyl(propyl)amino]cyclohexyl}amino)methyl]-N-(1H-imidazol-2-ylmethyl)benzamide (compound 50-39)

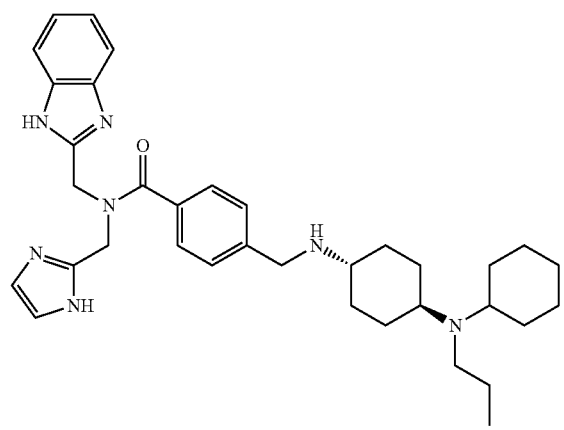 [SMILES: CCCN(C1CCCCC1)[C@H]1CC[C@H](NCc2ccc(C(=O)N(Cc3ncc[nH]3)Cc3nc4ccccc4[nH]3)cc2)CC1]

Description: amorphous;
TLC: Rf 0.38 (methanol:28% ammonia water=98:2);
NMR (CDCl$_3$): δ 0.76-0.88 (m, 3H), 1.09-1.15 (m, 2H), 1.17-1.27 (m, 5H), 1.29-1.41 (m, 4H), 1.56-1.63 (m, 1H), 1.67-1.80 (m, 6H), 1.90-2.03 (m, 2H), 2.34-2.47 (m, 3H), 2.50-2.63 (m, 2H), 3.79 (s, 2H), 4.62-4.69 (m, 1H), 4.72-4.79 (m, 1H), 4.84 (s, 2H), 6.97-7.11 (m, 2H), 7.22-7.35 (m, 4H), 7.49-7.65 (m, 4H)

Example 50(40)

N,N-bis(1H-imidazol-2-ylmethyl)-4-[({trans-4-[(3-methoxypropyl)(propyl)amino]cyclohexyl}amino)methyl]benzamide (compound 50-40)

Description: oily product;
TLC: Rf 0.49 (ethyl acetate:methanol:28% ammonia water=40:10:1);
NMR (CDCl$_3$): δ 0.84 (t, J=7.5 Hz, 3H), 1.08-2.02 (m, 12H), 2.33-2.50 (m, 6H), 3.31 (s, 3H), 3.39 (t, J=6.0 Hz, 2H), 3.82 (s, 2H), 4.56 (br-s, 2H), 4.60 (br-s, 2H), 7.01 (br-s, 2H), 7.08 (br-s, 2H), 7.37 (d, J=7.5 Hz, 2H), 7.29 (d, J=7.5 Hz, 2H)

Example 50(41)

4-[({trans-4-[(1-ethylpropyl)(propyl)amino]cyclohexyl}amino)methyl]-N,N-bis(1H-imidazol-2-ylmethyl)benzamide (compound 50-41)

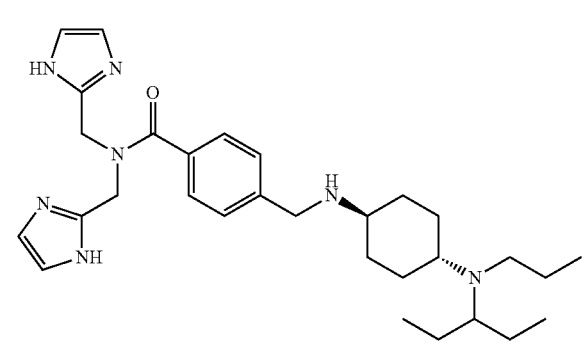 [SMILES: CCCN(C(CC)CC)[C@H]1CC[C@H](NCc2ccc(C(=O)N(Cc3ncc[nH]3)Cc3ncc[nH]3)cc2)CC1]

Description: oily product;
TLC: Rf 0.69 (ethyl acetate:methanol:28% ammonia water=40:10:1);
NMR (CDCl$_3$): δ 0.82 (t, J=7.5 Hz, 3H), 0.86 (t, J=7.5 Hz, 6H), 1.10-2.02 (m, 14H), 2.17-2.49 (m, 5H), 3.82 (s, 2H), 4.59 (br-s, 2H), 4.63 (br-s, 2H), 7.02 (br-s, 2H), 7.08 (br-s, 2H), 7.37 (d, J=8.1 Hz, 2H), 7.66 (d, J=8.1 Hz, 2H)

Example 50(42)

4-{[[4-(dipropylamino)butyl](methyl)amino]methyl}-N,N-bis(1H-imidazol-2-ylmethyl)benzamide (compound 50-42)

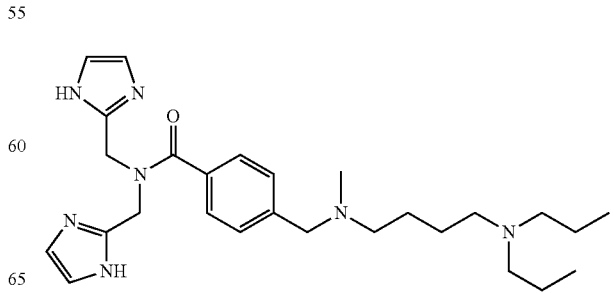

Description: oily product;

TLC: Rf 0.58 (ethyl acetate:methanol:28% ammonia water=40:10:1);

NMR (CDCl$_3$): δ 0.86 (t, J=7.5 Hz, 6H), 1.41-1.50 (m, 8H), 2.16 (s, 3H), 2.33-2.44 (m, 8H), 3.47 (s, 2H), 4.61 (br-s, 2H), 4.65 (br-s, 2H), 7.02 (br-s, 2H), 7.07 (br-s, 2H), 7.37 (d, J=8.1 Hz, 2H), 7.64 (d, J=8.1 Hz, 2H)

Example 50(43)

4-[(8-cyclopentyl-2,8-diazaspiro[4.5]dec-2-yl)methyl]-N,N-bis(1H-imidazol-2-ylmethyl)benzamide (compound 50-43)

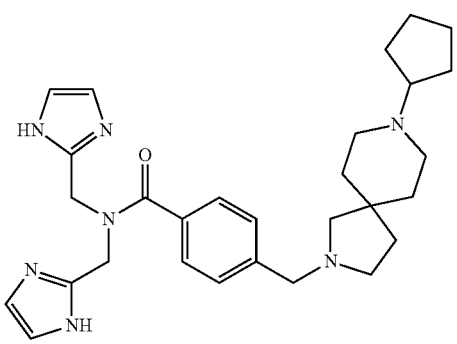 [SMILES: O=C(c1ccc(CN2CCC3(CCN(C4CCCC4)CC3)C2)cc1)N(Cc1ncc[nH]1)Cc1ncc[nH]1]

Description: amorphous;

TLC: Rf 0.39 (methanol:28% ammonia water=98:2);

NMR (CDCl$_3$): δ 1.24-1.74 (m, 12H), 1.75-1.94 (m, 2H), 2.19-2.49 (m, 7H), 2.54 (t, J=6.95 Hz, 2H), 3.57 (s, 2H), 4.54-4.81 (m, 4H), 6.88-7.13 (m, 4H), 7.35 (d, J=8.1 Hz, 2H), 7.54 (d, J=8.1 Hz, 2H)

Example 50(44)

N,N-bis(1H-imidazol-2-ylmethyl)-4-{[8-(tetrahydro-2H-pyran-4-yl)-2,8-diazaspiro[4.5]dec-2-yl]methyl}benzamide (compound 50-44)

Description: amorphous;

TLC: Rf 0.33 (methanol:28% ammonia water=98:2);

NMR (CDCl$_3$): δ 1.44-1.67 (m, 8H), 1.67-1.81 (m, 2H), 2.24-2.63 (m, 9H), 3.25-3.43 (m, 2H), 3.57 (s, 2H), 3.92-4.08 (m, 2H), 4.53-4.77 (m, 4H), 6.91-7.13 (m, 4H), 7.36 (d, J=8.1 Hz, 2H), 7.55 (d, J=8.1 Hz, 2H)

Example 50(45)

N,N-bis(1H-imidazol-2-ylmethyl)-4-{[8-(pyridine-2-ylmethyl)-2,8-diazaspiro[4.5]dec-2-yl]methyl}benzamide (compound 50-45)

Description: amorphous;

TLC: Rf 0.46 (ethyl acetate:methanol:28% ammonia water=50:10:1);

NMR (CDCl$_3$): δ 1.54-1.65 (m, 6H), 2.32-2.48 (m, 6H), 2.55 (t, J=6.9 Hz, 2H), 3.58 (s, 2H), 3.61 (s, 2H), 4.60-4.72 (m, 4H), 6.94-7.09 (m, 4H), 7.14 (dd, J=4.8, 7.5 Hz, 1H), 7.35 (d, J=8.4 Hz, 2H), 7.40 (d, J=7.5 Hz, 1H), 7.53 (d, J=8.4 Hz, 2H), 7.63 (dt, J=1.8, 7.5 Hz, 1H), 8.53 (d, J=4.8 Hz, 1H)

Example 50(46)

N,N-bis(1H-imidazol-2-ylmethyl)-4-{[8-(pyridine-3-ylmethyl)-2,8-diazaspiro[4.5]dec-2-yl]methyl}benzamide (compound 50-46)

Description: amorphous;

TLC: Rf 0.46 (ethyl acetate:methanol:28% ammonia water=50:10:1);

NMR (CDCl$_3$): δ 1.50-1.64 (m, 6H), 2.24-2.41 (m, 6H), 2.56 (t, J=6.9 Hz, 2H), 3.46 (s, 2H), 3.58 (s, 2H), 4.61-4.72 (m, 4H), 6.98-7.10 (m, 4H), 7.23 (dd, J=4.8, 7.5 Hz, 1H), 7.36 (d, J=8.4 Hz, 2H), 7.54 (d, J=8.4 Hz, 2H), 7.65 (dt, J=7.5, 1.8 Hz, 1H), 8.49 (dd, J=1.8, 4.8 Hz, 1H), 8.51 (d, J=1.8 Hz, 1H)

Example 50(47)

N,N-bis(1H-imidazol-2-ylmethyl)-4-{[8-(pyridine-4-ylmethyl)-2,8-diazaspiro[4.5]dec-2-yl]methyl}benzamide (compound 50-47)

Description: amorphous;

TLC: Rf 0.46 (ethyl acetate:methanol:28% ammonia water=50:10:1);

NMR (CDCl$_3$): δ 1.55-1.68 (m, 6H), 2.24-2.42 (m, 6H), 2.56 (t, J=6.9 Hz, 2H), 3.44 (s, 2H), 3.58 (s, 2H), 4.60-4.72 (m, 4H), 6.97-7.08 (m, 4H), 7.23 (d, J=6.0 Hz, 2H), 7.34 (d, J=8.4 Hz, 2H), 7.52 (d, J=8.4 Hz, 2H), 8.50 (d, J=6.0 Hz, 2H)

Example 50(48)

N,N-bis(1H-imidazol-2-ylmethyl)-4-{[8-(2-naphth-ylmethyl)-2,8-diazaspiro[4.5]dec-2-yl]methyl}benzamide (compound 50-48)

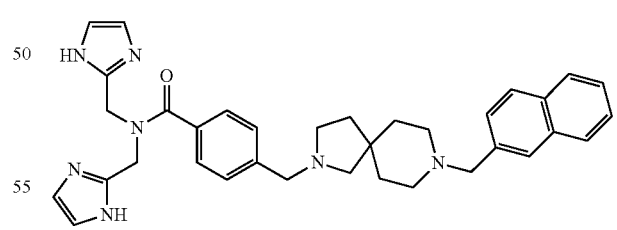

Description: amorphous;

TLC: Rf 0.52 (ethyl acetate:methanol:28% ammonia water=50:10:1);

NMR (CDCl$_3$): δ 1.56-1.65 (m, 6H), 2.32-2.48 (m, 6H), 2.58 (t, J=6.9 Hz, 2H), 3.57 (s, 2H), 3.62 (s, 2H), 4.60-4.70 (m, 4H), 6.97-7.08 (m, 4H), 7.35 (d, J=8.4 Hz, 2H), 7.40-7.50 (m, 3H), 7.54 (d, J=8.4 Hz, 2H), 7.71 (s, 1H), 7.74-7.82 (m, 3H)

Example 50(49)

4-[(8-cycloheptyl-2,8-diazaspiro[4.5]dec-2-yl)methyl]-N,N-bis(1H-imidazol-2-ylmethyl)benzamide (compound 50-49)

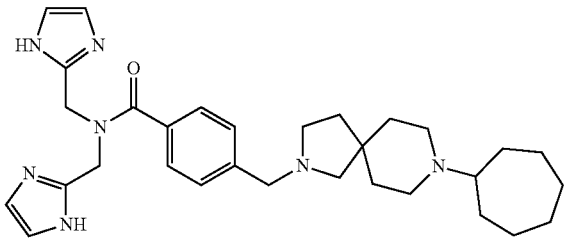 [SMILES: O=C(c1ccc(CN2CCC3(CCN(C4CCCCCC4)CC3)C2)cc1)N(Cc1ncc[nH]1)Cc1ncc[nH]1]

Description: amorphous;
TLC: Rf 0.32 (methanol:28% ammonia water=98:2);
NMR (CDCl$_3$): δ 1.27-1.86 (m, 18H), 2.23-2.63 (m, 9H), 3.57 (s, 2H), 4.51-4.75 (m, 4H), 6.90-7.11 (m, 4H), 7.36 (d, J=8.1 Hz, 2H), 7.59 (d, J=8.1 Hz, 2H)

Example 50(50)

4-[({trans-4-[cyclohexyl(methyl)amino]cyclohexyl}amino)methyl]-N,N-bis(1H-imidazol-2-ylmethyl)benzamide (compound 50-50)

Description: amorphous;
TLC: Rf 0.43 (ethyl acetate:methanol:28% ammonia water=80:20:2);
NMR (CDCl$_3$): δ d 1.00-2.06 (m, 18H), 2.30 (s, 3H), 2.42 (m, 1H), 2.55-2.75 (m, 2H), 3.81 (s, 2H), 4.52-4.75 (m, 4H), 6.95-7.10 (m, 4H), 7.35 (d, J=8.4 Hz, 2H), 7.61 (d, J=8.4 Hz, 2H)

Example 50(51)

4-[({trans-4-[benzyl(methyl)amino]cyclohexyl}amino)methyl]-N,N-bis(1H-imidazol-2-ylmethyl)benzamide (compound 50-51)

Description: amorphous;
TLC: Rf 0.24 (ethyl acetate:methanol:28% ammonia water=90:10:2);
NMR (CDCl$_3$): δ d 1.15-1.50 (m, 4H), 1.90-2.18 (m, 4H), 2.21 (s, 3H), 2.45-2.62 (m, 2H), 3.60 (s, 2H), 3.85 (s, 2H), 4.50-4.78 (m, 4H), 6.98-7.12 (m, 5H), 7.20-7.40 (m, 4H), 7.38 (d, J=8.4 Hz, 2H), 7.55 (d, J=8.4 Hz, 2H)

Example 50(52)

4-[({trans-4-[cyclohexyl(methylsulfonyl)amino]cyclohexyl}amino)methyl]-N,N-bis(1H-imidazol-2-ylmethyl)benzamide (compound 50-52)

Description: amorphous;
TLC: Rf 0.22 (ethyl acetate:methanol:28% ammonia water=90:10:2);
NMR (CDCl$_3$): δ d 1.00-2.12 (m, 18H), 2.49 (m, 1H), 2.86 (s, 3H), 3.10-3.42 (m, 2H), 3.83 (s, 2H), 4.58-4.75 (m, 4H), 6.98-7.10 (m, 4H), 7.37 (d, J=8.1 Hz, 2H), 7.65 (d, J=8.1 Hz, 2H)

Example 50(53)

N,N-bis(1H-imidazol-2-ylmethyl)-4-{[7-(2-phenylethyl)-2,7-diazaspiro[4.5]dec-2-yl]methyl}benzamide (compound 50-53)

Description: amorphous;
TLC: Rf 0.51 (methanol:28% ammonia water=98:2);
NMR (CDCl$_3$): δ 1.28-1.81 (m, 6H), 2.24 (d, J=9.3 Hz, 2H), 2.28-2.68 (m, 8H), 2.70-2.85 (m, 2H), 3.59 (s, 2H), 4.53-4.75 (m, 4H), 6.90-7.11 (m, 4H), 7.13-7.31 (m, 5H), 7.38 (d, J=8.1 Hz, 2H), 7.61 (d, J=8.1 Hz, 2H)

Example 50(54)

N,N-bis(1H-imidazol-2-ylmethyl)-4-{[7-(2-piperidine-1-ylethyl)-2,7-diazaspiro[4.5]dec-2-yl]methyl}benzamide (compound 50-54)

Description: amorphous;
TLC: Rf 0.24 (methanol:28% ammonia water=98:2);
NMR (CDCl$_3$): δ 1.15-1.77 (m, 12H), 2.06-2.76 (m, 16H), 3.58 (q, J=13.2 Hz, 2H), 4.47-4.82 (m, 4H), 6.87-7.14 (m, 4H), 7.36 (d, J=8.1 Hz, 2H), 7.58 (d, J=8.1 Hz, 2H)

Example 50(55)

4-{[8-(2,3-dihydro-1H-inden-2-yl)-2,8-diazaspiro[4.5]dec-2-yl]methyl}-N,N-bis(1H-imidazol-2-ylmethyl)benzamide (compound 50-55)

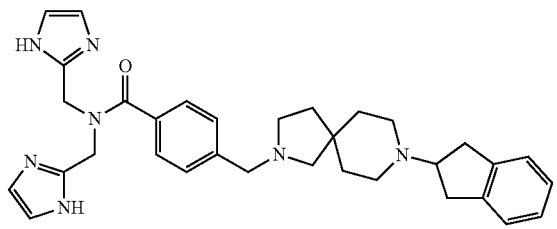 [SMILES: O=C(c1ccc(CN2CCC3(CCN(C4Cc5ccccc5C4)CC3)C2)cc1)N(Cc1ncc[nH]1)Cc1ncc[nH]1]

Description: amorphous;
TLC: Rf 0.37 (methanol:28% ammonia water=98:2);
NMR (CDCl$_3$): δ 1.58-1.71 (m, 6H), 2.35-2.39 (m, 3H), 2.42-2.51 (m, 3H), 2.53-2.59 (m, 2H), 2.84-2.98 (m, 2H), 3.01-3.17 (m, 3H), 3.59 (s, 2H), 4.61-4.74 (m, 4H), 6.94-7.07 (m, 4H), 7.09-7.19 (m, 4H), 7.30-7.41 (m, 2H), 7.51-7.62 (m, 2H)

Example 50(56)

4-[(8-cyclobutyl-2,8-diazaspiro[4.5]dec-2-yl)methyl]-N,N-bis(1H-imidazol-2-ylmethyl)benzamide (compound 50-56)

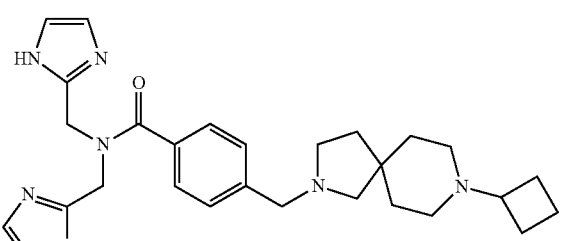

Description: amorphous;
TLC: Rf 0.45 (methanol:28% ammonia water=98:2);
NMR (CDCl₃): δ 1.56-1.71 (m, 8H), 1.85-1.93 (m, 2H), 1.95-2.05 (m, 3H), 2.19-2.35 (m, 5H), 2.52-2.59 (m, 2H), 2.62-2.69 (m, 1H), 3.58 (s, 2H), 4.59-4.72 (m, 4H), 6.95-7.10 (m, 4H), 7.31-7.40 (m, 2H), 7.56-7.64 (m, 2H)

Example 50(57)

N,N-bis(1H-imidazol-2-ylmethyl)-4-{[8-(1-propylpiperidin-4-yl)-2,8-diazaspiro[4.5]dec-2-yl]methyl}benzamide (compound 50-57)

Description: amorphous;
TLC: Rf 0.21 (methanol:28% ammonia water=98:2);
NMR (CDCl₃): δ 0.83-0.96 (m, 3H), 1.50-1.65 (m, 10H), 1.71-1.82 (m, 2H), 1.85-1.96 (m, 2H), 2.22-2.37 (m, 5H), 2.42-2.58 (m, 6H), 2.93-3.06 (m, 2H), 3.57 (s, 2H), 4.58-4.72 (m, 4H), 6.95-7.10 (m, 4H), 7.30-7.42 (m, 2H), 7.55-7.68 (m, 2H)

Example 50(58)

4-{[8-(2-adamantyl)-2,8-diazaspiro[4.5]dec-2-yl]methyl}-N,N-bis(1H-imidazol-2-ylmethyl)benzamide (compound 50-58)

Description: amorphous;
TLC: Rf 0.50 (methanol:28% ammonia water=98:2);
NMR (CDCl₃): δ 1.32-1.43 (m, 2H), 1.55-1.70 (m, 10H), 1.74-1.87 (m, 4H), 1.98-2.11 (m, 6H), 2.27-2.43 (m, 5H), 2.51-2.65 (m, 2H), 3.60 (s, 2H), 4.59-4.73 (m, 4H), 6.94-7.08 (m, 4H), 7.30-7.41 (m, 2H), 7.55-7.66 (m, 2H)

Example 50(59)

N,N-bis(1H-imidazol-2-ylmethyl)-4-[(8-isobutyl-2,8-diazaspiro[4.5]dec-2-yl)methyl]benzamide (compound 50-59)

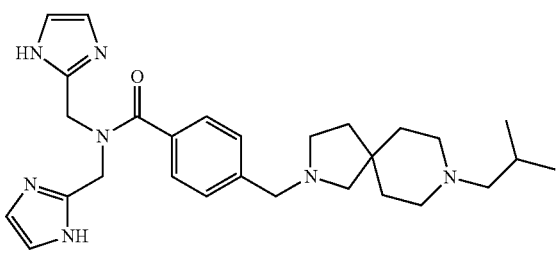 [SMILES: CC(C)CN1CCC2(CC1)CCN(Cc1ccc(C(=O)N(Cc3ncc[nH]3)Cc3ncc[nH]3)cc1)C2]

Description: amorphous;
TLC: Rf 0.48 (methanol:28% ammonia water=98:2);
NMR (CDCl₃): δ 0.80-0.94 (m, 6H), 1.51-1.65 (m, 6H), 1.68-1.83 (m, 1H), 1.97-2.11 (m, 2H), 2.22-2.37 (m, 6H), 2.47-2.61 (m, 2H), 3.58 (s, 2H), 4.57-4.72 (m, 4H), 6.95-7.10 (m, 4H), 7.30-7.45 (m, 2H), 7.51-7.66 (m, 2H)

Example 50(60)

4-(2,8-diazaspiro[4.5]dec-8-ylmethyl)-N,N-bis(1H-imidazol-2-ylmethyl)-2-methylbenzamide (compound 50-60)

Description: amorphous;
TLC: Rf 0.38 (chloroform:methanol:28% ammonia water=80:20:4);

NMR (DMSO-D₆): δ 1.36-1.51 (m, 6H), 2.11 (s, 3H), 2.21-2.34 (m, 4H), 2.51-2.56 (m, 2H), 2.77 (t, J=7.2 Hz, 2H), 3.16 (s, 2H), 4.40 (s, 2H), 4.68 (s, 2H), 6.79-7.02 (m, 4H), 7.02-7.08 (m, 1H), 7.08-7.19 (m, 2H), 11.47-13.11 (m, 2H)

Example 50(61)

4-[(2-cyclohexyl-2,8-diazaspiro[4.5]dec-8-yl)methyl]-N,N-bis(1H-imidazol-2-ylmethyl)-2-methylbenzamide (compound 50-61)

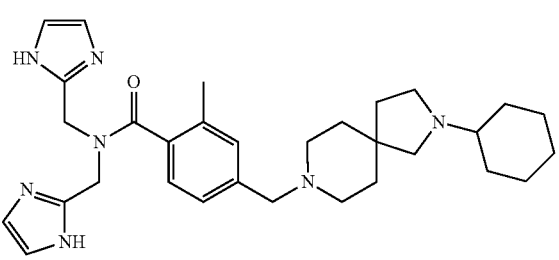 [SMILES: Cc1cc(CN2CCC3(CC2)CCN(C2CCCCC2)C3)ccc1C(=O)N(Cc1ncc[nH]1)Cc1ncc[nH]1]

Description: amorphous;
TLC: Rf 0.30 (chloroform:methanol:28% ammonia water=80:10:1);
NMR (DMSO-D₆): δ 1.04-1.28 (m, 6H), 1.36-1.56 (m, 8H), 1.58-1.71 (m, 2H), 1.71-1.85 (m, 2H), 1.88-1.97 (m, 1H), 2.11 (s, 3H), 2.17-2.31 (m, 4H), 2.31-2.39 (m, 2H), 3.34 (s, 2H), 4.39 (s, 2H), 4.67 (s, 2H), 6.64-7.00 (m, 4H), 7.00-7.07 (m, 1H), 7.07-7.18 (m, 2H), 12.05-12.42 (m, 2H)

Example 50(62)

4-{[[(3-azepan-1-yl-2,2-dimethylpropyl)amino]methyl}-N,N-bis(1H-imidazol-2-ylmethyl)benzamide (compound 50-62)

Description: amorphous;
TLC: Rf 0.52 (ethyl acetate:methanol:28% ammonia water=50:10:1);
NMR (CDCl₃): δ 0.86 (s, 6H), 1.48-1.62 (m, 8H), 2.36 (s, 2H), 2.44 (s, 2H), 2.67-2.70 (m, 4H), 3.79 (s, 2H), 4.61 (br-s, 2H), 4.66 (br-s, 2H), 7.00 (br-s, 2H), 7.07 (br-s, 2H), 7.38 (d, J=8.1 Hz, 2H), 7.62 (d, J=8.1 Hz, 2H)

Example 50(63)

N,N-bis(1H-imidazol-2-ylmethyl)-4-[({trans-4-[methyl(propyl)amino]cyclohexyl}amino)methyl]benzamide (compound 50-63)

Description: amorphous;
TLC: Rf 0.44 (dichloromethane:methanol:28% ammonia water=50:10:1);
NMR (CDCl₃): δ 0.87 (t, J=7.2 Hz, 3H), 1.07-1.33 (m, 4H), 1.41-1.53 (m, 2H), 1.82-1.86 (m, 2H), 1.99-2.02 (m, 2H), 2.25 (s, 3H), 2.36-2.41 (m, 4H), 3.81 (s, 2H), 4.59 (br-s, 2H), 4.65 (br-s, 2H), 6.99 (br-s, 2H), 7.06 (br-s, 2H), 7.35 (d, J=8.4 Hz, 2H), 7.61 (d, J=8.4 Hz, 2H).

Example 50(64)

N,N-bis(1H-imidazol-2-ylmethyl)-4-[({trans-4-[propyl(tetrahydro-2H-pyran-4-yl)amino]cyclohexyl}amino)methyl]benzamide (compound 50-64)

Description: amorphous;
TLC: Rf 0.46 (ethyl acetate:methanol:28% ammonia water=50:10:1);
NMR (CDCl$_3$): δ 0.81 (t, J=7.2 Hz, 3H), 1.06-1.18 (m, 2H), 1.25-1.42 (m, 4H), 1.58-1.73 (m, 6H), 1.95-1.99 (m, 2H), 2.35-2.44 (m, 3H), 2.58 (m, 1H), 2.73 (m, 1H), 3.35 (dt, J=11.0, 3.0 Hz, 2H), 3.81 (s, 2H), 3.96-3.99 (m, 2H), 4.59 (br-s, 2H), 4.64 (br-s, 2H), 6.99 (br-s, 2H), 7.06 (br-s, 2H), 7.35 (d, J=8.1 Hz, 2H), 7.62 (d, J=8.1 Hz, 2H)

Example 50(65)

4-({[trans-4-(benzylamino)cyclohexyl]amino}methyl)-N,N-bis(1H-imidazol-2-ylmethyl)benzamide (compound 50-65)

Description: amorphous;
TLC: Rf 0.54 (ethyl acetate:methanol:28% ammonia water=50:10:1);
NMR (CDCl$_3$): δ 1.13-1.20 (m, 4H), 1.97-2.02 (m, 4H), 2.40-2.60 (m, 2H), 3.81 (s, 2H), 3.82 (s, 2H), 4.57 (br-s, 2H), 4.62 (br-s, 2H), 7.00 (br-s, 2H), 7.06 (br-s, 2H), 7.24-7.32 (m, 5H), 7.36 (d, J=8.1 Hz, 2H), 7.62 (d, J=8.1 Hz, 2H)

Example 50(66)

N,N-bis(1H-imidazol-2-ylmethyl)-4-({[trans-4-(propylamino)cyclohexyl]amino}methyl)benzamide (compound 50-66)

Description: oily product;
TLC: Rf 0.27 (dichloromethane:methanol:28% ammonia water=50:10:1);
NMR (CDCl$_3$): δ 0.91 (t, J=7.2 Hz, 3H), 1.04-1.23 (m, 4H), 1.45-1.96 (m, 6H), 2.40-2.50 (m, 2H), 2.58 (t, J=7.2 Hz, 2H), 3.82 (s, 2H), 4.55 (br-s, 2H), 4.59 (br-s, 2H), 7.01 (br-s, 2H), 7.08 (br-s, 2H), 7.37 (d, J=8.1 Hz, 2H), 7.72 (d, J=8.1 Hz, 2H)

Example 50(67)

4-{[{trans-4-[cyclohexyl(propyl)amino]cyclohexyl}(methyl)amino]methyl}-N,N-bis(1H-imidazol-2-ylmethyl)benzamide (compound 50-67)

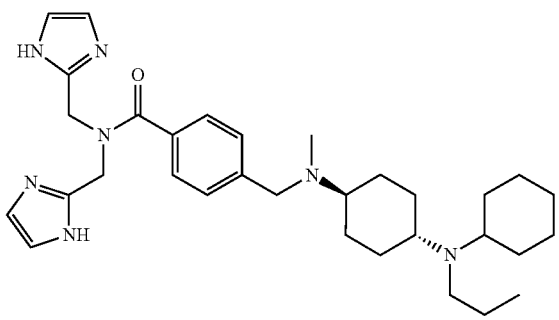 [SMILES: CCCN(C1CCCCC1)[C@H]1CC[C@H](N(C)Cc2ccc(C(=O)N(Cc3ncc[nH]3)Cc3ncc[nH]3)cc2)CC1]

Description: oily product;
TLC: Rf 0.65 (ethyl acetate:methanol:28% ammonia water=50:10:1);
NMR (CDCl$_3$): δ 0.81 (t, J=7.2 Hz, 3H), 1.07-2.51 (m, 25H), 2.26 (s, 3H), 3.55 (s, 2H), 4.63 (br-s, 2H), 4.65 (br-s, 2H), 6.98 (br-s, 2H), 7.06 (br-s, 2H), 7.36 (d, J=8.1 Hz, 2H), 7.61 (d, J=8.1 Hz, 2H)

Example 50(68)

4-[(benzyl{trans-4-[cyclohexyl(propyl)amino]cyclohexyl}amino)methyl]-N,N-bis(1H-imidazol-2-ylmethyl)benzamide (compound 50-68)

Description: oily product;
TLC: Rf 0.83 (ethyl acetate:methanol:28% ammonia water=50:10:1);
NMR (CDCl$_3$): δ 0.81 (t, J=7.2 Hz, 3H), 1.22-2.60 (m, 25H), 3.60 (s, 2H), 3.61 (s, 2H), 4.59 (br-s, 4H), 7.01 (br-s, 2H), 7.09 (br-s, 2H), 7.18-7.35 (m, 5H), 7.42 (d, J=8.1 Hz, 2H), 7.67 (d, J=8.1 Hz, 2H)

Example 50(69)

4-({[trans-4-(dipropylamino)cyclohexyl]amino}methyl)-N,N-bis(1H-imidazol-2-ylmethyl)-2-methylbenzamide (compound 50-69)

Description: amorphous;
TLC: Rf 0.60 (chloroform:methanol:28% ammonia water=80:20:4);
NMR (DMSO-D$_6$): δ 0.79 (t, J=7.50 Hz, 6H), 0.90-1.06 (m, 2H), 1.07-1.23 (m, 2H), 1.23-1.39 (m, 4H), 1.56-1.72 (m, 2H), 1.83-1.98 (m, 2H), 2.11 (s, 3H), 2.17-2.42 (m, 6H), 3.63 (s, 2H), 4.39 (s, 2H), 4.67 (s, 2H), 6.72-7.05 (m, 4H), 7.05-7.20 (m, 3H), 11.97-12.55 (m, 2H)

Example 50(70)

4-[(2-tert-butyl-2,8-diazaspiro[4.5]dec-8-yl)methyl]-N,N-bis(1H-imidazol-2-ylmethyl)benzamide (compound 50-70)

Description: amorphous;
TLC: Rf 0.52 (ethyl acetate:methanol:28% ammonia water=50:10:1);
NMR (CDCl$_3$): δ 1.07 (s, 9H), 1.52-1.66 (m, 6H), 2.24-2.44 (m, 4H), 2.54 (s, 2H), 2.71 (t, J=6.6 Hz, 2H), 3.48 (s, 2H), 4.58-4.66 (m, 4H), 6.98-7.10 (m, 4H), 7.37 (d, J=8.4 Hz, 2H), 7.65 (d, J=8.4 Hz, 2H)

Example 50(71)

4-({[4-(tert-butylamino)cyclohexyl]amino}methyl)-N,N-bis(1H-imidazol-2-ylmethyl)benzamide (compound 50-71)

Description: amorphous;
TLC: Rf 0.26 (ethyl acetate:methanol:28% ammonia water=90:10:2);
NMR (CDCl$_3$): δ d 1.12 (s, 9H), 1.48-1.75 (m, 8H), 2.62-2.78 (m, 2H), 3.76 (s, 2H), 4.50-4.75 (m, 4H), 6.95-7.12 (m, 4H), 7.36 (d, J=8.4 Hz, 2H), 7.60 (d, J=8.4 Hz, 2H)

Example 50(72)

4-({[4-(tert-butylamino)cyclohexyl]amino}methyl)-N,N-bis(1H-imidazol-2-ylmethyl)benzamide (compound 50-72)

Description: amorphous;
TLC: Rf 0.19 (ethyl acetate:methanol:28% ammonia water=90:10:2);

NMR (CDCl₃): δ d 1.12 (s, 9H), 1.10-1.30 (m, 4H), 1.75-2.00 (m, 4H), 2.42 (m, 1H), 2.54 (m, 1H), 3.81 (s, 2H), 4.50-4.72 (m, 4H), 6.90-7.12 (m, 4H), 7.35 (d, J=8.4 Hz, 2H), 7.63 (d, J=8.4 Hz, 2H)

Example 50(73)

4-[({trans-4-[(cyclohexylmethyl)amino]cyclohexyl}amino)methyl]-N,N-bis(1H-imidazol-2-ylmethyl)benzamide (compound 50-73)

Description: amorphous;
TLC: Rf 0.67 (ethyl acetate:methanol:28% ammonia water=80:20:2);
NMR (CDCl₃): δ d 0.80-2.04 (m, 19H), 2.38-2.54 (m, 4H), 3.81 (s, 2H), 4.50-4.68 (m, 4H), 6.92-7.12 (m, 4H), 7.35 (d, J=8.4 Hz, 2H), 7.64 (d, J=8.4 Hz, 2H)

Example 50(74)

4-{[(4-anilinocyclohexyl)amino]methyl}-N,N-bis(1H-imidazol-2-ylmethyl)benzamide (low polar compound) (compound 50-74)

Description: amorphous;
TLC: Rf 0.47 (ethyl acetate:methanol:28% ammonia water=90:10:2);
NMR (CDCl₃): δ d 1.50-1.85 (m, 8H), 2.70 (m, 1H), 3.49 (m, 1H), 3.82 (s, 2H), 4.50-4.68 (m, 4H), 6.59 (d, J=7.5 Hz, 2H), 6.66 (dd, J=7.5, 7.5 Hz, 1H), 6.98-7.10 (m, 4H), 7.15 (dd, J=8.7, 7.5 Hz, 2H), 7.39 (d, J=8.4 Hz, 2H), 7.68 (d, J=8.4 Hz, 2H)

Example 50(75)

4-{[(4-anilinocyclohexyl)amino]methyl}-N,N-bis(1H-imidazol-2-ylmethyl)benzamide (high polar compound) (compound 50-75)

Description: amorphous;
TLC: Rf 0.45 (ethyl acetate:methanol:28% ammonia water=90:10:2);
NMR (CDCl₃): δ d 1.04-1.38 (m, 4H), 1.98-2.08 (m, 2H), 2.12-2.22 (m, 2H), 2.52 (m, 1H), 3.24 (m, 1H), 3.85 (s, 2H), 4.46-4.70 (m, 4H), 6.58 (d, J=7.5 Hz, 2H), 6.66 (dd, J=7.5, 7.5 Hz, 1H), 6.98-7.10 (m, 4H), 7.15 (dd, J=8.4, 7.5 Hz, 2H), 7.39 (d, J=8.1 Hz, 2H), 7.70 (d, J=8.1 Hz, 2H)

Example 50(76)

4-{[8-(2-cyclohexylethyl)-2,8-diazaspiro[4.5]dec-2-yl]methyl}-N,N-bis(1H-imidazol-2-ylmethyl)benzamide (compound 50-76)

Description: amorphous;
TLC: Rf 0.28 (methanol:28% ammonia water=98:2);
NMR (CDCl₃): δ 0.83-0.97 (m, 2H), 1.13-1.27 (m, 4H), 1.36-1.45 (m, 2H), 1.58-1.72 (m, 10H), 2.32-2.48 (m, 9H), 2.52-2.61 (m, 2H), 3.59 (s, 2H), 4.58-4.70 (m, 4H), 6.98-7.12 (m, 4H), 7.32-7.43 (m, 2H), 7.62-7.74 (m, 2H)

Example 50(77)

4-{[8-(3-cyclohexylpropyl)-2,8-diazaspiro[4.5]dec-2-yl]methyl}-N,N-bis(1H-imidazol-2-ylmethyl)benzamide (compound 50-77)

Description: amorphous;
TLC: Rf 0.28 (methanol:28% ammonia water=98:2);
NMR (CDCl₃): δ 0.78-0.92 (m, 2H), 1.10-1.26 (m, 6H), 1.53-1.57 (m, 2H), 1.59-1.71 (m, 11H), 2.31-2.41 (m, 6H), 2.44-2.52 (m, 2H), 2.55-2.60 (m, 2H), 3.59 (s, 2H), 4.56-4.68 (m, 4H), 6.98-7.12 (m, 4H), 7.33-7.42 (m, 2H), 7.63-7.73 (m, 2H)

Example 50(78)

N,N-bis(1H-imidazol-2-ylmethyl)-4-({8-[(3-methyl-2-thienyl)methyl]-2,8-diazaspiro[4.5]dec-2-yl}methyl)benzamide (compound 50-78)

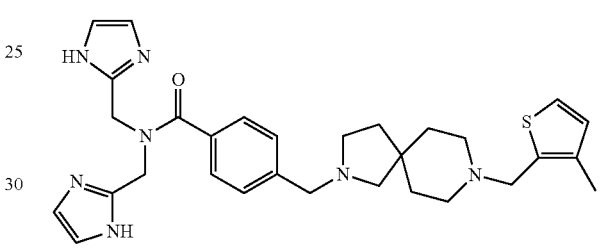

Description: amorphous;
TLC: Rf 0.40 (methanol:28% ammonia water=98:2);
NMR (CDCl₃): δ 1.52-1.65 (m, 6H), 2.15-2.21 (m, 3H), 2.30-2.45 (m, 6H), 2.49-2.59 (m, 2H), 3.52-3.63 (m, 4H), 4.57-4.69 (m, 4H), 6.73-6.80 (m, 1H), 6.97-7.12 (m, 5H), 7.32-7.43 (m, 2H), 7.60-7.69 (m, 2H)

Example 50(79)

4-{[8-(1-benzothien-2-ylmethyl)-2,8-diazaspiro[4.5]dec-2-yl]methyl}-N,N-bis(1H-imidazol-2-ylmethyl)benzamide (compound 50-79)

Description: amorphous;
TLC: Rf 0.40 (methanol:28% ammonia water=98:2);
NMR (CDCl₃): δ 1.54-1.67 (m, 6H), 2.34-2.49 (m, 6H), 2.51-2.60 (m, 2H), 3.59 (s, 2H), 3.74 (s, 2H), 4.57-4.69 (m, 4H), 6.97-7.12 (m, 5H), 7.22-7.34 (m, 2H), 7.35-7.41 (m, 2H), 7.61-7.69 (m, 3H), 7.72-7.80 (m, 1H)

Example 50(80)

4-{[8-(4-hydroxycyclohexyl)-2,8-diazaspiro[4.5]dec-2-yl]methyl}-N,N-bis(1H-imidazol-2-ylmethyl)benzamide (compound 50-80)

Description: amorphous;
TLC: Rf 0.23 (methanol:28% ammonia water=98:2);
NMR (CDCl₃): δ 1.22-1.38 (m, 2H), 1.51-2.05 (m, 12H), 2.26-2.58 (m, 9H), 3.53-4.02 (m, 3H), 4.56-4.66 (m, 4H), 6.95-7.10 (m, 4H), 7.33-7.44 (m, 2H), 7.64-7.74 (m, 2H)

Example 50(81)

4-{[8-(1-ethylpropyl)-2,8-diazaspiro[4.5]dec-2-yl]methyl}-N,N-bis(1H-imidazol-2-ylmethyl)benzamide (compound 50-81)

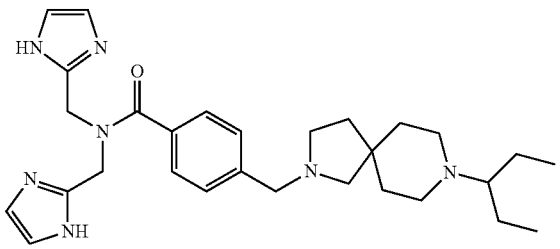 [SMILES: CCC(CC)N1CCC2(CCN(Cc3ccc(C(=O)N(Cc4ncc[nH]4)Cc4ncc[nH]4)cc3)C2)CC1]

Description: amorphous;
TLC: Rf 0.40 (methanol:28% ammonia water=98:2);
NMR (CDCl$_3$): δ 0.82-0.94 (m, 6H), 1.21-1.37 (m, 3H), 1.49-1.64 (m, 8H), 2.17-2.28 (m, 1H), 2.36 (s, 2H), 2.45-2.53 (m, 3H), 2.55-2.61 (m, 2H), 3.54-3.65 (m, 2H), 4.58-4.73 (m, 4H), 6.95-7.09 (m, 4H), 7.32-7.41 (m, 2H), 7.58-7.68 (m, 2H)

Example 50(82)

4-[(8-ethyl-2,8-diazaspiro[4.5]dec-2-yl)methyl]-N,N-bis(1H-imidazol-2-ylmethyl)benzamide (compound 50-82)

Description: amorphous;
TLC: Rf 0.16 (methanol:28% ammonia water=98:2);
NMR (CDCl$_3$): δ 1.02-1.12 (m, 3H), 1.54-1.66 (m, 6H), 2.27-2.42 (m, 8H), 2.46-2.60 (m, 2H), 3.58 (s, 2H), 4.57-4.70 (m, 4H), 6.95-7.10 (m, 4H), 7.32-7.41 (m, 2H), 7.54-7.65 (m, 2H)

Example 50(83)

4-{[8-(1-azabicyclo[2.2.2]octa-3-yl)-2,8-diazaspiro[4.5]dec-2-yl]methyl}-N,N-bis(1H-imidazol-2-ylmethyl)benzamide (compound 50-83)

Description: amorphous;
TLC: Rf 0.25 (methanol:28% ammonia water=9:1);
NMR (CDCl$_3$): δ 1.23-2.11 (m, 11H), 2.12-2.41 (m, 6H), 2.55 (t, J=6.9 Hz, 2H), 2.63-3.15 (m, 7H), 3.58 (s, 2H), 4.54-4.72 (m, 4H), 6.92-7.15 (m, 4H), 7.37 (d, J=8.1 Hz, 2H), 7.64 (d, J=8.1 Hz, 2H)

Example 50(84)

4-{[2-(cyclopentylmethyl)-2,8-diazaspiro[4.5]dec-8-yl]methyl}-N,N-bis(1H-imidazol-2-ylmethyl)benzamide (compound 50-84)

Description: amorphous;
TLC: Rf 0.47 (methanol:28% ammonia water=98:2);
NMR (CDCl$_3$): δ 1.06-1.30 (m, 2H), 1.41-1.67 (m, 10H), 1.66-1.85 (m, 2H), 1.88-2.08 (m, 1H), 2.25-2.44 (m, 8H), 2.55 (t, J=6.6 Hz, 2H), 3.47 (s, 2H), 4.52-4.73 (m, 4H), 6.89-7.17 (m, 4H), 7.38 (d, J=8.1 Hz, 2H), 7.66 (d, J=8.1 Hz, 2H)

Example 50(85)

N,N-bis(1H-imidazol-2-ylmethyl)-4-{[2-(2-thienylmethyl)-2,8-diazaspiro[4.5]dec-8-yl]methyl}benzamide (compound 50-85)

Description: amorphous;
TLC: Rf 0.58 (methanol:28% ammonia water=98:2);
NMR (CDCl$_3$): δ 1.49-1.70 (m, 6H), 2.20-2.38 (m, 4H), 2.41 (s, 2H), 2.62 (t, J=6.9 Hz, 2H), 3.46 (s, 2H), 3.78 (s, 2H), 4.51-4.73 (m, 4H), 6.89 (dd, J=3.6, 1.2 Hz, 1H), 6.93 (dd, J=4.8, 3.6 Hz, 1H), 6.96-7.13 (m, 4H), 7.20 (dd, J=4.8, 1.2 Hz, 1H), 7.37 (d, J=8.1 Hz, 2H), 7.65 (d, J=8.1 Hz, 2H)

Example 50(86)

4-{[2-(4-fluorobenzyl)-2,8-diazaspiro[4.5]dec-8-yl]methyl}-N,N-bis(1H-imidazol-2-ylmethyl)benzamide (compound 50-86)

Description: amorphous;
TLC: Rf 0.53 (methanol:28% ammonia water=98:2);
NMR (CDCl$_3$): δ 1.47-1.68 (m, 6H), 2.23-2.42 (m, 6H), 2.54 (t, J=6.9 Hz, 2H), 3.46 (s, 2H), 3.53 (s, 2H), 4.52-4.72 (m, 4H), 6.86-7.15 (m, 6H), 7.19-7.32 (m, 2H), 7.37 (d, J=8.1 Hz, 2H), 7.65 (d, J=8.1 Hz, 2H)

Example 50(87)

4-({2-[(4-(diethylamino)benzyl]-2,8-diazaspiro[4.5]dec-8-yl}methyl)-N,N-bis(1H-imidazol-2-ylmethyl)benzamide (compound 50-87)

Description: amorphous;
TLC: Rf 0.44 (methanol:28% ammonia water=98:2);
NMR (CDCl$_3$): δ 1.15 (t, J=7.2 Hz, 6H), 1.45-1.68 (m, 6H), 2.24-2.43 (m, 6H), 2.55 (t, J=6.6 Hz, 2H), 3.33 (q, J=7.2 Hz, 4H), 3.45 (s, 2H), 3.47 (s, 2H), 4.51-4.73 (m, 4H), 6.62 (d, J=9.0 Hz, 2H), 6.92-7.09 (m, 4H), 7.13 (d, J=9.0 Hz, 2H), 7.36 (d, J=8.1 Hz, 2H), 7.62 (d, J=8.1 Hz, 2H)

Example 50(88)

4-{[4-(cyclopentylmethyl)-1-oxa-4,9-diazaspiro[5.5]undec-9-yl]methyl}-N,N-bis(1H-imidazol-2-ylmethyl)benzamide (compound 50-88)

Description: amorphous;
TLC: Rf 0.71 (methanol:28% ammonia water=98:2);
NMR (CDCl$_3$): δ 1.08-1.30 (m, 2H), 1.40-1.79 (m, 8H), 1.84-2.25 (m, 7H), 2.27-2.56 (m, 6H), 3.52 (s, 2H), 3.62-3.75 (m, 2H), 4.50-4.75 (m, 4H), 6.89-7.18 (m, 4H), 7.39 (d, J=8.1 Hz, 2H), 7.66 (d, J=8.1 Hz, 2H)

Example 50(89)

N,N-bis(1H-imidazol-2-ylmethyl)-4-{[4-(2-thienylmethyl)-1-oxa-4,9-diazaspiro[5.5]undec-9-yl]methyl}benzamide (compound 50-89)

Description: amorphous;
TLC: Rf 0.73 (methanol:28% ammonia water=98:2);
NMR (CDCl$_3$): δ 1.43-1.65 (m, 2H), 1.82-2.03 (m, 2H), 2.24 (s, 2H), 2.28-2.57 (m, 6H), 3.49 (s, 2H), 3.63 (s, 2H), 3.67-3.80 (m, 2H), 4.50-4.74 (m, 4H), 6.88 (dd, J=3.6, 1.2 Hz, 1H), 6.92 (dd, J=5.1, 3.6 Hz, 1H), 6.95-7.12 (m, 4H), 7.21 (dd, J=5.1, 1.2 Hz, 1H), 7.37 (d, J=8.1 Hz, 2H), 7.63 (d, J=8.1 Hz, 2H)

Example 50(90)

4-{[{trans-4-[cyclohexyl(propyl)amino]cyclohexyl}(ethyl)amino]methyl}-N,N-bis(1H-imidazol-2-ylmethyl)benzamide (compound 50-90)

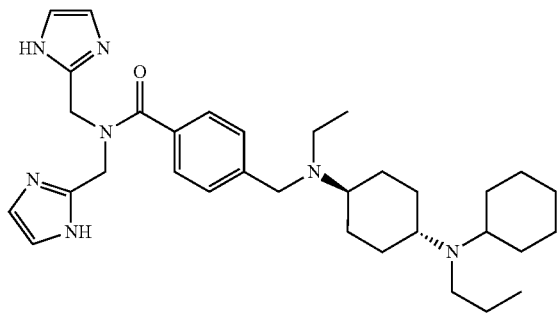 [SMILES: CCCN(C1CCCCC1)[C@H]1CC[C@H](N(CC)Cc2ccc(C(=O)N(Cc3ncc[nH]3)Cc3ncc[nH]3)cc2)CC1]

Description: amorphous;

TLC: Rf 0.69 (ethyl acetate:methanol:28% ammonia water=50:10:1);

NMR (CDCl₃): δ 0.81 (t, J=7.2 Hz, 3H), 0.93 (t, J=7.2 Hz, 3H), 1.18-1.81 (m, 20H), 2.39-2.53 (m, 7H), 3.59 (s, 2H), 4.64 (br-s, 4H), 6.99 (br-s, 2H), 7.07 (br-s, 2H), 7.40 (d, J=8.1 Hz, 2H), 7.62 (d, J=8.1 Hz, 2H)

Example 50(91)

4-{[{trans-4-[cyclohexyl(propyl)amino]cyclohexyl}(propyl)amino]methyl}-N,N-bis(1H-imidazol-2-ylmethyl)benzamide (compound 50-91)

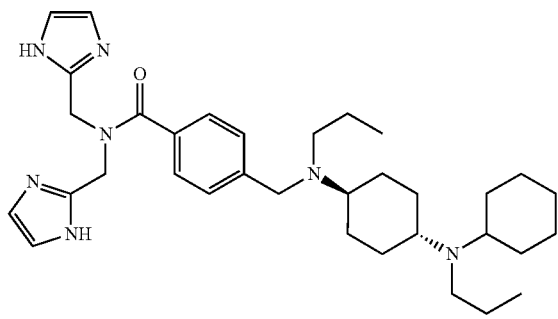 [SMILES: CCCN(Cc1ccc(C(=O)N(Cc2ncc[nH]2)Cc2ncc[nH]2)cc1)[C@H]1CC[C@H](N(CCC)C2CCCCC2)CC1]

Description: oily product;

TLC: Rf 0.73 (ethyl acetate:methanol:28% ammonia water=50:10:1);

NMR (CDCl₃): δ 0.78-0.85 (m, 6H), 1.06-1.92 (m, 22H), 2.36-2.59 (m, 7H), 3.60 (s, 2H), 4.62 (br-s, 4H), 7.01 (br-s, 2H), 7.09 (br-s, 2H), 7.41 (d, J=8.1 Hz, 2H), 7.68 (d, J=8.1 Hz, 2H)

Example 50(92)

4-[(2-cyclohexyl-2,8-diazaspiro[4.5]dec-8-yl)methyl]-N,N-bis(1H-imidazol-2-ylmethyl)benzamide (compound 50-92)

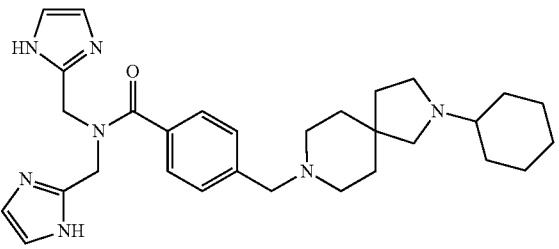 [SMILES: O=C(c1ccc(CN2CCC3(CC2)CCN(C2CCCCC2)C3)cc1)N(Cc1ncc[nH]1)Cc1ncc[nH]1]

Description: amorphous;

TLC: Rf 0.15 (methanol:28% ammonia water=99:1);

NMR (CDCl₃): δ 1.08-1.37 (m, 5H), 1.46-2.05 (m, 12H), 2.21-2.45 (m, 4H), 2.56 (s, 2H), 2.74 (t, J=6.6 Hz, 2H), 3.47 (s, 2H), 4.50-4.75 (m, 4H), 6.92-7.11 (m, 4H), 7.36 (d, J=8.1 Hz, 2H), 7.61 (d, J=8.1 Hz, 2H)

Example 50(93)

4-[(8-cyclohexyl-2,8-diazaspiro[5.5]undec-2-yl)methyl]-N,N-bis(1H-imidazol-2-ylmethyl)benzamide (compound 50-93)

Description: amorphous;

TLC: Rf 0.63 (methanol:28% ammonia water=98:2);

NMR (CDCl₃): δ 0.97-1.31 (m, 7H), 1.34-1.65 (m, 7H), 1.65-1.86 (m, 4H), 2.01-2.63 (m, 9H), 3.32-3.51 (m, 2H), 4.52-4.85 (m, 4H), 6.88-7.12 (m, 4H), 7.34 (d, J=8.1 Hz, 2H), 7.44 (d, J=8.1 Hz, 2H)

Example 50(94)

4-[(4-cyclohexyl-1-oxa-4,9-diazaspiro[5.5]undec-9-yl)methyl]-N,N-bis(1H-imidazol-2-ylmethyl)benzamide (compound 50-94)

Description: amorphous;

TLC: Rf 0.42 (methanol:28% ammonia water=99:1);

NMR (CDCl₃): δ 1.00-2.62 (m, 23H), 3.52 (s, 2H), 3.62-3.75 (m, 2H), 4.49-4.75 (m, 4H), 6.94-7.14 (m, 4H), 7.39 (d, J=7.8 Hz, 2H), 7.63 (d, J=7.8 Hz, 2H)

Example 50(95)

4-[(8-cyclohexyl-2,8-diazaspiro[4.5]dec-2-yl)methyl]-N,N-bis(1H-imidazol-2,ylmethyl)benzamide (compound 50-95)

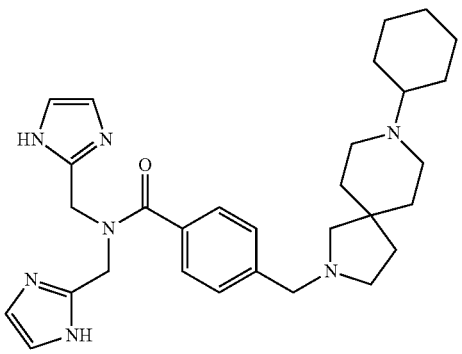 [SMILES: O=C(c1ccc(CN2CCC3(CCN(C4CCCCC4)CC3)C2)cc1)N(Cc1ncc[nH]1)Cc1ncc[nH]1]

Description: amorphous;
TLC: Rf 0.33 (ethyl acetate:methanol:28% ammonia water=50:10:1);
NMR (CDCl$_3$): δ 1.00-2.56 (m, 25H), 3.56 (s, 2H), 4.64 (s, 2H), 4.68 (s, 2H), 6.96 (s, 2H), 7.03 (s, 2H), 7.34 (d, J=8.1 Hz, 2H), 7.53 (d, J=8.1 Hz, 2H)

Example 50(96)

4-[(7-cyclohexyl-2,7-diazaspiro[4.5]dec-2-yl)methyl]-N,N-bis(1H-imidazol-2-ylmethyl)benzamide (compound 50-96)

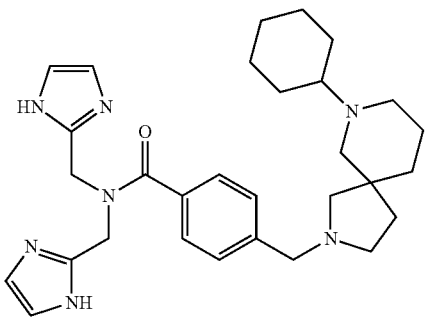 [SMILES: O=C(c1ccc(CN2CCC3(CCCN(C4CCCCC4)C3)C2)cc1)N(Cc1ncc[nH]1)Cc1ncc[nH]1]

Description: amorphous;
TLC: Rf 0.46 (ethyl acetate:methanol:28% ammonia water=50:10:1);
NMR (CDCl$_3$): δ 1.00-2.65 (m, 25H), 3.56 (d, J=13.8 Hz, 1H), 3.59 (d; J=13.8 Hz, 1H), 4.62-4.66 (m, 4H), 6.99 (s, 2H); 7.06 (s, 2H), 7.38 (d, J=8.1 Hz, 2H), 7.62 (d, J=8.1 Hz, 2H)

Example 50(97)

4-[(9-cyclohexyl-2,9-diazaspiro[5.5]undec-2-yl)methyl]-N,N-bis(1H-imidazol-2-ylmethyl)benzamide (compound 50-97)

Description: amorphous;
TLC: Rf 0.44 (ethyl acetate:methanol:28% ammonia water=50:10:1);
NMR (CDCl$_3$): δ 1.00-2.55 (m, 27H), 3.43 (s, 2H), 4.60-4.65 (m, 4H), 7.00 (s, 2H), 7.07 (s, 2H), 7.37 (d, J=8.1 Hz, 2H), 7.40 (d, J=8.1 Hz, 2H)

Example 50(98)

4-[(2-cyclohexyl-2,7-diazaspiro[3.5]nona-7-yl)methyl]-N,N-bis(1H-imidazol-2-ylmethyl)benzamide (compound 50-98)

Description: amorphous;
TLC: Rf 0.42 (methanol:28% ammonia water=98:2);
NMR (CDCl$_3$): δ 0.89-1.31 (m, 5H), 1.51-1.65 (m, 1H), 1.65-1.82 (m, 8H), 1.95-2.11 (m, 1H), 2.16-2.41 (m, 4H), 3.06 (s, 4H), 3.43 (s, 2H), 4.54-4.81 (m, 4H), 6.89-7.11 (m, 4H), 7.32 (d, J=8.1 Hz, 2H), 7.48 (d, J=8.1 Hz, 2H)

Example 50(99)

4-[(9-cyclohexyl-1-oxa-4,9-diazaspiro[5.5]undec-4-yl)methyl]-N,N-bis(1H-imidazol-2-ylmethyl)benzamide (compound 50-99)

Description: amorphous;
TLC: Rf 0.51 (methanol:28% ammonia water=98:2);
NMR (CDCl$_3$): δ 0.96-1.36 (m, 5H), 1.44-1.69 (m, 3H), 1.70-2.09 (m, 6H), 2.18 (s, 2H), 2.24-2.46 (m, 3H), 2.48-2.70 (m, 4H), 3.34-3.47 (m, 2H), 3.62-3.78 (m, 2H), 4.53-4.83 (m, 4H), 6.90-7.12 (m, 4H), 7.33 (d, J=8.1 Hz, 2H), 7.47 (d, J=8.1 Hz, 2H)

Example 50(100)

4-[(4-cyclohexyl-1-oxa-4,8-diazaspiro[5.5]undec-8-yl)methyl]-N,N-bis(1H-imidazol-2-ylmethyl)benzamide (compound 50-100)

Description: amorphous;
TLC: Rf 0.72 (methanol:28% ammonia water=98:2);
NMR (CDCl$_3$): δ 0.98-1.33 (m, 5H), 1.37-1.90 (m, 9H), 2.04-2.69 (m, 9H), 3.48 (d, J=13.8 Hz, 1H), 3.54 (d, J=13.8 Hz, 1H), 3.59-3.78 (m, 2H), 4.53-4.84 (m, 4H), 6.89-7.13 (m, 4H), 7.34 (d, J=8.1 Hz, 2H), 7.48 (d, J=8.1 Hz, 2H)

Example 50(101)

4-[(1'-cyclohexyl-1H-spiro[isoquinoline-4,4'-piperidine]-2(3H)-yl)methyl]-N,N-bis(1H-imidazol-2-ylmethyl)benzamide (compound 50-101)

Description: amorphous;
TLC: Rf 0.62 (methanol:28% ammonia water=98:2);
NMR (CDCl$_3$): δ 0.89-1.35 (m, 5H), 1.48-1.93 (m, 7H), 1.95-2.37 (m, 5H), 2.62 (s, 2H), 2.67-2.88 (m, 2H), 3.60 (s, 2H), 3.66 (s, 2H), 4.48-4.87 (m, 4H), 6.95 (d, J=7.87 Hz, 1H), 6.98-7.13 (m, 5H), 7.13-7.24 (m, 1H), 7.42 (d, J=8.1 Hz, 2H), 7.47 (d, J=8.4 Hz, 1H), 7.53 (d, J=8.1 Hz, 2H)

Example 50(102)

4-[({3-[(dipropylamino)methyl]phenyl}amino)methyl]-N,N-bis(1H-imidazol-2-ylmethyl)benzamide (compound 50-102)

Description: amorphous;
TLC: Rf 0.65 (ethyl acetate:methanol:28% ammonia water=50:10:1);

NMR (CDCl$_3$): δ 0.83 (t, J=7.2 Hz, 6H), 1.39-1.51 (m, 4H), 2.33-2.38 (m, 4H), 3.46 (s, 2H), 4.35 (s, 2H), 4.60 (br-s, 2H), 4.67 (br-s, 2H), 6.47 (m, 1H), 6.66-6.68 (m, 2H), 7.01 (br-s, 2H), 7.05 (br-s, 2H), 7.08 (m, 1H), 7.42 (d, J=8.4 Hz; 2H), 7.64 (d, J=8.4 Hz, 2H)

Example 50(103)

4-{[{trans-4-[cyclohexyl(propyl)amino]cyclohexyl}(2-hydroxyethyl)amino]methyl}-N,N-bis(1H-imidazol-2-ylmethyl)benzamide (compound 50-103)

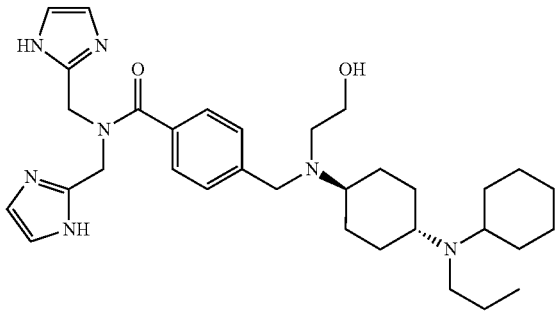 [SMILES: CCCN(C1CCCCC1)[C@H]1CC[C@H](N(CCO)Cc2ccc(C(=O)N(Cc3ncc[nH]3)Cc3ncc[nH]3)cc2)CC1]

Description: amorphous;
TLC: Rf 0.47 (dichloromethane:methanol:28% ammonia water=50:10:1);
NMR (CDCl$_3$): δ 0.81 (t, J=7.5 Hz, 3H), 1.18-2.00 (m, 20H), 2.38-2.58 (m, 5H), 2.65 (t, J=5.3 Hz, 2H), 3.41 (t, J=5.4 Hz, 2H), 3.63 (s, 2H), 4.57 (br-s, 2H), 4.69 (br-s, 2H), 7.02 (br-s, 2H), 7.05 (br-s, 2H), 7.34 (d, J=8.1 Hz, 2H), 7.61 (d, J=8.1 Hz, 2H)

Example 50(104)

4-[({trans-4-[(2-hydroxyethyl)(propyl)amino]cyclohexyl}amino)methyl]-N,N-bis(1H-imidazol-2-ylmethyl)benzamide (compound 50-104)

Description: oily product;
TLC: Rf 0.41 (dichloromethane:methanol:28% ammonia water=50:10:1);
NMR (CDCl$_3$): δ 0.86 (t, J=7.5 Hz, 3H), 1.06-2.04 (m, 10H), 2.35-2.52 (m, 4H), 2.59 (t, J=5.4 Hz, 2H), 3.48 (t, J=5.4 Hz, 2H), 3.82 (s, 2H), 4.58 (br-s, 2H), 4.61 (br-s, 2H), 7.02 (br-s, 2H), 7.09 (br-s, 2H), 7.37 (d, J=8.1 Hz, 2H), 7.71 (d, J=8.1 Hz, 2H)

Example 50(105)

4-[({trans-4-[(1-ethylpropyl)(2-hydroxyethyl)amino]cyclohexyl}amino)methyl]-N,N-bis(1H-imidazol-2-ylmethyl)benzamide (compound 50-105)

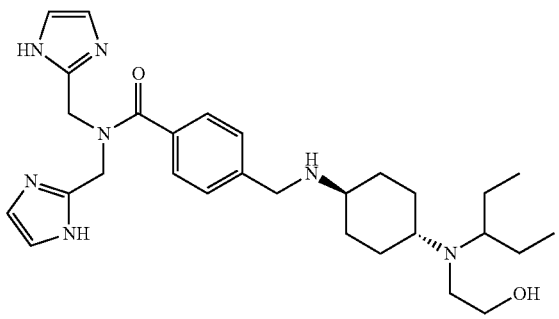 [SMILES: CCC(CC)N(CCO)[C@H]1CC[C@H](NCc2ccc(C(=O)N(Cc3ncc[nH]3)Cc3ncc[nH]3)cc2)CC1]

Description: amorphous;
TLC: Rf 0.50 (dichloromethane:methanol:28% ammonia water=50:10:1);
NMR (CDCl$_3$): δ 0.89 (t, J=7.2 Hz, 6H), 1.11-1.42 (m, 8H), 1.71-1.75 (m, 2H), 1.98-2.01 (m, 2H), 2.26 (m, 1H), 2.41 (m, 1H), 2.54 (m, 1H), 2.68 (t, J=5.1 Hz, 2H), 3.45 (t, J=5.1 Hz, 2H), 3.81 (s, 2H), 4.60 (br-s, 2H), 4.66 (br-s, 2H), 6.99 (br-s, 2H), 7.04 (br-s, 2H), 7.34 (d, J=7.8 Hz, 2H), 7.52 (d, J=7.8 Hz, 2H)

Example 50(106)

4-({[trans-4-(dipropylamino)cyclohexyl]amino}methyl)-N,N-bis(1H-imidazol-2-ylmethyl)-2-methoxybenzamide (compound 50-106)

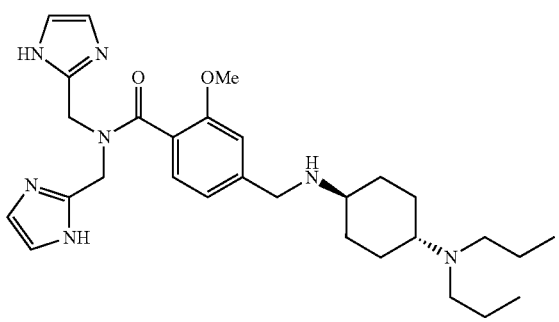 [SMILES: CCCN(CCC)[C@H]1CC[C@H](NCc2ccc(C(=O)N(Cc3ncc[nH]3)Cc3ncc[nH]3)c(OC)c2)CC1]

Description: amorphous;
TLC: Rf 0.67 (chloroform:methanol:28% ammonia water=80:20:4);
NMR (DMSO-D$_6$): δ 0.79 (t, J=7.2 Hz, 6H), 0.90-1.07 (m, 2H), 1.07-1.23 (m, 2H), 1.24-1.40 (m, 4H), 1.57-1.71 (m, 2H), 1.85-1.98 (m, 2H), 2.17-2.43 (m, 6H), 3.64 (s, 3H), 3.67 (s, 2H), 4.43 (s, 2H), 4.54-4.95 (m, 2H), 6.61-7.27 (m, 7H), 11.95-12.74 (m, 2H).

Example 50(107)

4-[({trans-4-[2,3-dihydro-1H-inden-2-yl(propyl)amino]cyclohexyl}amino)methyl]-N,N-bis(1H-imidazol-2-ylmethyl)benzamide (compound 50-107)

Description: amorphous;
TLC: Rf 0.64 (ethyl acetate:methanol:28% ammonia water=80:20:3);
NMR (CDCl$_3$): δ d 0.85 (t, J=7.2 Hz, 3H), 1.15-1.60 (m, 6H), 1.82-1.95 (m, 2H), 2.02-2.12 (m, 2H), 2.40-2.58 (m, 3H), 2.70 (m, 1H), 2.90-3.02 (m, 4H), 3.77 (m, 1H), 3.84 (s, 2H), 4.52-4.75 (m, 4H), 6.98-7.10 (m, 4H), 7.10-7.20 (m, 4H), 7.38 (d, J=8.4 Hz, 2H), 7.60 (d, J=8.4 Hz, 2H)

Example 50(108)

N,N-bis(1H-imidazol-2-ylmethyl)-4-[({trans-4-[(2-naphthylmethyl)(propyl)amino]cyclohexyl}amino)methyl]benzamide (compound 50-108)

Description: amorphous;
TLC: Rf 0.68 (ethyl acetate:methanol:28% ammonia water=80:20:3);
NMR (CDCl$_3$): δ d 0.81 (t, J=7.2 Hz, 3H), 1.10-1.50 (m, 6H), 1.82-1.98 (m, 2H), 2.00-2.12 (m, 2H), 2.42-2.50 (m, 2H), 2.50-2.70 (m, 2H), 3.75 (s, 2H), 3.84 (s, 2H), 4.45-4.70 (m, 4H), 6.98-7.10 (m, 4H), 7.35-7.85 (m, 11H)

Example 50(109)

4-[(8-cyclohexyl-2,8-diazaspiro[4.5]dec-2-yl)methyl]-N,N-bis(1H-imidazol-2-ylmethyl)-2-methoxy-benzamide (compound 50-109)

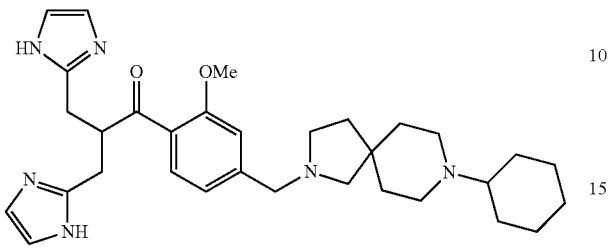

Description: amorphous;
TLC: Rf 0.63 (chloroform:methanol:28% ammonia water=80:20:4);
NMR (DMSO-D$_6$): δ 0.91-1.30 (m, 5H), 1.36-1.60 (m, 7H), 1.61-1.80 (m, 4H), 2.09-2.23 (m, 1H), 2.26 (s, 2H), 2.33-2.47 (m, 6H), 3.49 (s, 2H), 3.63 (s, 3H), 4.31-4.54 (m, 2H), 4.58-4.87 (m, 2H), 6.59-7.25 (m, 7H), 12.04-12.76 (m, 2H)

Example 50(110)

4-[({4-[(dipropylamino)methyl]benzyl}amino)methyl]-N,N-bis(1H-imidazol-2-ylmethyl)benzamide (compound 50-110)

Description: amorphous;
TLC: Rf 0.59 (ethyl acetate:methanol:28% ammonia water=50:10:1);
NMR (CDCl$_3$): δ 0.85 (t, J=7.5 Hz, 6H), 1.41-1.54 (m, 4H), 2.34-2.39 (m, 4H), 3.54 (s, 2H), 3.77 (s, 2H), 3.82 (s, 2H), 4.61 (br-s, 2H), 4.66 (br-s, 2H), 6.97 (br-s, 2H), 7.04 (br-s, 2H), 7.23-7.30 (m, 4H), 7.38 (d, J=7.8 Hz, 2H), 7.58-7.61 (m, 2H)

Example 50(111)

4-[({3-[(dipropylamino)methyl]benzyl}amino)methyl]-N,N-bis(1H-imidazol-2-ylmethyl)benzamide (compound 50-111)

Description: amorphous;
TLC: Rf 0.59 (ethyl acetate:methanol:28% ammonia water=50:10:1);
NMR (CDCl$_3$): δ 0.85 (t, J=7.5 Hz, 6H), 1.42-1.54 (m, 4H), 2.35-2.40 (m, 4H), 3.55 (s, 2H), 3.78 (s, 2H), 3.82 (s, 2H), 4.58 (br-s, 2H), 4.62 (br-s, 2H), 7.01 (br-s, 2H), 7.08 (br-s, 2H), 7.17-7.29 (m, 4H), 7.41 (d, J=8.1 Hz, 2H), 7.71 (d, J=8.1 Hz, 2H)

Example 50(112)

3-[{4-[(4-{[bis(1H-imidazol-2-ylmethyl)amino]carbonyl}benzyl)amino]cyclohexyl}(propyl)amino]propanoic acid (high polar compound) (compound 50-112)

Description: amorphous;
TLC: Rf 0.24 (dichloromethane:methanol:28% ammonia water=80:20:2);
NMR (DMSO-D$_6$): δ d 0.81 (t, J=7.5 Hz, 3H), 0.95-1.12 (m, 2H), 1.15-1.32 (m, 2H), 1.32-1.48 (m, 2H), 1.60-1.72 (m, 2H), 1.85-1.98 (m, 2H), 2.16 (t, J=7.2 Hz, 2H), 2.25 (m, 1H), 2.43 (t, J=7.2 Hz, 2H), 2.56 (m, 1H), 2.69 (t, J=6.6 Hz, 2H), 3.70 (s, 2H), 4.45-4.68 (m, 4H), 6.90-7.08 (m, 4H), 7.32 (d, J=8.4 Hz, 2H), 7.42 (d, J=8.4 Hz, 2H)

Example 50(113)

N,N-bis(1H-imidazol-2-ylmethyl)-4-{[8-(3-methyl-2-butene-1-yl)-2,8-diazaspiro[4.5]dec-2-yl]methyl}benzamide (compound 50-113)

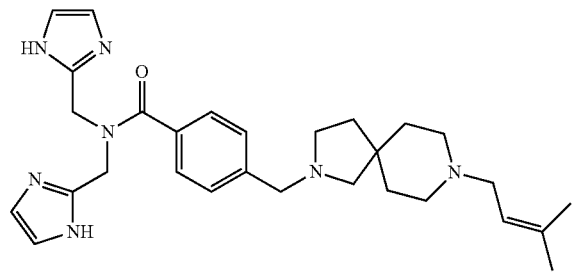 [SMILES: CC(C)=CCN1CCC2(CC1)CCN(Cc1ccc(C(=O)N(Cc3ncc[nH]3)Cc3ncc[nH]3)cc1)C2]

Description: amorphous;
TLC: Rf 0.44 (methanol:28% ammonia water=98:2);
NMR (CDCl$_3$): δ 1.49-1.66 (m, 9H), 1.72 (s, 3H), 2.2.1-2.46 (m, 6H), 2.55 (t, J=6.9 Hz, 2H), 2.92 (d, J=6.9 Hz, 2H), 3.57 (s, 2H), 4.52-4.73 (m, 4H), 5.15-5.33 (m, 1H), 6.86-7.14 (m, 4H), 7.36 (d, J=8.1 Hz, 2H), 7.61 (d, J=8.1 Hz, 2H)

Example 50(114)

4-{[8-(2-ethylbutyl)-2,8-diazaspiro[4.5]dec-2-yl]methyl}-N,N-bis(1H-imidazol-2-ylmethyl)benzamide (compound 50-114)

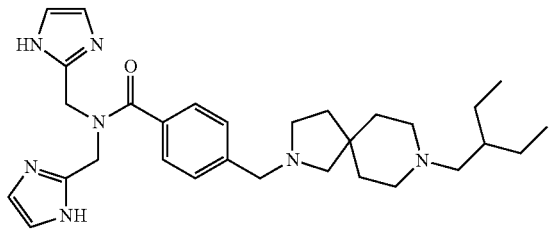 [SMILES: CCC(CC)CN1CCC2(CC1)CCN(Cc1ccc(C(=O)N(Cc3ncc[nH]3)Cc3ncc[nH]3)cc1)C2]

Description: amorphous;
TLC: Rf 0.58 (methanol:28% ammonia water=98:2);
NMR (CDCl$_3$): δ 0.83 (t, J=7.2 Hz, 6H), 1.15-1.46 (m, 5H), 1.48-1.68 (m, 6H), 2.08 (d, J=6.6 Hz, 2H), 2.16-2.39 (m, 6H), 2.54 (t, J=6.6 Hz, 2H), 3.57 (s, 2H), 4.50-4.77 (m, 4H), 6.82-7.16 (m, 4H), 7.36 (d, J=8.1 Hz, 2H), 7.59 (d, J=8.1 Hz, 2H)

Example 50(115)

N,N-bis(1H-imidazol-2-ylmethyl)-4-({8-[(5-methyl-2-thienyl)methyl]-2,8-diazaspiro[4.5]dec-2-yl}methyl)benzamide (compound 50-115)

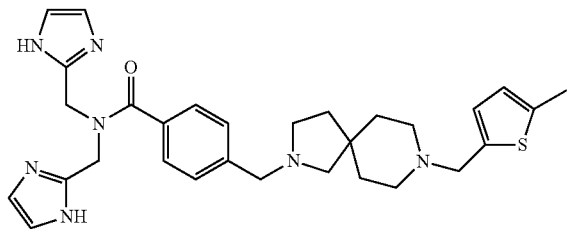 [SMILES: Cc1ccc(CN2CCC3(CC2)CCN(Cc2ccc(C(=O)N(Cc4ncc[nH]4)Cc4ncc[nH]4)cc2)C3)s1]

Description: amorphous;
TLC: Rf 0.41 (methanol:28% ammonia water=98:2);
NMR (CDCl$_3$): δ 1.52-1.64 (m, 6H), 2.31-2.45 (m, 9H), 2.49-2.59 (m, 2H), 3.52-3.63 (m, 4H), 4.58-4.71 (m, 4H), 6.52-6.59 (m, 1H), 6.62-6.68 (m, 1H), 6.95-7.09 (m, 4H), 7.31-7.40 (m, 2H), 7.56-7.65 (m, 2H)

Example 50(116)

4-({8-[(5-chloro-2-thienyl)methyl]-2,8-diazaspiro[4.5]dec-2-yl}methyl)-N,N-bis(1H-imidazol-2-ylmethyl)benzamide (compound 50-116)

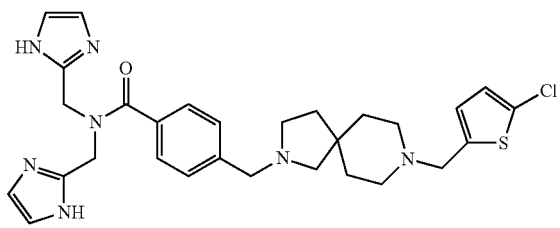 [SMILES: O=C(c1ccc(CN2CCC3(CCN(Cc4ccc(Cl)s4)CC3)C2)cc1)N(Cc1ncc[nH]1)Cc1ncc[nH]1]

Description: amorphous;
TLC: Rf 0.40 (methanol:28% ammonia water=98:2);
NMR (CDCl$_3$): δ 1.52-1.65 (m, 6H), 2.29-2.43 (m, 6H), 2.47-2.60 (m, 2H), 3.51-3.61 (m, 4H), 4.58-4.71 (m, 4H), 6.60-6.66 (m, 1H), 6.67-6.74 (m, 1H), 6.95-7.09 (m, 4H), 7.31-7.41 (m, 2H), 7.55-7.65 (m, 2H)

Example 50(117)

N,N-bis(1H-imidazol-2-ylmethyl)-4-{[8-(1,3-thiazol-2-ylmethyl)-2,8-diazaspiro[4.5]dec-2-yl]methyl}benzamide (compound 50-117)

Description: amorphous;
TLC: Rf 0.41 (methanol:28% ammonia water=98:2);
NMR (CDCl$_3$): δ 1.54-1.67 (m, 6H), 2.34 (s, 2H), 2.43-2.58 (m, 6H), 3.58 (s, 2H), 3.79 (s, 2H), 4.58-4.70 (m, 4H), 6.94-7.08 (m, 4H), 7.22-7.28 (m, 1H), 7.30-7.40 (m, 2H), 7.56-7.65 (m, 2H), 7.65-7.71 (m, 1H)

Example 50(118)

N,N-bis(1H-imidazol-2-ylmethyl)-4-{[8-(1,3-oxazol-2-ylmethyl)-2,8-diazaspiro[4.5]dec-2-yl]methyl}benzamide (compound 50-118)

Description: amorphous;
TLC: Rf 0.41 (methanol:28% ammonia water=98:2);
NMR (CDCl$_3$): δ 1.54-1.67 (m, 6H), 2.32 (s, 2H), 2.37-2.49 (m, 4H), 2.49-2.57 (m, 2H), 3.57 (s, 2H), 3.65 (s, 2H), 4.57-4.69 (m, 4H), 6.95-7.09 (m, 5H), 7.31-7.39 (m, 2H), 7.57-7.66 (m, 3H)

Example 50(119)

3-chloro-4-({[trans-4-(dipropylamino)cyclohexyl]amino}methyl)-N,N-bis(1H-imidazol-2-ylmethyl)benzamide (compound 50-119)

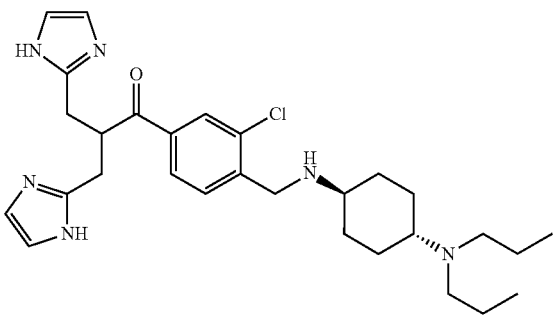 [SMILES: CCCN(CCC)[C@H]1CC[C@H](NCc2ccc(C(=O)C(Cc3ncc[nH]3)Cc3ncc[nH]3)cc2Cl)CC1]

Description: oily product;
TLC: Rf 0.49 (chloroform:methanol:28% ammonia water=40:10:2);
NMR (METHANOL-D$_4$): δ 0.77-0.93 (m, 6H), 1.04-1.54 (m, 8H), 1.68-1.92 (m, 2H), 1.96-2.14 (m, 2H), 2.26-2.59 (m, 6H), 3.83-3.93 (m, 2H), 4.31-4.87 (m, 4H), 7.01 (s, 4H), 7.33-7.51 (m, 2H), 7.55 (s, 1H)

Example 50(120)

3-chloro-4-[(8-cyclohexyl-2,8-diazaspiro[4.5]dec-2-yl)methyl]-N,N-bis(1H-imidazol-2-ylmethyl)benzamide (compound 50-120)

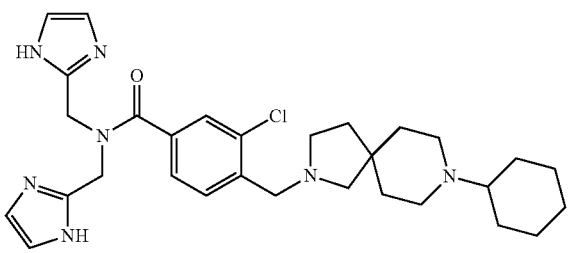 [SMILES: O=C(c1ccc(CN2CCC3(CCN(C4CCCCC4)CC3)C2)c(Cl)c1)N(Cc1ncc[nH]1)Cc1ncc[nH]1]

Description: amorphous;
TLC: Rf 0.49 (chloroform:methanol:28% ammonia water=40:10:2);
NMR (METHANOL-D$_4$): δ 1.01-1.35 (m, 6H), 1.46-1.70 (m, 6H), 1.72-1.83 (m, 2H), 1.85-1.99 (m, 2H), 2.15-2.36 (m, 1H), 2.40-2.76 (m, 8H), 3.60-3.93 (m, 2H), 4.33-4.85 (m, 4H), 6.80-7.22 (m, 4H), 7.34-7.46 (m, 1H), 7.47-7.65 (m, 2H)

Example 50(121)

4-[(8-cyclooctyl-2,8-diazaspiro[4.5]dec-2-yl)methyl]-N,N-bis(1H-imidazol-2-ylmethyl)benzamide (compound 50-121)

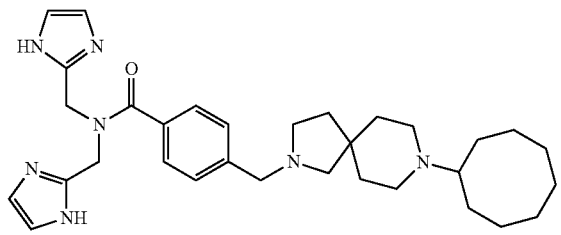 [SMILES: O=C(c1ccc(CN2CCC3(CCN(C4CCCCCCC4)CC3)C2)cc1)N(Cc1ncc[nH]1)Cc1ncc[nH]1]

Description: amorphous;
TLC: Rf 0.22 (methanol:28% ammonia water=98:2);
NMR (CDCl$_3$): δ 1.40-1.75 (m, 18H), 2.31-2.60 (m, 11H), 3.59 (s, 2H), 4.55-4.69 (m, 4H), 6.94-7.10 (m, 4H), 7.31-7.41 (m, 2H), 7.59-7.68 (m, 2H)

Example 50(122)

N,N-bis(1H-imidazol-2-ylmethyl)-4-[(8-methyl-2,8-diazaspiro[4.5]dec-2-yl)methyl]benzamide (compound 50-122)

Description: amorphous;
TLC: Rf 0.12 (methanol:28% ammonia water=98:2);
NMR (CDCl$_3$): δ 1.53-1.66 (m, 6H), 2.19-2.34 (m, 9H), 2.48-2.61 (m, 2H), 3.60 (s, 2H), 4.59-4.71 (m, 4H), 6.95-7.10 (m, 4H), 7.30-7.42 (m, 2H), 7.55-7.66 (m, 2H)

Example 50(123)

4-[(8-acetyl-2,8-diazaspiro[4.5]dec-2-yl)methyl]-N,N-bis(1H-imidazol-2-ylmethyl)benzamide (compound 50-123)

Description: amorphous;
TLC: Rf 0.41 (methanol:28% ammonia water=98:2);
NMR (CDCl$_3$): δ 1.50-1.75 (m, 6H), 2.06 (s, 3H), 2.31-2.46 (m, 2H), 2.53-2.68 (m, 2H), 3.25-3.64 (m, 6H), 4.60-4.74 (m, 4H), 6.92-7.07 (m, 4H), 7.30-7.42 (m, 2H), 7.55-7.67 (m, 2H)

Example 50(124)

[2-(4-{[bis(1H-imidazol-2-ylmethyl)amino]carbonyl}benzyl)-2,8-diazaspiro[4.5]dec-8-yl]acetic acid (compound 50-124)

Description: amorphous;
TLC: Rf 0.53 (methanol:28% ammonia water=98:2);
NMR (CDCl$_3$): δ 1.79-1.93 (m, 6H), 2.63-2.71 (m, 2H), 2.79-2.88 (m, 2H), 3.15-3.35 (m, 4H), 3.56 (s, 2H), 3.81 (s, 2H), 4.59-4.85 (m, 4H), 7.00-7.09 (m, 4H), 7.39-7.51 (m, 4H)

Example 50(125)

3-{[trans-4-(dipropylamino)cyclohexyl]amino}-N,N-bis(1H-imidazol-2-ylmethyl)propaneamide (compound 50-125)

Description: amorphous;
TLC: Rf 0.57 (dichloromethane:methanol:ammonia water=40:10:1);
NMR (CDCl$_3$): δ 0.85 (t, J=7.2 Hz, 6H), 1.00-1.48 (m, 8H), 1.74-1.84 (m, 2H), 1.90-2.00 (m, 2H), 2.30-2.50 (m, 6H), 2.72 (t, J=6.0 Hz, 2H), 2.92 (t, J=6.0 Hz, 2H), 4.64 (s, 2H), 4.69 (s, 2H), 6.96 (s, 4H)

Example 50(126)

3-(8-cyclohexyl-2,8-diazaspiro[4.5]dec-2-yl)-N,N-bis(1H-imidazol-2-ylmethyl)propaneamide (compound 50-126)

Description: amorphous;
TLC: Rf 0.61 (dichloromethane:methanol:ammonia water=40:10:1);
NMR (CDCl$_3$): δ 1.00-1.34 (m, 6H), 1.59-1.73 (m, 6H), 1.78-1.85 (m, 2H), 1.88-1.97 (m, 2H), 2.48 (m, 1H), 2.56 (s, 2H), 2.58-2.70 (m, 4H), 2.77 (t, J=6.9 Hz, 2H), 2.81 (t, J=6.6 Hz, 2H), 2.91 (t, J=6.9 Hz, 2H), 4.67 (s, 2H), 4.71 (s, 2H), 6.99 (s, 4H)

Example 50(127)

4-(8-cyclohexyl-2,8-diazaspiro[4.5]dec-2-yl)-N,N-bis(1H-imidazol-2-ylmethyl)butaneamide (compound 50-127)

Description: amorphous;
TLC: Rf 0.57 (dichloromethane:methanol:ammonia water=40:10:1);
NMR (CDCl$_3$): δ 1.03-1.44 (m, 8H), 1.63-1.73 (m, 2H), 1.79-2.10 (m, 10H), 2.64 (t, J=6.9 Hz, 2H), 2.70 (s, 2H), 2.78-2.94 (m, 5H), 3.02 (t, J=6.9 Hz, 2H), 4.72 (s, 2H), 4.76 (s, 2H), 6.99 (s, 2H), 7.00 (s, 2H)

Example 50(128)

5-(8-cyclohexyl-2,8-diazaspiro[4.5]dec-2-yl)-N,N-bis(1H-imidazol-2-ylmethyl)pentaneamide (compound 50-128)

Description: amorphous;
TLC: Rf 0.60 (dichloromethane:methanol:ammonia water=40:10:1);
NMR (CDCl$_3$): δ 1.06-1.50 (m, 8H), 1.58-1.76 (m, 4H), 1.84-1.96 (m, 4H), 2.00-2.20 (m, 4H), 2.47 (t, J=6.6 Hz, 2H), 2.80-3.18 (m, 11H), 4.80 (s, 2H), 4.82 (s, 2H), 7.00 (s, 2H), 7.02 (s, 2H)

Example 50(129)

4-[({4-[(4,4-difluorocyclohexyl)amino]cyclohexyl}amino)methyl]N,N-bis(1H-imidazol-2-ylmethyl)benzamide (low polar compound) (compound 50-129)

Description: amorphous;
TLC: Rf 0.38 (ethyl acetate:methanol:28% ammonia water=80:20:3);

NMR (CDCl₃): δ d 1.40-2.20 (m, 16H), 2.65-2.80 (m, 3H), 3.79 (s, 2H), 4.52-4.72 (m, 4H), 6.95-7.12 (m, 4H), 7.37 (d, J=8.1 Hz, 2H), 7.62 (d, J=8.1 Hz, 2H)

Example 50(130)

4-[({4-[(4,4-difluorocyclohexyl)amino]cyclohexyl}amino)methyl]-N,N-bis(1H-imidazol-2-ylmethyl)benzamide (high polar compound) (compound 50-130)

Description: amorphous;
TLC: Rf 0.28 (ethyl acetate:methanol:28% ammonia water=80:20:3);
NMR (CDCl₃): δ d 1.00-2.20 (m, 16H), 2.40-3.00 (m, 3H), 3.84 (s, 2H), 4.50-4.70 (m, 4H), 6.95-7.12 (m, 4H), 7.38 (d, J=8.1 Hz, 2H), 7.67 (d, J=8.1 Hz, 2H)

Example 50(131)

(2E)-3-{4-[(8-cyclohexyl-2,8-diazaspiro[4.5]dec-2-yl)methyl]phenyl}-N,N-bis(1H-imidazol-2-ylmethyl)acrylamide (compound 50-131)

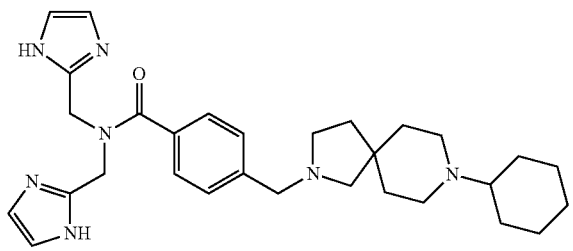 [SMILES: O=C(c1ccc(CN2CCC3(CCN(C4CCCCC4)CC3)C2)cc1)N(Cc1ncc[nH]1)Cc1ncc[nH]1]

Description: amorphous;
TLC: Rf 0.60 (ethyl acetate:methanol:ammonia water=50:10:1);
NMR (CDCl₃): δ 1.05-2.33 (m, 16H), 2.44-2.57 (m, 9H), 3.56 (s, 2H), 4.80 (br-s, 2H), 4.90 (br-s, 2H), 6.99 (br-s, 2H), 7.01 (br-s, 2H), 7.08 (d, J=15.3 Hz, 1H), 7.29 (d, J=6.9 Hz, 2H), 7.45 (d, J=6.9 Hz, 2H), 7.61 (d, J=15.3 Hz, 1H)

Example 50(132)

(2E)-3-[4-({[trans-4-(dipropylamino)cyclohexyl]amino}methyl)phenyl]-N,N-bis(1H-imidazol-2-ylmethyl)acrylamide (compound 50-132)

Description: amorphous;
TLC: Rf 0.59 (ethyl acetate:methanol:ammonia water=50:10:1);
NMR (CDCl₃): δ 0.85 (t, J=7.5 Hz, 6H), 1.06-1.50 (m, 8H), 1.80-1.83 (m, 2H), 1.98-2.02 (m, 2H), 2.37-2.51 (m, 6H), 3.79 (s, 2H), 4.79 (br-s, 2H), 4.89 (br-s, 2H), 7.00 (br-s, 4H), 7.07 (d, J=15.3 Hz, 1H), 7.27 (d, J=8.4 Hz, 2H), 7.45 (d, J=8.4 Hz, 2H), 7.59 (d, J=15.3 Hz, 1H)

Example 50(133)

3-{4-[(8-cyclohexyl-2,8-diazaspiro[4.5]dec-2-yl)methyl]phenyl}-N,N-bis(1H-imidazol-2-ylmethyl)propaneamide (compound 50-133)

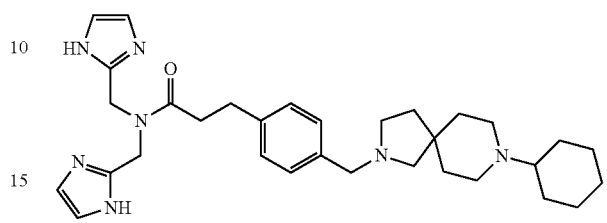

Description: amorphous;
TLC: Rf 0.55 (ethyl acetate:methanol:ammonia water=50:10:1);
NMR (CDCl₃): δ 1.05-1.27 (m, 6H), 1.57-1.63 (m, 8H), 1.70-1.80 (m, 2H), 1.85-1.90 (m, 2H), 2.28 (m, 1H), 2.45-2.57 (m, 6H), 2.76-2.88 (m, 4H), 3.49 (s, 2H), 4.48 (br-s, 2H), 4.56 (br-s, 2H), 6.97 (br-s, 2H), 6.98 (br-s, 2H), 7.01 (d, J=8.1 Hz, 2H), 7.12 (d, J=8.1 Hz, 2H)

Example 50(134)

3-[4-({[trans-4-(dipropylamino)cyclohexyl]amino}methyl)phenyl]-N,N-bis(1H-imidazol-2-ylmethyl)propaneamide (compound 50-134)

Description: amorphous;
TLC: Rf 0.56 (ethyl acetate:methanol:ammonia water=50:10:1);
NMR (CDCl₃): δ 0.86 (t, J=7.5 Hz, 6H), 1.10-2.03 (m, 12H), 2.39-2.51 (m, 6H), 2.76-2.85 (m, 4H), 3.74 (s, 2H), 4.46 (br-s, 2H), 4.52 (br-s, 2H), 6.97 (br-s, 2H), 6.98 (br-s, 2H), 7.02 (d, J=8.1 Hz, 2H), 7.12 (d, J=8.1 Hz, 2H)

Example 50(135)

2-{4-[(8-cyclohexyl-2,8-diazaspiro[4.5]dec-2-yl)methyl]phenyl}-N,N-bis(1H-imidazol-2-ylmethyl)acetamide (compound 50-135)

Description: amorphous;
TLC: Rf 0.59 (ethyl acetate:methanol:ammonia water=50:10:1);
NMR (CDCl₃): δ 1.10-1.30 (m, 6H), 1.59-2.02 (m, 14H), 2.44-2.63 (m, 5H), 3.54 (s, 2H), 3.79 (s, 2H), 4.64 (br-s, 2H), 4.73 (br-s, 2H), 6.98 (br-s, 2H), 6.99 (br-s, 2H), 7.13 (d, J=8.1 Hz, 2H), 7.23 (d, J=8.1 Hz, 2H)

Example 50(136)

2-[4-({[trans-4-(dipropylamino)cyclohexyl]amino}methyl)phenyl]-N,N-bis(1H-imidazol-2-ylmethyl)acetamide (compound 50-136)

Description: amorphous;
TLC: Rf 0.57 (ethyl acetate:methanol:ammonia water=50:10:1);
NMR (CDCl₃): δ 0.86 (t, J=7.5 Hz, 6H), 1.09-1.49 (m, 8H), 1.81-1.85 (m, 2H), 2.00-2.04 (m, 2H), 2.40-2.52 (m, 6H), 3.76 (s, 2H), 3.78 (s, 2H), 4.61 (br-s, 2H), 4.72 (br-s, 2H), 6.97 (br-s, 2H), 7.00 (br-s, 2H), 7.11 (d, J=8.1 Hz, 2H), 7.21 (d, J=8.1 Hz, 2H)

Example 50(137)

4-{[8-(cyclobutylmethyl)-2,8-diazaspiro[4.5]dec-2-yl]methyl}-N,N-bis(1H-imidazol-2-ylmethyl)benzamide (compound 50-137)

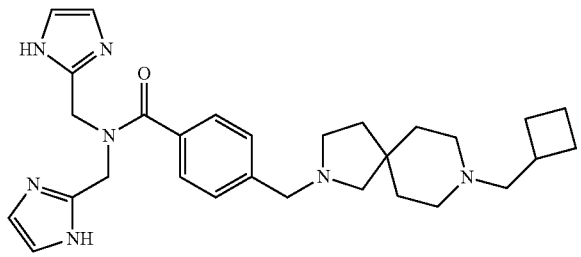 [SMILES: O=C(c1ccc(CN2CCC3(CCN(CC4CCC4)CC3)C2)cc1)N(Cc1ncc[nH]1)Cc1ncc[nH]1]

Description: amorphous;
TLC: Rf 0.34 (methanol:28% ammonia water=98:2);
NMR (CDCl₃): δ 1.57-1.90 (m, 10H), 1.96-2.11 (m, 3H), 2.31-2.46 (m, 7H), 2.50-2.62 (m, 3H), 3.58 (s, 2H), 4.57-4.71 (m, 4H), 6.93-7.08 (m, 4H), 7.29-7.39 (m, 2H), 7.54-7.64 (m, 2H)

Example 50(138)

4-[({4-[(4,4-difluorocyclohexyl)(propyl)amino]cyclohexyl}amino)methyl]-N,N-bis(1H-imidazol-2-ylmethyl)benzamide (low polar compound) (compound 50-138)

Description: amorphous;
TLC: Rf 0.73 (ethyl acetate:methanol:28% ammonia water=80:20:3);
NMR (CDCl₃): δ 0.82 (t, J, 7.5 Hz, 3H), 1.30-1.84 (m, 16H), 2.00-2.20 (m, 2H), 2.43 (t, J, 7.5 Hz, 2H), 2.54 (m, 1H), 2.72 (m, 1H), 2.76 (m, 1H), 3.77 (s, 2H), 4.60-4.80 (m, 4H), 6.95-7.12 (m, 4H), 7.37 (d, J=8.4 Hz, 2H), 7.51 (d, J=8.4 Hz, 2H)

Example 50(139)

4-[({4-[(4,4-difluorocyclohexyl)(propyl)amino]cyclohexyl}amino)methyl]-N,N-bis(1H-imidazol-2-ylmethyl)benzamide (high polar compound) (compound 50-139)

Description: amorphous;
TLC: Rf 0.60 (ethyl acetate:methanol:28% ammonia water=80:20:3);
NMR (CDCl₃): δ d 0.82 (t, J=7.5 Hz, 3H), 1.02-1.90 (m, 14H), 1.92-2.20 (m, 4H), 2.38 (m, 1H), 2.40 (t, J, 7.5 Hz, 2H), 2.52 (m, 1H), 2.64 (m, 1H), 3.81 (s, 2H), 4.60-4.80 (m, 4H), 6.98-7.12 (m, 4H), 7.34 (d, J=8.1 Hz, 2H), 7.52 (d, J=8.1 Hz, 2H)

Example 50(140)

4-({[4-(1-azocanyl)cyclohexyl]amino]methyl)-N,N-bis(1H-imidazol-2-ylmethyl)benzamide (low polar compound) (compound 50-140)

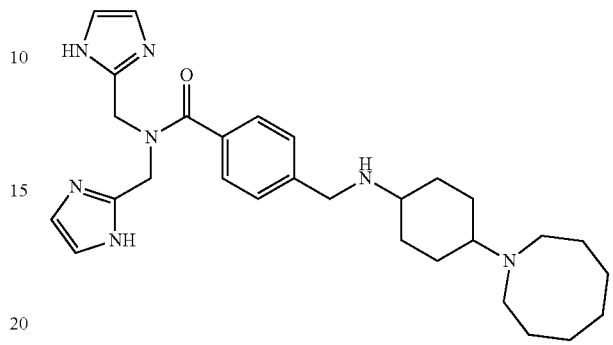

Description: amorphous;
TLC: Rf 0.53 (ethyl acetate:methanol:28% ammonia water=90:10:2);
NMR (CDCl₃): δ d 1.40-1.82 (m, 18H), 2.41 (m, 1H), 2.55-2.70 (m, 4H), 2.73 (m, 1H), 3.78 (s, 2H), 4.60-4.80 (m, 4H), 6.98-7.12 (m, 4H), 7.37 (d, J=8.1 Hz, 2H), 7.53 (d, J, 8.1 Hz, 2H)

Example 50(141)

4-({[4-(1-azocanyl)cyclohexyl]amino}methyl)-N,N-bis(1H-imidazol-2-ylmethyl)benzamide (high polar compound) (compound 50-141)

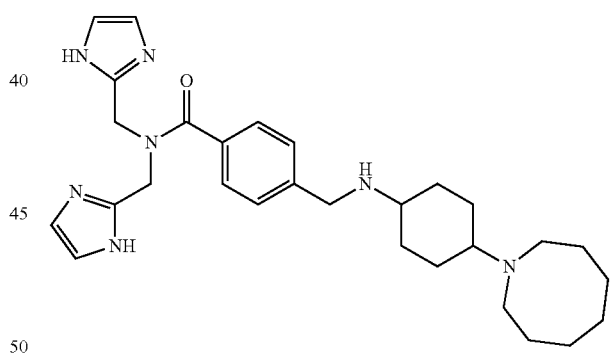

Description: amorphous;
TLC: Rf 0.37 (ethyl acetate:methanol:28% ammonia water=90:10:2);
NMR (CDCl₃): δ d 1.04-1.38 (m, 4H), 1.45-1.68 (m, 10H), 1.75-1.88 (m, 2H), 1.92-2.08 (m, 2H), 2.32-2.48 (m, 2H), 2.50-2.68 (m, 4H), 3.81 (s, 2H), 4.58-4.78 (m, 4H), 6.92-7.12 (m, 4H), 7.33 (d, J=8.1 Hz, 2H), 7.53 (d, J=8.1 Hz, 2H)

Example 50(142)

4-({[(2E)-4-(diethylamino)-2-butene-1-yl]amino}methyl)-N,N-bis(1H-imidazol-2-ylmethyl)benzamide (compound 50-142)

Description: oily product;
TLC: Rf 0.26 (methanol:28% ammonia water=98:2);

NMR (CDCl$_3$): δ 1.02 (t, J=6.9 Hz, 3H), 1.10 (t, J=7.2 Hz, 3H), 2.48 (q, J=6.9 Hz, 2H), 2.64 (q, J=7.2 Hz, 2H), 3.03 (d, J=4.8 Hz, 2H), 3.22 (d, J=4.8 Hz, 2H), 3.55 (s, 2H), 4.64 (m, 4H), 5.64 (m, 2H), 7.01 (m, 4H), 7.37 (d, J=8.1 Hz, 2H), 7.59 (d, J=8.1 Hz, 2H)

Example 50(143)

N,N-bis(1H-imidazol-2-ylmethyl)-4-{[8-(2,2,6,6-tetramethyl-4-piperidinyl)-2,8-diazaspiro[4.5]dec-2-yl]methyl}benzamide (compound 50-143)

Description: amorphous;

TLC: Rf 0.25 (methanol:28% ammonia water=98:2);

NMR (CDCl$_3$): δ 1.05 (t, J=12.3 Hz, 2H), 1.12 (s, 6H), 1.18 (s, 6H), 1.51-1.66 (m, 6H), 1.74 (dd, J=12.3, 3.0 Hz, 2H), 2.33 (s, 2H), 2.37-2.63 (m, 6H), 2.68-2.87 (m, 1H), 3.58 (s, 2H), 4.51-4.76 (m, 4H), 6.86-7.16 (m, 4H), 7.38 (d, J=8.1 Hz, 2H), 7.64 (d, J=8.1 Hz, 2H)

Example 50(144)

4-[(7-cycloheptyl-2,7-diazaspiro[3.5]nona-2-yl)methyl]-N,N-bis(1H-imidazol-2-ylmethyl)benzamide (compound 50-144)

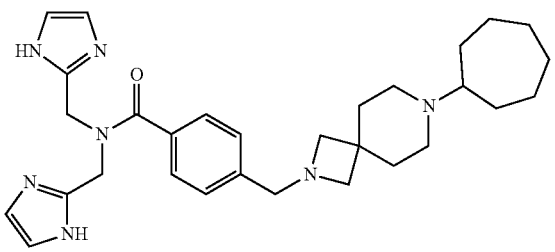 [SMILES: O=C(c1ccc(CN2CC3(CCN(C4CCCCCC4)CC3)C2)cc1)N(Cc1ncc[nH]1)Cc1ncc[nH]1]

Description: amorphous;

TLC: Rf 0.34 (methanol:28% ammonia water=98:2);

NMR (CDCl$_3$): δ 1.24-1.86 (m, 16H), 2.30-2.45 (m, 4H), 2.44-2.59 (m, 1H), 2.99 (s, 4H), 3.63 (s, 2H), 4.49-4.73 (m, 4H), 6.88-7.15 (m, 4H), 7.32 (d, J=8.1 Hz, 2H), 7.62 (d, J=8.1 Hz, 2H)

Example 50(145)

4-[(5-cycloheptyl-2,5-diazabicyclo[2.2.1]hepta-2-yl)methyl]-N,N-bis(1H-imidazol-2-ylmethyl)benzamide (compound 50-145)

Description: amorphous;

TLC: Rf 0.38 (methanol:28% ammonia water=98:2);

NMR (CDCl$_3$): δ 1.19-1.88 (m, 14H), 2.42-2.62 (m, 3H), 2.82 (d, J=9.6 Hz, 1H), 2.96 (dd, J=9.6, 2.7 Hz, 1H), 3.21 (s, 1H), 3.56 (s, 1H), 3.66 (d, J=13.9 Hz, 1H), 3.76 (d, J=13.90 Hz, 1H), 4.51-4.77 (m, 4H), 6.89-7.16 (m, 4H), 7.41 (d, J=8.1 Hz, 2H), 7.64 (d, J=8.1 Hz, 2H)

Example 50(146)

4-({[(1-cycloheptyl-4-piperidinyl)methyl]amino}methyl)-N,N-bis(1H-imidazol-2-ylmethyl)benzamide (compound 50-146)

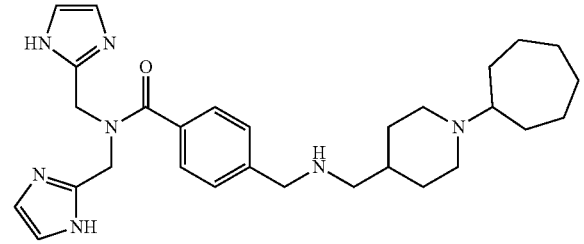 [SMILES: O=C(c1ccc(CNCC2CCN(C3CCCCCC3)CC2)cc1)N(Cc1ncc[nH]1)Cc1ncc[nH]1]

Description: amorphous;

TLC: Rf 0.30 (methanol:28% ammonia water=98:2);

NMR (CDCl$_3$): δ 1.08-1.90 (m, 17H), 2.12-2.31 (m, 2H), 2.47 (d, J=6.9 Hz, 2H), 2.50-2.61 (m, 1H), 2.69-2.87 (m, 2H), 3.77 (s, 2H), 4.46-4.76 (m, 4H), 6.86-7.14 (m, 4H), 7.30-7.43 (m, 2H), 7.54-7.70 (m, 2H)

Example 50(147)

3-[{4-[(4-{[bis(1H-imidazol-2-ylmethyl)amino]carbonyl}benzyl)amino]cyclohexyl}(propyl)amino]propanoic acid (low polar compound) (compound 50-147)

Description: amorphous;

TLC: Rf 0.47 (dichloromethane:methanol:28% ammonia water=80:20:2);

NMR (DMSO-D$_6$): δ d 0.84 (t, J=7.5 Hz, 3H), 1.22-1.82 (m, 10H), 2.21 (t, J=6.6 Hz, 2H), 2.53 (m, 2H), 2.60-2.75 (m, 2H), 2.78 (t, J, 6.6 Hz, 2H), 3.66 (s, 2H), 4.50-4.68 (m, 4H), 6.90-7.08 (m, 4H), 7.35 (d, J=8.1 Hz, 2H), 7.43 (d, J=8.1 Hz, 2H)

Example 51(1) to Example 51(2)

The same procedure as a series of reactions of Example 16→Example 17→Example 18→Example 19 was carried out, except that 1-(1-{[2-(trimethylsilyl)ethoxy]methyl}-1H-imidazol-2-yl)methaneamine was used or a corresponding amine compound was used in place of it in the process of Example 16, 1H-imidazole-2-carboxylic acid was used or a corresponding carboxylic acid was used in place of it in the process of Example 17, and N,N-dipropyl-1,4-butanediamine was used or a corresponding amine was used in place of it in the process of Example 19, to obtain the title compound having the following physical properties

Example 51(1)

N-(1H-benzoimidazol-2-ylmethyl)-N-{4-[(8-cyclohexyl-2,8-diazaspiro[4.5]dec-2-yl)methyl]benzyl}-1H-imidazole-2-carboxamide (compound 51-1)

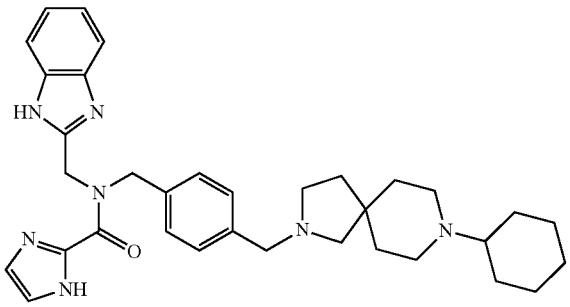 [SMILES: O=C(c1ncc[nH]1)N(Cc1ccc(CN2CCC3(CCN(C4CCCCC4)CC3)C2)cc1)Cc1nc2ccccc2[nH]1]

Description: amorphous;
TLC: Rf 0.32 (methanol:28% ammonia water=98:2);
NMR (DMSO-d$_6$): δ 1.06-1.19 (m, 5H), 1.40-1.56 (m, 7H), 1.61-1.74 (m, 4H), 2.12-2.20 (m, 1H), 2.22-2.28 (m, 2H), 2.32-2.47 (m, 6H), 3.48 (s, 2H), 4.61-4.74 (m, 2H), 5.57-5.69 (m, 2H), 7.11-7.26 (m, 8H), 7.43-7.55 (m, 2H)

Example 51(2)

N-(1H-benzoimidazol-2-ylmethyl)-N-{4-[({trans-4-[cyclohexyl(propyl)amino]cyclohexyl}amino)methyl]benzyl}-1H-imidazole-2-carboxamide (compound 51-2)

Description: amorphous;
TLC: Rf 0.28 (methanol:28% ammonia water=98:2);
NMR (DMSO-d$_6$): δ 0.73-0.83 (m, 3H), 0.97-1.10 (m, 4H), 1.13-1.29 (m, 7H), 1.53-1.69 (m, 7H), 1.85-1.98 (m, 2H), 2.21-2.31 (m, 1H), 2.35-2.45 (m, 4H), 3.67 (s, 2H), 4.62-4.73 (m, 2H), 5.56-5.69 (m, 2H), 7.09-7.17 (m, 3H), 7.20-7.31 (m, 5H), 7.41-7.57 (m, 2H)

Example 52(1) to Example 52(4)

The same procedure as a series of reactions of Example 44→Example 45→Example 46 was carried out, except that a corresponding carboxylic acid was used in place of [1-(tert-butoxycarbonyl)-4-piperidinyl]acetic acid, to obtain the title compound having the following physical properties.

Example 52(1)

3-{1-[3-(dipropylamino)propyl]piperidin-4-yl}-N,N-bis(1H-imidazol-2-ylmethyl)propaneamide (compound 52-1)

Description: amorphous;
TLC: Rf 0.84 (chloroform:methanol:28% ammonia water=40:10:2);
NMR (METHANOL-D$_4$): δ 0.89 (t, J=7.2 Hz, 6H), 1.09-1.36 (m, 3H), 1.36-1.55 (m, 6H), 1.57-1.71 (m, 4H), 1.83-1.98 (m, 2H), 2.25-2.34 (m, 2H), 2.35-2.51 (m, 8H), 2.84-2.97 (m, 2H), 4.66 (s, 2H), 4.70 (s, 2H), 6.96 (s, 2H), 7.02 (s, 2H)

Example 52(2)

1-[6-(dipropylamino)hexyl]-N,N-bis(1H-imidazol-2-ylmethyl)piperidine-4-carboxamide (compound 52-2)

Description: oily product;
TLC: Rf 0.73 (chloroform:methanol:28% ammonia water=40:10:2);
NMR (METHANOL-D$_4$): δ 0.88 (t, J=7.5 Hz, 6H), 1.16-1.36 (m, 6H), 1.39-1.59 (m, 8H), 1.60-1.84 (m, 2H), 1.86-2.06 (m, 2H), 2.22-2.33 (m, 2H), 2.36-2.55 (m, 6H), 2.57-2.77 (m, 1H), 2.82-3.00 (m, 2H), 4.66 (s, 2H), 4.75 (s, 2H), 6.97 (s, 2H), 7.03 (s, 2H)

Example 52(3)

4-{[trans-4-(dipropylamino)cyclohexyl]amino}-N,N-bis(1H-imidazol-2-ylmethyl)butaneamide (compound 52-3)

Description: amorphous;
TLC: Rf 0.39 (dichloromethane:methanol:28% ammonia water=40:10:1);
NMR (CDCl$_3$): δ 0.88 (t, J=7.2 Hz, 6H), 1.32-1.68 (m, 8H), 1.90-2.04 (m, 2H), 2.13-2.24 (m, 2H), 2.47-2.79 (m, 9H), 2.86-3.03 (m, 3H), 4.69 (s, 2H), 4.72 (s, 2H), 6.94 (s, 2H), 6.97 (s, 2H)

Example 52(4)

5-{[trans-4-(dipropylamino)cyclohexyl]amino}-N,N-bis(1H-imidazol-2-ylmethyl)pentaneamide (compound 52-4)

Description: amorphous;
TLC: Rf 0.39 (dichloromethane:methanol:28% ammonia water=40:10:1);
NMR (CDCl$_3$): δ 0.88 (t, J=7.2 Hz, 6H), 1.29-1.81 (m, 10H), 1.90-2.00 (m, 2H), 2.12-2.22 (m, 2H), 2.41-2.53 (m, 6H), 2.60-2.72 (m, 3H), 2.78-2.93 (m, 3H), 4.71 (s, 4H), 6.96 (s, 2H), 6.98 (s, 2H)

Example 53

1-{4-[(8-cyclohexyl-2,8-diazaspiro[4.5]dec-2-yl)methyl]phenyl}-N,N-bis(1H-imidazol-2-ylmethyl)methaneamine (compound 53)

The same procedure as a series of reactions of Example 16→Example 18→Example 19 was carried out, except that 1-(1-{[2-(trimethylsilyl)ethoxy]methyl}-1H-imidazol-2-yl)methaneamine was used or a corresponding amine compound was used in place of it in the process of Example 16, to obtain the title compound having the following physical properties.

Description: amorphous;
TLC: Rf 0.22 (chloroform:methanol:28% ammonia water=80:10:1);
NMR (DMSO-D$_6$): 8.0.92-1.28 (m, 5H), 1.35-1.60 (m, 7H), 1.61-1.77 (m, 4H), 2.10-2.23 (m, 1H), 2.25 (s, 2H), 2.32-2.48 (m, 6H), 3.44-3.51 (m, 4H), 3.55 (s, 4H), 6.72-7.16 (m, 4H), 7.21 (d, J=7.80 Hz, 2H), 7.32 (d, J=7.80 Hz, 2H), 11.61-12.37 (m, 2H).

Example 54(1) to Example 54(2)

The reaction was carried out in the order of Example 3→Example 5→Example 6→Example 10, using a corresponding amine in place of 4-formylbenzoic acid and t-butoxycarbonyl-1,4-butylenediamine in Example 3 and using a corresponding amine in place of diimidazoleamine in Example 6, to obtain the title compound.

Example 54(1)

1-[4-(2,8-diazaspiro[4.5]dec-2-ylcarbonyl)phenyl]-N,N-bis(1H-imidazol-2-ylmethyl)methaneamine (compound 54-1)

Description: amorphous;
TLC: Rf 0.60 (chloroform:methanol:28% ammonia water=80:20:4);
NMR (DMSO-D$_6$): δ 1.21-1.36 (m, 2H), 1.37-1.54 (m, 2H), 1.61-1.81 (m, 2H), 2.55-2.76 (m, 3H), 3.10-3.27 (m, 3H), 3.38-3.51 (m, 2H), 3.51-3.56 (m, 2H), 3.56-3.66 (m, 4H), 6.71-6.97 (m, 2H), 6.99-7.24 (m, 2H), 7.34-7.54 (m, 4H), 11.85-12.20 (m, 2H)

Example 54(2)

1-{4-[(8-cyclohexyl-2,8-diazaspiro[4.5]dec-2-yl)carbonyl]phenyl}-N,N-bis(1H-imidazol-2-ylmethyl)methaneamine (compound 54-2)

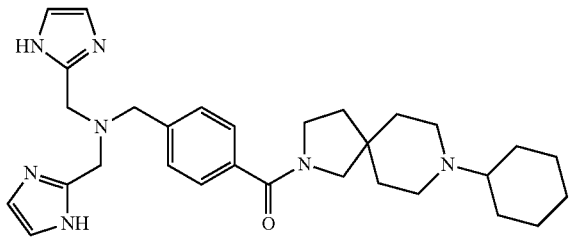 [SMILES: O=C(c1ccc(CN(Cc2ncc[nH]2)Cc2ncc[nH]2)cc1)N1CCC2(CCN(C3CCCCC3)CC2)C1]

Description: amorphous;
TLC: Rf 0.64 (chloroform:methanol:28% ammonia water=80:20:4);
NMR (DMSO-D$_6$): δ 1.15 (m, 5H), 1.40 (m, 2H), 1.56 (m, 3H), 1.71 (m, 6H), 2.27 (m, 2H), 2.43 (m, 2H), 3.23 (m, 3H), 3.45 (m, 2H), 3.54 (m, 2H), 3.58 (m, 4H), 6.97 (m, 4H), 7.43 (m, 4H), 12.00 (m, 2H)

Biological Examples

Efficacy of the compound of the present invention, for example the fact that the compound of the present invention has CXCR4 antagonistic activity, has been demonstrated by the following experiment.

A measuring method of the present invention was modified to improve accuracy and/or sensitivity of the measurement for evaluating the compound of the present invention. The detailed experimental methods are shown bellow.

As mentioned above, a more direct procedure is a screening a compound that prevents for HIV from binding to CXCR4, which is a receptor on CD4+ cell, on an assay system using HIV viruses. However, using HIV viruses for a large-scale screening is not practical due to its difficult handling. On the other hand, both of T cell-directed (X4) HIV-1 and SDF-1 bind to CXCR4 and therefore CXCR4 binding sites at both of HIV-side and SDF-1-side as well as SDF-1- and HIV-binding sites at the CXCR4 side may presumably have any common characteristics. Thus, to find a compound inhibiting absorption of HIV viruses to a cell that is a different mechanism from those of pre-existing anti-AIDS drugs (reverse transcriptase inhibitors and protease inhibitors), an assay system using an endogenous ligand for CXCR4, SDF-1 instead of HIV may be available.

Specifically, as a system of screening a compound that inhibits the binding between SDF-1 and CXCR4, for example a system of measuring the binding between iodine-labeled SDF-1 and a human T cell strain in which CXCR4 is known to be expressed is operable. The identical idea is possible since macrophage (R5) HIV and RANTES, MIP-1α, and MIP-113 all bind to CCR5.

Test Methods

Test Example 1

Study for Inhibition of Binding Human SDF-1 to CEM Cells

To human T cell strain CEM cells in a binding buffer (containing HEPES and BSA), the test compound and $^{125}$I-SDF-1 (NEN) were added and the mixture was incubated at 4° C. for 60 minutes. The reacted CEM cells were rapidly filtrated with a GF/B membrane filter plate (Packard) to adsorb. The plate was washed with PBS three times and then dried. Microscint+20 (Packard) was added thereto. An amount of the radioactivity bound to the CEM cells was measured using Top Count (Packard) and inhibition (%) of the test compound was calculated according to the following equation:

$$\text{Inhibition} = \{(Et-Ea)/(Et-Ec)\} \times 100$$

wherein
Et: amount of radioactivity when the test compound is not added,
Ec: amount of radioactivity when non-radioactive SDF-1 (Pepro Tech) is added in an amount of 1000 times as much as $^{125}$I-SDF-1 as a test compound, and
Ea: amount of radioactivity when the test compound is added.

All compounds of the present invention shown in the Example exhibited inhibition of 50% or more in a concentration of 10 μM. For example, IC$_{50}$ value for compound 10 was 27 nM.

Test Example 2

Measuring of Influence of a compound of the Present Invention on Blood Pressure and Heart Rate A rat was anesthetized with urethane (1.2 g/kg subcutaneous administration). After neck midline dissection, a catheter for measuring blood pressure was inserted into a right common carotid artery. Then, after dissecting inguinal region, a catheter for chemical injection was inserted into a femoral vein and fixed. A catheter for measurement of blood pressure was connected to a pressure transducer and then the pressure waveform was recorded on a thermal writing pen recorder through an amplifier for strain compression (AP-641G (manufactured by NIHON KOHDEN CORPORATION)). In this case, regarding a heart rate, a value through an cardiotachometer (AT-601G (manufactured by NIHON KOHDEN CORPORATION)) using the pressure waveform obtained from the amplifier for strain compression as a trigger was recorded on a thermal writing pen recorder. The test compound was dissolved in a 10% solubilizing agent/physiological saline solution (volume ratio of polyoxyethylene hydroxystearate:propylene glycol:physiological saline=7:3:190) so as to adjust the concentration to 0.1, 0.3, 1, 3 or 10 mg/mL to prepare solutions. Each solution was intravenous administered at 1 mL/Kg through the caudal vein over about 10 seconds. Accumulative administration of stepwise increasing of a dosage was carried out to an individual.

In case of administration of the compound 19, when the concentration was 3 mg/kg or less, the effect of decreasing blood pressure was not recognized, and a rate of increase in the heart rate was 2% when 10 mg/kg of the test compound is administered, and there was no influence on the heart rate in case of a low dosage.

Formulation Examples

Formulation Example 1

4-({[4-(dipropylamino)butyl]amino}methyl)-N,N-bis (1H-imidazol-2-ylmethyl)benzoamide (200 g), calcium carboxymethyl cellulose (disintegrant, 20.0 g), magnesium stearate (lubricants, 10.0 g) and microcrystalline cellulose (870 g) were mixed by a conventional method and then compressed to obtain 10,000 tablets each containing 20 mg of an active ingredient.

Formulation Example 2

4-({[4-(dipropylamino)butyl]amino}methyl)-N,N-bis (1H-imidazol-2-ylmethyl)benzoamide (100 g), mannitol (2 kg) and distilled water (50 L) were mixed by a conventional method and filtered with a dust filter, and then each ampoule was filled with 5 mL of the obtained mixture and subjected to heat sterilization in an autoclave to obtain 10,000 ampoules each containing 10 mg of an active ingredient.

INDUSTRIAL APPLICABILITY

The compound of the present invention has CXCR4 antagonistic activity and is therefore useful as a preventive and/or therapeutic agent for CXCR4-mediated diseases. Accordingly, the compound of the present invention can be available as a drug. For example, the compound of the present invention is useful as a preventive and/or therapeutic agent for inflammatory and immune diseases (for example, rheumatoid arthritis, arthritis, retinopathy, pulmonary fibrosis, transplanted organ rejection, etc.), allergic diseases, infections (for example, human immunodeficiency virus infection, acquired immunodeficiency syndrome, etc.), psychoneurotic diseases, cerebral diseases, cardiovascular disease, metabolic diseases, and cancerous diseases (for example, cancer, cancer metastasis, etc.), or an agent for regeneration therapy.

The invention claimed is:

1. A compound represented by formula (I-0):

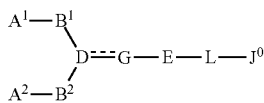

(I-0)

wherein $A^1$ and $A^2$ each independently represents an imidazole ring which may have a substituent(s);
$B^1$ and $B^2$ each independently represents a methylene group which may have a substituent(s);
E represents a phenylene which may have a substituent(s);
L represents a —CO— or —CH$_2$—;
$J^0$ represents 1-oxa-4,9-diazaspiro[5.5]undecane which may have a substituent(s);
⸺ represents a single bond;
D represents a nitrogen atom, G represents a —CO— or —CH$_2$—
or a salt thereof, an N-oxide thereof or a solvate thereof.

2. The compound according to claim 1, which is represented by formula (I-4):

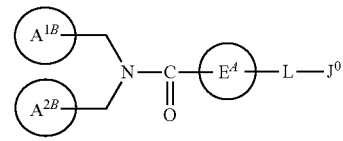

(I-4)

wherein ring $A^{1B}$ and ring $A^{2B}$ each independently represents imidazole which may have a substituent(s);
ring $E^4$ represents a phenylene which may have a substituent(s).

3. The compound according to claim 2, which is represented by formula (I-4-4):

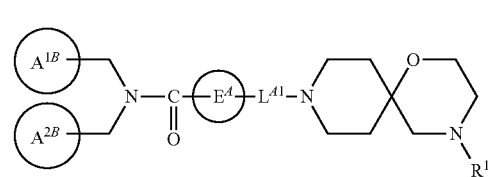

(I-4-4)

wherein $L^{A1}$ represents a —CO— or —CH$_2$ and $R^1$ represents a hydrogen atom or a substituent.

4. The compound according to claim 1, which is represented by formula (I-8):

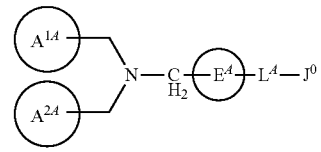

(I-8)

wherein ring $A^{1A}$, ring $A^{2A}$ each independently represents imidazole which may have a substituent(s);
ring $E^4$ represents a phenylene which may have a substituent(s);
$L^A$ represents a —CO— or —CH$_2$.

5. The compound according to claim 1, which is
(1) 4-[(4-cyclohexyl-1-oxa-4,9-diazaspiro[5.5]undec-9-yl)methyl]-N,N-bis(1H-imidazol-2-ylmethyl)benzamide,
(2) 4-[(9-cyclohexyl-1-oxa-4,9-diazaspiro[5.5]undec-4-yl)methyl]-N,N-bis(1H-imidazol-2-ylmethyl)benzamide,
(3) 4-{[4-(cyclopentylmethyl)-1-oxa-4,9-diazaspiro[5.5] undec-9-yl]methyl}-N,N-bis(1H-imidazol-2-ylmethyl)benzamide,
(4) N,N-bis(1H-imidazol-2-ylmethyl)-4-{[4-(2-thienylmethyl)-1-oxa-4,9-diazaspiro[5.5]undec-9-yl] methyl}benzamide, (5) 4-[(4-cyclohexyl-1-oxa-4,9-diazaspiro[5.5]undec-9-yl)methyl]-N,N-bis(1H-imidazol-2-ylmethyl)benzamide, or (6) 4-[(9-cyclohexyl-1-oxa-4,9-diazaspiro[5.5]undec-4-yl)methyl]-N,N-bis(1H-imidazol-2-ylmethyl)benzamide.

6. A pharmaceutical composition comprising a compound represented by formula (I-0) described in claim 1, a salt thereof, an N-oxide thereof or a solvate thereof.

7. A pharmaceutical composition comprising a compound represented by formula (I-0) described in claim 1, a salt thereof, an N-oxide thereof or a solvate thereof and one or more agents selected from reverse transcriptase inhibitor and protease inhibitor, wherein said reverse transferase inhibitor is at least one compound selected from the group consisting of zidovudine, didanosine, zalcitabine, stavudine, lamivudine, abacavir, didanosine, adefovir, dipivoxil, emtricitabine, tenofovir, nevirapine, delavirdine, efavirenz and capravirine, and wherein said protease inhibitor is at least one compound selected from the group consisting of indinavir, ritonavir, nelfinavir, saquinavir, amprenavir, lopinavir, atazanavir, fosamprenavir and tipranavir.

8. A method of treating CXCR4-mediated diseases selected from the group consisting of human immunodeficiency virus infection, acquired immunodeficiency syndrome, small cell lung cancer, breast cancer, melanoma, multiple myeloma, malignant myeloma, pancreatic cancer, prostate cancer, acute and chronic leukemia, rheumatoid arthritis, collagen-induced arthritis, diabetic retinopathy, or pulmonary fibrosis in a mammal, which comprises administering an effective dosage of a compound represented by formula (I-0) described in claim 1, a salt thereof, an N-oxide thereof or a solvate thereof to the mammal.

9. A method of treating human immunodeficiency virus infection, which comprises administering an effective dosage of a compound represented by formula (I-0) described in claim 1, or a salt thereof, or an N-oxide thereof to a mammal.

* * * * *